US 10,695,417 B2

(12) United States Patent
Jones et al.

(10) Patent No.: US 10,695,417 B2
(45) Date of Patent: Jun. 30, 2020

(54) HUMAN ADENOVIRUS SEROTYPE 5 VECTORS CONTAINING E1 AND E2B DELETIONS ENCODING THE EBOLA VIRUS GLYCOPROTEIN

(71) Applicant: Etubics Corporation, Seattle, WA (US)

(72) Inventors: Frank R. Jones, Seattle, WA (US); Elizabeth Gabitzsch, Seattle, WA (US)

(73) Assignee: Etubics Corporation, Seattle, WA (US)

( * ) Notice: Subject to any disclaimer, the term of this patent is extended or adjusted under 35 U.S.C. 154(b) by 0 days.

(21) Appl. No.: 15/542,003

(22) PCT Filed: Jan. 7, 2016

(86) PCT No.: PCT/US2016/012482
§ 371 (c)(1),
(2) Date: Jul. 6, 2017

(87) PCT Pub. No.: WO2016/112188
PCT Pub. Date: Jul. 14, 2016

(65) Prior Publication Data
US 2017/0368161 A1    Dec. 28, 2017

Related U.S. Application Data

(60) Provisional application No. 62/101,968, filed on Jan. 9, 2015.

(51) Int. Cl.
A61K 39/12      (2006.01)
A61K 38/19      (2006.01)
C12N 15/861     (2006.01)
A61K 35/761     (2015.01)

(52) U.S. Cl.
CPC ............ A61K 39/12 (2013.01); A61K 35/761 (2013.01); A61K 38/19 (2013.01); C12N 15/861 (2013.01); C12N 2710/10043 (2013.01); C12N 2710/10341 (2013.01); C12N 2760/14122 (2013.01); C12N 2760/14134 (2013.01)

(58) Field of Classification Search
CPC .... A61K 39/12; A61K 35/761; C12N 15/861; C12N 2710/10341; C12N 2760/14122
See application file for complete search history.

(56) References Cited

U.S. PATENT DOCUMENTS

| | | | |
|---|---|---|---|
| 5,145,684 A | 9/1992 | Liversidge et al. |
| 5,466,468 A | 11/1995 | Schneider et al. |
| 5,552,157 A | 9/1996 | Yagi et al. |
| 5,565,213 A | 10/1996 | Nakamori et al. |
| 5,567,434 A | 10/1996 | Szoka, Jr. |
| 5,738,868 A | 4/1998 | Shinkarenko |
| 5,795,587 A | 8/1998 | Gao et al. |
| 6,045,802 A | 4/2000 | Schlom et al. |
| 6,057,158 A | 5/2000 | Chamberlain et al. |
| 6,063,622 A | 5/2000 | Chamberlain et al. |
| 6,083,750 A | 7/2000 | Chamberlain et al. |
| 6,348,450 B1 | 2/2002 | Tang et al. |
| 6,451,596 B1 | 9/2002 | Chamberlain et al. |
| 6,544,947 B2 | 4/2003 | Holaday et al. |
| 6,706,693 B1 | 3/2004 | Tang et al. |
| 6,716,823 B1 | 4/2004 | Tang et al. |
| 6,756,038 B1 | 6/2004 | Schlom et al. |
| 7,211,569 B2 | 5/2007 | Neeper et al. |
| 7,410,758 B2 | 8/2008 | Sastry et al. |
| 7,488,482 B2 | 2/2009 | Balloul et al. |
| 7,547,681 B2 | 6/2009 | Scholler et al. |
| 7,662,586 B2 | 2/2010 | Monaci et al. |
| 7,723,096 B2 | 5/2010 | Schlom et al. |
| 7,771,715 B2 | 8/2010 | Schlom et al. |
| 7,786,278 B2 | 8/2010 | Parrington et al. |
| 7,999,071 B2 | 8/2011 | Schlom et al. |
| 8,012,468 B2 | 9/2011 | Kim et al. |
| 8,017,590 B1 | 9/2011 | Berinstein et al. |
| 8,188,244 B2 | 5/2012 | La Monica et al. |
| 8,207,314 B2 | 6/2012 | Berinstein et al. |
| 8,298,549 B2 | 10/2012 | Balint et al. |
| 8,609,395 B2 | 12/2013 | Schlom et al. |
| 9,248,177 B2 | 2/2016 | Tang et al. |
| 9,605,276 B2 | 3/2017 | Jones et al. |
| 2004/0091995 A1 | 5/2004 | Schlom et al. |
| 2004/0265274 A1 | 12/2004 | Wei et al. |
| 2005/0037439 A1 | 2/2005 | Bourner et al. |
| 2006/0104986 A1 | 5/2006 | Duke et al. |

(Continued)

FOREIGN PATENT DOCUMENTS

| | | |
|---|---|---|
| EP | 1017810 B1 | 5/2004 |
| EP | 1447414 B1 | 6/2007 |

(Continued)

OTHER PUBLICATIONS

Audet, J., et al., Nov. 2014, Molecular characterization of the monoclonal antibodies composing ZMAb: A protective cocktail against Ebola virus, Sci. Reports 4(6881):1-8 (DOI:10.1038/srep06881).*
Dube, D., et al., Apr. 2009, The primed ebolavirus glycoprotein (19-kilodalton GP1,2): Sequence residues critical for host binding, J. Virol. 83(7):2883-2891.*
Amalfitano, A. Use of multiply deleted adenovirus vectors to probe adenovirus vector performance and toxicities. Curr Opin Mol Ther. Aug. 2003;5(4):362-6.
Amalfitano, et al. Separating fact from fiction: assessing the potential of modified adenovirus vectors for use in human gene therapy. Curr Gene Ther 2:111-133 (2002).
Amara, et al. A new generation of HIV vaccines. Trends Mol Med 8;489-95 (2002).

(Continued)

Primary Examiner — Jeffrey S Parkin
(74) Attorney, Agent, or Firm — Sheridan Ross P.C.

(57) ABSTRACT

Methods for generating immune responses to Ebola virus antigens using adenovirus vectors that allow multiple vaccinations with the same adenovirus vector and vaccinations in individuals with preexisting immunity to adenovirus are provided.

25 Claims, 9 Drawing Sheets
Specification includes a Sequence Listing.

(56) References Cited

U.S. PATENT DOCUMENTS

| | | |
|---|---|---|
| 2007/0104685 A1 | 5/2007 | La Monica et al. |
| 2010/0055069 A1 | 3/2010 | Rooke et al. |
| 2010/0183673 A1 | 7/2010 | Balint et al. |
| 2010/0209386 A1 | 8/2010 | Schlom et al. |
| 2010/0285065 A1 | 11/2010 | Parrington et al. |
| 2013/0224144 A1* | 8/2013 | Balint et al. ......... A61K 39/235 |
| 2013/0251741 A1 | 9/2013 | Pietersz et al. |
| 2014/0212434 A1* | 7/2014 | Blaney et al. ......... C12N 15/86 |
| 2014/0377294 A1 | 12/2014 | Fueyo-Margareto et al. |
| 2015/0086541 A1* | 3/2015 | Aguilar-Cordova et al. ............... A61K 39/3955 |
| 2015/0182621 A1 | 7/2015 | Wu et al. |
| 2015/0352198 A1 | 12/2015 | Berinstein et al. |
| 2015/0374790 A1 | 12/2015 | Liu et al. |
| 2017/0065693 A1 | 3/2017 | Balint et al. |
| 2017/0065706 A1 | 3/2017 | Balint et al. |
| 2017/0165341 A1 | 6/2017 | Jones et al. |

FOREIGN PATENT DOCUMENTS

| | | |
|---|---|---|
| EP | 1227837 B1 | 5/2008 |
| EP | 1015035 B1 | 1/2009 |
| EP | 2465520 A2 | 6/2012 |
| WO | WO-9614876 A1 | 5/1996 |
| WO | WO-0034494 A1 | 6/2000 |
| WO | WO-0208436 A2 | 1/2002 |
| WO | WO-03008649 A1 | 1/2003 |
| WO | WO-2005012527 A1 | 2/2005 |
| WO | WO-2005051991 A2 | 6/2005 |
| WO | WO-2005058937 A2 | 6/2005 |
| WO | WO-2005058950 A2 | 6/2005 |
| WO | WO-2006033672 A2 | 3/2006 |
| WO | WO-2006044923 A2 | 4/2006 |
| WO | WO-2006033672 A3 | 6/2006 |
| WO | WO-2007008780 A2 | 1/2007 |
| WO | WO-2007008780 A3 | 3/2007 |
| WO | WO-2007092792 A2 | 8/2007 |
| WO | WO-2009006479 A2 | 1/2009 |
| WO | WO-2009006479 A3 | 3/2009 |
| WO | WO-2010033841 A1 | 3/2010 |
| WO | WO-2010065626 A1 | 6/2010 |
| WO | WO-2010121180 A1 | 10/2010 |
| WO | WO-2011032119 A1 | 3/2011 |
| WO | WO-2011115914 A1 | 9/2011 |
| WO | WO-2012019127 A2 | 2/2012 |
| WO | WO-2012109404 A1 | 8/2012 |
| WO | WO-2012174220 A1 | 12/2012 |
| WO | WO-2013025972 A1 | 2/2013 |
| WO | WO 2014/031178 A1 * | 2/2014 ............ C12N 15/63 |
| WO | WO-2014031178 A1 | 2/2014 |
| WO | WO-2014043518 A1 | 3/2014 |
| WO | WO-2014160747 A2 | 10/2014 |
| WO | WO-2015031778 A2 | 3/2015 |
| WO | WO-2015061416 A2 | 4/2015 |
| WO | WO-2015103602 A1 | 7/2015 |
| WO | WO-2015127027 A1 | 8/2015 |
| WO | WO-2015157639 A1 | 10/2015 |
| WO | WO-2016007499 A1 | 1/2016 |
| WO | WO-2016112188 A1 | 7/2016 |
| WO | WO-2016112195 A1 | 7/2016 |
| WO | WO-2016172249 A1 | 10/2016 |

OTHER PUBLICATIONS

Appledorn, et al. (2008) Adenovirus vector-induced innate inflammatory mediators, MAPK signaling, as well as adaptive immune responses are dependent upon both TLR2 and TLR9 in vivo. J Immunol. 181:2134-2144.

Appledorn, et al. (2008) Wild-type adenoviruses from groups A-F evoke unique innate immune responses, of which HAd3 and SAd23 are partially complement dependent. Gene Ther. 15:885-901.

Balint, et al. Extended evaluation of a phase ½ trial on dosing, safety, immunogenicity, and overall survival after immunizations with an advanced-generation Ad5 [E1-, E2b-]-CEA (6D) vaccine in late-stage colorectal cancer. Cancer Immunology, Immunotherapy 64.8 (2015): 977-987.

Bangari, et al. (2006) Development of nonhuman adenoviruses as vaccine vectors. Vaccine 24:849-862.

Bangari, et al. Current strategies and future directions for eluding adenoviral vector immunity. Curr Gene Ther. Apr. 2006; 6(2):215-226.

Barjot, et al. Gutted adenoviral vector growth using E1/E2b/E3-deleted helper viruses. J Gene Med 4;480-9 (2002).

Barouch, et al. (2011) International seroepidemiology of adenovirus serotypes 5, 26, 35, and 48 in pediatric and adult populations. Vaccine 29:5203-5209.

Barouch, et al. Adenovirus vector-based vaccines for human immunodeficiency virus type 1. Hum Gene Ther. 16:149-156 (2005).

Barratt-Boyes, et al. Broad cellular immunity with robust memory responses to simian immunodeficiency virus following serial vaccination with adenovirus 5- and 35-based vectors. J Gen Virol 87:.Pt 1 139-149 (2006).

Bewig, et al. (2000) Accelerated titering of adenoviruses. BioTechniques 28:871-873.

Brave, et al. Vaccine delivery methods using viral vectors. Mol Pharm 4:.1 18-32 (2007).

Campos, et al. (2007) Current advances and future challenges in adenoviral vector biology and targeting. Curr Gene Ther 7:189-204.

Chamberlain, et al. Packaging cell lines for generating replication-defective and gutted adenoviral vectors. Methods Mol Med 76;153-66 (2003).

Co-pending U.S. Appl. No. 15/564,413, filed Oct. 4, 2017.

Dellorusso, et al. Functional correction of adult mdx mouse muscle using gutted adenoviral vectors expressing full-length dystrophin. Proc Natl Acad Sci U S A. Oct. 1, 2002;99(20):12979-84. Epub Sep. 23, 2002.

Ding, et al. Long-term efficacy after [E1-, polymerase-] adenovirus-mediated transfer of human acid-alpha-glucosidase gene into glycogen storage disease type II knockout mice. Hum Gene Ther 12;955-65 (2001).

Eo, et al. Prime-boost immunization with DNA vaccine: mucosal route of administration changes the rules. J Immunol 166;5473-9 (2001).

Evans, et al. Development of stable liquid formulations for adenovirus-based vaccines. J Pharm Sci. Oct. 2004;93(10):2458-75.

Everett, et al. Liver toxicities typically induced by first-generation adenoviral vectors can be reduced by use of E1, E2b-deleted adenoviral vectors. Hum Gene Ther, 2003. 14(18): p. 1715-1726.

Everett, et al. Strain-specific rate of shutdown of CMV enhancer activity in murine liver confirmed by use of persistent [E1(-), E2b(-)] adenoviral vectors. Virology. Jul. 20, 2004; 325(1):96-105.

Gabaglia CR, Sercarz EE, Diaz-De-Durana Y, Hitt M, Graham FL, Gauldie J, and Braciak TA. Life-long systemic protection in mice vaccinated with L. major and adenovirus IL-12 vector requires active infection, macrophages and intact lymph nodes.Vaccine 23:.2 247-257 (2004).

Gabitzsch, et al. (2009) Novel adenovirus type 5 vaccine platform induces cellular immunity aginst HIV-Gag, Pol, Nef despite the presence of Ad5 immunity. Vaccine 27:6394-6398.

Gabitzsch, et al. (2010) Anti-tumor immunity despite immunity to adenovirus using a novel adenoviral vector Ad5 [E1-, E2b-]-CEA. Cancer Immunol Immunother 59:1131-1135.

Gabitzsch, et al. (2011) Induction and Comparison of SIV immunity in Ad5 Naïve and Ad5 Immune Non-human Primates using an Ad5 [E1-, E2b-] based vaccine. Vaccine 29:8101-8107.

Gabitzsch, et al. (2011) New Recombinant Ad5 Vector Overcomes Ad5 Immunity Allowing for Multiple Safe, Homologous Immunizations. J Clin Cell Immunol. S4:001. doi:10.4172/2155-9899.S4-001.

Gabitzsch, et al. (2012) Control of SIV infection and subsequent induction of pandemic H1N1 immunity in rhesus macaques using an Ad5 [E1-, E2b-] vector platform. Vaccine 2012; 30:7265-7270.

Gabitzsch, et al. The generation and analyses of a novel combination of recombinant adenovirus vaccines targeting three tumor antigens as an immunotherapeutic. Oncotarget. Oct. 13, 2015; 6(31): 31344-31359.

(56) References Cited

OTHER PUBLICATIONS

Gao et al. Protection of mice and poultry from lethal H5N1 avian influenza virus through adenovirus-based immunization. J Virol, 2006. 80(4): p. 1959-1964.
Garnett, et al. TRICOM vector based cancer vaccines. Curr Pharm Des. 2006;12(3):351-61.
Gomez-Roman, et al. Adenoviruses as vectors for HIV vaccines. AIDS Rev 5;178-85 (2003).
Gulley, et al. (2008) Pilot study of vaccination with recombinant CEA-MUC-1-TRICOM poxviral-based vaccines in patients with metastatic carcinoma. Clin Cancer Res. 14:3060-3069.
Haglund, et al. Robust recall and long-term memory T-cell responses induced by prime-boost regimens with heterologous live viral vectors expressing human immunodeficiency virus type 1 Gag and Env proteins. J Virol 76;7506-17 (2002).
Harris, et al. (2002) Acute Regression of Advanced and Retardation of Early Aortic Atheroma in Immunocompetent Apolipoprotein-E (Apoe) Deficient Mice by Administration of a Second Generation [E1(-), E3(-), Polymerase(-)] Adenovirus Vector Expressing Human Apoe. Human Molecular Genetics 11:43-58.
Hartigan-O'Connor, et al. Developments in gene therapy for muscular dystrophy. Microsc Res Tech 48;223-38 (2000).
Hartigan-O'Connor, et al. Efficient rescue of gutted adenovirus genomes allows rapid production of concentrated stocks without negative selection. Hum Gene Ther. Mar. 1, 2002;13(4):519-31.
Hartigan-O'Connor, et al. Generation and growth of gutted adenoviral vectors. Methods Enzymol 346;224-46 (2002).
Hartigan-O'Connor, et al. Immune evasion by muscle-specific gene expression in dystrophic muscle. Mol Ther. Dec. 2001;4(6):525-33.
Hartman, et al. (2008) Adenovirus vector induced innate immune responses: impact upon efficacy and toxicity in gene therapy and vaccine applications. Virus Res 132:1-14.
Hartman, et al. Adenoviral infection induces a multi-faceted innate cellular immune response that is mediated by the toll-like receptor pathway in A549 cells. Virology. Feb. 20, 2007;358(2):357-72. Epub Oct. 5, 2006.
Hartman, et al. Adenovirus infection triggers a rapid, MyD88-regulated transcriptome response critical to acute-phase and adaptive immune responses in vivo. J Virol. Feb. 2007;81(4):1796-812. Epub Nov. 22, 2006.
Harui, et al. 2004. Vaccination with helper-dependent adenovirus enhances the generation of transgene-specific CTL. Gene Ther 11:1617-1626.
Hauser, et al. Analysis of muscle creatine kinase regulatory elements in recombinant adenoviral vectors. Mol Ther 2;16-25 (2000).
Hirschowitz, et al. 2000. Murine dendritic cells infected with adenovirus vectors show signs of activation. Gene Ther 7:1112-1120.
Hodges, et al. (2000) Multiply deleted [E1, polymerase-, and pTP-] adenovirus vector persists despite deletion of the preterminal protein. J Gene Med 2:250-259.
Hodges, et al. Adenovirus vectors with the 100K gene deleted and their potential for multiple gene therapy applications. J Virol. Jul. 2001;75(13):5913-20.
Hoelscher, et al. Development of adenoviral-vector-based pandemic influenza vaccine against antigenically distinct human H5N1 strains in mice. Lancet, 2006. 367(9509): p. 475-481.
Huang Chun-Ming et al. A differential proteome in tumors suppressed by an adenovirus-based skin patch vaccine encoding human carcinoembryonic antigen. Proteomics, 5(4); 1013-1023 (Mar. 2005).
Jonuleit, et al. 2000. Efficient transduction of mature CD83+ dendritic cells using recombinant adenovirus suppressed T cell stimulatory capacity. Gene Ther 7:249-254.
Joshi, et al. (2009) Adenovirus DNA polymerase is recognized by human CD8+T cells. J Gen Virol 90:84-94.
Kaufman, et al. (2004) Phase II randomized study of vaccine treatment of advanced prostate cancer (E7897): A trial of the Eastern Cooperative Oncology Group. J Clin Oncol 22:2122-2132.
Kawano, et al. (2007) MUC1 oncoprotein regulates Bcr-Abl stability and pathogenesis in chronic myelogenous leukemia cells. Cancer Res. 67:11576-11584.
Khanam, et al. An adenovirus prime/plasmid boost strategy for induction of equipotent immune responses to two dengue virus serotypes. BMC Biotechnol 7:.1-11 (2007).
Kiang et al. Fully deleted Ad persistently expressing GAA accomplishes long-term skeletal muscle glycogen correction in tolerant and nontolerant GSD-II mice. Mol Ther, 2006. 13(1):127.
Kiang, et al. Multiple innate inflammatory responses induced after systemic adenovirus vector delivery depend on a functional complement system. Mol Ther. Oct. 2006;14(4):588-98. Epub Jun. 2, 2006.
Kirk, et al. Gene-modified dendritic cells for use in tumor vaccines. Hum Gene Ther 11;797-806 (2000).
Kong, et al. Immunogenicity of multiple gene and clade human immunodeficiency virus type 1 DNA vaccines. J Virol. 77:12764-72 (2003).
Lemiale et al., Enhanced mucosal immunoglobulin A response of intranasal adenoviral vector human immunodeficiency virus vaccine and localization in the central nervous system. J Virol., 77 (2003): 10078-87.
Letvin, et al. Heterologous envelope immunogens contribute to AIDS vaccine protection in rhesus monkeys. J Virol. 78;7490-7 (2004).
Lozier, et al. Toxicity of a first-generation adenoviral vector in rhesus macaques. Hum Gene Ther 13;113-24 (2002).
Lubaroff, et al. Clinical protocol: phase I study of an adenovirus/prostate-specific antigen vaccine in men with metastatic prostate cancer. Hum Gene Ther. 17:220-229 (2006).
Luebke, et al. (2001) A Modified Adenovirus Can Transfect Cochlear Hair Cells In Vivo Without Compromising Cochlear Function. Gene Ther. 8:789-794.
Maione, et al. An improved helper-dependent adenoviral vector allows persistent gene expression after intramuscular delivery and overcomes preexisting immunity to adenovirus. Proc Natl Acad Sci U S A. May 22, 2001;98(11):5986-91. Epub May 15, 2001.
Maione, et al. Prolonged expression and effective readministration of erythropoietin delivered with a fully deleted adenoviral vector. Hum Gene Ther. Apr. 10, 2000;11(6):859-68.
McDermott, et al. Cytotoxic T-Lymphocyte Escape Does Not Always Explain the Transient Control of Simian Immunodeficiency Virus SIVmac239 Viremia in Adenovirus-Boosted and DNA-Primed Mamu-A*01-Positive Rhesus Macaques. J Virol. 79:15556-66 (2005).
Miller, et al. 2000. Intratumoral administration of adenoviral interleukin 7 gene-modified dendritic cells augments specific antitumor immunity and achieves tumor eradication. Hum Gene Ther 11:53-65.
Mohebtash, et al. A pilot study of MUC-1/CEA/TRICOM poxviral-based vaccine in patients with metastatic breast and ovarian cancer. Clin Cancer Res. Nov. 15, 2011;17(22):7164-73. doi: 10.1158/1078-0432.CCR-11-0649. Epub Nov. 8, 2011.
Moore, et al. Progress in DNA-based heterologous prime-boost immunization strategies for malaria. Immunol Rev. 199:126-143 (2004).
Moore, et al. Effects of antigen and genetic adjuvants on immune responses to human immunodeficiency virus DNA vaccines in mice. J Virol 76;243-50 (2002).
Morelli, et al. 2000. Recombinant adenovirus induces maturation of dendritic cells via an NF-kappaB-dependent pathway. J Virol 74:9617-9628.
Morral, et al. Lethal toxicity, severe endothelial injury, and a threshold effect with high doses of an adenoviral vector in baboons. Hum Gene Ther 13;143-54 (2002).
Morse, et al. (2005) Phase I study of immunization with dendritic cells modified with recombinant fowlpox encoding carcinoembryonic antigen and the triad of costimulatory molecules CD54, CD58, and CD80 in patients with advanced malignancies. Clin Cancer Res 11:3017-3024.
Morse, et al. (2013) Novel Adenoviral Vector Induces T Cell Responses Despite Anti-Adenoviral Neutralizing Antibodies in Colorectal Cancer Patients. Cancer Immunol Immunother. 62:1293-1301.
Morse, et al. Effect of the vaccine Ad5 [E1-, E2b-]-CEA(6D) on CEA-directed CMI responses in patients with advanced CEA-

(56) References Cited

OTHER PUBLICATIONS expressing malignancies in a phase I/II clinical trial. Etubics Corporation, Seattle, WA. Poster. 2012. http://www.etubics.com/pdf/ASCO%202012.pdf.
Nazir, et al. Innate immune response to adenovirus. J Investig Med. Sep. 2005;53(6):292-304.
Nemunaitis, et al. Pilot trial of intravenous infusion of a replication-selective adenovirus (ONYX-015) in combination with chemotherapy or IL-2 treatment in refractory cancer patients. Cancer Gene Ther. 10:341-352 (2003).
Nwanegbo, et al. (2004) Prevalence of neutralizing antibodies to adenoviral serotypes 5 and 35 in the adult populations of The Gambia, South Africa, and the United States. Clin Diagn Lab Immunol 11:351-357.
Oh, et al. Dendritic cells transduced with recombinant adenoviruses induce more efficient anti-tumor immunity than dendritic cells pulsed with peptide. Vaccine, 24; 2860-2868 (2006).
Ojima et al. Successful cancer vaccine therapy for carcinoembryonic antigen (CEA)-expressing colon cancer using genetically modified dendritic cells that express CEA and T helper-type 1 cytokines in CEA transgenic mice, International Journal of Cancer 120(3), 585-593 (2006).
Osada, et al. (2009) Optimization of vaccine responses with an E1, E2b and E3-deleted Ad5 vector circumvents pre-existing anti-vector immunity. Cancer Gene Ther 16:673-682.
Osada, et al. Optimization of vaccine responses with an E1, E2b and E3-deleted Ad5 vector circumvents pre-existing anti-vector immunity. Cancer Gene Ther.vol. 16, Issue No. 9, pp. 673-682 (Sep. 2009).
Perkins, et al. Boosting with an adenovirus-based vaccine improves protective efficacy against Venezuelan equine encephalitis virus following DNA vaccination. Vaccine. 2006; 24:3440-5.
Etubics press release. Etubics and Duke Cancer Institute report positive phase I/II results for colorectal cancer immunotherapy. Etubics corporation. Seattle (May 16, 2012). URL:<http://etubics.com/etubics-and-duke-cancer-institute-report-positive-phase-iii-results-for-colorectal-cancer-immunotherapy/.>.
Phillpotts, et al. Intranasal immunization with defective adenovirus serotype 5 expressing the Venezuelan equine encephalitis virus E2 glycoprotein protects against airborne challenge with virulent virus. Vaccine 23:1615-1623. (2005).
Qualikene, et al. Protease-deleted adenovirus vectors and complementing cell lines: potential applications of single-round replication mutants for vaccination and gene therapy. Human Gene Therapy Jun. 10, 2000;11(9):1341-53.
Ramlau, et al. (2008) A phase II study of Tg4010 (Mva-Muc1-II2) in association with chemotherapy in patients with stage III/IV Non-small cell lung cancer. J Thorac Oncol. 3:735-744.
Reddy, et al. Sustained human factor VIII expression in hemophilia A mice following systemic delivery of a gutless adenoviral vector. Mol Ther. Jan. 2002;5(1):63-73.
Rice, et al. An HPV-E6/E7 immunotherapy plus PD-1 checkpoint inhibition results in tumor regression and reduction in PD-L1 expression. Cancer Gene Therapy 22, 454-462 (Sep. 2015).
Roberts, et al. Hexon-chimaeric adenovirus serotype 5 vectors circumvent pre-existing anti-vector immunity. Nature, 2006. 441(7090):239-43.
Sandig, et al. Optimization of the helper-dependent adenovirus system for production and potency in vivo. Proc Natl Acad Sci U S A. Feb. 1, 2000;97(3):1002-7.
Santosuosso, et al. Mucosal luminal manipulation of T cell geography switches on protective efficacy by otherwise ineffective parenteral genetic immunization. J Immunol 178:.4 2387-395 (2007).
Scott, et al. Gutted adenoviral vectors for gene transfer to muscle. Methods Mol Biol 219;19-28 (2003).
Scott et al. Viral vectors for gene transfer of micro-, mini-, or full-length dystrophin. Neuromuscul. Disord. 12(Suppl 1):S23-9 (2002).

Seregin, et al. (2009) Overcoming pre-existing Adenovirus immunity by genetic engineering of Adenovirus-based vectors. Expert Opin Biol Ther 9(12): 1521-1531.
Shiver, et al. Recent advances in the development of HIV-1 vaccines using replication-incompetent adenovirus vectors. Annu Rev Med. 55;355-72 (2004).
Shiver, et al. 2002. Replication-incompetent adenoviral vaccine vector elicits effective anti-immunodeficiency-virus immunity. Nature 415:331-335.
Morse, et al. Synergism from combined immunologic and pharmacologic inhibition of HER2 in vivo. Int J Cancer 126(12):2893-2903 (2010). First published online Oct. 23, 2009. URL:<https://doi.org/10.1002/ijc.24995>.
Steel, et al. Interleukin-15 and its Receptor Augment Dendritic Cell Vaccination Against the neu Oncogene Through the Induction of Antibodies Partially Independent of CD4-help. Cancer Res. Feb. 1, 2010; 70(3): 1072.
Sullivan, et al. Development of a preventive vaccine for Ebola virus infection in primates. Nature 408;605-9 (2000).
Sumida, et al. Neutralizing antibodies and CD8+T lymphocytes both contribute to immunity to adenovirus serotype 5 vaccine vectors. J Virol. Mar. 2004;78(6):2666-73.
Tatsis, et al. (2004) Adenoviruses as vaccine vectors. Molecular Ther 10:616-629.
Tatsis, et al. A CD46-binding Chimpanzee Adenovirus Vector as a Vaccine Carrier. Mol Ther (2007).
Thomas, et al. Peripheral infection with adenovirus causes unexpected long-term brain inflammation in animals injected intracranially with first-generation, but not with high-capacity, adenovirus vectors: toward realistic long-term neurological gene therapy for chronic diseases. Proc Natl Acad Sci U S A 97;7482-7 (2000).
Thorner, et al. Immunogenicity of heterologous recombinant adenovirus prime-boost vaccine regimens is enhanced by circumventing vector cross-reactivity. J Virol. Dec. 2006;80(24):12009-16. Epub Oct. 11, 2006.
Tillman, et al. 2000. Adenoviral vectors targeted to CD40 enhance the efficacy of dendritic cell-based vaccination against human papillomavirus 16-induced tumor cells in a murine model. Cancer Res 60:5456-5463.
Tsang, et al. (2004) A human cytotoxic T-lymphocyte epitope and its agonist epitope from the nonvariable number of tandem repeat sequence of MUC-1. Clin Cancer Res. 10:2139-2149.
Van Cutsem, et al. (2007) Open-label Phase III trial of panitumumab plus best supportive care compared with best supportive care alone in patients with chemotherapy-refractory metastatic colorectal cancer. J Clin Oncol 25:1658-1664.
Van Kampen, et al. Safety and immunogenicity of adenovirus-vectored nasal and epicutaneous influenza vaccines in humans. Vaccine, 2005. 23(8): p. 1029-1036.
Varnavski, et al. Evaluation of toxicity from high-dose systemic administration of recombinant adenovirus vector in vector-naive and pre-immunized mice. Gene Ther 12:.5 427-436.(2005).
Vaxgen I. VaxGen Announces Initial Results of its Phase III AIDS Vaccine Trial. http://www.corporate-ir.net/ireye/ir_site.zhtml?ticker=VXGN&script=410&layout=6&item_id=385014. Accessed Jul. 14, 2003.
Vergati, et al. (2010) Strategies for cancer vaccine development. J Biomed Biotechnol 2010. pii: 596432.
Wang, et al. Episomal segregation of the adenovirus enhancer sequence by conditional genome rearrangement abrogates late viral gene expression. J Virol. 2000; 74:11296-303.
Ward, et al. *E. coli* expression and purification of human and cynomolgus IL-15. Protein Expr Purif. Nov. 2009;68(1):42-8. doi: 10.1016/j.pep.2009.05.004. Epub May 10, 2009.
Weaver, et al. Comparison of replication-competent, first generation, and helper-dependent adenoviral vaccines. PLoS One. 2009;4(3):e5059. doi: 10.1371/journal.pone.0005059. Epub Mar. 31, 2009.
Wieking, et al. (2012) A non-oncogenic HPV 16 E6/E7 vaccine enhances treatment of HPV expressing tumors. Cancer Gene Ther. 2012; 19:667-674.

(56) References Cited

OTHER PUBLICATIONS

Zhao, et al. Enhanced cellular immunity to SIV Gag following co-administration of adenoviruses encoding wild-type or mutant HIV Tat and SIV Gag. Virology 342:.1 1-12 (2005).
Zhi, et al. Efficacy of severe acute respiratory syndrome vaccine based on a nonhuman primate adenovirus in the presence of immunity against human adenovirus. Hum Gene Ther 17:.5 500-06 (2006).
Zhu, et al. (2000) Specific cytolytic T-cell responses to human CEA from patients immunized with recombinant avipox-CEA vaccine. Clin. Cancer Res. 6:24-33.
EP16735409.1 Extended European Search Report dated Jun. 20, 2018.
Barouch, et al. Plasmid chemokines and colony-stimulating factors enhance the immunogenicity of DNA priming-viral vector boosting human immunodeficiency virus type 1 vaccines. J Virol. Aug. 2003;77(16):8729-35.
Berinstein, Neil L. Carcinoembryonic antigen as a target for therapeutic anticancer vaccines: a review. Journal of Clinical Oncology, J Clin Oncol. Apr. 15, 2002;20(8):2197-207.
Casimiro, et al. Comparative immunogenicity in rhesus monkeys of DNA plasmid, recombinant vaccinia virus, and replication-defective adenovirus vectors expressing a human immunodeficiency virus type 1 gag gene. J Virol. Jun. 2003;77(11):6305-13.
Chandran, et al. Recent trends in drug delivery systems: liposomal drug delivery system—preparation and characterisation. Indian J Exp Biol. Aug. 1997;35(8):801-9.
Chirmule, et al. Immune responses to adenovirus and adeno-associated virus in humans. Gene Ther.Sep. 1999;6(9):1574-83.
Couvreur, P. Polyalkylcyanoacrylates as colloidal drug carriers. Crit Rev Ther Drug Carrier Syst. 1988;5(1):1-20.
Gabitzsch, et al. A preliminary and comparative evaluation of a novel Ad5 [E1-, E2b-] recombinant-based vaccine used to induce cell mediated immune responses. Immunol Lett. Jan. 29, 2009;122(1):44-51. doi: 10.1016/j.imlet.2008.11.003. Epub Dec. 13, 2008.
Gaynor, et al. Cis-acting induction of adenovirus transcription. Cell. Jul. 1983;33(3):683-93.
Hoenen, et al. Current ebola vaccines. Expert Opin Biol Ther. Jul. 2012;12(7):859-72.
International Application No. PCT/US2016/012482 International Search Report and Written Opinion dated Mar. 21, 2016.
Jones, et al. Prevention of influenza virus shedding and protection from lethal H1N1 challenge using a consensus 2009 H1N1 HA and NA adenovirus vector vaccine. Vaccine. Sep. 16, 2011; 29(40):7020-7026.
Lasic, DD. Novel applications of liposomes. Trends Biotechnol. Jul. 1998;16(7):307-21.
Lauer, et al. Natural variation among human adenoviruses: genome sequence and annotation of human adenovirus serotype 1. J Gen Virol. Sep. 2004;85(Pt 9):2615-25.

Ledgerwood, J. et al. A replication defective recombinant Ad5 vaccine expressing Ebola virus GP is safe and immunogenic in healthy adults. Vaccine. Dec. 16, 2010;29(2):304-13.
Leza, et al. Cellular transcription factor binds to adenovirus early region promoters and to a cyclic AMP response element. J Virol. Aug. 1988;62(8):3003-13.
Margalit, R. Liposome-mediated drug targeting in topical and regional therapies. Crit Rev Ther Drug Carrier Syst. 1995;12(2-3):233-61.
McCoy, et al. Effect of preexisting immunity to adenovirus human serotype 5 antigens on the immune responses of nonhuman primates to vaccine regimens based on human- or chimpanzee-derived adenovirus vectors. J Virol. Jun. 2007;81(12):6594-604. Epub Apr. 11, 2007.
McMichael, et al. The quest for an AIDS vaccine: is the CD8+T-cell approach feasible? Nat Rev Immunol. Apr. 2002;2(4):283-91.
Miralles, et al. The adenovirus inverted terminal repeat functions as an enhancer in a cell-free system. J Biol Chem. Jun. 25, 1989;264(18):10763-72.
Nevins, Jr. Mechanism of activation of early viral transcription by the adenovirus E1A gene product. Cell. Oct. 1981;26(2 Pt 2):213-20.
Schaack, et al. E1A and E1B proteins inhibit inflammation induced by adenovirus. Proc Natl Acad Sci U S A. Mar. 2, 2004;101(9):3124-9. Epub Feb. 19, 2004.
Schaack. Induction and inhibition of innate inflammatory responses by adenovirus early region proteins. Viral Immunol. 2005;18(1):79-88.
Takakura, et al. [Drug delivery systems in gene therapy]. Nihon Rinsho. Mar. 1998;56(3):691-5.
Yang, et al. Overcoming immunity to a viral vaccine by DNA priming before vector boosting. J Virol. Jan. 2003; 77(1): 799-803.
Yang, et al. Role of viral antigens in destructive cellular immune responses to adenovirus vector-transduced cells in mouse lungs. J Virol. Oct. 1996;70(10):7209-12.
Zambaux, et al. Influence of experimental parameters on the characteristics of poly(lactic acid) nanoparticles prepared by a double emulsion method. J Control Release. Jan. 2, 1998;50(1–3):31-40.
Zur Muhlen, et al. Solid lipid nanoparticles (SLN) for controlled drug delivery—drug release and release mechanism. Eur J Pharm Biopharm. Mar. 1998;45(2):149-55.
Li et al., "Progress in the Production of Adenovirus Vector", The Chinese Journal of Process Engineering, 2004, vol. 4, No. 5, pp. 475-480. (English Abstract).
Official Action (with English translation) for Chinese Patent Application No. 201680014847.2 dated Jan. 21, 2020, 12 pages.
Notice of Intention to Grant for European Patent Application No. 16735409.1 dated Oct. 11, 2019, 7 pages.
Notice of Intention to Grant for European Patent Application No. 16735409.1 dated Jan. 9, 2020, 7 pages.
Official Action (with English translation) for South Korean Patent Application No. 10-2017-7022208 dated Apr. 2, 2020, 13 pages.

* cited by examiner

FIG. 8

SEQUENCE LISTING

```
<160> NUMBER OF SEQ ID NOS: 7

<210> SEQ ID NO 1
<211> LENGTH: 18959
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
cggacacaca aaaagaaaga agaatttttta ggatcttttg tgtgcgaata actatgagga      60
agattaataa ttttcctctc attgaaattt atatcggaat ttaaattgaa attgttactg     120
taatcatacc tggtttgttt cagagccata tcaccaagat agagaacaac ctaggtctcc     180 ggaggggggca agggcatcag tgtgctcagt tgaaaatccc ttgtcaacat ctaggcctta     240
tcacatcaca agttccgcct taaactctgc agggtgatcc aacaaccta atagcaacat     300 tattgttaaa ggacagcatt agttcacagt caaacaagca agattgagaa ttaactttga     360
ttttgaacct gaacacccag aggactggag actcaacaac cctaaagcct ggggtaaaac     420
attagaaata gtttaaagac aaattgctcg gaatcacaaa attccgagta tggattctcg     480
tcctcagaaa gtctggatga cgccgagtct cactgaatct gacatggatt accacaagat     540
cttgacagca ggtctgtccg ttcaacaggg gattgttcgg caaagagtca tcccagtgta     600
tcaagtaaac aatcttgagg aaatttgcca acttatcata caggccttg aagctggtgt     660 tgatttttcaa gagagtgcgg acagtttcct tctcatgctt tgtcttcatc atgcgtacca     720
aggagattac aaactttctct tggaaagtgg cgcagtcaag tatttggaag ggcacgggtt     780
ccgttttgaa gtcaagaagc gtgatggagt gaagcgcctt gaggaattgc tgccagcagt     840
atctagtggg agaaacatta agagaacact tgctgccatg ccggaagagg agacgactga     900
agctaatgcc ggtcagttcc tctcctttgc aagtctattc cttccgaaat tggtagtagg     960
agaaaaggct tgccttgaga aggttcaaag gcaaattcaa gtacatgcag agcaaggact    1020
gatacaatat ccaacagctt ggcaatcagt aggacacatg atggtgattt tccgtttgat    1080
gcgaacaaat tttttgatca aatttcttct aatacaccaa gggatgcaca tggttgccgg    1140
acatgatgcc aacgatgctg tgatttcaaa ttcagtggct caagctcgtt tttcaggtct    1200
attgattgtc aaaacagtac ttgatcatat cctacaaaag acagaacgag gagttcgtct    1260
ccatcctctt gcaaggaccg ccaaggtaaa aaatgaggtg aactccttca aggctgcact    1320
cagctccctg gccaagcatg gagagtatgc tcctttcgcc cgactttga acctttctgg    1380 agtaaataat cttgagcatg gtcttttccc tcaactgtcg gcaattgcac tcggagtcgc    1440
cacagcccac gggagcaccc tcgcaggagt aaatgttgga gaacagtatc aacagctcag    1500
agaggcagcc actgaggctg agaagcaact ccaacaatat gcggagtctc gtgaacttga    1560
ccatcttgga cttgatgatc aggaaaagaa aattcttatg aacttccatc agaaaaagaa    1620
cgaaatcagc ttccagcaaa caaacgcgat ggtaactcta agaaaagagc gcctggccaa    1680
```

```
gctgacagaa gctatcactg ctgcatcact gcccaaaaca agtggacatt acgatgatga   1740
tgacgacatt ccctttccag gacccatcaa tgatgacgac aatcctggcc atcaagatga   1800
tgatccgact gactcacagg atacgaccat tcccgatgtg gtagttgatc ccgatgatgg   1860
aggctacggc gaataccaaa gttactcgga aaacggcatg agtgcaccag atgacttggt   1920
cctattcgat ctagacgagg acgacgagga caccaagcca gtgcctaaca gatcgaccaa   1980
gggtggacaa cagaaaaaca gtcaaaaggg ccagcataca gagggcagac agacacaatc   2040
cacgccaact caaaacgtca caggccctcg cagaacaatc caccatgcca gtgctccact   2100
cacggacaat gacagaagaa acgaaccctc cggctcaacc agccctcgca tgctgacccc   2160
aatcaacgaa gaggcagacc cactggacga tgccgacgac gagacgtcta gccttccgcc   2220
cttagagtca gatgatgaag aacaggacag ggacggaact tctaaccgca cacccactgt   2280
cgccccaccg gctcccgtat acagagatca ctccgaaaag aaagaactcc cgcaagatga   2340
acaacaagat caggaccaca ttcaagaggc aggaaccaa  gacagtgaca cacccagcc   2400 agaacattct tttgaggaga tgtatcgcca cattctaaga tcacaggggc catttgatgc   2460
cgttttgtat tatcatatga tgaaggatga gcctgtagtt ttcagtacca gtgatggtaa   2520
agagtacacg tatccggact cccttgaaga ggaatatcca ccatggctca ctgaaaaaga   2580
ggccatgaat gatgagaata gatttgttac actggatggt caacaatttt attggccagt   2640
aatgaatcac aggaataaat tcatggcaat cctgcaacat catcagtgaa tgagcatgta   2700
ataatgggat gatttaatcg acaaatagct aacattaaat agtcaaggaa cgcaaacagg   2760 aagaatttt  gatgtctaag gtgtgaatta ttatcacaat aaaagtgatt cttagttttg   2820
aatttaaagc tagcttatta ttactagccg tttttcaaag ttcaatttga gtcttaatgc   2880
aaataagcgt taagccacag ttatagccat aatggtaact caatatctta gccagcgatt   2940
tatctaaatt aaattacatt atgcttttat aacttaccta ctagcctgcc caacatttac   3000
acgatcgttt tataattaag aaaaaactaa tgatgaagat taaaaccttc atcatcctta   3060
cgtcaattga attctctagc actagaagct tattgtcttc aatgtaaaag aaaagctggc   3120
ctaacaagat gacaactaga acaaagggca ggggccatac tgtggccacg actcaaaacg   3180
acagaatgcc aggccctgag cttttcgggct ggatctctga gcagctaatg accggaagga   3240
ttcctgtaaa cgacatcttc tgtgatattg agaacaatcc aggattatgc tacgcatccc   3300
aaatgcaaca aacgaagcca aacccgaaga tgcgcaacag tcaaacccaa acggacccaa   3360
tttgcaatca tagttttgag gaggtagtac aaacattggc ttcattggct actgttgtgc   3420
aacaacaaac catcgcatca gaatcattag aacaacgcat tacgagtctt gagaatggtc   3480
taaagccagt ttatgatatg gcaaaaacaa tctcctcatt gaacagggtt tgtgctgaga   3540
tggttgcaaa atatgatctt ctggtgatga caaccggtcg ggcaacagca accgctgcgg   3600 caactgagc ttattgggct gaacatggtc aaccaccacc tggaccatca ctttatgaag   3660
aaagtgcgat tcggggtaag attgaatcta gagatgagac tgtccctcaa agtgttaggg   3720
aggcattcaa caatctagac agtaccactt cactaactga ggaaaatttt gggaaacctg   3780
acatttcggc aaaggatttg agaaacatta tgtatgatca cttgcctggt tttggaactg   3840
ctttccacca attagtacaa gtgatttgta aattgggaaa agatagcaat tcattggaca   3900
ttattcatgc tgagttccag gccagcctgg ctgaaggaga ctcccctcaa tgtgccctaa   3960
ttcaaattac aaaaagagtt ccaatcttcc aagatgctgc tccacctgtc atccacatcc   4020
```

```
gctctcgagg tgacattccc cgagcttgcc agaagagctt gcgtccagtc ccaccatcac    4080
ccaagattga tcgaggttgg gtatgtgttt ttcagcttca agatggtaaa acacttggac    4140
tcaaaatttg agccaatctc ttttccctcc gaaagaggca actaatagca gaggcttcaa    4200
ctgctgaact atagggtatg ttacattaat gatacacttg tgagtatcag ccctagataa    4260
tataagtcaa ttaaacaacc aagataaaat tgttcatatc ccgctagcag ctttaaagat    4320
aaatgtaata ggagctatac ctctgacagt attataatta attgttatta agtaacccaa    4380
accaaaaatg atgaagatta agaaaaacct acctcgactg agagagtgtt ttttcattaa    4440
ccttcatctt gtaaacgttg agcaaaattg ttaaaaatat gaggcgggtt atattgccta    4500
ctgctcctcc tgaatatatg gaggccatat accctgccag gtcaaattca acaattgcta    4560
ggggtggcaa cagcaataca ggcttcctga caccggagtc agtcaatgga gacactccat    4620
cgaatccact caggccaatt gctgatgaca ccatcgacca tgccagccac acaccaggca    4680
gtgtgtcatc agcattcatc ctcgaagcta tggtgaatgt catatcgggc cccaaagtgc    4740
taatgaagca aattccaatt tggcttcctc taggtgtcgc tgatcaaaag acctacagct    4800
ttgactcaac tacggccgcc atcatgcttg cttcatatac tatcacccat ttcggcaagg    4860
caaccaatcc gcttgtcaga gtcaatcggc tgggtcctgg aatcccggat cacccctca    4920 ggctcctgcg aattggaaac caggcttttc tccaggagtt cgttcttcca ccagtccaac    4980
taccccagta tttcacccttt gatttgacag cactcaaact gatcactcaa ccactgcctg    5040
ctgcaacatg gaccgatgac actccaactg gatcaaatgg agcgttgcgt ccaggaattt    5100
catttcatcc aaaacttcgc cccattcttt tacccaacaa agtgggaag aaggggaaca    5160 gtgccgatct aacatctccg gagaaaatcc aagcaataat gacttcactc caggacttta    5220
agatcgttcc aattgatcca accaaaaata tcatgggtat cgaagtgcca gaaactctgg    5280
tccacaagct gaccggtaag aaggtgactt ccaaaaatgg acaaccaatc atccctgttc    5340
ttttgccaaa gtacattggg ttggacccgg tggctccagg agacctcacc atggtaatca    5400
cacaggattg tgacacgtgt cattctcctg caagtcttcc agctgtggtt gagaagtaat    5460
tgcaataatt gactcagatc cagtttttaca gaatcttctc agggatagtg ataacatctt    5520
tttaataatc cgtctactag aagagatact tctaattgat caatatacta aaggtgcttt    5580
acaccattgt ctcttttctc tcctaaatgt agagcttaac aaaagactca taatatacct    5640 gttttttaaaa gattgattga tgaaagatca tgactaataa cattacaaac aatcctacta    5700
taatcaatac ggtgattcaa atgtcaatct ttctcattgc acatactctt tgtccttatc    5760
ctcaaattgc ctacatgctt acatctgagg acagccagtg tgacttggat tggagatgtg    5820
gaggaaaaat cggggcccat ttctaagttg ttcacaatct aagtacagac attgctcttc    5880
taattaagaa aaaatcggcg atgaagatta agccgacagt gagcgtaatc ttcatctctc    5940
ttagattatt tgtcttccag agtaggggtc atcaggtcct tttcaattgg ataaccaaaa    6000
taagcttcac tagaaggata ttgtgaggcg acaacacaat gggtgttaca ggaatattgc    6060
agttacctcg tgatcgattc aagaggacat cattctttct tgggtaatt atccttttcc    6120 aaagaacatt ttccatcccg cttggagtta tccacaatag tacattacag gttagtgatg    6180
tcgacaaact agtttgtcgt gacaaactgt catccacaaa tcaattgaga tcagttggac    6240
tgaatctcga ggggaatgga gtggcaactg acgtgccatc tgcgactaaa agatggggct    6300
tcaggtccgg tgtcccacca aaggtggtca attatgaagc tggtgaatgg gctgaaaact    6360
gctacaatct tgaaatcaaa aaacctgacg ggagtgagtg tctaccagca gcgccagacg    6420
```

```
ggattcgggg cttcccccgg tgccggtatg tgcacaaagt atcaggaacg ggaccatgtg    6480
ccggagactt tgccttccac aaagagggtg ctttcttcct gtatgatcga cttgcttcca    6540
cagttatcta ccgaggaacg actttcgctg aaggtgtcgt tgcatttctg atactgcccc    6600
aagctaagaa ggacttcttc agctcacacc ccttgagaga gccggtcaat gcaacgaggg    6660
acccgtcgag tggctattat tctaccacaa ttagatatca ggctaccggt tttggaacta    6720
atgagacaga gtacttgttc gaggttgaca atttgaccta cgtccaactt gaatcaagat    6780
tcacaccaca gtttctgctc cagctgaatg agacaatata tgcaagtggg aagaggagca    6840
acaccacggg aaaactaatt tggaaggtca accccgaaat tgatacaaca atcggggagt    6900
gggccttctg ggaaactaaa aaaacctcac tagaaaaatt cgcagtgaag agttgtcttt    6960
cacagctgta tcaaacggac ccaaaaacat cagtggtcag agtccggcgc gaacttcttc    7020
cgacccagag accaacacaa caaatgaaga ccacaaaatc atggcttcag aaaattcctc    7080
tgcaatggtt caagtgcaca gtcaaggaag gaaagctgca gtgtcgcatc tgacaaccct    7140
tgccacaatc tccacgagtc ctcaacctcc cacaaccaaa acaggtccgg acaacagcac    7200
ccataataca cccgtgtata aacttgacat ctctgaggca actcaagttg acaacatca    7260 ccgtagagca gacaacgaca gcacagcctc cgacactccc cccgccacga ccgcagccgg    7320
acccttaaaa gcagagaaca ccaacacgag taagagcgct gactccctgg acctcgccac    7380
cacgacaagc ccccaaaact acagcgagac tgctggcaac aacaacactc atcaccaaga    7440
taccggagaa gagagtgcca gcagcgggaa gctaggctta attaccaata ctattgctgg    7500
agtagcagga ctgatcacag gcgggagaag gactcgaaga gaagtaattg tcaatgctca    7560
acccaaatgc aaccccaatt tacattactg gactactcag gatgaaggtg ctgcaatcgg    7620
attggcctgg ataccatatt tcgggccagc agccgaagga atttacacag aggggctaat    7680
gcacaaccaa gatggtttaa tctgtgggtt gaggcagctg gccaacgaaa cgactcaagc    7740
tctccaactg ttcctgagag ccacaactga gctgcgaacc ttttcaatcc tcaaccgtaa    7800
ggcaattgac ttcctgctgc agcgatgggg tggcacatgc cacattttgg gaccggactg    7860
ctgtatcgaa ccacatgatt ggaccaagaa cataacagac aaaattgatc agattattca    7920
tgattttgtt gataaaaccc ttccggacca ggggacaat gacaattggt ggacaggatg    7980
gagacaatgg ataccggcag gtattggagt tacaggtgtt ataattgcag ttatcgcttt    8040
attctgtata tgcaaatttg tcttttagtc tttcttcaga ttgtttcacg gcaaaactca    8100
acctcaaatc aatgaaacta ggatttaatt atatgaatca cttgaatcta agattacttg    8160
acaaatgata acataataca ctggagcttc aaacatagcc aatgtgattc taactccttt    8220
aaactcacag ttaatcataa acaaggtttg acatcaatct agctatatct ttaagaatga    8280
taaacttgat gaagattaag aaaaaggtaa tctttcgatt atctttagtc ttcatccttg    8340
attctacaat catgacagtt gtctttaatg aaaaaggaaa aaagccttt tattaagttg    8400 taataatcag atctgcaaac cggtagaatt tagttgtaac ctaacacaca caagcattg    8460 gtaaaaaagt caatagaaat ttaaacagtg agtgcagaca actcttaaat ggaagcttca    8520
tatgagagag gacgcccccg agctgccaga cagcattcaa gggatggaca cgaccaccat    8580
gttcgagcac gatcatcatc cagagagaat tatcgaggtg agtaccgtca atcaaggagc    8640
gcctcacaag tgcgcgttcc tactgtattt cataagaaga gagttgaacc attaacagtt    8700
cctccagcac ctaaagacat atgtccgacc ttgaaaaaag gattttgtg tgacagtagt    8760
```

```
ttttgcaaaa aagaccacca gttagaaagt ttaactgata gggaattact cctactaatc   8820
gcccgtaaga cttgtggatc agtagaacaa caattaaata taactgcacc caaggactcg   8880
cgcttagcaa atccaacggc tgatgatttc cagcaagagg aaggtccaaa aattaccttg   8940
ttgacactga tcaagacggc agaacactgg gcgagacaag acatccgaac catagaggat   9000
tccaaattaa gggcattgtt aactctatgt gctgtgatga cgaggaaatt ctcaaaatcc   9060
cagctgagtc ttttgtgtga gacacaccta aggcgcgaag ggcttgggca agatcaggca   9120
gaacccgttc tcgaagtata tcaacgatta cacagtgata aaggaggcag ttttgaagct   9180
gcactatggc aacaatggga ccgacaatcc ctaattatgt ttatcactgc attcttgaat   9240
atcgctctcc agttaccgtg tgaaagttct gctgtcgttg tttcagggtt aagaacattg   9300
gttcctcaat cagataatga ggaagcttca accaacccgg ggacatgctc atggtctgat   9360
gagggtaccc cttaataagg ctgactaaaa cactatataa ccttctactt gatcacaata   9420
ctccgtatac ctatcatcat atatttaatc aagacgatat cctttaaaac ttattcagta   9480
ctataatcac tctcatttca aattgataag atatgcaata ttgccttaat atataaagag   9540
gtatgatata acccaaacat tgaccaaaga aaatcataat ctcgtatcgc tcgcaatata   9600
acctgccaag catcctctt gcacaaagtg attcttgtac acaataatg tttgactcta   9660 caggaggtag caacgatcca tctcatcaaa aaataagtat tttatgattt actaatgatc   9720
tcttaaaata ttaagaaaaa ctgacggaac ataaattctt tctgcttcaa gttgtggagg   9780
aggtctatgg tattcgctat tgttatatta caatcaataa caagcttgta aaaatattgt   9840
tcttgtttca ggaggtatat tgtgaccgga aaagctaaac taatgatgaa gattaatgcg   9900
gaggtctgat gagaataaac ctcattattc agattaggcc ccaagaggca ttcttcatct   9960 cctttttagca aaatactatt tcaggatagt ccagctagtg acacgtcttt tagctgtata  10020
ccagttgccc ctgagatacg ccacaaaagt gtctctgagc taaagtggtc tgtacacatc  10080
tcatacattg tattagggc aataatatct aattgaactt agccatttaa aatttagtgc   10140
ataaatctgg gctaactcca ccaggtcaac tccattggct gaaaagaagc ccacctacaa  10200
cgaacattac tttgagcgcc ctcacaatta aaaaataaga gcgtcgttcc aacaatcgag  10260
cgcaaggtta caaggttgaa ctgagagtgt ctagacaaca aaatatcgat actccagaca  10320
ccaagcaaga cctgagaaaa aaccatggcc aaagctacgg gacgatacaa tctaatatcg  10380
cccaaaaagg acctggagaa aggggttgtc ttaagcgacc tctgtaactt cttagttagt  10440
caaactattc aagggtggaa agtttattgg gctggtattg agtttgatgt gactcacaaa  10500
ggaatggccc tattgcatag actgaaaact aatgactttg cccctgcatg gtcaatgaca  10560
aggaacctat ttccccatt atttcaaaat ccgaattcca ctattgaatc accgctgtgg  10620
gcactgagag tcatccttgc agcagggata caggaccagt taattgacca gtctttgatt  10680
gaacccttag caggagccct tggtctgatc tctgattggc tgctaacaac caacactaac  10740
catttcaaca tgcgaacaca acgtgtcaag gaacaattga gcctaaaaat gctgtcgttg  10800
attcgatcca atattctcaa gtttattaac aaattggatg ctctacatgt cgtgaactac  10860
aatggattat tgagcagtat tgaaattgga actcaaaatc atacaatcat cataactcga  10920
actaacatgg gttttctggt ggagctccaa gaacccgaca aatcggcaat gaaccgcaag  10980
aagcctgggc cggcgaaatt ttccctcctt catgagtcca cactgaaagc atttacacaa  11040
gggtcctcga cacgaatgca aagtttaatt cttgaattca atagctctct tgctatctaa  11100
ctaagatgga atacttcata ttgggctaac tcatatatgc tgactcaata gttaacttga  11160
```

```
catctctgcc ttcataatca gatatataag cataataaat aaatactcat atttcttgat    11220
aatttgttta accacagata aatcctcact gtaagccagc ttccaagttg acacccttac    11280
aaaaaccagg actcagaatc cctcaaataa gagattccaa gacaacatca tagaattgct    11340
ttattatatt aataagcatt ttatcactag aaatccaata tacgaaatgg ttaattgtaa    11400
ctaaacccgc aggtcatgtg tgttaggttt cacaaattat atatattact aactccatac    11460
tcgtaactaa cattagataa gtaggttaag aaaaaagctt gaggaagatt aagaaaaact    11520
gcttattggg tctttccgtg ttttagatga agcagttgac attcttcctc ttgatattaa    11580
atggctacac aacatacccc ataccccagac gccaggttat catcaccaat tgtattggac    11640
caatgtgacc ttgtcactag agcttgcggg ttgtattcat catactccct taatccgcaa    11700
ctacgcaact gtaaactccc gaaacatata taccgtttaa aatatgatgt aactgttacc    11760
aagttcttaa gtgatgtacc agtggcgaca ttgcccatag atttcatagt cccaattctt    11820
ctcaaggcac tatcaggcaa tgggttctgt cctgttgagc cgcggtgcca acagttctta    11880
gatgaaatta ttaagtacac aatgcaagat gctctcttcc tgaaatatta tctcaaaaat    11940
gtgggtgctc aagaagactg tgttgatgac cactttcaag aaaaaatctt atcttcaatt    12000
cagggcaatg aattttaca tcaaatgttt ttctggtatg acctggctat tttaactcga    12060 agggtagat taaatcgagg aaactctaga tcaacgtggt ttgttcatga tgatttaata    12120
gacatcttag gctatgggga ctatgttttt tggaagatcc caatttcact gttaccactg    12180
aacacacaag gaatccccca tgctgctatg gattggtatc agacatcagt attcaaagaa    12240
gcggttcaag ggcatacaca cattgtttct gtttctactg ccgatgtctt gataatgtgc    12300
aaagatttaa ttcatgtcg attcaacaca actctaatct caaaaatagc agaggttgag    12360
gacccagttt gctctgatta tcccaatttt aagattgtgt ctatgcttta ccagagcgga    12420
gattacttac tctccatatt agggtctgat gggtataaaa tcattaagtt tctcgaacca    12480
ttgtgcttgg ctaaaattca attgtgctca agtacaccg agaggaaggg ccgattctta    12540
acacaaatgc atttagctgt aaatcacacc ctggaagaaa ttacagaaat acgtgcacta    12600
aagccttcac aggctcacaa gatccgtgaa ttccatagaa cattgataag gctggagatg    12660
acgccacaac aactttgtga gctattttcc atacaaaaac actgggggca tcctgtgcta    12720
catagtgaaa cagcaatcca aaaagttaaa aaacatgcta cggtgctaaa agcattacgc    12780
cctatcgtga ttttcgagac atattgtgtt tttaaatata gcattgcaaa acattatttt    12840
gatagtcaag atcttggta cagtgttacc tcagatagaa atctaacacc aggtcttaat    12900
tcttatatca aagaaatca attccctccg ttgccaatga ttaaagaact gctatgggaa    12960
ttttaccacc ttgaccatcc tccactttc tcaaccaaaa ttattagtga cttaagtatt    13020
tttataaaag acagagctac tgcagtagaa aggacatgct gggatgcagt attcgagcct    13080
aatgttctgg gatataatcc acctcacaaa ttcagtacca acgtgtacc ggaacaattt    13140 ttagagcaag aaaacttttc tattgagaat gttctttcct acgcgcaaaa actcgagtat    13200
ctactaccac aatatcggaa ttttctttc tcattgaaag agaaagagtt gaatgtaggt    13260
agaactttcg gaaaattgcc ttatccgact cgcaatgttc aaacactttg tgaagctctg    13320
ttagctgatg gtcttgctaa agcatttcct agcaatatga tggtagttac ggaacgtgaa    13380
caaaaagaaa gcttattgca tcaagcatca tggcaccaca caagtgatga tttcggtgag    13440
catgccacag ttagagggag tagctttgta actgatttag agaaatacaa tcttgcattt    13500
```

```
aggtatgagt ttacagcacc ttttatagaa tattgcaacc gttgctatgg tgttaagaat    13560
gtttttaatt ggatgcatta tacaatccca cagtgttata tgcatgtcag tgattattat    13620
aatccaccgc ataacctcac actggaaaat cgaaacaacc ccctgaagg gcctagttca     13680
tacaggggtc atatgggagg gattgaagga ctgcaacaaa aactctggac aagtatttca    13740
tgtgctcaaa tttctttagt tgaaattaag actggtttta agttgcgctc agctgtgatg    13800
ggtgacaatc agtgcattac cgttttatca gtcttcccct tagagactga tgcagacgag    13860
caggaacaga gcgccgagga caatgcagcg agggtggccg ccagcctagc aaaagttaca    13920
agtgcctgtg gaatcttttt aaaacctgat gaaacatttg tacattcagg ttttatctat    13980
tttgaaaaaa aacaatattt gaatggggtc caattgcctc agtcccttaa aacggctaca    14040
agaatggcac cattgtctga tgcaattttt gatgatcttc aagggaccct ggctagtata    14100
ggtactgctt ttgagcgatc catctctgag acacgacata tctttccttg cagaataacc    14160
gcagctttcc atacgttctt ttcggtgaga atcttgcaat atcatcacct cggatttaat    14220
aaaggttttg accttggaca gttaacactc ggcaaacctc tggatttcgg aacaatatca    14280
ttggcactag cggtaccgca ggtgcttgga gggttatcct tcttgaatcc tgagaaatgt    14340
ttctaccgga atctaggaga tccagttacc tcaggtttat tccagttaaa aacttatctc    14400
cgaatgattg agatggatga tttattctta cctttaattg cgaagaaccc tgggaactgc    14460
actgccattg actttgtgct aaatcctagc ggattaaatg ttcctgggtc gcaagactta    14520
acttcatttc tgcgccagat tgtacgtagg actatcaccc taagtgcgaa aaacaaactt    14580
attaatacct tatttcatgc atcagctgac ttcgaagacg aaatggtttg taagtggctc    14640
ttatcatcaa ctcctgttat gagtcgtttc gcagccgata tattttcacg cacgccgagc    14700
gggaagcgat tgcaaattct aggatacttg gaaggaacac gcacattatt agcctctaag    14760
atcatcaaca ataatacaga gacgccggtt ttggacagac tgaggaagat aacattgcaa    14820
aggtggagtc tatggtttag ttatcttgat cattgtgata atatcctggc ggaggcttta    14880
acccaaataa cttgcacagt tgatttagca cagatcctga gggaatattc atgggcacat    14940
attttagagg ggagacctct tattggagcc acactcccat gtatgattga gcaattcaaa    15000
gtggtttggc tgaaacccta cgaacaatgt ccgcagtgtt caaatgccaa gcaacctggt    15060
gggaaaccat tcgtgtcagt agcagtcaag aaacatattg ttagtgcatg gccaaatgca    15120
tcccgaataa gctggactat cggggatgga atcccataca ttggatcaag gacagaagat    15180
aagatagggc aacctgctat taaaccaaaa tgtccttccg cagccttaag agaggccatt    15240
gaattggcgt cccgtttaac atgggtaact caaggcagtt cgaacagtga cttgctaata    15300
aaaccatttt tggaagcacg agtaaattta agtgttcaag aaatacttca aatgaccect    15360
tcacattact cgggaaatat tgttcatagg tacaacgatc aatacagtcc tcattctttc    15420
atggccaatc gtatgagtaa ctcagcaacg cgattgattg tttctacaaa cactttaggt    15480
gagttttcag gaggtggcca atcggcacgc gacagcaata ttattttcca gaatgttata    15540
aattatgcag ttgcactgtt cgatattaaa tttagaaaca ctgaggctac agatatccag    15600
tataatcgtg ctcaccttca tctaactaag tgttgcaccc ggggaggtac cagctcagtat    15660
ttaacataca catctacatt ggatttagat ttaacaagat accgagaaaa tgaattgatt    15720
tatgacaata atcctctaaa aggaggactc aattgcaata tctcatttga taacccatttt   15780
ttccaaggca aacagctgaa cattatagaa gatgacctta ttcgactgcc tcacttatct    15840
ggatgggagc tagctaagac catcatgcaa tcaattattt cagatagcaa taattcgtct    15900
```

```
acagacccaa ttagcagtgg agaaacaaga tcattcacta cccatttctt aacttatccc   15960
aagataggac ttctgtacag ttttggggcc tttgtaagtt attatcttgg caatacaatt   16020
cttcggacta agaaattaac acttgacaat tttttatatt acttaactac ccaaattcat   16080
aatctaccac atcgctcatt gcgaatactt aagccaacat tcaaacatgc aagcgttatg   16140
tcacgattaa tgagtattga tccccatttt tctatttaca taggcggtgc tgcaggtgac   16200
agaggactct cagatgcggc caggttattt ttgagaacgt ccatttcatc ttttcttaca   16260
tttgtaaagg aatggataat taatcgcgga acaattgtcc ctttatggat agtatatcca   16320
ttagagggtc aaaatccaac acctgttaat aatttcctcc atcagatcgt agaactgctg   16380
gtgcatgatt catcaagaca ccaggctttt aaaactacca taaatgatca tgtacatcct   16440
cacgacaatc ttgtttacac atgtaagagt acagccagca atttcttcca tgcgtcattg   16500
gcgtactgga ggagcaggca cagaaacagc aaccgaaaag acttgacaag aaactcttca   16560
actggatcaa gcacaaacaa cagtgatggt catattaaga gaagtcaaga acaaaccacc   16620
agagatccac atgatggcac tgaacggagt ctagtcctgc aaatgagcca tgaaataaaa   16680
agaacgacaa ttccacaaga gaacacgcac cagggtccgt cgttccagtc atttctaagt   16740
gactctgctt gcggtacagc aaacccaaaa ctaaatttcg atagatcgag acacaatgtg   16800
aaatctcagg atcataactc agcatccaag agggaaggtc atcaaataat ctcacatcgt   16860
ctagtcctac ctttctttac attatctcaa gggacacgcc aattaacgtc atccaatgag   16920
tcacaaaccc aagatgagat atcaaagtac ttacggcaat tgagatccgt cattgatacc   16980
acagtttatt gtaggtttac cggtatagtc tcgtccatgc attacaaact tgatgaggtc   17040
ctttgggaaa tagagaattt taagtcggct gtgacgctgg cagagggaga aggtgctggt   17100
gccttactat tgattcagaa ataccaagtt aagacttat ttttcaacac gctagctact   17160
gagtccagta tagagtcaga aatagtatca ggaatgacta ctcctaggat gcttctacct   17220
gttatgtcaa aattccataa tgaccaaatt gagattattc ttaacaactc agcaagccaa   17280
ataacagaca taacaaatcc tacttggttt aaagaccaaa gagcaaggct acctaggcaa   17340
gtcgaggtta taaccatgga tgcagagacg acagagaata taaacagatc gaaattgtac   17400
gaagctgtac ataaattgat cttacaccat gttgatccca gcgtattgaa agcagtggtc   17460
cttaaagtct ttctaagtga taccgagggt atgttatggc taaatgataa tctagccccg   17520 tttttttgcca ctgggtattt aattaagcca ataacgtcaa gtgccaggtc tagtgagtgg   17580
tatctttgtc tgacgaactt cttatcaact acacgtaaga tgccacacca aaaccatctc   17640
agttgtaagc aggtaatact tacggcattg caactgcaaa ttcaacggag cccatactgg   17700
ctaagtcatt taactcagta tgctgactgc gatttacatt taagctatat ccgccttggt   17760
tttccatcat tagagaaagt actataccac aggtataacc ttgtcgattc aaaaagaggt   17820
ccactagtct ctgtcactca gcacttagca catcttaggg cagagattcg agaattgacc   17880
aatgattata atcaacagcg acaaagtcgg actcaaacat atcactttat tcgtactgca   17940
aaaggacgaa tcacaaaaact agtcaatgat tatttaaaat tctttcttat tgtacaagca   18000
ttaaaacata atgggacatg gcaagctgag tttaagaaat taccgagagtt gattagtgtg   18060 tgcaataggt tctatcatat tagagattgt aattgtgaag aacgtttctt agttcaaacc   18120
ttatatttac atagaatgca ggattctgaa gttaagctta tcgaaaggct gacagggctt   18180
ctgagtttat ttccagatgg tctctacagg ttcgattgaa taaccgtgca tagtattttg   18240
```

| | |
|---|---:|
| atacttgtaa aggttggtta tcaacataca gattataaaa aactcataaa ttgctctcat | 18300 |
| acatcatctt gatctgattt caataaataa ctatttagat aacgaaagga gtccttacat | 18360 |
| tatacactat atttggcctc tctccctgcg tgataatcaa aaaattcaca atacagcatg | 18420 |
| tgtgacatat tactgctgca atgagtctaa cgcaacataa taaactccgc actctttata | 18480 |
| attaagcttt aacgataggt ctgggctcat attgttattg atatagtaat gttgtatcaa | 18540 |
| tatcttgcca gatggaatag tgctttggtt gataacacga cttcttaaaa caaaactgat | 18600 |
| ctttaagatt aagttttta taattgtcat tgctttaatt tgtcgattta aaaatggtga | 18660 |
| tagcctttaat ctttgtgtaa aataagagat taggtgtaat aactttaaca ttttttgtcta | 18720 |
| gtaagctact attccattca gaatgataaa attaaaagaa aagacatgac tgtaaaatca | 18780 |
| gaaatacctt ctttacaata tagcagacta gataataatc ttcgtgttaa tgataattaa | 18840 |
| ggcattgacc acgctcatca gaaggctcac tagaataaac gttgcaaaaa ggatccctgg | 18900 |
| aaaaatggtc gcacacaaaa atttaaaaat aaatctattt cttctttttt gtgtgtcca | 18959 |

<210> SEQ ID NO 2
<211> LENGTH: 18874
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2

| | |
|---|---:|
| cggacacaca aaaagaaaga aaagtttttt agacttttg tgtgcgaata actatgagga | 60 |
| agattaatca ttttcctcaa actcaaacta atattaacat tgagattgat ctcatcattt | 120 |
| accaattgga gacaatttaa ctagtcaatc ccccatttgg gggcattcct aaagtgttgc | 180 |
| aaaggtatgt gggtcgtatt gttttgcctt ttcctaacct ggctcctcct acaattctaa | 240 |
| cctgcttgat aagtgtgatt acctgagtaa tagactaatt tcgtcctggt aattagcatt | 300 |
| ttctagcaaa accaatacta tctcaagtcc taagagaagg tgagaagagg gtcccgaggt | 360 |
| atccctccag tccacaaaat ctagctaatt ttagctgagt ggactgatta ctctcatcac | 420 |
| acgctaacta ctaagggttt acctgagagc ctacaacatg gataaacggg tgagaggttc | 480 |
| atgggccctg ggaggacaat ctgaagttga tcttgactac cacaaaatat taacagccgg | 540 |
| gctttcggtc caacaaggga ttgtgcgaca aagagtcatc ccgtatatg ttgtgagtga | 600 |
| tcttgagggt atttgtcaac atatcattca ggcctttgaa gcaggcgtag atttccaaga | 660 |
| taatgctgac agcttccttt tacttttatg tttacatcat gcttaccaag gagatcatag | 720 |
| gctcttcctc aaaagtgatg cagttcaata cttagagggc catggtttca ggtttgaggt | 780 |
| ccgagaaaag gagaatgtgc accgtctgga tgaattgttg cccaatgtca ccggtggaaa | 840 |
| aaatcttagg agaacattgg ctgcaatgcc tgaagaggag acaacagaag ctaatgctgg | 900 |
| tcagttttta tcctttgcca gtttgtttct acccaaactt gtcgttgggg agaaagcgtg | 960 |
| tctggaaaaa gtacaaaggc agattcaggt ccatgcagaa caagggctca ttcaatatcc | 1020 |
| aacttcctgg caatcagttg gacacatgat ggtgatcttc cgtttgatga gaacaaactt | 1080 |
| tttaatcaag ttcctactaa tacatcaggg gatgcacatg tcgcaggcc atgatgcgaa | 1140 |
| cgacacagta atatctaatt ctgttgccca agcaaggttc tctggtcttc tgattgtaaa | 1200 |
| gactgttctg gaccacatcc tacaaaaaac cgatcttgga gtacgacttc atccactggc | 1260 |
| caggacagca aaagtcaaga atgaggtcag ttcattcaag gcagctcttg gctcacttgc | 1320 |

```
caagcatgga gaatatgctc catttgcacg tctcctcaat ctttctggag tcaacaactt    1380
ggaacatggg ctttatccac aactctcagc cattgctttg ggtgttgcaa ctgcccacgg    1440
gagcacgctg gctggtgtta atgtagggga gcaatatcag caactgcgtg aggctgctac    1500
tgaagctgaa aagcaactcc aacaatatgc tgagacacgt gagttggaca accttgggct    1560
tgatgagcag gaaaagaaga ttctcatgag cttccaccag aagaagaatg agatcagctt    1620
ccagcaaact aacgcaatgg taaccttgag gaaagagcgg ctggccaaac tgaccgaagc    1680
catcacgact gcatcaaaga tcaaggttgg agatcgttat cctgatgaca atgatattcc    1740
atttcccggg ccgatctatg atgaaaccca ccccaaccct tctgatgata atcctgatga    1800
ttcacgtgat acaactatcc caggtggtgt tgttgacccg tatgatgatg agagtaataa    1860
ttatcctgac tacgaggatt cggctgaagg caccacagga gatcttgatc tcttcaattt    1920
ggacgacgac gatgacgaca gccaaccagg accaccagac agggggcaga gcaaggagag    1980
agcggctcgg acacatggcc tccaagatcc gaccttggac ggagcgaaaa aggtgccgga    2040
gttaaccccca ggttcccacc aaccaggcaa cctccacatc accaagccgg gttcaaacac    2100
caaccaacca caaggcaata tgtcatctac tctccagagt atgacccta tacaggaaga    2160
atcagagccc gatgatcaga aagatgatga tgacgagagt ctcacatccc ttgactctga    2220
aggtgacgaa gatgttgaga gcgtatcagg ggagaacaac ccaactgtag ctccaccagc    2280
accagtctac aaagatactg gagtagacac taatcagcaa aatggaccaa gcaatgctgt    2340
agatggtcaa ggttctgaaa gtgaagctct cccaatcaac cccgaaaaga gatctgcact    2400
ggaagaaaca tattatcatc tcctaaaaac acagggtcca tttgaggcaa tcaattatta    2460
tcacctaatg agtgatgagc ccattgcttt tagcactgaa agtggcaagg aatatctctt    2520
cccagattct cttgaagaag cctacccgcc ttggttgagt gagaaggagg ccttagagaa    2580
agaaaatcgt tatctggtca ttgatggcca gcaattcttc tggccagtaa tgagcctaca    2640
ggacaagttc cttgctgttc ttcaacatga ctgaggaccc atgattagta gattttgttt    2700
attctgagct tgattataat tgttttgata attcaagtat gagcacccaa cccgaaatat    2760
aaaccctatt ttagttatga ggaaattaaa taaataatct gtaagttgta ggactatgaa    2820
gagctgcttg tgtcaatttta tcacgggtta atacccatac cgcaagaata attatttagt    2880
aattttgatc agcttatgat atgtaccaat aggaaaacat tatagcatta aaacataaag    2940
tatccttcga tgagcttagg aggataatat cctgatgaat tctatagaac ttaggattaa    3000
gaaaaaattc atgatgaaga ttaaaaccctt catcatcctt taaaaagaga gctattcttt    3060
atctgaatgc ccttattaat gtctaagagc tattattttg taccctctta gcctagacac    3120
tgcccaacat ataaatcatg cagcaggata ggacttatag acatcatgga cccgaagtgt    3180
ctggctggtt ttctgagcaa ttaatgaccg gcaaaatacc gctaacagag gtgtttgttg    3240
atgttgaaaa caaccaagt cctgccccga taaccattat tagtaagaat cccaagacaa    3300
cacgtaaaag tgataagcaa gtccaaacag atgatgccag tagcttattg acagaagaag    3360
tcaaggctgc cataaattcg gtgatatcag ctgtgcgtcg gcaaaccaat gctattgaat    3420
cactagaagg tcgagtaaca actcttgagg ccagcttaaa accagttcaa gacatggcaa    3480
agaccatatc atccctgaat cgcagctgtg ccgaaatggt tgcaaaatac gacctactgg    3540
tgatgaccac tgggcgagca actgccactg ctgcagcaac agaagcatat tggaatgaac    3600
atggacaagc acctccaggc ccatcattgt acgaggatga tgctattaag gctaaattga    3660
aagatccgaa cgggaaggtt ccagaaagtg tcaaacaggc ctacacaaat ctagatagca    3720
```

```
caagtgccct caatgaggaa aatttcgggc gaccttacat ttcagcaaaa gatctcaagg   3780
aaatcatcta tgaccatctc ccaggatttg ggacagcttt tcatcagttg gtgcaggtta   3840
tctgcaaaat tggtaaggat aataatatcc tagacataat tcatgcagaa ttccaagcaa   3900
gcttggctga gggagactcc ccccagtgtg cattaatcca gataacaaaa cggatccctg   3960
ctttccaaga tgcctctcct ccaattgtgc atatcaagtc tcgaggagat atacccaaag   4020
cctgtcagaa aagcctccgg ccggtcccgc cgtcaccaaa gatcgataga ggttgggtct   4080 gtattttca attccaagac gggaaggccc ttgggctaaa aatatgatac agaagcaagg   4140
taagctcatt ttgcgatggc caaatgatac ttatgactgt ttaaaatcaa gttagactaa   4200
tagtctatca tgtcataagc ttataagtca gttttaaatt tcccctctat cctaatcaat   4260
tgataatgct gtcaatagga aaattcccct gtattgtaat aagacctcat taacacattt   4320
cctctgctta gtactatgca gaaaccccg agcaaattaa aattgatgaa gattaagaaa   4380
aagagggatt ttctcaggaa aaatcttttt ccttaccttc atctcattta aacaaattta   4440
ggactcagga aaaatgaaaa gggtcactgt gccgactgca ccacctgcct atgctgacat   4500
tggctatcct atgagcatgc ttcccatcaa gtcaagcagg gctgtgagtg gaattcaaca   4560
gaaacaagag gtccttcctg gaatggatac accatcaaat tctatgagac ctgttgctga   4620
tgataacatt gatcatacaa gtcatacccc gaacggagtg gcctcagcat tcatcttgga   4680
ggcaactgtc aatgtgatct cggggcccaa agtcctcatg aaacaaatcc ctatttggtt   4740
gccactcgga attgctgacc aaaaaacgta cagttttgac tcaacaacag cagcaattat   4800
gctcgcatct tatacgatca cccattttgg aaaggccaac aaccccctcg ttagagtgaa   4860
tcgacttggt cagggaatac cggatcaccc actcagattg ctcaggatgg ggaaccaggc   4920
tttccttcaa gagtttgtgc taccaccagt tcaactgccg caatatttca cttttgatct   4980
gactgcactc aaattagtga cacagcctct ccctgctgcg acatggacag atgagactcc   5040
gagcaaccct tcaggagcac ttcgtcccgg gctttcattt cacccaaagc tgagacccgt   5100
tctacttcca ggcaaaacgg gaaagaaagg gcatgtttct gatctgactg ctccagacaa   5160
aattcagaca attgtgaacc tgatgcaaga tttcaaaatc gtgccaattg atccagctaa   5220
gagtatcatt gggatcgagg ttccagaatt gctggtccac aagctcactg ggaagaaaat   5280
gagtcagaag aatggacagc ctataattcc tgtcttactt ccaaaataca ttgggctaga   5340
tccaatctca cctggagacc tgactatggt cataacacca gattatgatg attgtcattc   5400
acctgccagt tgctcttatc tcagtgaaaa gtgattctca caaagtgaga gaaacacctc   5460
cagtaaagaa atcaaatctt atctatagca actcaatcga cttttaggaa gctagcagta   5520
catatactat gggacaactc aaccctcttg ttaaaatgta ctaatcgggt caagaactc    5580 tcactgatca agcctgaatc caagatagaa ccagcccaaa gggcctcccc agagtctctt   5640
acaaacttag ccaatcaatt aacatgcata agcgatccat acttcaccca atcagtgtcc   5700
gatgttcacc ccttcaagcc tccttcctag caaattgaac tagctgtacc aagaggttcc   5760
ctcagcctcc ttctcaaata acctgatcct tgagggttac accttcacca ctctatgctc   5820
atttcaccca aacataaaat gaaatgtctt aacatgattg caccattaag aaaaacaaat   5880
ctgatgaaga ttaagcctga ttaaggccca accttcatct ttttaccata atcttgttct   5940
cagtaccatt tgataagggt acacttgcca aaacgccccc atcctaaggg tctcgcaatg   6000
gggggtctta gcctactcca attgcccagg gacaagtttc ggaaaagctc tttctttgtt   6060
```

```
tgggtcatca tcttattcca aaaggccttt tccatgcctt tgggtgttgt gactaacagc    6120
actttagaag taacagagat tgaccagcta gtctgcaagg atcatcttgc atctactgac    6180
cagctgaaat cagttggtct caacctcgag gggagcggag tatctactga tatcccatct    6240
gcaacaaagc gttggggctt cagatctggt gttcctccca aggtggtcag ctatgaagcg    6300
ggagaatggg ctgaaaattg ctacaatctt gaaataaaga agccggacgg gagcgaatgc    6360 ttaccccac cgccagatgg tgtcagaggc tttccaaggt gccgctatgt gcacaaagcc    6420
caaggaaccg ggccctgccc aggtgactac gcctttcaca aggatggagc tttctttctc    6480
tatgacaggc tggcttcaac tgtaatttac agaggagtca attttgctga ggggtgatt    6540 gcattcttga tattggctaa accaaaagaa acgttccttc agtcaccccc cattcgagag    6600
gcagtaaact acactgaaaa tacatcaagt tattatgcca catcctactt ggagtatgaa    6660
atcgaaaatt ttggtgctca acactccacg acccttttca aaattgacaa taatactttt    6720
gttcgtctgg acaggcccca cacgcctcag ttccttttcc agctgaacga caccattcac    6780
cttcaccaac agttgagtaa tacaactggg agactaattt ggacactaga tgctaatatc    6840
aatgctgata ttggtgaatg gcttttttgg gaaaataaaa aaatctctcc gaacaactac    6900
gtggagaaga gctgtctttc gaagctttat cgctcaacga gacagaagac gatgatgcgg    6960
catcgtcgag aattacaaag ggaagaatct ccgaccgggc caccaggcag tattcggacc    7020
tggttccaaa gaatccccct gggatggttc cattgcacat accagaaggg gaaacaacat    7080
tgccgtctca gaattcgaca gaaggtcgaa gagtaagtgt gaacactcag gagaccatca    7140
cagagacagc tgcaacaatt ataggcacta acggcaacca tatgcagatc tccaccatcg    7200
ggataagacc gagctccagc caaatcccga gttcctcacc gaccacggca ccaagccctg    7260
aggctcagac ccccacaacc cacacatcag gtccatcagt gatggccacc gaggaaccaa    7320
caacaccacc gggaagctcc cccggcccaa caacagaagc acccactctc accaccccag    7380
aaaatataac aacagcggtt aaaactgtcc tgccacagga gtccacaagc aacggtctaa    7440
taacttcaac agtaacaggg attcttggga gtcttgggct tcgaaaacgc agcagaagac    7500 aaaactaacac caaagccacg ggtaagtgca atcccaactt acactactgg actgcacaag    7560
aacaacataa tgctgctggg attgcctgga tcccgtactt tggaccgggt gcggaaggca    7620
tatacactga aggcctgatg cataaccaaa atgccttagt ctgtggactt aggcaacttg    7680
caaatgaaac aactcaagct ctgcagcttt tcttaagagc cacaacggag ctgcggacat    7740
ataccatact caacaggaag gccatagatt tccttctgcg acgatggggc gggacatgca    7800
ggatcctggg accagattgt tgcattgagc cacatgattg acaaaaaac atcactgata    7860 aaatcaacca aatcatccat gatttcatcg acaaccccct acctaatcag gataatgatg    7920
ataattggtg gacaggctgg agacagtgga tccctgcagg aataggcatt actggaatta    7980
ttattgcaat tattgctctt ctttgcgttt gcaagctgct tgctgaata tcaatttgaa    8040 tcatcaattt aagcttgata catttctagc attttaaatt ataaaccgat actgatactt    8100
gaaaatcagg ctaatgccaa gttctgtgca aaacttgaaa gtaagcttac aaaaatcctt    8160
tgaactggaa tgctttgata ctctttctca atactatata agttccttcc caagaataat    8220
attgatgaag attaagaaaa agtgacattg tgcccacttt tgtaatcttc atccacctac    8280
acattcatat tcaggaatct ttgaattaac cctcacactt gcttaggaaa gagcctatcc    8340 tctcacaagaa tcccgaggcg gcaattcagt taatttcata tcaagataac atccatttcc    8400
aagaccacag ataactatat tattaatctt taccacaaat atggagaggg gtcgtgagcg    8460
```

```
cgggagatca aggaattcac gtgccgacca gcaaaattca acaggtcctc aatttaggac   8520
aagatccatt tcccgggata agacaacaac agactaccgt agtagtcgaa gtacttcgca   8580
agttagagtc cctacggttt tccataagaa aggtactggg acccttactg tccctccagc   8640
acctaaggat atttgtccta ctctcagaaa aggatttcta tgtgacagta atttctgtaa   8700
aaaggaccat caacttgaaa gcctaaccga ccgggagctc ctacttctta tagcacggaa   8760
gacctgtgga tcaactgatt catcgcttaa tatagctgct cctaaagacc taagactagc   8820
aaatcctacg gctgatgact tcaagcaaga cggcagtcca aaattaaccc taaaattact   8880
agtcgagact gctgagtttt gggccaatca gaatattaat gaagtagatg atgcaaaact   8940
ccgtgctctc ttgacgttga gtgctgtctt agtgcggaaa ttctctaagt cacagcttag   9000
tcaattatgt gagagtcatc ttaggaggga aaacttagga caagaccaag ctgaatcagt   9060
tctcgaggtt tatcaacgtt tacatagtga taaaggaggt gcttttgagg cagcactatg   9120
gcaacagtgg gatagacaat cattaactat gtttatatct gctttcctcc atgtagcatt   9180
gcaactttcc tgtgagagct ccactgtagt gatatcaggc ctacgcttac ttgcccccc    9240
aagcgttaat gaagggctcc ctcctgcacc aggggaatat acttggtcag aagatagtac   9300
aacttagcct atagggagga caagtaaaac aagatgccct tatcctctat agatggtatt   9360
tttaaagagg gggacaggat aggaataaag ataatgacta agccaatat  aaagatacga   9420
acacaagtag aaattaaaat agaaatcaaa acaatctccc cttgttcaat atgaaatata   9480
atagtgagta tttgtttcat gatgtcaatc atttattgtt aaaaataaac aaagtcagta   9540
agagtgttag gatcgttata ttgcaaggat cctccctaga agcgttgaat catctcaagt   9600
agcctagaac aagaacagca gagcattaaa ttgaaataga taataaggat attgcttgtt   9660
tttaagatag ttttaggaag tttaaaatta agaaaaagaa cccatggaca cactctagca   9720
ttgaggatgg ggttcccttg atgatagtat agtcttaggt atagggtagt cctacacgtc   9780
ctatattata cagtctaaac ttgtaaaatt aaactacaag aacatgatga aaattaatga   9840
gaaggttcca agattgactt caatccaaac accttgctct gccaattttc atctccttaa   9900
gatatatgat tttgttcctg cgagataagg ttatcaaata gggtgtgtat ctcttttaca   9960
tatttgggct cccactaggc tagggtttat agttaaggaa gactcatcac attttaatt   10020
gaactagtct actcgcagaa tcctaccggg aatagaaatt agaacatttg tgatactttg  10080
actataggaa ataattttca acactacctg agatcaggtt attcttccaa cttattctgc  10140
aagtaattgt ttagcatcat aacaacaacg ttataattta agaatcaagt cttgtaacag  10200
aaataaagat aacagaaaga accttttatta tacgggtcca ttaattttat aggagaagct  10260
ccttttacaa gcctaagatt ccattagaga taaccagaat ggctaaagcc acaggccggt  10320
acaacttggt aacaccaaaa cgggagctag agcaaggagt tgtgtttagc gacctatgca  10380
acttcctagt gactccaact gtgcaaggat ggaaggttta ctgggctgga cttgagtttg  10440
atgtcaacca aaagggtatt accctgttaa atcgtcttaa agtgaatgat tttgctcctg  10500
catgggcgat gacccggaac ctcttccac acttgttcaa aaaccaacag tctgaagtcc    10560
aaactcccat ttgggcctta agggtaattc ttgccgccgg gattcttgac caattaatgg  10620
atcattccct cattgagccg ctatcagggg ccctgaacct aattgctgat tggttactaa  10680
caacatctac taatcacttc aacatgagaa ctcaacgagt aaaggaccaa ctgagtatga  10740
ggatgttatc tcttataagg tcaaatatta ttaactttat aaataagctc gagactcttc  10800
```

```
atgtcgttaa ttacaaggga cttctaagca gtgttgagat aggaacacca agctatgcaa    10860
tcatcattac caggactaat atgggttatc ttgtcgaagt tcaggaacca gataaatctg    10920
caatggatat acgacaccct ggtcctgtca aattctccct actacatgaa tcgacactta    10980
aacctgttgc cactcctaaa ccgtcaagca ttacttcatt gatcatggag ttcaacagtt    11040
ctttggcaat ttaattgccg taataacaat tgtacgatag ggctaacatt gattccataa    11100
tccatcgtag gacagaatca ttttcctgta tgatcttagt ttaatctctc tttatacaat    11160
gattaataag gagcttgttt agaatgttac aaaagtatac tgtttgaccc cctagtatcc    11220
ctgtaaatat cctcattcaa ttttttgctt ttacatgtgt agtcacctgt atagcatgac    11280
cctagtcatg cctttaatta atacttaatc taacagttaa tataatgtat aactttccat    11340
gttcaaagag tagtcaaaac aatgtgagat ccagtttcac tcacagcatc tattcactat    11400
ttacagtatg atgagcccaa attaacacag tagaggtcta gatttattaa tagaatgagg    11460
aagattaaga aaaagtccat aatgctgggg aggcaatcct tgccaccata ggactttttc    11520
aattcctcta ttttatgatg ctacccaac atacacaata tcctgatgca agattgtctt    11580
ccccaattgt cttagaccaa tgtgacctag tgacaagagc ttgtggactt tactctgagt    11640
attcgctgaa ccctaaacta aggacatgcc gtttaccgaa acatatctac agattaaaat    11700
atgacactat tgttttacga tttatcagtg atgtccctgt agctacaatc ccaatagact    11760
acattgctcc gatgttaata aatgttctgg cagatagtaa aaatgtacca ttggaacctc    11820
cctgcttgag tttcttggat gaaatagtca attataccgt gcaggatgca gcattcctta    11880
attattacat gaatcagatt aaaacacagg aaggagtaat tacagatcaa ttgaaacaga    11940
acattcgtag ggtcattcac aaaaacagat atctatctgc tctattcttc tggcatgatc    12000
ttgccatcct cacccgtcga gggagaatga accgaggaaa tgtgcgctct acttggtttg    12060
taacgaatga ggttgttgac attctaggat atggtgatta tatcttctgg aagatcccta    12120
ttgctctatt accaatgaac acagctaatg ttccacatgc atcaactgac tggtaccaac    12180
ctaatatctt caaggaggct attcaaggac acacacatat tatttcagtc tctacagccg    12240
aggtccttat tatgtgtaag gatcttgtca caagtcgttt taatacccct ctgattgctg    12300
agttagccag gttggaagat ccagtgtctg ctgattatcc actagtagat aatattcaat    12360
ctctgtatga cgcaggagac tacctgttgt ccatattggg atcagagggg tacaaaataa    12420
tcaaatatct cgaacctctg tgtttggcta agattcaact atgttcccaa tatacagaac    12480
gaaaagggcg gttttaacc cagatgcatc ttgcagttat tcagacattg cgtgaactcc    12540
tccttaatag agggttgaaa aaatcacaat tgtctaaaat ccgcgagttt caccaactgt    12600
tgctcagact ccgatctaca ccacaacaat tatgtgaatt attttcaatc caaaaacact    12660
ggggccaccc agttctgcat agtgaaaagg ccatccaaaa ggttaaaaat catgcaacag    12720
ttctaaaggc attgcggccg attatcatct ttgaaacgta ttgtgtgttc aagtatagtg    12780
ttgcaaaaca tttctttgat agtcaaggca cttggtacag tgtgatatca gaccgatgtt    12840
taacgccggg attgaattcc tacattaggc gaaatcaatt ccctccactt ccaatgatca    12900
aagatctttt atgggaattt taccatttgg atcatcctcc attattctcc acgaagatca    12960
ttagtgacct cagcattttc attaaagacc gcgcaacagc agttgaacag acctgttggg    13020
atgcagtttt tgagcctaac gttttgggct acagtccacc ttatcgattc aataccaaac    13080
gtgtacctga acaattcctg gagcaagagg atttttctat tgagagtgtc ttacaatacg    13140
cccaagaact taggtactta ttgccccaga atcgaaattt ttcttttca ttgaaggaaa    13200
```

```
aagaattaaa tgttggtagg acatttggaa aattgcctta tttaaccagg aatgtccaaa    13260
ccctctgcga agcattactt gcagatggtt tggctaaagc cttttccaagc aatatgatgg   13320 tggtcacaga gagggaacaa aaggagagcc tccttcacca agcatcctgg caccatacaa    13380
gtgatgattt cggagagcat gccacagttc gtggaagtag ttttgtcaca gacctggaaa   13440
aatacaatct ggccttcagg tatgaattca cagctccctt catcaaatat tgcaaccaat   13500
gctatggggt tcgcaatgtc tttgattgga tgcacttcct aattccacag tgttacatgc   13560
atgttagtga ttattataac ccaccacata atgtaacctt agagaatagg gaatatcccc   13620
ccgaaggacc aagtgcttat agaggccacc ttggcggtat tgagggggctt caacaaaagt   13680 tatggactag tatctcatgt gctcaaatct cattggtaga gatcaagacc gggttcaaat   13740
tgcgatcagc agtcatgggg gataatcaat gtattacagt attatcagtc tttccactag   13800
aatctagtcc gaatgagcag gagagatgcg cagaagacaa tgcagccaga gtggctgcta   13860
gcttggccaa agtcacaagt gcctgtggga tattcctcaa gcctgatgag actttcgtac   13920
actcaggctt tatctatttt ggcaaaaagc aatacttgaa cggaattcaa ttacctcaat   13980
cactcaagac agcagctagg atggcccctc tctcagatgc aattttttgat gacttgcaag   14040 gtacacttgc tagtatagga actgcctttg agcgatcaat ctccgaaact agacatattt   14100
taccatgtcg tgttgcagct gcctttcata catatttctc tgttcggatc ttacaacatc   14160
atcaccttgg tttccataag ggttcagacc ttggacaatt ggcaatcaat aaacctcttg   14220
atttcgggac cattgcacta tccctagcag ttcctcaggt attgggtgga ttatccttcc   14280
taaatccaga aaagtgcctt tatcgcaact tgggtgatcc tgtaacttca ggcctattcc   14340
agttgaagca ttatctgtca atggtgggta tgagtgatat cttcatgca cttgttgcaa    14400 aaagcccagg gaattgtagc gcgattgact ttgttctaaa cccaggcggg ttaaatgtcc   14460
ctggatcaca ggatttaaca tcttttcctc gtcagattgt cagaaggagt atcacacttt   14520
cggcaaggaa caagttaatc aacacgttat ttcacgcttc tgcagatctt gaagacgaat   14580
tagtatgtaa atggttactt tcttcaacgc ccgtgatgag tcgtttcgca gccgatattt   14640
tctcacgaac accaagcggg aaaagattac aaatcttggg atacctcgag ggaaccagaa   14700
ctttattagc atctaaaatg ataagcaata atgcagagac accaatcttg gagaggctca   14760
gaaaaataac acttcaaaga tggaatctat ggtttagtta cctagaccat tgtgacccag   14820
ctttaatgga agcaattcaa ccaattaagt gtactgttga tattgctcaa attcttagag   14880
aatactcctg ggctcatatt cttgatggta gacagttaat aggggcaaca ctgccatgta   14940
tacctgagca gttccaaacc acatggttaa aaccttacga gcaatgtgtg aatgttcat    15000 ccacaaacaa tactagtcca tatgtatcag ttgcattaaa aaggaacgtg ttagtgctt    15060 ggcctgatgc atctagattg gggtggacga ttggtgatgg gattccctac ataggctcaa   15120
gaactgagga caagataggt cagcccgcta ttaagccgag gtgccatca gctgcattaa    15180 gagaagctat tgaattgacc tctaggttga cctgggtcac tcaaggtagt gcaaacagcg   15240
atcagttaat tcgccctttt cttgaggcaa gagtaaactt gagtgtacaa gagattcttc   15300 aaaatgacccc ctcacattac tccggtaata ttgtgcatcg gtataatgat cagtatagcc   15360
ctcactcctt tatggctaac cgcatgagta acacagcaac gcgcttgatg gtatctacca   15420
acacactagg agagttttcc ggagggggtc aggctcacg tgatagcaac attatatttc   15480
aaaatgtgat taacttttgca gtggccttgt atgacattag gtttcggaac acttgtacat   15540
```

```
cttctattca atatcacagg gcccatattc acctgacgaa ttgttgtacg agggaagtac   15600
cggcccaata cttaacatac acaaccacgc taaatctaga tttgagtaag taccgtaata   15660
atgaactgat ttatgattca gagccactaa gaggaggtct caactgcaac ttatcgattg   15720
acagtccttt gatgaagggc ccacgtttaa atattattga ggatgactta atacggttgc   15780
cacatttatc cggctgggaa ttagcaaaaa cagtcttgca atcaataatc tctgatagta   15840
gcaattcatc aacagatccc attagcagcg gtgaaacaag atccttcaca acccacttct   15900
taacgtatcc caaaataggg ctcctataca gttttggagc cctcataagt ttttatttgg   15960
gtaatactat tctgtgcacg aaaaagatcg gactcacaga atttctatac tatctccaga   16020
atcagatcca caacttatca catagatccc ttcgaatctt caaaccgaca tttagacact   16080
caagtgtcat gtccaggttg atggatatag accccaactt ctcaatatat attggtggga   16140
ctgcaggtga ccgtggatta tcggacgctg caagattatt tctccgaatt gcaatttcaa   16200
ctttcttgag ctttgttgag gagtgggtta tctttaggaa ggcaaacatc ccactatggg   16260
ttatctatcc tctcgaaggc caacgccctg atcctcctgg cgaattttttg aaccgagtaa   16320 aatctctaat tgttgggact gaagatgata aaaataaagg ctctatactt tcaagatctg   16380
gagagaaatg ctcttcaaat ctagtttata attgcaagag tacagcaagc aatttttttcc   16440 atgcatcatt ggcttattgg agaggtcgac acagacctaa aagagactata ggtgcaacca   16500 acgcgacaac agctccacac atcatcctgc caccaggaaa ctctgatcga ccgcctggcc   16560
tagaccttaa taggaacgat gatactttca ttcctaccag aattaaacag atagtccaag   16620
gagactctag aaacgacaga acgaccacca cgagatttcc acccaaaagt aggtccactc   16680
caacatcagc aaccgagcct cctacaaaaa tgtatgaggg ttcgacaacc caccaaggga   16740
aattaacaga tacacatttg gatgaggatc acaatgccaa agagttccca tccaatccgc   16800
atcgtttagt agtaccattc tttaaattaa caaaagatgg ggaatacagt atcgaacctt   16860
ctactgaaga aagccgcagt aatataaaag ggttacttca acatttaaga accatggttg   16920
atactaccat atattgtcgc ttcactggaa ttgtttcatc aatgcattat aagttagatg   16980
aagtactatg ggaatataat aaatttgaat cagctgtaac cctagcagaa ggggagggtt   17040 caggtgccttt actactgatc caaaaatacg gcgttaagaa gttatttttg aatacacttg   17100
ctactgaaca tagtattgag agtgaagtta tatcaggtta caccactcca aggatgctac   17160
tctcaattat gcctaaaaca catcgtggtg agctagaggt catattaaat aactcagcta   17220
gtcaaataac tgacattaca caccgagatt ggttttcaaa tcaaaaaaat aggattccaa   17280
atgatgctga tattattacc atggatgctg aaactacaga aaacttagat cgttccagat   17340
tatatgaagc agtatatacg attatttgta atcatatcaa tcctaaaact ttgaaagtgg   17400
tcatcttaaa agtcttcctc agcgatttgg atgggatgtg ctggattaac aattatcttg   17460
ctcctatgtt tggatcagga tatttaatca aacctataac atcaagtgca aagtcaagtg   17520 agtggtatttt atgcttatct aatctacttt caaccttgag aactactcag catcaaaccc   17580
aggcaaactg tctccatgtc gtacaatgtg ctcttcaaca gcaagtacaa agagggtcat   17640
actggctaag tcatcttacc aaatacacca caagtagatt gcacaatagt tatatcgtat   17700 ttggtttttcc ttcattagag aaggtcctat atcataggta taacctcgtt gattcgagaa   17760
acggaccatt agtttctata acgagacacc ttgccctcct ccaaactgag atccgggagt   17820
tggtaactga ttataatcag ctgcgacaaa gtcgaaccca gacttatcat ttcataaaaa   17880
catccaaggg acggataact aaaactagtga atgattatct aagatttgag ttggttatac   17940
```

```
gggctcttaa aaataattct acatggcacc atgagttata cttgctacca gaacttatag    18000
gtgtttgcca tcgatttaat catacacgta actgtacatg cagtgaaagg ttcctggttc    18060
aaactttata tctacaccga atgagtgatg ctgagataaa acttatggac cggctcacca    18120
gcctagtcaa tatgttttcct gaaggtttca ggtctagttc agtctaattc taactgcacc    18180
aaaggctcta gaaatatttt aaataaccag gtgtatatca aagtcaatac aagtgtaaaa    18240
acaatatgca agggaccaca tttaggatca gtttattgac tcttccaata cacagagttg    18300
gaagcaccga ttcaaggttt ctaagacgct ctatcaatta tgttgataat gtaaataata    18360
gcttttcctg tctattatga cttaaataaa catatctata acgaccatca cagctaagtc    18420
gttgccctag ttcatatatt aaattaaaat ttggaagcta ggttaactct aattacataa    18480
gtattaagaa aaaattacta agactaatac tctcatgcca agaactagta atgtgtttca    18540
catgacagat tatttctaac actaaattgc aatttcaatt ttaaagctaa gtttaacacc    18600
tatacagcca aaatatttca tagggccgat gggaataaca taagaggaac atgatcaatg    18660 aacccttat tccaactagg cagttgattg ataatctaca aattccataa gatgttctta    18720
cgatattctt ttgttttaa tctcaatgtc aatgatttaa taagtaataa taaaaaaatc    18780
acattaaaga tgcaggaaga tcttgacctc gccaggaaaa ttaagcgcac acaaataaat    18840
taaaaaatct gtattttctc ttttttgtgt gtcc                               18874

<210> SEQ ID NO 3
<211> LENGTH: 32315
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
catcatcaat aatataccctt attttggatt gaagccaata tgataatgag ggggtggagt     60
ttgtgacgtg gcgcggggcg tgggaacggg gcgggtgacg tagtagtgtg gcggaagtgt    120
gatgttgcaa gtgtggcgga acacatgtaa gcgacggatg tggcaaaagt gacgttttttg   180 gtgtgcgccg gtgtacacag gaagtgacaa ttttcgcgcg gttttaggcg gatgttgtag    240
taaatttggg cgtaaccgag taagatttgg ccatttttcgc gggaaaactg aataagagga    300
agtgaaatct gaataatttt gtgttactca tagcgcgtaa tactgtaata gtaatcaatt    360
acggggtcat tagttcatag cccatatatg gagttccgcg ttacataact tacggtaaat    420
ggcccgcctg gctgaccgcc caacgacccc cgcccattga cgtcaataat gacgtatgtt    480
cccatagtaa cgccaatagg gactttccat tgacgtcaat gggtggagta tttacggtaa    540
actgcccact tggcagtaca tcaagtgtat catatgccaa gtacgccccc tattgacgtc    600
aatgacggta aatggcccgc ctggcattat gcccagtaca tgaccttatg gactttcct    660 acttggcagt acatctacgt attagtcatc gctattacca tggtgatgcg gttttggcag    720
tacatcaatg ggcgtggata gcggtttgac tcacgggat tccaagtct ccaccccatt     780 gacgtcaatg ggagtttgtt ttggcaccaa aatcaacggg actttccaaa atgtcgtaac    840
aactccgccc cattgacgca aatgggcggt aggcgtgtac ggtgggaggt ctatataagc    900
agagctggtt tagtgaaccg tcagatccgc tagagatctg gtaccgtcga cgcggccgct    960
cgagcctaag cttggtaccg agctcggatc cactagtaac ggccgccagt gtgctggaat   1020
tcggcttaaa ggtacccaga gcagacagcc gccaccatgg agtctccctc ggcccctccc   1080
```

-continued

```
cacagatggt gcatccctg gcagaggctc ctgctcacag cctcacttct aaccttctgg    1140
aacccgccca ccactgccaa gctcactatt gaatccacgc cgttcaatgt cgcagagggg    1200
aaggaggtgc ttctacttgt ccacaatctg ccccagcatc tttttggcta cagctggtac    1260
aaaggtgaaa gagtggatgg caaccgtcaa attataggat atgtaatagg aactcaacaa    1320
gctaccccag ggcccgcata cagtggtcga gagataatat accccaatgc atccctgctg    1380
atccagaaca tcatccagaa tgacacagga ttctacaccc tacacgtcat aaagtcagat    1440
cttgtgaatg aagaagcaac tggccagttc cgggtatacc cggagctgcc caagccctcc    1500
atctccagca caactccaa acccgtggag gacaaggatg ctgtggcctt cacctgtgaa    1560
cctgagactc aggacgcaac ctacctgtgg tgggtaaaca atcagagcct cccggtcagt    1620
cccaggctgc agctgtccaa tggcaacagg accctcactc tattcaatgt cacaagaaat    1680
gacacagcaa gctacaaatg tgaaaccag aacccagtga gtgccaggcg cagtgattca    1740
gtcatcctga atgtcctcta tggccccgat gcccccacca tttcccctct aaacacatct    1800
tacagatcag gggaaaatct gaacctctcc tgccacgcag cctctaaccc acctgcacag    1860
tactcttggt ttgtcaatgg gactttccag caatccaccc aagagctctt tatcccccaac   1920 atcactgtga ataatagtgg atcctatacg tgccaagccc ataactcaga cactggcctc    1980
aataggacca cagtcacgac gatcacagtc tatgcagagc cacccaaacc cttcatcacc    2040
agcaacaact ccaacccgt ggaggatgag gatgctgtag ccttaacctg tgaacctgag    2100
attcagaaca caacctacct gtggtgggta aataatcaga gcctcccggt cagtcccagg    2160
ctgcagctgt ccaatgacaa caggaccctc actctactca gtgtcacaag gaatgatgta    2220
ggaccctatg agtgtggaat ccagaacgaa ttaagtgttg accacagcga cccagtcatc    2280
ctgaatgtcc tctatggccc agacgacccc accatttccc cctcatacac ctattaccgt    2340
ccaggggtga acctcagcct ctcctgccat gcagcctcta acccacctgc acagtattct    2400
tggctgattg atgggaacat ccagcaacac acacaagagc tctttatctc caacatcact    2460
gagaagaaca gcggactcta tcctgccag gccataact cagccagtgg ccacagcagg    2520
actacagtca agacaatcac agtctctgcg gagctgccca gccctccat ctccagcaac    2580 aactccaaac ccgtggagga caaggatgct gtggccttca cctgtgaacc tgaggctcag    2640
aacacaacct acctgtggtg ggtaaatggt cagagcctcc cagtcagtcc caggctgcag    2700
ctgtccaatg gcaacaggac cctcactcta ttcaatgtca agaaatga cgcaagagcc    2760 tatgtatgtg gaatccagaa ctcagtgagt gcaaaccgca gtgacccagt caccctggat    2820
gtcctctatg gccggacac ccccatcatt tccccccag actcgtctta cctttcggga    2880
gcggacctca acctctcctg ccactcggcc tctaacccat cccgcagta ttcttggcgt    2940 atcaatggga taccgcagca acacacacaa gttctcttta tcgccaaaat cacgccaaat    3000
aataacggga cctatgcctg ttttgtctct aacttggcta ctggccgcaa taattccata    3060
gtcaagagca tcacagtctc tgcatctgga acttctcctg gtctctcagc tggggccact    3120
gtcggcatca tgattggagt gctggttggg gttgctctga tatagcagcc ctggtgtagt    3180
ttcttcattt caggaagact gacagttgtt ttgcttcttc cttaaagcat ttgcaacagc    3240
tacagtctaa aattgcttct ttaccaagga tatttacaga aaagactctg accagagatc    3300
gagaccatcc tctagataag atatccgatc caccggatct agataactga tcataatcag    3360
ccataccaca tttgtagagg ttttacttgc tttaaaaaac ctcccacacc tcccctgaa    3420
```

```
cctgaaacat aaaatgaatg caattgttgt tgttaacttg tttattgcag cttataatgg   3480
ttacaaataa agcaatagca tcacaaattt cacaaataaa gcattttttt cactgcattc   3540
tagttgtggt ttgtccaaac tcatcaatgt atcttaacgc ggatctgggc gtggttaagg   3600
gtgggaaaga atatataagg tggggtctt atgtagtttt gtatctgttt tgcagcagcc    3660
gccgccgcca tgagcaccaa ctcgtttgat ggaagcattg tgagctcata tttgacaacg   3720
cgcatgcccc catgggccgg ggtgcgtcag aatgtgatgg gctccagcat tgatggtcgc   3780
cccgtcctgc ccgcaaactc tactaccttg acctacgaga ccgtgtctgg aacgccgttg   3840
gagactgcag cctccgccgc cgcttcagcc gctgcagcca ccgcccgcgg gattgtgact   3900
gactttgctt tcctgagccc gcttgcaagc agtgcagctt cccgttcatc cgcccgcgat   3960
gacaagttga cggctctttt ggcacaattg gattctttga cccgggaact taatgtcgtt   4020
tctcagcagc tgttggatct gcgccagcag gtttctgccc tgaaggcttc ctcccctccc   4080
aatgcggttt aaaacataaa taaaaaacca gactctgttt ggatttggat caagcaagtg   4140
tcttgctgtc tttatttagg ggttttgcgc gcgcggtagg cccgggacca gcggtctcgg   4200
tcgttgaggg tcctgtgtat ttttccagg acgtggtaaa ggtgactctg gatgttcaga    4260
tacatgggca taagcccgtc tctggggtgg aggtagcacc actgcagagc ttcatgctgc   4320
ggggtggtgt tgtagatgat ccagtcgtag caggagcgct gggcgtggtg cctaaaaatg   4380
tctttcagta gcaagctgat tgccagggc aggcccttgg tgtaagtgtt tacaaagcgg    4440
ttaagctggg atgggtgcat acgtggggat atgagatgca tcttggactg tattttagg    4500
ttggctatgt tcccagccat atccctccgg ggattcatgt tgtgcagaac caccagcaca   4560
gtgtatccgg tgcacttggg aaatttgtca tgtagcttag aaggaaatgc gtggaagaac   4620
ttggagacgc ccttgtgacc tccaagattt tccatgcatt cgtccataat gatggcaatg   4680
ggcccacggg cggcggcctg ggcgaagata tttctgggat cactaacgtc atagttgtgt   4740
tccaggatga gatcgtcata ggccattttt acaaagcgcg gcggagggt gccagactgc    4800
ggtataatgg ttccatccgg cccaggggcg tagttaccct cacagatttg catttcccac   4860
gctttgagtt cagatggggg gatcatgtct acctgcgggg cgatgaagaa aacggtttcc   4920
ggggtagggg agatcagctg ggaagaaagc aggttcctga gcagctgcga cttaccgcag   4980
ccggtgggcc cgtaaatcac acctattacc ggctgcaact ggtagttaag agagctgcag   5040
ctgccgtcat ccctgagcag gggggccact tcgttaagca tgtccctgac tcgcatgttt   5100
tccctgacca aatccgccag aaggcgctcg ccgcccagcg atagcagttc ttgcaaggaa   5160
gcaaagtttt tcaacggttt gagaccgtcc gccgtaggca tgcttttgag cgtttgacca   5220
agcagttcca gcggtccca cagctcggtc acctgctcta cggcatctcg atccagcata    5280
tctcctcgtt tcgcgggttg gggcggcttt cgctgtacgg cagtagtcgg tgctcgtcca   5340
gacgggccag ggtcatgtct ttccacgggc gcagggtcct cgtcagcgta gtctgggtca   5400
cggtgaaggg gtgcgctccg ggctgcgcgc tggccagggt gcgcttgagg ctggtcctgc   5460
tggtgctgaa gcgctgccgg tcttcgccct gcgcgtcggc caggtagcat tgaccatgg    5520
tgtcatagtc cagcccctcc gcggcgtggc ccttggcgcg cagcttgccc ttggaggagg   5580
cgccgcacga ggggcagtgc agactttga gggcgtagag cttgggcgcg agaaataccg    5640
attccgggga gtaggcatcc gcgccgcagg ccccgcagac ggtctcgcat tccacgagcc   5700
aggtgagctc tggccgttcg gggtcaaaaa ccaggttcc cccatgcttt ttgatgcgtt    5760
tcttacctct ggtttccatg agccggtgtc cacgctcggt gacgaaaagg ctgtccgtgt   5820
```

```
ccccgtatac agacttgaga ggcctgtcct cgagcggtgt tccgcggtcc tcctcgtata    5880
gaaactcgga ccactctgag acaaaggctc gcgtccaggc cagcacgaag gaggctaagt    5940
gggaggggta gcggtcgttg tccactaggg ggtccactcg ctccagggtg tgaagacaca    6000
tgtcgccctc ttcggcatca aggaaggtga ttggtttgta ggtgtaggcc acgtgaccgg    6060
gtgttcctga agggggggcta taaaagggggg tgggggcgcg ttcgtcctca ctctcttccg    6120
catcgctgtc tgcgagggcc agctgttggg gtgagtactc cctctgaaaa gcgggcatga    6180
cttctgcgct aagattgtca gtttccaaaa acgaggagga tttgatattc acctggcccg    6240
cggtgatgcc tttgagggtg gccgcatcca tctggtcaga aaagacaatc ttttttgttgt    6300
caagcttggt ggcaaacgac ccgtagaggg cgttggacag caacttggcg atggagcgca    6360
gggtttggtt tttgtcgcga tcggcgcgct ccttggccgc gatgtttagc tgcacgtatt    6420
cgcgcgcaac gcaccgccat tcgggaaaga cggtggtgcg ctcgtcgggc accaggtgca    6480
cgcgccaacc gcggttgtgc agggtgacaa ggtcaacgct ggtggctacc tctccgcgta    6540
ggcgctcgtt ggtccagcag aggcggccgc ccttgcgcga gcagaatggc ggtaggggt     6600
ctagctgcgc tcgtccgggg gggtctgcgt ccacggtaaa gaccccgggc agcaggcgcg    6660
cgtcgaagta gtctatcttg catccttgca agtctagcgc ctgctgccat gcgcgggcgg    6720
caagcgcgcg ctcgtatggg ttgagtgggg gacccccatgg catggggtgg gtgagcgcgg    6780
aggcgtacat gccgcaaatg tcgtaaacgt agaggggctc tctgagtatt ccaagatatg    6840
tagggtagca tcttccaccg cggatgctgg cgcgcacgta atcgtatagt tcgtgcgagg    6900
gagcgaggag gtcgggaccg aggttgctac gggcgggctg ctctgctcgg aagactatct    6960
gcctgaagat ggcatgtgag ttggatgata tggttggacg ctggaagacg ttgaagctgg    7020
cgtctgtgag acctaccgcg tcacgcacga aggaggcgta ggagtcgcgc agcttgttga    7080
ccagctcggc ggtgacctgc acgtctaggg cgcagtagtc cagggttttcc ttgatgatgt    7140
catacttatc ctgtcccttt ttttttccaca gctcgcggtt gaggacaaac tcttcgcggt    7200
cttccagta ctcttggatc ggaaacccgt cggcctccga acggtaagag cctagcatgt    7260
agaactggtt gacggcctgg taggcgcagc atcccttttc tacgggtagc gcgtatgcct    7320
gcgcggcctt ccggcatgac cagcatgaag ggcacgagct gcttcccaaa ggcccccatc    7380
caagtatagg tctctacatc gtaggtgaca aagagacgct cggtgcgagg atgcgagccg    7440
atcgggaaga actggatctc ccgccaccaa ttggaggagt ggctattgat gtggtgaaag    7500
tagaagtccc tgcgacgggc cgaacactcg tgctggcttt tgtaaaaacg tgcgcagtac    7560
tggcagcggt gcacgggctg tacatcctgc acgaggttga cctgacgacc gcgcacaagg    7620
aagcagagtg ggaatttgag cccctcgcct ggcgggtttg gctggtggtc ttctacttcg    7680
gctgcttgtc cttgaccgtc tggctgctcg aggggagtta cggtggatcg gaccaccacg    7740
ccgcgcgagc ccaaagtcca gatgtccgcg cgcggcggtc ggagcttgat gacaacatcg    7800
cgcagatggg agctgtccat ggtctggagc tcccgcggcg tcaggtcagg cgggagctcc    7860
tgcaggttta cctcgcatag acgggtcagg gcgcgggcta gatccaggtg atacctaatt    7920
tccagggct ggttggtggc ggcgtcgatg gcttgcaaga ggccgcatcc ccgcggcgcg    7980
actacggtac cgcgcggcgg cggtgggcc gcggggtgt ccttggatga tgcatctaaa      8040
agcggtgacg cgggcgagcc cccggaggta gggggggctc cggacccgcc gggagagggg    8100
gcaggggcac gtcggcgccg cgcgcgggca ggagctggtc ctgcgcgcgt aggttgctgg    8160
```

```
cgaacgcgac gacgcggcgg ttgatctcct gaatctggcg cctctgcgtg aagacgacgg    8220
gcccggtgag cttgaacctg aaagagagtt cgacagaatc aatttcggtg tcgttgacgg    8280
cggcctggcg caaaatctcc tgcacgtctc ctgagttgtc ttgataggcg atctcggcca    8340
tgaactgctc gatctcttcc tcctggagat ctccgcgtcc ggctcgctcc acggtggcgg    8400
cgaggtcgtt ggaaatgcgg gccatgagct gcgagaaggc gttgaggcct ccctcgttcc    8460
agacgcggct gtagaccacg ccccttcgg catcgcgggc gcgcatgacc acctgcgcga    8520
gattgagctc cacgtgccgg gcgaagacgg cgtagtttcg caggcgctga aagaggtagt    8580
tgagggtggt ggcggtgtgt tctgccacga agaagtacat aacccagcgt cgcaacgtgg    8640
attcgttgat aattgttgtg taggtactcc gccgccgagg gacctgagcg agtccgcatc    8700
gaccggatcg gaaaacctct cgagaaaggc gtctaaccag tcacagtcgc aaggtaggct    8760
gagcaccgtg gcgggcggca gcgggcggcg gtcggggttg tttctggcgg aggtgctgct    8820
gatgatgtaa ttaaagtagg cggtcttgag acggcggatg gtcgacagaa gcaccatgtc    8880
cttgggtccg gcctgctgaa tgcgcaggcg gtcggccatg ccccaggctt cgttttgaca    8940
tcggcgcagg tctttgtagt agtcttgcat gagcctttct accggcactt cttcttctcc    9000
ttcctcttgt cctgcatctc ttgcatctat cgctgcggcg gcggcggagt ttggccgtag    9060
gtggcgccct cttcctccca tgcgtgtgac cccgaagccc ctcatcggct gaagcagggc    9120
taggtcggca caacgcgct cggctaatat ggcctgctgc acctgcgtga gggtagactg    9180
gaagtcatcc atgtccacaa agcggtggta tgcgcccgtg ttgatggtgt aagtgcagtt    9240
ggccataacg gaccagttaa cggtctggtg accggctgc gagagctcgg tgtacctgag    9300
acgcgagtaa gccctcgagt caaatacgta gtcgttgcaa gtccgcacca ggtactggta    9360
tcccaccaaa aagtgcggcg gcggctggcg gtagaggggc cagcgtaggg tggccggggc    9420
tccggggcg agatcttcca acataaggcg atgatatccg tagatgtacc tggacatcca    9480
ggtgatgccg gcgcggtgg tggaggcgcg cggaaagtcg cggacgcggt tccagatgtt    9540
gcgcagcggc aaaaagtgct ccatggtcgg gacgctctgg ccggtcaggc gcgcgcaatc    9600
gttgacgctc tagcgtgcaa aaggagagcc tgtaagcggg cactcttccg tggtctggtg    9660
gataaattcg caagggtatc atggcggacg accggggttc gagccccgta tccggccgtc    9720
cgccgtgatc catgcggtta ccgcccgcgt gtcgaaccca ggtgtgcgac gtcagacaac    9780
gggggagtgc tccttttggc ttccttccag gcgcggcggc tgctgcgcta gctttttgg    9840
ccactggccg cgcgcagcgt aagcggttag gctggaaagc gaaagcatta agtggctcgc    9900
tccctgtagc cggagggtta ttttccaagg gttgagtcgc gggacccccg gttcgagtct    9960
cggaccggcc ggactgcggc gaacgggggt ttgcctcccc gtcatgcaag accccgcttg   10020
caaattcctc cggaaacagg gacgagcccc ttttttgctt ttcccagatg catccggtgc   10080
tgcggcagat gcgccccct cctcagcagc ggcaagagca agagcagcgg cagacatgca   10140
gggcaccctc ccctcctcct accgcgtcag gaggggcgac atccgcggtt gacgcggcag   10200
cagatggtga ttacgaaccc ccgcggcgcc gggcccggca ctacctggac ttggaggagg   10260
gcgagggcct ggcgcggcta ggagcgccct ctcctgagcg gcacccaagg gtgcagctga   10320
agcgtgatac gcgtgaggcg tacgtgccgc ggcagaacct gtttcgcgac cgcgagggag   10380
aggagcccga ggagatgcgg gatcgaaagt tccacgcagg gcgcgagctg cggcatggcc   10440
tgaatcgcga gcggttgctg cgcgaggagg actttgagcc cgacgcgcga accgggatta   10500
gtcccgcgcg cgcacacgtg gcggccgccg acctggtaac cgcatacgag cagacggtga   10560
```

```
accaggagat taactttcaa aaaagcttta acaaccacgt gcgtacgctt gtggcgcgcg   10620
aggaggtggc tataggactg atgcatctgt gggactttgt aagcgcgctg gagcaaaacc   10680
caaatagcaa gccgctcatg gcgcagctgt tccttatagt gcagcacagc agggacaacg   10740
aggcattcag ggatgcgctg ctaaacatag tagagcccga gggccgctgg ctgctcgatt   10800
tgataaacat cctgcagagc atagtggtgc aggagcgcag cttgagcctg gctgacaagg   10860
tggccgccat caactattcc atgcttagcc tgggcaagtt ttacgcccgc aagatatacc   10920 ataccccttta cgttcccata gacaaggagg taaagatcga ggggttctac atgcgcatgg   10980
cgctgaaggt gcttaccttg agcgacgacc tgggcgttta tcgcaacgag cgcatccaca   11040
aggccgtgag cgtgagccgg cggcgcgagc tcagcgaccg cgagctgatg cacagcctgc   11100
aaagggccct ggctggcacg ggcagcggcg atagagaggc cgagtcctac tttgacgcgg   11160
gcgctgacct gcgctgggcc ccaagccgac gcgccctgga ggcagctggg gccggacctg   11220
ggctggcggt ggcacccgcg cgcgctgca acgtcggcgg cgtggaggaa tatgacgagg   11280
acgatgagta cgagccagag gacggcgagt actaagcggt gatgtttctg atcagatgat   11340
gcaagacgca acggacccgg cggtgcgggc ggcgctgcag agccagccgt ccggccttaa   11400
ctccacggac gactggcgcc aggtcatgga ccgcatcatg tcgctgactg cgcgcaatcc   11460
tgacgcgttc cggcagcagc cgcaggccaa ccggctctcc gcaattctgg aagcggtggt   11520
cccggcgcgc gcaaacccca cgcacgagaa ggtgctggcg atcgtaaacg cgctggccga   11580
aaacagggcc atccgccccg acgaggccgg cctggtctac gacgcgctgc ttcagcgcgt   11640
ggctcgttac aacagcggca acgtgcagac caacctggac cggctggtgg gggatgtgcg   11700
cgaggccgtg gcgcagcgtg agcgcgcgca gcagcagggc aacctgggct ccatggttgc   11760
actaaacgcc ttcctgagta cacagcccgc caacgtgccg cggggacagg aggactacac   11820
caactttgtg agcgcactgc ggctaatggt gactgagaca ccgcaaagtg aggtgtacca   11880
gtctgggcca gactattttt tccagaccag tagacaaggc ctgcagaccg taaacctgag   11940
ccaggctttc aaaaacttgc aggggctgtg ggggtgcgg gctcccacag gcgaccgcgc   12000
gaccgtgtct agcttgctga cgcccaactc gcgcctgttg ctgctgctaa tagcgcccct   12060
cacggacagt ggcagcgtgt cccgggacac ataccctaggt cacttgctga cactgtaccg   12120
cgaggccata ggtcaggcgc atgtggacga gcatactttc caggagatta caagtgtcag   12180
ccgcgcgctg gggcaggagg acacgggcag cctggaggca accctaaaact acctgctgac   12240 caaccggcgg cagaagatcc cctcgttgca cagtttaaac agcgaggagg agcgcatttt   12300
gcgctacgtg cagcagagcg tgagccttaa cctgatgcgc gacggggtaa cgcccagcgt   12360
ggcgctggac atgaccgcgc gcaacatgga accgggcatg tatgcctcaa accggccgtt   12420
tatcaaccgc ctaatggact acttgcatcg cgcggccgcc gtgaaccccg agtatttcac   12480
caatgccatc ttgaacccgc actggctacc gccccctggt ttctacaccg ggggattcga   12540
ggtgcccgag ggtaacgatg gattcctctg gacgacata gacgacagcg tgttttcccc   12600
gcaaccgcag accctgctag agttgcaaca gcgcgagcag gcagaggcgg cgctgcgaaa   12660
ggaaagcttc gcaggccaa gcagcttgtc cgatctaggc gctgcggccc gcggtcaga   12720 tgctagtagc ccatttccaa gcttgatagg gtctcttacc agcactcgca ccacccgccc   12780
gcgcctgctg ggcgaggagg agtacctaaa caactcgctg ctgcagccgc agcgcgaaaa   12840
aaacctgcct ccggcatttc ccaacaacgg gatagagagc ctagtggaca agatgagtag   12900
```

```
atggaagacg tacgcgcagg agcacaggga cgtgccaggc ccgcgcccgc ccacccgtcg    12960
tcaaaggcac gaccgtcagc ggggtctggt gtgggaggac gatgactcgg cagacgacag    13020
cagcgtcctg gatttgggag ggagtggcaa cccgtttgcg caccttcgcc ccaggctggg    13080
gagaatgttt taaaaaaaaa aaagcatgat gcaaaataaa aaactcacca aggccatggc    13140
accgagcgtt ggttttcttg tattcccctt agtatgcggc gcgcggcgat gtatgaggaa    13200
ggtcctcctc cctcctacga gagtgtggtg agcgcggcgc cagtggcggc ggcgctgggt    13260
tctcccttcg atgctcccct ggacccgccg tttgtgcctc cgcggtacct gcggcctacc    13320 gggggagaa acagcatccg ttactctgag ttggcacccc tattcgacac cacccgtgtg     13380
tacctggtgg acaacaagtc aacggatgtg gcatccctga actaccagaa cgaccacagc    13440
aactttctga ccacggtcat tcaaaacaat gactacagcc cggggaggc aagcacacag     13500 accatcaatc ttgacgaccg gtcgcactgg ggcggcgacc tgaaaaccat cctgcatacc    13560
aacatgccaa atgtgaacga gttcatgttt accaataagt ttaaggcgcg ggtgatggtg    13620
tcgcgcttgc ctactaagga caatcaggtg gagctgaaat acgagtgggt ggagttcacg    13680
ctgcccgagg gcaactactc cgagaccatg accatagacc ttatgaacaa cgcgatcgtg    13740
gagcactact tgaaagtggg cagacagaac ggggttctgg aaagcgacat cggggtaaag    13800
tttgacaccc gcaacttcag actggggttt gaccccgtca ctggtcttgt catgcctggg    13860
gtatatacaa cgaagccttt ccatccagac atcattttgc tgccaggatg cggggtggac    13920
ttcacccaca gccgcctgag caacttgttg ggcatccgca agcggcaacc cttccaggag    13980
ggctttagga tcacctacga tgatctggag ggtggtaaca ttcccgcact gttggatgtg    14040
gacgcctacc aggcgagctt gaaagatgac accgaacagg gcggggtgg cgcaggcggc    14100 agcaacagca gtggcagcgg cgcggaagag aactccaacg cggcagccgc ggcaatgcag    14160
ccggtggagg acatgaacga tcatgccatt cgcggcgaca cctttgccac acgggctgag    14220
gagaagcgcg ctgaggccga agcagcggcc gaagctgccg cccccgctgc gcaacccgag    14280
gtcgagaagc ctcagaagaa accggtgatc aaacccctga cagaggacag caagaaacgc    14340
agttacaacc taataagcaa tgacagcacc ttcacccagt accgcagctg gtaccttgca    14400
tacaactacg gcgaccctca gaccggaatc cgctcatgga ccctgctttg cactcctgac    14460
gtaacctgcg gctcggagca ggtctactgg tcgttgccag acatgatgca agaccccgtg    14520
accttccgct ccacgcgcca gatcagcaac tttccggtgg tgggcgccga gctgttgccc    14580
gtgcactcca gagcttcta caacgaccag gccgtctact cccaactcat ccgccagttt    14640
acctctctga cccacgtgtt caatcgcttt cccgagaacc agattttggc gcgcccgcca    14700 gccccacca tcaccaccgt cagtgaaaac gttcctgctc tcacagatca cgggacgcta    14760
ccgctgcgca acagcatcgg aggagtccag cgagtgacca ttactgacgc cagacgccgc    14820 acctgccccct acgtttacaa ggccctgggc atagtctcgc cgcgcgtcct atcgagccgc    14880
actttttgag caagcatgtc catccttata tcgcccagca ataacacagg ctggggcctg    14940
cgcttcccaa gcaagatgtt tggcggggcc aagaagcgct ccgaccaaca cccagtgcgc    15000
gtgcgcgggc actaccgcgc gccctgggc gcgcacaaac gcggccgcac tgggcgcacc      15060
accgtcgatg acgccatcga cgcggtggtg gaggaggcgc gcaactacac gcccacgccg    15120
ccaccagtgt ccacagtgga cgcggccatt cagaccgtgg tgcgcggagc ccggcgctat    15180
gctaaaatga gagacggcg gaggcgcgta gcacgtcgcc accgccgccg acccggcact     15240
gccgcccaac gcgcggcggc ggccctgctt aaccgcgcac gtcgcaccgg ccgacgggcg    15300
```

```
gccatgcggg ccgctcgaag gctggccgcg ggtattgtca ctgtgccccc caggtccagg   15360
cgacgagcgg ccgccgcagc agccgcggcc attagtgcta tgactcaggg tcgcaggggc   15420
aacgtgtatt gggtgcgcga ctcggttagc ggcctgcgcg tgcccgtgcg caccgcccc    15480 ccgcgcaact agattgcaag aaaaaactac ttagactcgt actgttgtat gtatccagcg   15540
gcggcggcgc gcaacgaagc tatgtccaag cgcaaaatca agaagagat gctccaggtc    15600 atcgcgccgg agatctatgg ccccccgaag aaggaagagc aggattacaa gccccgaaag   15660
ctaaagcggg tcaaaaagaa aagaaagat gatgatgatg aacttgacga cgaggtggaa    15720
ctgctgcacg ctaccgcgcc caggcgacgg gtacagtgga aaggtcgacg cgtaaaacgt   15780
gttttgcgac ccggcaccac cgtagtcttt acgcccggtg agcgctccac ccgcacctac   15840
aagcgcgtgt atgatgaggt gtacggcgac gaggacctgc ttgagcaggc caacgagcgc   15900
ctcggggagt ttgcctacgg aaagcggcat aaggacatgc tggcgttgcc gctggacgag   15960
ggcaacccaa cacctagcct aaagcccgta acactgcagc aggtgctgcc cgcgcttgca   16020
ccgtccgaag aaaagcgcgg cctaaagcgc gagtctggtg acttggcacc caccgtgcag   16080
ctgatggtac ccaagcgcca gcgactggaa gatgtcttgg aaaaaatgac cgtggaacct   16140
gggctggagc ccgaggtccg cgtgcggcca atcaagcagg tggcgccggg actgggcgtg   16200
cagaccgtgg acgttcagat acccactacc agtagcacca gtattgccac cgccacagag   16260
ggcatggaga cacaaacgtc cccggttgcc tcagcggtgg cggatgccgc ggtgcaggcg   16320
gtcgctgcgg ccgcgtccaa gacctctacg gaggtgcaaa cggacccgtg gatgtttcgc   16380
gtttcagccc ccggcgccc gcgccgttcg aggaagtacg gcgccgccag cgcgctactg    16440
cccgaatatg ccctacatcc ttccattgcg cctaccccg gctatcgtgg ctacacctac    16500
cgccccagaa gacgagcaac tacccgacgc cgaaccacca ctggaacccg ccgccgccgt   16560
cgccgtcgcc agcccgtgct ggccccgatt tccgtgcgca gggtggctcg cgaaggaggc   16620
aggaccctgg tgctgccaac agcgcgctac cacccccagca tcgtttaaaa gccggtctttt  16680 gtggttcttg cagatatggc cctcacctgc cgcctccgtt tcccggtgcc gggattccga   16740
ggaagaatgc accgtaggag gggcatggcc ggccacgggc tgacgggcgg catgcgtcgt   16800
gcgcaccacc ggcggcggcg cgcgtcgcac cgtcgcatgc gcggcggtat cctgcccctc   16860
cttattccac tgatcgccgc ggcgattggc gccgtgcccg gaattgcatc cgtggccttg   16920
caggcgcaga gacactgatt aaaaacaagt tgcatgtgga aaaatcaaaa taaaagtct    16980 ggactctcac gctcgcttgg tcctgtaact attttgtaga atggaagaca tcaactttgc   17040
gtctctggcc ccgcgacacg gctcgcgccc gttcatggga aactggcaag atatcggcac   17100
cagcaatatg agcggtggcg ccttcagctg gggctcgctg tggagcggca ttaaaaattt   17160
cggttccacc gttaagaact atggcagcaa ggcctggaac agcagcacag gccagatgct   17220
gagggataag ttgaaagagc aaaatttcca acaaaaggtg gtagatggcc tggcctctgg   17280
cattagcggg gtggtggacc tggccaacca ggcagtgcaa aataagatta acagtaagct   17340
tgatccccgc cctcccgtag aggagcctcc accggccgtg gagacagtgt ctccagaggg   17400
gcgtggcgaa aagcgtccgc gccccgacag ggaagaaact ctggtgacgc aaatagcga    17460 gcctccctcg tacgaggagg cactaaagca aggcctgccc accacccgtc ccatcgcgcc   17520
catggctacc ggagtgctgg gccagcacac acccgtaacg ctggacctgc ctccccgc    17580 cgacacccag cagaaacctg tgctgccagg cccgaccgcc gttgttgtaa cccgtcctag   17640
```

```
ccgcgcgtcc ctgcgccgcg ccgccagcgg tccgcgatcg ttgcggcccg tagccagtgg    17700
caactggcaa agcacactga acagcatcgt gggtctgggg gtgcaatccc tgaagcgccg    17760
acgatgcttc tgatagctaa cgtgtcgtat gtgtgtcatg tatgcgtcca tgtcgccgcc    17820
agaggagctg ctgagccgcc gcgcgcccgc tttccaagat ggctacccct tcgatgatgc    17880
cgcagtggtc ttacatgcac atctcgggcc aggacgcctc ggagtacctg agccccgggc    17940
tggtgcagtt tgcccgcgcc accgagacgt acttcagcct gaataacaag tttagaaacc    18000
ccacggtggc gcctacgcac gacgtgacca cagaccggtc ccagcgtttg acgctgcggt    18060
tcatccctgt ggaccgtgag gatactgcgt actcgtacaa ggcgcggttc accctagctg    18120
tgggtgataa ccgtgtgctg gacatggctt ccacgtactt tgacatccgc ggcgtgctgg    18180
acaggggccc tacttttaag ccctactctg gcactgccta acgccctg gctcccaagg       18240 gtgccccaaa tccttgcgaa tgggatgaag ctgctactgc tcttgaaata aacctagaag    18300
aagaggacga tgacaacgaa gacgaagtag acgagcaagc tgagcagcaa aaaactcacg    18360
tatttgggca ggcgccttat tctggtataa atattacaaa ggagggtatt caaataggtg    18420
tcgaaggtca aacacctaaa tatgccgata aacatttca acctgaacct caaataggag    18480
aatctcagtg gtacgaaaca gaaattaatc atgcagctgg gagagtccta aaaaagacta    18540
ccccaatgaa accatgttac ggttcatatg caaaacccac aaatgaaaat ggagggcaag    18600
gcattcttgt aaagcaacaa aatggaaagc tagaaagtca agtggaaatg caattttcct      18660
caactactga ggcagccgca ggcaatggtg ataacttgac tcctaaagtg gtattgtaca    18720
gtgaagatgt agatatagaa accccagaca ctcatatttc ttacatgccc actattaagg    18780
aaggtaactc acgagaacta atgggccaac aatctatgcc caacaggcct aattacattg    18840
cttttaggga caattttatt ggtctaatgt attacaacag cacgggtaat atgggtgttc    18900
tggcgggcca agcatcgcag ttgaatgctg ttgtagattt gcaagacaga aacacagagc    18960
tttcatacca gcttttgctt gattccattg gtgatagaac caggtacttt tctatgtgga    19020
atcaggctgt tgacagctat gatccagatg ttagaattat tgaaaatcat ggaactgaag    19080
atgaacttcc aaaattactgc tttccactgg gaggtgtgat taatacagag actcttacca    19140
aggtaaaacc taaaacaggt caggaaaatg gatgggaaaa agatgctaca gaattttcag    19200
ataaaaatga aataagagtt ggaaataatt ttgccatgga aatcaatcta aatgccaacc    19260
tgtggagaaa tttcctgtac tccaacatag cgctgtattt gcccgacaag ctaaagtaca    19320
gtccttccaa cgtaaaaatt tctgataacc caaacaccta cgactacatg aacaagcgag    19380
tggtggctcc cgggctagtg gactgctaca ttaaccttgg agcacgctgg tcccttgact    19440
atatggacaa cgtcaaccca tttaaccacc accgcaatgc tggcctgcgc taccgctcaa    19500
tgttgctggg caatggtcgc tatgtgccct tccacatcca ggtgcctcag aagttctttg    19560
ccattaaaaa cctccttctc ctgccgggct catacaccta cgagtggaac ttcaggaagg    19620
atgttaacat ggttctgcag agctccctag gaaatgacct aagggttgac ggagccagca    19680
ttaagtttga tagcatttgc ctttacgcca ccttcttccc catggcccac aacaccgcct    19740
ccacgcttga ggccatgctt agaaacgaca ccaacgacca gtcctttaac gactatctct    19800
ccgccgccaa catgctctac cctatacccg ccaacgctac caacgtgccc atatccatcc    19860
cctcccgcaa ctgggcggct ttccgcggct gggccttcac gcgccttaag actaaggaaa    19920
ccccatcact gggctcgggc tacgaccctt attacaccta ctctggctct ataccctacc    19980
tagatggaac cttttacctc aaccacacct ttaagaaggt ggccattacc tttgactctt    20040
```

```
ctgtcagctg gcctggcaat gaccgcctgc ttacccccaa cgagtttgaa attaagcgct    20100
cagttgacgg ggagggttac aacgttgccc agtgtaacat gaccaaagac tggttcctgg    20160
tacaaatgct agctaactat aacattggct accagggctt ctatatccca gagagctaca    20220
aggaccgcat gtactccttc tttagaaact tccagcccat gagccgtcag gtggtggatg    20280
atactaaata caaggactac caacaggtgg gcatcctaca ccaacacaac aactctggat    20340
ttgttggcta ccttgccccc accatgcgcg aaggacaggc ctaccctgct aacttcccct    20400
atccgcttat aggcaagacc gcagttgaca gcattaccca gaaaagtttt ctttgcgatc    20460 gcacccttig gcgcatccca ttctccagta actttatgtc catgggcgca ctcacagacc    20520
tgggccaaaa ccttctctac gccaactccg cccacgcgct agacatgact tttgaggtgg    20580
atcccatgga cgagcccacc cttctttatg ttttgtttga agtctttgac gtggtccgtg    20640
tgcaccagcc gcaccgcggc gtcatcgaaa ccgtgtacct gcgcacgccc ttctcggccg    20700
gcaacgccac aacataaaga agcaagcaac atcaacaaca gctgccgcca tgggctccag    20760
tgagcaggaa ctgaaagcca ttgtcaaaga tcttggttgt gggccatatt ttttgggcac    20820
ctatgacaag cgcttccag gctttgtttc tccacacaag ctcgcctgcg ccatagtcaa    20880
tacggccggt cgcgagactg ggggcgtaca ctggatggcc tttgcctgga cccgcactc    20940 aaaaacatgc tacctctttg agccctttgg cttttctgac cagcgactca agcaggttta    21000
ccagtttgag tacgagtcac tcctgcgccg tagcgccatt gcttcttccc ccgaccgctg    21060
tataacgctg gaaagtcca cccaaagcgt acagggggcc aactcggccg cctgtggact    21120
attctgctgc atgtttctcc acgcctttgc caactggccc caaactccca tggatcacaa    21180
ccccaccatg aaccttatta ccggggtacc caactccatg ctcaacagtc cccaggtaca    21240 gcccacccctg cgtcgcaacc aggaacagct ctacagcttc ctggagcgcc actcgcccta    21300
cttccgcagc cacagtgcgc agattaggag cgccacttct ttttgtcact tgaaaaacat    21360
gtaaaaataa tgtactagag acactttcaa taaaggcaaa tgcttttatt tgtacactct    21420
cgggtgatta tttacccccca cccttgccgt ctgcgccgtt taaaaatcaa aggggttctg    21480
ccgcgcatcg ctatgcgcca ctggcaggga cacgttgcga tactggtgtt tagtgctcca    21540
cttaaactca ggcacaacca tccgcggcag ctcggtgaag ttttcactcc acaggctgcg    21600
caccatcacc aacgcgttta gcaggtcggg cgccgatatc ttgaagtcgc agttggggcc    21660
tccgccctgc gcgcgcgagt tgcgatacac agggttgcag cactggaaca ctatcagcgc    21720
cgggtggtgc acgctggcca gcacgctctt gtcggagatc agatccgcgt ccaggtcctc    21780
cgcgttgctc agggcgaacg gagtcaactt tggtagctgc cttcccaaaa agggcgcgtg    21840
cccaggcttt gagttgcact cgcaccgtag tggcatcaaa aggtgaccgt gcccggtctg    21900
ggcgttagga tacagcgcct gcataaaagc cttgatctgc ttaaaagcca cctgagcctt    21960
tgcgccttca gagaagaaca tgccgcaaga cttgccggaa aactgattgg ccggacaggc    22020
cgcgtcgtgc acgcagcacc ttgcgtcggt gttggagatc tgcaccacat tcggcccca    22080 ccggttcttc acgatcttgg ccttgctaga ctgctcctc agcgcgcgct gcccgttttc    22140
gctcgtcaca tccatttcaa tcacgtgctc cttatttatc ataatgcttc cgtgtagaca    22200
cttaagctcg ccttcgatct cagcgcagcg gtgcagccac aacgcgcagc ccgtgggctc    22260
gtgatgcttg taggtcacct ctgcaaacga ctgcaggtac gcctgcagga atcgccccat    22320
catcgtcaca aaggtcttgt tgctggtgaa ggtcagctgc aacccgcggt gctcctcgtt    22380
```

```
cagccaggtc ttgcatacgg ccgccagagc ttccacttgg tcaggcagta gtttgaagtt   22440
cgcctttaga tcgttatcca cgtggtactt gtccatcagc gcgcgcgcag cctccatgcc   22500
cttctcccac gcagacacga tcggcacact cagcgggttc atcaccgtaa tttcactttc   22560
cgcttcgctg ggctcttcct cttcctcttg cgtccgcata ccacgcgcca ctgggtcgtc   22620
ttcattcagc cgccgcactg tgcgcttacc tcctttgcca tgcttgatta gcaccggtgg   22680
gttgctgaaa cccaccattt gtagcgccac atcttctctt tcttcctcgc tgtccacgat   22740
tacctctggt gatggcgggc gctcgggctt gggagaaggg cgcttctttt tcttcttggg   22800
cgcaatggcc aaatccgccg ccgaggtcga tggccgcggg ctgggtgtgc gcggcaccag   22860
cgcgtcttgt gatgagtctt cctcgtcctc ggactcgata cgccgcctca tccgcttttt   22920
tgggggcgcc cggggaggcg gcggcgacgg ggacggggac gacacgtcct ccatggttgg   22980
gggacgtcgc gccgcaccgc gtccgcgctc ggggtggtt tcgcgctgct cctcttcccg   23040
actggccatt tccttctcct ataggcagaa aaagatcatg gagtcagtcg agaagaagga   23100
cagcctaacc gcccctctg agttcgccac caccgcctcc accgatgccg caacgcgcc   23160 taccaccttc cccgtcgagg cacccccgct tgaggaggag gaagtgatta tcgagcagga   23220
cccaggtttt gtaagcgaag acgacgagga ccgctcagta ccaacagagg ataaaaagca   23280
agaccaggac aacgcagagg caaacgagga acaagtcggg cgggggacg aaaggcatgg   23340 cgactaccta gatgtgggag acgacgtgct gttgaagcat ctgcagcgcc agtgcgccat   23400
tatctgcgac gcgttgcaag agcgcagcga tgtgcccctc gccatagcgg atgtcagcct   23460
tgcctacgaa cgccacctat tctcaccgcg cgtaccccc aaacgccaag aaaacggcac   23520
atgcgagccc aacccgcgcc tcaacttcta ccccgtattt gccgtgccag aggtgcttgc   23580
cacctatcac atcttttttcc aaaactgcaa gatacccta tcctgccgtg caaccgcag   23640 ccgagcggac aagcagctgg ccttgcggca gggcgctgtc atacctgata tcgcctcgct   23700
caacgaagtg ccaaaaatct ttgagggtct tggacgcgac gagaagcgcg cggcaaacgc   23760
tctgcaacag gaaaacagcg aaaatgaaag tcactctgga gtgttggtgg aactcgaggg   23820
tgacaacgcg cgcctagccg tactaaaacg cagcatcgag gtcacccact ttgcctaccc   23880
ggcacttaac ctaccccccca aggtcatgag cacagtcatg agtgagctga tcgtgcgccg   23940
tgcgcagccc ctggagaggg atgcaaattt gcaagaacaa acagaggagg cctacccgc   24000 agttggcgac gagcagctag cgcgctggct tcaaacgcgc gagcctgccg acttggagga   24060
gcgacgcaaa ctaatgatgg ccgcagtgct cgttaccgtg gagcttgagt gcatgcagcg   24120
gttctttgct gacccggaga tgcagcgcaa gctagaggaa acattgcact acacctttcg   24180
acagggctac gtacgccagg cctgcaagat ctccaacgtg gagctctgca acctggtctc   24240
ctaccttgga attttgcacg aaaaccgcct tgggcaaaac gtgcttcatt ccacgctcaa   24300
gggcgaggcg cgccgcgact acgtccgcga ctgcgtttac ttatttctat gctacacctg   24360
gcagacggcc atgggcgttt ggcagcagtg cttggaggag tgcaacctca aggagctgca   24420
gaaactgcta aagcaaaact tgaaggacct atggacggcc ttcaacgagc gctccgtggc   24480
cgcgcacctg gcggacatca ttttccccga acgcctgctt aaaacccctgc aacagggtct   24540 gccagacttc accagtcaaa gcatgttgca gaactttagg aactttatcc tagagcgctc   24600
aggaatcttg cccgccacct gctgtgcact tcctagcgac tttgtgccca ttaagtaccg   24660
cgaatgccct ccgccgcttt ggggccactg ctaccttctg cagctagcca actaccttgc   24720
ctaccactct gacataatgg aagacgtgag cggtgacggt ctactggagt gtcactgtcg   24780
```

```
ctgcaaccta tgcaccccgc accgctccct ggtttgcaat tcgcagctgc ttaacgaaag    24840
tcaaattatc ggtacctttg agctgcaggg tccctcgcct gacgaaaagt ccgcggctcc    24900
ggggttgaaa ctcactccgg ggctgtggac gtcggcttac cttcgcaaat ttgtacctga    24960
ggactaccac gcccacgaga ttaggttcta cgaagaccaa tcccgcccgc ctaatgcgga    25020
gcttaccgcc tgcgtcatta cccagggcca cattcttggc caattgcaag ccatcaacaa    25080
agcccgccaa gagtttctgc tacgaaaggg acgggggggtt tacttggacc cccagtccgg    25140
cgaggagctc aacccaatcc ccccgccgcc gcagccctat cagcagcagc cgcgggccct    25200
tgcttcccag gatggcaccc aaaaagaagc tgcagctgcc gccgccaccc acggacgagg    25260
aggaatactg ggacagtcag gcagaggagg tttttggacga ggaggaggag acatgatgg    25320 aagactggga gagcctagac gaggaagctt ccgaggtcga agaggtgtca gacgaaacac    25380
cgtcaccctc ggtcgcattc ccctcgccgg cgccccagaa atcggcaacc ggttccagca    25440
tggctacaac ctccgctcct caggcgccgc cggcactgcc cgttcgccga cccaaccgta    25500
gatgggacac cactggaacc agggccggta agtccaagca gccgccgccg ttagcccaag    25560
agcaacaaca gcgccaaggc taccgctcat ggcgcgggca caagaacgcc atagttgctt    25620
gcttgcaaga ctgtggggggc aacatctcct tcgcccgccg ctttcttctc taccatcacg    25680
gcgtggcctt cccccgtaac atcctgcatt actaccgtca tctctacagc ccatactgca    25740
ccggcggcag cggcagcaac agcagcggcc acacagaagc aaaggcgacc ggatagcaag    25800
actctgacaa agcccaagaa atccacagcg gcggcagcag caggaggagg agcgctgcgt    25860
ctggcgccca acgaacccgt atcgacccgc gagcttagaa acaggatttt tcccactctg    25920
tatgctatat ttcaacagag caggggccaa gaacaagagc tgaaaataaa aaacaggtct    25980
ctgcgatccc tcacccgcag ctgcctgtat cacaaaagcg aagatcagct tcggcgcacg    26040
ctggaagacg cggaggctct cttcagtaaa tactgcgcgc tgactcttaa ggactagttt    26100
cgcgcccttt ctcaaattta agcgcgaaaa ctacgtcatc tccagcggcc acacccggcg    26160
ccagcacctg ttgtcagcgc cattatgagc aaggaaattc ccacgccctg catgtggagt    26220
taccagccac aaatgggact tgcggctgga gctgcccaag actactcaac ccgaataaac    26280
tacatgagcg cgggaccccca catgatatcc cgggtcaacg gaatacgcgc ccaccgaaac    26340
cgaattctcc tggaacaggc ggctattacc accacacctc gtaataacct taatccccgt    26400
agttggcccg ctgccctggt gtaccaggaa agtcccgctc ccaccactgt ggtacttccc    26460
agagacgccc aggccgaagt tcagatgact aactcagggg cgcagcttgc gggcggcttt    26520
cgtcacaggg tgcggtcgcc cgggcagggt ataactcacc tgacaatcag agggcgaggt    26580
attcagctca acgacgagtc ggtgagctcc tcgcttggtc tccgtccgga cgggacattt    26640
cagatcggcg gcgccggccg ctcttcattc acgcctcgtc aggcaatcct aactctgcag    26700
acctcgtcct ctgagccgcg ctctggaggc attggaactc tgcaatttat tgaggagttt    26760
gtgccatcgg tctactttaa cccccttctcg ggacctcccg gccactatcc ggatcaattt    26820
attcctaact ttgacgcggt aaaggactcg gcggacggct acgactgaat gttaagtgga    26880
gaggcagagc aactgcgcct gaaacacctg gtccactgtc gccgccacaa gtgctttgcc    26940
cgcgactccg gtgagttttg ctactttgaa ttgcccgagg atcatatcga gggcccggcg    27000
cacggcgtcc ggcttaccgc ccagggagag cttgcccgta gcctgattcg ggagtttacc    27060
cagcgccccc tgctagttga gcgggacagg ggaccctgtg ttctcactgt gatttgcaac    27120
```

```
tgtcctaacc ctggattaca tcaagatcct ctagttaatg tcaggtcgcc taagtcgatt    27180
aactagagta cccgggatc ttattcccctt taactaataa aaaaaaataa taaagcatca     27240
cttacttaaa atcagttagc aaatttctgt ccagtttatt cagcagcacc tccttgccct    27300
cctcccagct ctggtattgc agcttcctcc tggctgcaaa ctttctccac aatctaaatg    27360
gaatgtcagt ttcctcctgt tcctgtccat ccgcacccac tatcttcatg ttgttgcaga    27420
tgaagcgcgc aagaccgtct gaagatacct caacccccgt gtatccatat gacacggaaa    27480
ccggtcctcc aactgtgcct tttcttactc ctcccctttgt atcccccaat gggtttcaag    27540
agagtccccc tggggtactc tctttgcgcc tatccgaacc tctagttacc tccaatggca    27600
tgcttgcgct caaaatgggc aacggcctct ctctggacga ggccggcaac cttacctccc    27660
aaaatgtaac cactgtgagc ccacctctca aaaaaccaa gtcaaacata aacctggaaa      27720
tatctgcacc cctcacagtt acctcagaag ccctaactgt ggctgccgcc gcacctctaa    27780
tggtcgcggg caacacactc accatgcaat cacaggcccc gctaaccgtg cacgactcca    27840
aacttagcat tgccacccaa ggaccccctca cagtgtcaga aggaaagcta gccctgcaaa    27900
catcaggccc cctcaccacc accgatagca gtacccttac tatcactgcc tcacccccctc   27960 taactactgc cactggtagc ttgggcattg acttgaaaga gcccatttat acacaaaatg    28020
gaaaactagg actaaagtac ggggctcctt tgcatgtaac agacgaccta aacactttga    28080
ccgtagcaac tggtccaggt gtgactatta ataatacttc cttgcaaact aaagttactg    28140
gagccttggg ttttgattca caaggcaata tgcaacttaa tgtagcagga ggactaagga    28200
ttgattctca aaacagacgc cttatacttg atgttagtta tccgtttgat gctcaaaacc    28260
aactaaatct aagactagga cagggccctc tttttataaa ctcagcccac aacttggata    28320
ttaactacaa caaaggcctt tacttgttta cagcttcaaa caattccaaa aagcttgagg    28380
ttaacctaag cactgccaag gggttgatgt tgacgctac agccatagcc attaatgcag    28440
gagatgggct tgaatttggt tcacctaatg caccaaacac aaatccctc aaaacaaaaa     28500 ttggccatgg cctagaattt gattcaaaca aggctatggt tcctaaacta ggaactggcc    28560
ttagttttga cagcacaggt gccattacag taggaaacaa aaataatgat aagctaactt    28620
tgtggaccac accagctcca tctcctaact gtagactaaa tgcagagaaa gatgctaaac    28680
tcactttggt cttaacaaaa tgtggcagtc aaatacttgc tacagtttca gttttggctg    28740
ttaaaggcag tttggctcca atatctggaa cagttcaaag tgctcatctt attataagat    28800
ttgacgaaaa tggagtgcta ctaaacaatt ccttcctgga cccagaatat tggaacttta    28860
gaaatggaga tcttactgaa ggcacagcct atacaaacgc tgttggattt atgcctaacc    28920
tatcagctta tccaaaatct cacggtaaaa ctgccaaaag taacattgtc agtcaagttt    28980
acttaaacgg agacaaaact aaacctgtaa cactaaccat tacactaaac ggtacacagg    29040
aaacaggaga cacaactcca agtgcatact ctatgtcatt tcatgggac tggtctggcc     29100 acaactacat taatgaaata tttgccacat cctcttacac tttttcatac attgcccaag    29160
aataaagaat cgtttgtgtt atgtttcaac gtgtttattt tcaattgca gaaaatttca    29220 agtcattttt cattcagtag tatagcccca ccaccacata gcttatacag atcaccgtac    29280
cttaatcaaa ctcacagaac cctagtattc aacctgccac ctccctccca acacacagag    29340
tacacagtcc tttctccccg gctggcctta aaaagcatca tatcatgggt aacagacata    29400
ttcttaggtg ttatattcca cacgttttcc tgtcgagcca aacgctcatc agtgatatta    29460
ataaactccc cgggcagctc acttaagttc atgtcgctgt ccagctgctg agccacaggc    29520
```

```
tgctgtccaa cttgcggttg cttaacgggc ggcgaaggag aagtccacgc ctacatgggg   29580
gtagagtcat aatcgtgcat caggataggg cggtggtgct gcagcagcgc gcgaataaac   29640
tgctgccgcc gccgctccgt cctgcaggaa tacaacatgg cagtggtctc ctcagcgatg   29700
attcgcaccg cccgcagcat aaggcgcctt gtcctccggg cacagcagcg caccctgatc   29760
tcacttaaat cagcacagta actgcagcac agcaccacaa tattgttcaa aatcccacag   29820
tgcaaggcgc tgtatccaaa gctcatggcg gggaccacag aacccacgtg gccatcatac   29880
cacaagcgca ggtagattaa gtggcgaccc ctcataaaca cgctggacat aaacattacc   29940
tcttttggca tgttgtaatt caccacctcc cggtaccata taaacctctg attaaacatg   30000
gcgccatcca ccaccatcct aaaccagctg gccaaaacct gcccgccggc tatacactgc   30060
agggaaccgg gactgaaaca atgacagtgg agagcccagg actcgtaacc atggatcatc   30120
atgctcgtca tgatatcaat gttggcacaa cacaggcaca cgtgcataca cttcctcagg   30180
attacaagct cctcccgcgt tagaaccata tcccagggaa caacccattc ctgaatcagc   30240
gtaaatccca cactgcaggg aagacctcgc acgtaactca cgttgtgcat tgtcaaagtg   30300
ttacattcgg gcagcagcgg atgatcctcc agtatggtag cgcgggtttc tgtctcaaaa   30360
ggaggtagac gatccctact gtacggagtg cgccgagaca accgagatcg tgttggtcgt   30420
agtgtcatgc caaatggaac gccggacgta gtcatatttc ctgaagcaaa accaggtgcg   30480
ggcgtgacaa acagatctgc gtctccggtc tcgccgctta gatcgctctg tgtagtagtt   30540
gtagtatatc cactctctca aagcatccag gcgcccctg gcttcgggtt ctatgtaaac   30600
tccttcatgc gccgctgccc tgataacatc caccaccgca gaataagcca cacccagcca   30660
acctacacat tcgttctgcg agtcacacac gggaggagcg ggaagagctg gaagaaccat   30720 gtttttttt ttattccaaa agattatcca aaacctcaaa atgaagatct attaagtgaa   30780
cgcgctcccc tccggtggcg tggtcaaact ctacagccaa agaacagata atggcatttg   30840
taagatgttg cacaatggct tccaaaaggc aaacggccct cacgtccaag tggacgtaaa   30900
ggctaaaccc ttcagggtga atctcctcta taaacattcc agcaccttca accatgccca   30960
aataattctc atctcgccac cttctcaata tatctctaag caaatcccga atattaagtc   31020
cggccattgt aaaaatctgc tccagagcgc cctccacctt cagcctcaag cagcgaatca   31080
tgattgcaaa aattcaggtt cctcacagac ctgtataaga ttcaaaagcg gaacattaac   31140
aaaaataccg cgatcccgta ggtcccttcg cagggccagc tgaacataat cgtgcaggtc   31200
tgcacggacc agcgcggcca cttccccgcc aggaaccatg acaaaagaac ccacactgat   31260
tatgacacgc atactcggag ctatgctaac cagcgtagcc ccgatgtaag cttgttgcat   31320
gggcggcgat ataaaatgca aggtgctgct caaaaaatca ggcaaagcct cgcgcaaaaa   31380
agaaagcaca tcgtagtcat gctcatgcag ataaaggcag gtaagctccg gaaccaccac   31440
agaaaaagac accatttttc tctcaaacat gtctgcgggt ttctgcataa acacaaaata   31500
aaataacaaa aaaacattta aacattagaa gcctgtctta caacaggaaa acaacccctt   31560
ataagcataa gacggactac ggccatgccg gcgtgaccgt aaaaaaactg gtcaccgtga   31620
ttaaaaagca ccaccgacag ctcctcggtc atgtccggag tcataatgta agactcggta   31680
aacacatcag gttgattcac atcggtcagt gctaaaaagc gaccgaaata gcccggggga   31740
atacataccc gcaggcgtag agacaacatt acagccccca taggaggtat aacaaaatta   31800
ataggagaga aaaacacata aacacctgaa aaaccctcct gcctaggcaa aatagcaccc   31860
```

| | |
|---|---:|
| tcccgctcca gaacaacata cagcgcttcc acagcggcag ccataacagt cagccttacc | 31920 |
| agtaaaaaag aaaacctatt aaaaaaacac cactcgacac ggcaccagct caatcagtca | 31980 |
| cagtgtaaaa aagggccaag tgcagagcga gtatatatag gactaaaaaa tgacgtaacg | 32040 |
| gttaaagtcc acaaaaaaca cccagaaaac cgcacgcgaa cctacgccca gaaacgaaag | 32100 |
| ccaaaaaacc cacaacttcc tcaaatcgtc acttccgttt tcccacgtta cgtcacttcc | 32160 |
| cattttaaga aaactacaat tcccaacaca tacaagttac tccgccctaa aacctacgtc | 32220 |
| acccgccccg ttcccacgcc ccgcgccacg tcacaaactc cacccccctca ttatcatatt | 32280 |
| ggcttcaatc caaaataagg tatattattg atgat | 32315 |

<210> SEQ ID NO 4
<211> LENGTH: 18935
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

| | |
|---|---:|
| cggacacaca aaaagaaaga aggtttttg atctttattg tgtgcgaata actatgagga | 60 |
| agattaataa ttttcctctc attgacactt acattaagat taagattctc attgatctgt | 120 |
| tacttactct gaggataata attggtgttc agaagtaccc cattccccag tgggggcaaa | 180 |
| gacagtccaa aagactcaac ttgtcctatt caactaatct gttttgtctc agtagttcac | 240 |
| atattgatca tacccaggag ttggacctaa ttccaaagct tagagtggga cctagtgtat | 300 |
| cctcggggct gtaatataat cagccattta acacataaca agccctactg ttttcttgtt | 360 |
| ttgccgtgca tttagaataa gagacaactt aaacctccga ttcggcaaca cagggaataa | 420 |
| tctcaccaga cccggcagtg tcttcaggct tcatagcccc aagatggaga gtcgggccca | 480 |
| caaagcatgg atgacgcaca ccgcatcagg tttcgaaaca gattaccata agattttaac | 540 |
| agcaggattg tcagtccaac aaggcattgt gagacaacgg gtcattcaag tccaccaggt | 600 |
| tacaaaccta gaagaaatat gccaattgat cattcaagcc tttgaagctg gtgttgattt | 660 |
| tcaagagagt gcagacagtt tcttgctgat gctatgttta catcatgctt atcagggtga | 720 |
| ctacaagcaa ttcttggaaa gcaatgcagt caagtacctt gagggtcatg gctttcgctt | 780 |
| tgaggtcagg aaaaaggaag gagtcaagcg actcgaagaa ttgcttcctg ctgcatccag | 840 |
| tggcaagagc atcaggagaa cactggctgc aatgcctgaa gaggagacaa cagaagcaaa | 900 |
| tgccggacag ttcctctctt ttgctagctt atttcttcct aagctagttg tcggagaaaa | 960 |
| agcctgtcta gaaaaggtgc agcggcaaat tcaagttcat tctgagcagg gattgatcca | 1020 |
| ataccccaca gcctggcagt cagttggaca catgatggtc attttcagac tgatgagaac | 1080 |
| aaattttcta attaagttcc tccttataca tcaagggatg catatggtag caggacacga | 1140 |
| tgctaacgat gctgtcatcg caaactctgt agctcaagca cgttttttcag gattattgat | 1200 |
| cgttaaaaca gtgctagatc acatccttca gaaaacagag cacggagtgc gtcttcatcc | 1260 |
| tttggcaaga actgctaagg tcaagaacga agtaaattcc tttaaggctg cccttagctc | 1320 |
| gctagcacaa catggagagt atgctccttt tgctcgcttg ctgaatcttt ctggagtcaa | 1380 |
| caatctcgag cacggactgt ttcctcagct ttctgcaatt gccctaggtg tcgcaacggc | 1440 |
| acacggcagt accctggcag gagtaaatgt gggggaacag tatcagcaac tacgagaagc | 1500 |
| agccactgag gcagaaaaac aattgcagaa atacgctgaa tctcgcgagc ttgaccatct | 1560 |

```
aggtctcgat gatcaagaga agaagatctt gaaagacttc catcagaaga aaaatgaaat   1620
cagcttccag cagacaacag ccatggtcac actacggaag gaaaggctag ccaagctcac   1680
tgaggcaatc acctccacat cccttctcaa gacaggaaaa cagtatgatg atgacaacga   1740
tatccccttt cctgggccca tcaatgataa cgaaaactca gaacagcaag acgatgatcc   1800
aacagattct caggacacta ccatccctga tatcattgtt gacccggatg atggcagata   1860
caacaattat ggagactatc ctagtgagac ggcgaatgcc cctgaagacc ttgttctttt   1920
tgaccttgaa gatggtgacg aggatgatca ccgaccgtca agttcatcag agaacaacaa   1980
caaacacagt cttacaggaa ctgacagtaa caaaacaagt aactggaatc gaaacccgac   2040
taatatgcca aagaaagact ccacacaaaa caatgacaat cctgcacagc gggctcaaga   2100
atacgccagg gataacatcc aggatacacc aacaccccat cgagctctaa ctcccatcag   2160
cgaagaaacc ggctccaatg gtcacaatga agatgacatt gatagcatcc ctcctttgga   2220
atcagacgaa gaaaacaaca ctgagacaac cattaccacc acaaaaaata ccactgctcc   2280
accagcacct gtttatcgga gtaattcaga aaaggagccc ctcccgcaag aaaaatccca   2340
gaagcaacca aaccaagtga gtggtagtga gaataccgac aataaacctc actcagagca   2400
atcagtggaa gaaatgtatc gacacatcct ccaaacacaa ggaccatttg atgccatcct   2460
atactattac atgatgacgg aggagccgat tgtctttagc actagtgatg ggaaagaata   2520
cgtataccct gattctcttg aaggggagca tccaccgtgg ctcagtgaaa aagaggcctt   2580
gaatgaggac aataggttta tcacaatgga tgatcaacaa ttctactggc ctgtaatgaa   2640
tcacaggaac aaattcatgg ctatccttca gcaccacaga taatttcttc ataatgacag   2700
atcattgtaa ggttattacc accatccctg caacaaagca tgaaaaccac actcaacaac   2760
gccctaccac aggatacctt ggagaccata caccaagatc agcagctgtg caaccacccc   2820
catgcgaatc caccaccaca accaccaaac aataatccca agaccaaacc gcacacatcc   2880
agatcaaccc aaaccctcaa acaccacccc actccgcgat cccagaccaa actccgcccc   2940
agacaagcac cccacccatc ccagaaaccg cacggccgag aatcgatccc cagcattcaa   3000
aatgcgttat taagaaaaaa catatgatga agattaaaac cttcatcaac attgcacaga   3060
ctttgatcct taggagtttta ttctagctat ctacaaaacg ggtccaaaac ggaatgattt   3120
ccactagggc tgcagcaatc aatgatcctt cattaccaat cagaaaccag tgtacacgtg   3180
gccctgaact atcaggatgg atctccgaac aattaatgac aggcaaaatt ccggtacatg   3240
aaatcttcaa cgacactgag ccccacataa gctcagggtc cgactgcctt cccagaccca   3300
aaaacacggc cccccggact cgcaacaccc agacacagac cgatccggtt tgcaatcaca   3360
attttgaaga cgttacacaa gcactaacat cattaaccaa tgtcatacaa aaacaggctc   3420
ttaacttaga gtctctcgaa caacgcatca tagatctaga gaatggctta aagccaatgt   3480
atgacatggc taaagtcatt tctgcattga atagatcttg tgctgagatg gtagcaaaat   3540
atgatctcct ggtgatgaca actggccgcg caaccgccac cgccgctgca actgaggctt   3600
attgggagga acatggacaa ccaccacctg gaccatcact ttatgaagag agtgcgatta   3660
gaggcaagat taacaagcaa gaggataaag tacctaagga agttcaagaa gcttttcgta   3720
atctggacag taccagctca ctaacagaag agaactttgg caagccagat atatctgcaa   3780
aggacctacg agacatcatg tatgaccacc taccaggctt cggtacggct tttcaccaac   3840
tggtccaggt aatttgcaag ctaggaaaag acaattctgc attggacatt attcatgctg   3900
agttccaagc cagccttgct gaaggtgatt ctccccaatg tgccctgatc caaataacaa   3960
```

```
aacggatccc catcttccag gatgccactc cgcccacaat tcacatccgc tctcgtggtg    4020
acatcccacg tgcctgccaa aaaagtctcc gtccagttcc tccatcacca aaaatagaca    4080
gaggttgggt ttgcattttc caattgcagg acgggaagac acttgggctc aagatatagg    4140 gtccccagt caaagacacg tgcggtccca tcctccctca ccttcagaca tcaacgcatg     4200
gcagtcccaa acaccggtga gggaggcgcc cggcgacaac acatgatgat aggctgatct    4260
tcgggataag agacatgaaa aaccaaaaag ccgtttacat ccagatccaa gatcaagagt    4320
ggcttggaaa taaggggcac ttgttctttg tctcaaagga cttacaaaaa caagggtgat    4380
gaagattaag aaaaagcctc cttcagttgc aaggagctaa ttcttaaaac ttcatctaga    4440
ctaaggataa atcgattcca atcacgatga ggagaatcat cctacccacg gcaccacctg    4500
aatacatgga ggctgtttac ccaatgagaa caatgaattc tggtgcagac aacactgcca    4560
gtggccctaa ttacacaaca actggtgtga tgacaaatga tactccctct aattcactcc    4620
gaccagttgc agatgataat attgatcatc cgagccacac gcctaacagt gttgcctctg    4680
catttatatt ggaagctatg gtgaatgtaa tatctggccc gaaagtgctg atgaagcaaa    4740
tcccaatctg gcttcctctg ggtgtctctg accagaagac atatagcttt gattcaacca    4800
ctgctgccat tatgctagca tcatatacca tcactcattt tggcaaaacc tcaaatcccc    4860
ttgtgagaat caaccgactt ggtcctggca tacctgatca cccactacga ctcctaagaa    4920
taggaaatca agccttccta caagagtttg tgctacctcc tgtacaactg ccacaatact    4980
tcacttttga tctgacagcg ctgaagctga tcacccagcc actccagcg gcaacctgga     5040 cagatgaaac tccagctgtg tcaactggca cgctccgccc agggatctca ttccatccca    5100
aattaaggcc tatcctgcta ccaggaagag ctggaaagaa gggctccaac tccgatctaa    5160
catctcctga caaaatccag gctataatga atttcctaca agacctcaaa attgtaccaa    5220
tcgatccaac caagaatatc atgggtattg aagtgccaga actcctggtt cacaggctga    5280
ctgggaagaa gacaactacc aagaatggtc aaccaatcat tccaattctg ctaccaaagt    5340
acattggtct tgatcctcta tctcaaggtg atctcacaat ggtgatcact caggactgtg    5400
attcctgcca ctccccggcc agtcttcccc cagtcaatga aaaatgacca tgagactcaa    5460
catcacactg ccagagcacc tcaccgcaag tctatacaac aatcaacccc ggcatctaca    5520
acctgcaaaa accagcccat ctgatactcc tggcatcggg ggcaagacaa ggcagccaag    5580
cagcagcccc cgagccgagc ccaaacccat tacacccgag cccaacaccc atccagcaac    5640
ccacaaccgt caaacgcaca gatggacaag caaagaacat caagccagga gcaacacaga    5700
ccccaagtct aagctgatca acccctcccg caatcccacc aacgccagca aaaatccccc    5760
aactcgatac caaccccaag caaatcagct caaaccgtct atctctcccc gcttcactcc    5820
acaccccaga ttcagcaaac gatcaacgca cttcttatgc cacagcttat attaagaaaa    5880
agaacttgat gaagattaag gcaaccagtg gtgctatctt catctctttg atttgagtct    5940
taagtgaata cacaggttct aatactgttc ttctgtccaa cggtataatt cagccaggcc    6000
taagacagta gctaatcaca gtcatcatgg gagcgtcagg gattctgcaa ttgccccgtg    6060
agcgcttcag gaaaacatct ttctttgttt gggtaataat cctattccat aaagtctttt    6120
caatcccgtt gggggttgta cacaacaata ccctacaagt gagtgatatt gacaagtttg    6180
tgtgccgaga caaactctct tcaactagcc aattgaagtc agtcggggttg aacttggagg    6240 gcaatggagt agcaactgat gtaccaacgg caaccaaaag atggggtttt cgagctggtg    6300
```

```
ttccaccaaa ggtggtaaat tgcgaagctg gagaatgggc tgagaactgt tataacctgg      6360
ctataaagaa agttgatggt agtgagtgcc taccagaagc ccctgaggga gtgagggatt      6420
ttccccgttg ccgctatgta cacaaagtct caggaactgg accatgccca ggaggactcg      6480
cctttcacaa agaaggagcc ttcttcctgt atgaccgact cgcatcaaca atcatttatc      6540
ggggtacaac ctttgccgaa ggagttattg catttctgat cttgcctaag gcgcgaaagg      6600
attttttcca gtctcctcca ttgcatgagc ctgccaacat gacccacgga t ccctccagtt    6660 actatcacac gacaacaata aactacgtgg ttgataattt tggaaccaac accacagagt      6720
ttctgttcca agtcgatcat ttgacgtatg tgcagctcga ggcaagattc acaccacaat      6780
tccttgtcct cctaaatgaa accatctact ctgataaccg cagaagtaac acaacaggaa      6840
aactaatctg gaaataaat cccactgttg ataccagcat gggtgagtgg gctttctggg       6900
aaaataaaaa aacttcacaa aaacccttc aagtgaagag ttgtctttcg tacctgtacc       6960
agaaacccag aaccaggtcc ttgacacgac agcgacggtc tctcctccca tctccgccca     7020
caaccacgca gccgaagacc acaaagaatt ggtttcagag gattccactc cagtggttca     7080
gatgcaaaac atcaagggaa aggacacaat gccaaccaca gtgacgggtg taccaacaac     7140
cacaccctct ccatttccaa tcaatgctcg caacactgat cataccaaat catttatcgg     7200
cctggagggg ccccaagaag accacagcac cacacagcct gccaagacca ccagccaacc     7260
aaccaacagc acagaatcga cgacactaaa cccaacatca gagccctcca gtagaggcac     7320
gggaccatcc agccccacgg tccccaacac cacagaaagc cacgccgaac ttggcaagac     7380
aaccccaacc acactcccag aacagcacac tgccgccagt gccattccaa gagccgtgca     7440
ccccgacgaa ctcagtggac ctggcttcct gacgaacaca atacggggg ttacaaatct      7500 cctgacagga tccagaagaa agcgaaggga tgtcactccc aatacacaac ccaaatgcaa     7560
cccaaacctg cactattgga cagccttgga tgagggtgct gccataggtt tagcctggat     7620
accatacttc gggccagcag ctgagggaat ttacactgaa ggcataatgg agaatcaaaa     7680
tggattgatc tgtggattga ggcagctggc caacgaaacg acacaagctc ttcaattgtt     7740
cttaagggca actactgagt tgcgtacatt ctctatacta aatcggaaag caatagactt     7800
cttgctccaa agatggggag gaacatgtca cattctaggg cctgattgtt gcattgaacc     7860
ccaagattgg accaaaaata tcactgataa aattgatcaa ataatccatg actttgtcga     7920
taataatctt ccaaatcaga atgatggcag caactggtgg actggatgga acaatgggt    7980 tcctgctgga ataggaatca caggagtaat cattgctatt attgctttgc tgtgcatttg    8040
caaattcatg ctttgaacta atatagcatc atactttcta atattcccc aatatgaatt     8100 tttgttttcg atttttattta atgatatatc ctctgtatac ctcactaatg tactcgagca    8160
taatttccct gatagacttg attgtatttg atgattaagg acctcacaaa attcctgggg    8220
attgaaaaga actggataac tcaataaatt ttatgctagg accacaaata cacttgatga    8280
agattaagaa aaagataatc ttatgattat cattgatctt catctatacc ttaaatactc    8340
tattcaagga gagtatgaca aaaccaagta gtattggata aacttgtcct gcattcaaat    8400
ctgaagacat acggcttatc tattcactat tgtattagaa aatctaggga atatcatttg    8460
aaactaatta gtgactaaaa cacacaactc aagtcggcca gaatggaagt tgttcatgaa    8520
agaggtcgct ccaggatctc ccgacaaaac acagggatg gacctagtca tttagtacgg     8580
gcgagatcat cctctcgagc tagttatcga agtgaatacc atacaccaag gagtgcctcg    8640
cagatccgtg tccccactgt cttcatcgg aaaaagacag atttattgac agttccacca    8700
```

```
gcacctaaag atgtatgccc gactttaaag aaagggtttc tatgtgacag caatttctgt   8760
aaaaaggatc accaacttga aagcttaaca gatagagagt tactcttgct gattgcacgc   8820
aagacatgtg gatccacgga acaacaacta agcatagttg ctccaaaaga ttcacgtctg   8880
gctaatccta ttgctgagga tttccaacaa aaagatgggc ctaaggtaac actgtcgatg   8940
cttatagaga cagcagagta ttggtccaaa caggacatta agaacatcga tgattcaaga   9000
ttaagagctt tattgaccct ttgtgctgtt atgacgcgca aattttcaaa atctcaactt   9060
agcttgctat gtgaaagcca cttacggcga aaggacttg gtcaagacca atcagagtca    9120
gttctggagg tatatcaacg cttacacagc gataaaggtg ggaatttcga ggcagcacta   9180
tggcagcagt gggatcggca atcattgata atgttcataa cagcattttt aaatattgca   9240
ttacaattac catgtgagag ttcatctgtt gttatttcag gtttgagaat gctgataccc   9300
cagtcggaag ccactgaggt tgtaaccccc tccgaaacct gcacatggtc agaaggagga   9360
agttcccatt gaagcccaa atcacaaggc gagctaaaaa atccctttg aacatgcata    9420 acatcacata caatttcaaa ggcattggaa taaatggtga tttcaggaag attagtgttt   9480
gccctcaaaa tcagatccga gcaataatca tctactctac agccagttaa tttctaatat   9540
aaaggttaaa aaatgctgc aggccagcta ttgttccaca ggtcccaatt cttcttgtta    9600
aattgtagga gctagcacaa gtgatgcaat taaatgatac tagtatatac aatgccacca   9660
acttaattct aagattttgt atatctcgga aattcaaaat taaatgctac gttattgatt   9720
caattaagaa aaagacaatg gaccatcaaa attagttcaa tacctgaact aatgcactta   9780
tagaaacagg agaaccagcc agacagcaga caaataacaa tgaaccacaa tatgttactg   9840
ctataatgaa gttcgttaat tcaaaaacaa atgatgaaga ttaatgcaga tgtctaaagg   9900
ataaacactc catgcatcag tgttataatt gggctctgta gaaaatcttc atctcctcca   9960
acctacctca aagaaggatt ttaccgcgat tgggagttat aacgacaata gggacaacca  10020
cctttgacac tagccaagct tgtcgtgggc acacagcatt ttatcttgca acgtcgacat  10080
tcccatcaat ctgaggagta acagctatca aaacaacgca tatgtagaca ttgtcggtaa  10140
tagtactgcc taagacaact atttataata acagttggaa ttcattttt cacccaagct   10200 attctcaagt taacagttga acaggactc gacccaggac aactccggat acgtaacata   10260
agaaaagaac aacccttgac ccagagtgaa caagctcata ctatcaaggc taatcctcgg  10320
gcctgcctgg agtccacaat ggccaaggct actgggaggt acaaccttat ctccccaaag  10380
aaagatcttg aaaagggct ggttctgaat gacctttgca ctctctcagt ggcccagacg   10440
gtccagggat ggaaggttac ctgggctggg attgaatttg atgttacaca gaaagggatg  10500
gccttattgc acaggctcaa gaccagtgat tttgctccag cctggtcaat gaccaggaac  10560
ttatttccac atctctttca aaacccgaac tctacaattg agtcgccact ttgggcactg  10620
cgggtcatac tagcagcagg tattcaagat cagctaattg atcaatcgtt gatcgaaccc  10680
ttggcaggag cgctaggctt aattgctgat tggcttctta ctactggaac aaaccacttt  10740
caaatgcgca cacaacaggc taaggagcaa ctaagtctaa aaatgttgtc cctggtgcga  10800
tcaaacatcc taaagttcat caaccaacta gatgcactac atgttgtgaa ttacaatgga  10860
cttctcagta gcattgaaat tggcaccaaa agccatacaa ttataattac ccggacaaat  10920
atgggttttt tggtagagtt gcaagagcct gacaaatcag cctgaacac cagaaaacca   10980 ggaccagtca aattctccct cctccatgaa tcaaccttga agacacttgc taaaaaacct  11040
```

```
gcgacccaga tgcaagcact aatcttagaa ttcaatagtt ctctcgctat ttaactcaac    11100
tcatcaaaat gctaacttgt gatccttaag ctgcaccttta gacttttgat aagaatacta   11160
actattgatg attgtctttg acatgaggat aagaacactg cccattagat agatggggtt    11220
caccattaat acacaattac ccaatcatgt taacagcagt tagatccctc aagtatatca    11280
agttcattct accctttgca ttgtcactct aattaaatca cctgatacaa ttatgttaat    11340
tagctagatt ctctcatttt tagacttgtt tgctagaata attgatcatc cacttgatta    11400
cacatccaac tagggtctag ttcatagatt gctaataatc tttagttcaa tactaatgac    11460
aaagagatta gattagctat agcttgagga agattaagaa aaagtgtctg tggggtcttt    11520
ccgtgtagaa gggcacacag ccataattct tcctctttat acaacatggc tacacaacat    11580
acgcaatatc cagacgcaag gttatcatca cctatagttt tagatcagtg tgatcttgtc    11640
actcgtgctt gtggattgta ttccgcatac tccttaaatc cccaactaaa gaactgtaga    11700
ctaccgaaac atatataccg actaaaatat gacaccactg ttacagagtt tttgagtgat    11760
gtgccggtag caacattgcc agcggatttt ttagtaccta catttcttag gactctatca    11820
ggaaatggtt cttgtccaat tgatccaaaa tgcagtcaat ttttagaaga aattgtcaat    11880
tatactctac aagatattcg cttcctaaac tattacctca atcgagccgg agtgcataac    11940
gatcatgtgg atagggattt tggacaaaaa attcgcaatc taatttgcga caatgaggtt    12000
ttacatcaaa tgtttcactg gtatgatctt gcaattctag cacgtagagg gcgactaaat    12060
agagggaata atcgctcaac atggtttgca agtgataatt tggtagatat cctaggttat    12120
ggagattata ttttttggaa aataccatta tcactactac cagtggatac acaaggcctc    12180
ccacatgcag ccaaggactg gtatcatgaa tcggttttca aggaggctat tcaaggccat    12240
acacacatcg tgtccatctc tacagcagat gtcttaatca tgtgtaagga cataatcacc    12300
tgtcgattta atactttact gattgctgct gtggcaaatc tagaggattc agttcattca    12360
gattaccctt taccagaaac agtgtctgac ctatacaaag caggagatta tttaatctca    12420
ttgctaggat cagaaggtta caaagtcata aaattccttg agccgttatg cttagcaaag    12480
atccaactct gctcaaatta cactgagagg aaaggaagat tcctcactca aatgcattta    12540
gctgtaaatc atacacttga ggaacttaca gggtcccgag aattaaggcc acaacagatt    12600
cggaaggtaa gggaattcca tcaaatgctg ataaaaccttta aggcaactcc tcaacaactc    12660
tgtgagttgt tttcagtgca aaagcattgg gggcaccctg tcttgcatag cgaaaaggct    12720
atccaaaaag taaagaagca tgcaacagtg ataaaagcat tgcgcccaat aataatcttt    12780
gaaacatatt gtgtgtttaa atacagcatt gcaaaacatt atttttgatag tcagggtacg    12840 tggtacagtg tgacttctga cagatgctta acaccaggcc tttcctctta catcaaaaga    12900
aaccaatttc ctccactacc tatgatcaaa gaacttttgt gggaattttta tcacttagat    12960 catcctccgt tattctccac caaagtgatt agtgatttga gtatctttat taaagatcgt    13020
gctactgcag tcgagaaaac atgctgggac gcagttttttg aacccaatgt tcttggttat    13080 aaccccaccga ataaatttgc tacaaaaagg gtacctgagc aattccttga acaggagaat    13140
ttctcaatag agagtgtcct acattatgct caacgtctgg aatatcttct cccggagtac    13200
cggaacttct cttttttcact caaggagaag gagttaaaca ttggacgagc ttttgggaaa    13260
ttgccatatc caacacgcaa tgttcaaact ctgtgcgaag ctttgttagc agatggtttg    13320
gcgaaagcat tcccaagcaa tatgatggtt gtgacagagc gcgagcaaaa agaaagcctt    13380
ttgcatcaag cgtcttggca tcacacaagt gatgattttg gtgagaatgc tactgttaga    13440
```

```
ggcagtagtt ttgtaacaga cttggaaaaa tacaatttag cattccgata tgagtttaca   13500 gctccttta  ttgaatactg taatcgttgt tacggtgtaa gaaatttgtt taattggatg   13560
cactacacta taccacagtg ttatatacat gtgagtgatt attataaccc cccacatgga   13620
gtctctctcg aaaaccgaga aaatccacca gaaggtccaa gctcttaccg tggtcatcta   13680
ggcgggattg agggacttca acaaaaactc tggacaagca tctcatgtgc acagatttca   13740
ttagttgaaa tcaaaaccgg ttttaaactg cgatctgcgg taatgggtga caatcaatgt   13800
ataactgtac tctctgtatt tccctcgaa  actgagtcta gtgagcaaga attaagttct    13860
gaagataatg ccgctagagt agctgctagc ttagcaaaag tcacaagtgc ctgcggcatc   13920
tttttaaaac ctgatgaaac ttttgttcac tcaggtttca tttattttgg caaaaaacaa   13980
tatttgaatg gagtacaatt acctcaatca ctgaaaactg ctactagaat tgcacccttg   14040
tcagatgcta tctttgatga tcttcaaggg acactagcta gcataggcac ggcttttgaa   14100
agatctatct ccgaaactag gcacgtagtc ccttgtagag tagcagctgc attccatacc   14160 ttttttccg  taagaatctt acaatatcat catcttggct tcaacaaggg aacagacctg   14220
ggtcaattgt cattaagcaa gccattagat tttggaacta taactttggc cttggcagta   14280
ccacaagtct tgggtggctt atcattccta aatccagaaa aatgttttta tagaaatctg   14340
ggtgatcctg ttacttcagg gctgtttcag ctcaagacat atcttcaaat gatccacatg   14400
gatgatttgt ttttaccttt gatcgcaaag aacccaggga actgtagcgc aattgacttt   14460
gtgttaaacc ctagtgggtt aaacgtaccg gggtcacagg atttgacatc cttcctacgt   14520
cagatagtgc gccgaacaat tactctaagt gctaaaaata aattaataaa cactttgttc   14580
cattcttctg ctgatttaga agatgaaatg gtttgcaaat ggttgctttc ttctacacca   14640
gtcatgagta ggtttgccgc cgatatattt tctcgcactc ccagtgggaa acgtttacag   14700
atcttaggtt accttgaagg gactagaaca ttgttagcct ctaaaattat aaatcataat   14760
actgagacac ctatcctaga tcgattgagg aaaattacgc tgcaaaggtg gagcctgtgg   14820
tttagttatc tcgaccactg tgatcaagtt ctggctgatg ccctaactca gataacctgc   14880
actgtggact tagcacagat tcttcgcgag tacacctggg cacacatact agagggaagg   14940
cagctcattg gagcaacact tccttgtata ctagaacaac taaatgtcat ctggctcaaa   15000
ccatatgagc attgccctaa atgtgcaaag tcagcaaacc ctaaagggga acctttgtt   15060 tctattgcaa ttaaaaaaca tgtagtaagt gcttggcctg atcaatcacg acttagttgg   15120
acaattggag atggcatccc ttatatcgga tctcgaacag aggataagat tgggcagcca   15180
gccatcaaac caaaatgccc ttcagcagcc ttacgtgaag caattgagtt gacatcaaga   15240
ttgacttggg ttactcaagg tggagcaaac agcgacttac tagttaaacc cttcatagaa   15300
gcacgagtaa atttaagcgt acaggaaatt ctccaaatga caccttctca ttactccggc   15360
aacattgtgc atcgatataa tgatcaatat agtccacact catttatggc aaataggatg   15420
agtaattctg ctactaggtt agttgtttcg acaaacactc ttggagaatt ttcaggagga   15480
ggtcagtcag caagagatag taatatattc ttccagaatg tcattaattt tgctgttgca   15540 cttttgatc  tacgatttag gaacgtggct acttcttcta tacaacatca tcgggctcat   15600
cttcatttgt caaagtgttg cacgcgagag gttccagccc aatatttagt ttatacatca   15660
acattgccat tggaccttac acggtatcgg gataatgagt tgatttacga tgacaatcca   15720
ttaagaggtg gtttaaattg caatctttct tttgataatc cgcttttcaa gggccagaga   15780
```

```
cttaacataa ttgaagaaga cttgattaga ctaccttact tatcaggatg ggagctagct    15840
aaaactgtta tccaatctat aatttctgac agcaacaatt catcaacgga tccaatcagt    15900
agtggggaaa cacgatcatt caccactcac ttcttgacat atcctaagat tggactacta    15960
tatagttttg gtgcactcat cagttattat ctaggcaaca ccattattag aaccaaaaaa    16020
ttgactctta acaacttcat atattaccta gctactcaaa tacataattt acctcatcgc    16080
tcgttgagaa tccttaaacc tactttgaaa cacgctagtg ttatctcgag attaataagt    16140
attgactctc acttctcaat ttatattgga ggaactgctg gtgatcgagg actttccgat    16200
gcggcaagat tgtttcttag aactgccatt actgtcttcc ttcaattcgt tagaaagtgg    16260
atagttgaac gcaagacagc tattccactg tgggtcatct accctctaga aggtcaaagt    16320
cctagtccga tcaacagttt tctacaccac gtcatcgcat tgttgcaaca tgagtcctcc    16380
cacgatcatg tttgtgctgc agaagcccac agtcgagtgg agacatttga taatttagtt    16440
tatatgtgta aaagcacagc aagtaacttc tttcatgctt cattagcata ctggagaagt    16500
cgatctaaaa atcaagacaa agagagatg acaaagatat tatctttgac gcaaacggaa    16560
aagaaaaatt cattcggcta tacagcacat ccagaaagca ctgctgttct tggttccctc    16620
cagaccagcc ttgctccacc tccatctgct gacgaggcta catatgatag gaaaaacaaa    16680
gttttgaaag cttccagacc tggcaagtat tcccagaata caaccaaagc cccacccaac    16740
caaaccagtt gtcgcgatgt atctcccaat atcacaggca cagatgggtg ccttctgcc     16800 aatgagggtt ctaacagcaa taacaataat ttagtctcgc acagaattgt actgccgttt    16860
tttacattgt ctcataatta taacgaaaga ccctctatca gaaagtctga ggggacaaca    16920
gagattgtaa ggcttactcg gcagctgagg gcaataccag acaccacaat atattgccgc    16980
ttcacgggaa tagtttcttc aatgcactat aagctcgatg aagtcctttg ggaatttgat    17040
aattttaagt ctgctataac acttgccgaa ggtgaaggtt cgggtgcatt actcttatta    17100
caaaaatata agtagaaaac cttgtttttt aatacactag ccacagaaca cagcattgaa    17160
gcagaaatta tttctggaat aactacacca agaatgcttc tccctattat gtctaggttc    17220
catggtggac aaataaaagt cactttaaac aattctgcaa gccagattac cgatattact    17280
aatccaagtt ggttggcaga ccaaaaatct aggatcccta agcaagtaga gattataacc    17340
atggatgctg aaacaacaga aaacattaat cggtcaaaat tgtacgaagc agtccaacag    17400
ctgattgtct cacatattga tccgaatgca ctcaaagttg tggttcttaa agttttctta    17460
agtgacattg atggaatcct atggctgaat gataacctta ccccttttgtt tgggctgggt    17520 tacttgatca agccgatcac ctctagccca aaatctagtg agtggtacct atgtctctca    17580
aaccttcttt caacttcaag acgattacct catcagagtc atactacttg catgcatgtt    17640
attcaaacag cactccagct acaaattcag aggagctcat attggcttag ccaccttgtc    17700
cagtatgcca atcataattt gcatttagat tatattaatc tcggtttccc ttcattggag    17760
agggttttat accatagata caatttagtc gattctcaga aaggccctt gacttccatt     17820 gtccaacatc tagcgcacct gcagaccgag attagggagt tggttaatga ctataatcaa    17880
caaagacaaa gtcgaaccca acatatcat ttcattaaaa caataaaagg tcgtattaca     17940
aaattggtaa atgattacct taagttcttt ctaataatac aagccttaaa gcacaattgc    18000
acatggcaag aggaactaag agctcttcca gatctaatta gtgtctgcac tcgattctat    18060
catactcgaa actgttcatg tgaaaaccgg ttcctagtac agactttata cttatcacgc    18120
atgcaggatt cggaaatcaa actaatagat agattgaccg gccttcttag tctatgtcca    18180
```

```
aatggttttt ttcggtaagg actcttgacg tacaaactcc acatagttat acaatggtac    18240
caggacacta tatgtaaatt gaccctaaga aagagtaatt cgacacacag agttctcaag    18300
tgaaacccct catctcagat tatctgtggt tgcaattcta atatccgatt gttacccccgt   18360 gagtataact ccagattaat ataagaaaat acctttttgtc ctgcaaattt atcttaaatt   18420
caagtacata cgctccaaat cgtataaaat attaagaaaa agttaatctg cttgctttaa    18480
ttataacttt aatattcgac aaatagttaa cggtctcatc actcaaaaat ttcattaaca    18540
aaagaagtac tctgagtata ttcacatatc atatgtgatt aacatataag caacgcatga    18600
tgcgccttcc tcttacttat tgtgttgtca cgcagtcgtt gtactacctc gaaaattcca    18660
aacaataaat cgtgtctatc ccgcatttag tgtctttaat ttaagatctc aaatccaaaa    18720
aactgggttt atgttgatgt aaatcaataa taccgaaatt gcttgatatt aaaataaagc    18780
ttaaaggatt tttccttaaa cggtgatgtt aggtatatag gaaagctcga tcacgatgtc    18840
ccttactcag aaaaagaaaa acggaagccc tattggccat ttaatcgtac acaaaaatat    18900
ctttaccaaa ttgttttctc ttttttgtgt gtcca                              18935

<210> SEQ ID NO 5
<211> LENGTH: 18940
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
cggacacaca aaagaatga aggattttga atctttattg tgtgcgagta actacgagga       60
agattaaaga ttttcctctc attgaaattg aaattgagat tctaatctcg acggatcgat      120
ccccaatacc aacactgaga attggcctga agaagtcatc tgctccttgg caaaaccaag      180
agcaggccca aagggccatt aggccacatc tgctgagcct gcagaacacg caggacttac      240
ttagcagaag agagcgcgtg ccgaaaccag ccaacaaatt gacacagctg ctcactctga      300
ccctgaattc ataaacaata ttaagttgac aacagagata ctaatccaat atttggatca      360
agaatcaaaa tagtgaaacg actgactatc cctccttaga attagcaaag atccttttgt      420
agactattgt gctacattct ctatccaaga cctcaaaatg gatcctcgtc caatcagaac      480
ctggatgatg cataacacat ctgaagttga agcagactac cataagattc taactgccgg      540
attgtccgtc cagcaaggca ttgtgagaca aagaatcatt cctgtttacc aaatctcaaa      600
cctggaggaa gtatgtcaac tcatcataca ggcattcgag gctggcgtcg acttccagga      660
tagtgcagat agcttttttgt taatgctatg tctgcatcat gcctatcaag gggattataa      720 acaattttttg gaaagtaatg cggtaaaata ccttgaaggt catggattcc gttttgagat      780
gaagaaaaag gaaggtgtca agcgcctgga ggaactactc cctgctgcct cgagtggaaa      840
gaacatcaag agaacattgg ctgcaatgcc cgaggaggaa acaacagaag caaatgctgg      900
acaatttctt tcatttgcta gtctgttttct cccaaaattg gttgtcggag aaaaggcctg      960
tctggagaag gttcaacgac aaatccaagt gcacgcagaa caaggtctga ttcaataccc     1020
gacatcttgg caatcggtgg acatatgat ggtcatcttc agactaatgc gaaccaactt      1080
cctgattaag ttcctcctaa tacatcaagg aatgcatatg gttgcagggc atgatgctaa     1140
tgatgccgtc attgccaact ctgtagctca agctcgtttc tccggattgt tgatagtcaa     1200
aacagtgctt gatcatatcc tccaaaaaac agagcacgga gttcgcctgc atcccttggc     1260
```

```
gcgaacagcc aaagtcaaaa atgaggtgag ctcttttaag gccgctttag cctcactagc      1320
acaacatgga gaatatgccc cgtttgctcg tctgctgaat ctatctgggg ttaataatct      1380
tgagcatggg cttttccctc aactttctgc aattgctttg ggagtagcaa ctgcacatgg      1440
gagcactctg gctggagtca atgtaggaga gcaataccaa caactgcgag aagcagccac      1500
tgaggccgaa aagcagttgc agaaatatgc tgaatctcgt gaacttgatc acctaggtct      1560
tgatgatcag gaaagaaaaa tcctaaaaga cttccatcag aaaaagaatg agatcagctt      1620
ccagcagacg acagccatgg tcacactgcg gaaagagaga ttggccaaat tgaccgaagc      1680
tattacttcc acctctatcc tcaaaacagg aaggcggtat gatgatgaca atgcatacc       1740 cttctccaggg ccaatcaatg ataacgagaa ctctggtcag aacgatgacg atccaacaga     1800
ctcccaggat accacaatcc cggatgtaat aatcgatcca aacgatggtg ggtataataa      1860
ttacagcgat tatgcaaatg atgctgcaag tgctcctgat gacctagttc ttttttgacct    1920 tgaggacgag gatgatgctg ataacccggc tcaaaacacg ccagaaaaaa atgatagacc      1980
agcaacaaca aagctgagaa atggacagga ccaggatgga aaccaaggcg aaactgcatc      2040
cccacgggta gcccccaacc aatacagaga caagccaatg ccacaagtac aggacagatc      2100
cgaaaatcat gaccaaaccc ttcaaacaca gtccagggtt ttgactccta tcagcgagga      2160
agcagacccc agcgaccaca acgatggtga caatgaaagc attcctcccc tggaatcaga      2220
cgacgagggt agcactgata ctactgcagc agaaacaaag cctgccactg cacctcccgc      2280
tcccgtctac cgaagtatct ccgtagatga ttctgtcccc tcagagaaca ttcccgcaca      2340
gtccaatcaa acgaacaatg aggacaatgt caggaacaat gctcagtcgg agcaatccat      2400
tgcagaaatg tatcaacata tcttgaaaac acaaggacct tttgatgcca tcctttacta      2460
ccatatgatg aaagaagagc ccatcatttt cagcactagt gatgggaagg agtatacata      2520
tccagactct cttgaagatg agtatccacc ctggctcagc gagaaggaag ccatgaacga      2580
agacaataga ttcataacca tggatggtca gcagttttac tggcctgtga tgaatcatag      2640
aaataaattc atggcaatcc tccagcatca caggtgatcc gacctctaaa actgagctcc      2700
taactacaag ctacccccatc actctgccgg aatgccagaa cctccctcca aaacagctcc      2760
acatcgagaa cctccgacgc ggtacacagg caagacaggc aacctaatga tgttcctgtt      2820
cacccacaac cgcaaccaac acttgatcga cttccaagac aactcaaacc cccttagcca      2880
actccaccac agaagcacca cccccataaca acaaccccaa accaacaaca ctgcatgtaa      2940
gtattgtctc accccaagat gatccctgga caccaacaac cccctaacct ccccaagttg      3000
tcattaagaa aaaatatatg atgaagatta aaaccttcat cagagctatt tcttctacgc      3060
ttggttagga ccagtattca caaactattt tacaatccct acccaatatg acctctaaca      3120
gagcaagggt gacttacaac ccaccaccaa caaccacagg cacacgatcg tgtgggccgg      3180
aactttccgg gtggatctct gagcaattga tgacaggcaa gattccgatt accgatatct      3240
tcaatgaaat tgaaacctta cctagtataa gtccctcgat ccactccaaa atcaaaaccc      3300
caagtgttca aacacgcagt gtccagaccc aaactgaccc aaattgtaat catgattttg      3360
cagaggttgt gaaaatgcta acatctctaa cccttgtcgt acaaaaacaa acccttgcaa      3420
ctgaatcact tgagcaacgc attactgacc tggaaggtag cctgaaacca gtgtctgaga      3480
tcaccaagat tgtttctgca ctaaatagat cctgtgcaga gatggtggcc aaatatgatc      3540
ttctagtaat gacgactggt cgtgcaactg ccactgctgc agctactgaa gcatactggg      3600
```

```
cagaacatgg acgtcctcca ccggggccct cattgtacga ggaggatgca atcaggacta    3660
aaattggaaa acaaggggat atggtaccca aggaagtgca agaggccttc cgtaatctgg    3720
atagtactgc ccttctaacg aagagaatt ttgggaaacc agacatatcc gcaaaagact    3780
tgcgcaatat catgtatgat cacctcccag gttttggcac agcatttcat caactagtgc    3840
aagttatctg caagttaggg aaggacaatt cctcacttga tgtaattcat gcagaatttc    3900
aggccagcct tgctgaagga gactctcctc agtgtgccct gattcagata accaaacgga    3960
ttcctatttt ccaagatgca gcaccaccg taatccatat tcggtcacgc ggtgatatac    4020
caaaggcgtg tcaaaagagc ctccgccctg ttccaccatc accaaagatt gatagggggtt    4080
gggtatgcat attccagcta aagacggaa aaacactcgg actcaaaatc taaggtgaac    4140
aattgcgcaa cctccacagt cgcctatatt gcttccttcc ggaatcaggg tatgatcgcg    4200
taaaaaataa gcttccaaca tattgataca cgatccatat ccataatgcc atctccagga    4260
atatgagaac gcaaggccat atcaggaccc gatctcaatt ccaatgcaac ctactgttaa    4320
gaataaaata accaatgtcc tctagcctta tatgttctca aaaatacaag tgatgaagat    4380
taagaaaaag catcctttac ttgagaggag ctaattcttt atacttcatc taatctttaa    4440
gtaagttgat cactaccacc atgaggaggg caattctacc tactgcaccg ccagaataca    4500
tagaggctgt ctacccaatg agaacggtta gtactagtat caacagtact gccagtggtc    4560
cgaactttcc agcaccggat gtaatgatga gtgatacacc ctccaactca ctccgaccaa    4620
ttgctgatga taacatcgat catccaagtc atacaccaac cagtgtttca tcagccttta    4680
tactcgaggc aatggtgaat gtgatatcgg ggccgaaggt actaatgaag caaattccta    4740
tatggctccc cttgggtgtt gctgatcaaa aaacatatag ttttgactca actacagctg    4800
caattatgct cgcatcgtac accatcactc actttggcaa acctccaat ccgcttgtga    4860
gaatcaatcg acttggtcct gggatccccg atcacccgtt gcggcttcta agaataggaa    4920
atcaagcctt cttgcaagag tttgtgctgc ctccagttca attgccgcag tatttcactt    4980
ttgacctgac ggctctaaag ctgatcactc aacctctccc ggcagcaacc tggacggatg    5040
atactccgac cggtcctaca ggaatacttc gtcctggaat ttccttcat cccaaactga    5100
gacctatcct attgccaggg aagaccggga aaagaggatc cagctccgat cttacttctc    5160
ctgataaaat acaagcaata atgaactttc tccaagacct caaactcgtg ccgattgatc    5220
cagccaagaa cattatgggt attgaagtgc cggaactctt ggtccacaga ctaactggaa    5280
agaaaatcac aacaaaaaat ggtcaaccaa taattcctat tcttctacca aagtatattg    5340
gcatggatcc catttctcag ggagacctca caatggtcat cactcaagac tgtgacactt    5400
gccattctcc tgctagtctt cctccagtca gcgagaaatg agcatgaagt ccgaggctgc    5460
ccggcccaca cgacccccag ggccttcgtc cggctaccga accaaccatc cgaccttcat    5520
caaaaccaaa aaataccgcc acgcgaaagc taaaatgcag gaccacaatc caaccagcaa    5580
caccatccat acacaggtat caattgggct gccgcagcat atagacccaa tagcaagctg    5640
ctgtccagaa aatagttccg gaaagtaact caaccatcgc aagcccaatg cagctttcag    5700
aaatccgcca gcaacccaac tccactgtac ccccaatatt aacctgaatc gactaaccgc    5760
acttttaattt gaagtacatt tgttcaatgg gttcattatt aacagtgttg cttttagatt    5820
gtacctttgc tcacagatag taaattgtta tggtatcaaa tcttattaag aaaaagaaca    5880
cgatgaagat taacgcgacc tagagcgctg ccttcatctc atcaatttaa cttgtcaata    5940
gagcaaccta gtttgtgatt actcatcttc cgtagttgac aaacactttg ctggttaatt    6000
```

```
gtaaatatac cacagtcatc atggttacat caggaattct acaattgccc cgtgaacgct    6060
tcagaaaaac atcattttt gtttgggtaa taatcctatt tcacaaagtt ttccctatcc    6120
cattgggcgt agttcacaac aacactctcc aggtaagtga tatagataaa ttggtgtgcc    6180
gggataaact ttcctccaca agtcagctga atcggtcgg gcttaatcta gaaggtaatg     6240
gagttgccac agatgtacca acagcaacga agagatgggg attccgagct ggtgttccac    6300
ccaaagtggt gaactacgaa gctggggagt gggctgaaaa ctgctacaac ctggacatca    6360
agaaagcaga tggtagcgaa tgcctacctg aagccctga gggtgtaaga ggcttccctc      6420
gctgccgtta tgtgcacaag gtttctggaa cagggccgtg ccctgaaggt tacgcttccc    6480
acaaagaagg cgctttcttc ctgtatgatc gactggcatc aacaatcatc tatcgaagca    6540
ccacgttttc agaaggtgtt gtggctttct tgatcctccc cgaaactaaa aaggactttt    6600
tccaatcgcc accactacat gaaccggcca atatgacaac agacccatcc agctactacc    6660
acacagtcac acttaattat gtggctgaca attttgggac caatatgact aactttctgt    6720
ttcaagtgga tcatctaact tatgtgcaac ttgaaccaag attcacacca caatttcttg    6780
tccaactcaa tgagaccatt tatactaatg ggcgtcgcag caacaccaca ggaacactaa    6840
tttggaaagt aaatcctact gttgacaccg gcgtaggtga atgggccttc tgggaaaata    6900
aaaaaacttc acaaaaaccc tttcaagtga agagctgtct gtcatatttg taccaagagc    6960
ccaggatcca ggcagcaacc agaagacgaa ggtcactccc accagcttcg ccaacaacca    7020
aacctccaag aaccacgaag acttggttcc agaggatccc gcttcagtgg ttcaagtgcg    7080
agacctccag agggaaaaca cagtgccgac cccacccca gacacagtcc ccacaactct     7140
gatccccgac acaatggagg aacaaaccac cagccactac gaaccaccaa acatttccag    7200
aaaccatcaa gagaggaaca caccgcaca ccccgaaact ctcgccaaca atcccccaga     7260
caacacaacc ccgtcgacac cacctcaaga cggtgagcgg acaagttccc acacaacacc    7320 ctcccccgc ccagtcccaa ccagcacaat ccatcccacc acacgagaga ctcacattcc     7380
caccacaatg acaacaagcc atgacaccga cagcaatcga cccaacccaa ttgacatcag    7440
cgagtctaca gagccaggac cactcaccaa caccacaaga ggggctgcaa atctgctgac    7500
aggctcaaga gaacccgaa gggaaatcac cctgagaaca caagccaaat gcaacccaaa     7560
cctacactat tggacaaccc aagatgaagg ggctgccatt ggtttagcct ggatacctta    7620
cttcgggccc gcagcagagg gaatttatac ggaagggata atgcacaatc aaaatgggct    7680
aatttgcggg ttgaggcagc tagcaaatga gacgactcaa gccctacagt tattcttgcg    7740
tgctaccacg gaattgcgca ctttctctat attgaatcga aaagccatcg acttttact     7800 ccaaagatgg ggaggaacgt gccacatctt aggcccagat tgctgtattg agccccatga    7860
ttggactaag aacattactg acaaaataga tcaaatcatt catgatttca ttgataaacc    7920
tctaccagat caaacagata atgacaattg gtggacaggt ggaggcaat gggttcctgc     7980 cgggatcggg atcacggggg taataatcgc agttatagca ctgctgtgta tttgcaaatt    8040
tctactctaa tctagtccga ctctgtacca gcataatggc ctctaaaata agcttttgct    8100
tctgcttcct atagttaata catttcagca aaatcaact attaagtcaa agaagatcc     8160 ctctaataat cctaattacc ttcaaaaatc tagaacttta ttaattctca gggtatttag    8220
aacagccaga tgacttgact aagtttgtac tgtaataaaa agatacttga tgaagattaa    8280
gaaaaagaca gtcttgtgat tgtcactaat cttcatctca aaacatatta ttttaccaga    8340
```

```
agctactata gcctacctcc ttgacacata gcaaacctta ctcatgttga taattgtttg    8400
cctgctattt acatatttac taacttacaa aattatcttg gggatttctc tgaacatata    8460
atcagaattg gcatttaaaa cacaagttag tcctaatgga ctcatttcat gagagagggc    8520
gtagcagaac tattcgacag agtgcaagag atgggccgag tcatcaagta agaacaagat    8580
catcctccag agacagccac cgcagcgaat atcatacacc taggagctct tcccaagttc    8640
gagtcccgac tgtgtttcat cggaagcgta ctgattcttt gacagttcca ccagcaccaa    8700
aggacatatg tcctacctta aggaaaggat ttttgtgtga cagcaatttt tgtaaaaagg    8760
accatcaact agaaagttta acagataggg agctgctttt gctgattgca cggaaaacct    8820
gcggctccct tgaacaacaa ttgaacatca ctgctcctaa agatacacga ttagcaaatc    8880
caattgcaga tgatttccaa caaaaagacg gcccaaaaat tacactattg acactttggg    8940
agactgcgga gtattggtca aaacaagata tcaagggcat tgatgactca agactaagag    9000
cattactaac cctttgtgcc gtcatgacga ggaaattctc aaaatcccag cttagtctat    9060
tgtgtgagag tcatctacga cgagaagggc taggacagga tcaatcagaa tctgttcttg    9120
aagtgtatca gcgcttacat agcgacaaag gcggaaattt tgaggcagcc ctatggcaac    9180
aatgggaccg acagtccttg atcatgttta taacagcatt tcttaatatt gctttacaat    9240
taccctgtga aagttcatct gttgttattt caggattaag gctgctagtg cctcaatcag    9300
aagataccga gacctcaacc tacaccgaga cacgtgcatg gtcagaggaa ggtggccccc    9360
attaacatct tccacagtcg aatctaccat aatttcccta ttcaacgcag ataagaatca    9420
gtactaaacc acaagtgcaa aaattaacaa acaccagca taagtgaaat cctgtctgtg    9480
attagcaaca cgaatgatct tcaatcctgt tgcaattcgc cagtgataat tgtattcaca    9540
ttgtggccac aatatactgt cttttcccat tgaaaaataa ggctgaatct attacgctac    9600
acaaacttac aggattagca ccacgacggc tcaatactat acctattggt cacggctcga    9660
tgtgttaatc acttatattg tattcatttg aaattactca ttaggcaaat actttgatta    9720
agaaaaaata attggaaaac cagaaaatcc ctaggtattt aaattcctat ctccggagat    9780
ccgagataat taatcaagca atgagggaac aatggtgaac aacaacatat tgttgccccc    9840
tttagattgg tcagttccaa aaacaagtga tgaagattaa tgcagatgtc caaggaacac    9900
atatttgtga tttaaacgtt ccagttagac tctgttcaag gatcttcatc ttttgtagct    9960
ccactctgag tcacaacata attgagtttt tgctcagaac agttatcagg attaaattct    10020
ctcaaataac tgaaactact agcatcactc tcaatttcat tacttacgac aatcattatc    10080
ttaataatat ttctctaaat tactgactta attagcttgt aatcagataa tatcgaaacc    10140
aatttatcat aaggcataat ttgtataagt gatttaggat ttaccccaga agtgaaataa    10200
ttcttagaat aaaagaccga ctagaatatc cttaaggctg tctaacgtgc cacacagcta    10260
gggttagcct gacatctgga acaagatcga tactaatata gggatttgtt tcatactagc    10320
tctctgcaaa cacaatggct aaggcaacag gtaggtacaa cttggtttca cctaaaaagg    10380
acctcgagag ggggcttgtt ttgagtgatt tgtgcacgtt tttagttgat cagactatcc    10440
aggggtggcg ggtgacttgg gttgggattg aatttgacat cgcccagaaa gggatggctc    10500
tactgcatcg gttaaaaact gctgacttcg ctcctgcatg gtcgatgaca aggaatttat    10560
ttcctcattt atttcaaaat tcaaattcta ctattgagtc tcccctctgg gcattacgag    10620
tgattctggc agctggtatt caagaccagt taattgacca atccttggta gaaccgttgg    10680
ccggagccct gagcttagtc tccgattggc ttcttacaac aaacacaaac cattttcaaa    10740
```

```
tgcgcacgca gcacgctaaa gagcaactga gcttgaagat gctatcatta gtgcgctcta   10800
atatcttgaa attcatcagt caattggacg cactacatgt cgtgaactac aatggactct   10860
tgagcagtat cgaaattggc actagaaatc ataccattat catcacaaga accaacatgg   10920
gtttcctggt agaattacag gagcctgata aatctgccat gaatcaaaag aaaccaggac   10980
cagtcaagtt ctccctcctg catgaatcaa ccttcaaggc tctaatcaaa aaacccgcaa   11040
ctaagatgca ggccttgatt ctggaattta acagctccct ggcaatatag tccaacgcta   11100
ccaaccatca ttttttgtaa ctgcatctct tttatttcct ttctaacttg atacaattat   11160
aatcaagatc cctaatccct tttgacgaag tgggctaatt tttgctcatt ctaataataa   11220
atcataacct gaataaaaga caccacaata ttataaccca ataacaccta gagaatttct   11280
gaattgctaa agattatata ctcgcactaa gagacaagtt aatcaatctt tacttaataa   11340
tatactaaat gctagatagc tctggctaac taacctgagt tgtggattac tcctttttaaa  11400 agtctatcaa tttaagctta tcactaatat taaggaggac ttttttaaata agagcaagtg  11460 ttatgtagtc ttactaagaa tgatttgagg aagattaaga aaaagtgctt gtggggtctt   11520
tccgttgtag aggacacacg agcaaacttc ttcctctaat tttaatatgg caactcaaca   11580
tacacaatat ccagatgcaa gattatcttc acccattgtc ttagatcaat gtgatcttgt   11640
cacccgtgct tgcggtctgt attcttcata ctcattaaat cctcagttga aaaattgtag   11700
actaccaaaa catatttacc gcctcaaatt tgatgctacg gttacaaaat ttttaagcga   11760
tgttccaata gttacattgc cgatagatta cttgacccct ttacttttac gaactttatc   11820
cggggagggc ttatgccctg tcgaaccaaa gtgcagccaa ttcttagatg aaatagtaag   11880
ttatgttttg caggatgcac gtttttttaag atactatttt aggcatgttg gagtacacga   11940
tgacaatgtt ggaaaaaatt ttgagccaaa gattaaggct ttgatttatg ataatgaatt   12000
tctgcaacaa ttgttttatt ggtacgattt agcaatccta acgcgtagag ggcgcctgaa   12060
tcgagggaat aaccgttcaa catggtttgc aaatgacgat ttaatagaca ttctcgggta   12120
cggtgattat attttctgga aaataccgtt gtcattgttg tcactcaaca cagaggggat   12180
tcctcatgca gctaaggact ggtatcacgc atcaatcttc aaagaagcgg ttcaaggtca   12240
cacacatatc gtgtcagttt ccactgcaga tgttttaatt atgtgtaagg acatcataac   12300
ctgtcgtttc aataccacac tcattgcagc attggcaaat ttagaagatt ctatctgttc   12360
tgactatcca caacctgaaa caatctctaa tctgtataag gcagggggatt acttaatctc   12420 gatactgggt tcagaaggtt ataaggtcat aaagttttta gaaccactat gtttagctaa   12480
gatccaattg tgctcaaatt acactgagag gaaagggaga ttccttactc aaatgcattt   12540
ggccgttaat cacacacttg aagaacttat tgagggccgg ggattgaagt cacaacaaga   12600
ctggaagatg agggaatttc accgaatctt agtaaattta aagtcaacac cacaacaact   12660
ctgtgaattg ttttcagtgc aaaagcattg ggggcatcct gtgctacata gcgagaaggc   12720
tattcagaaa gtaaagaaac atgcaaccgt aataaaagca ttgcgtcccg taatcatctt   12780
tgagacatat tgtgtgttca agtacagcat tgccaaacat tattttgata gccaagggtc   12840
atggtatagt gtaatctcag ataaacatct aacaccaggt ttacactctt acattaagag   12900
gaaccaattt ccgccactgc ctatgattaa agacttattg tgggaattct atcaccttga   12960
tcatcctccc ttattttcca ccaagattat tagtgacttg agtattttca ttaaggatcg   13020
cgctaccgca gtggaaaaaa catgttggga tgcagttttc gagcctaatg ttcttggata   13080
```

```
tagtcctcca aacaagttct caactaagag ggttcctgaa cagtttcttg aacaagaaaa   13140
tttctcgatt gatagtgttc tcacttatgc ccagcgcctg gattatctac ttccacaata   13200
ccggaatttt tctttctcac ttaaggaaaa agaattaaat gtaggacgag cttttggtaa   13260
gctaccttat cctacacgta atgttcaaac tttatgtgaa gccttattgg cagatggatt   13320
agctaaagcc tttcctagta acatgatggt tgtaacagag cgtgagcaga aggaaagcct   13380
cttgcaccag gcgtcgtggc accacacaag tgacgatttc ggtgagaatg ccactgttag   13440
aggcagcagt tttgttaccg acctagaaaa atacaacttg gcatttagat atgagtttac   13500
agctccattt attgaatact gtaatcgatg ttatggtgta aaaaatttat tcaattggat   13560
gcattatacg ataccgcaat gttatataca tgtaagtgat tattataatc cccctcatgg   13620
agtttcgcta gaaaatcggg aagatccccc ggaaggccct agctcttacc gtggtcatct   13680
tgggggaatt gagggactcc aacagaaact ctggaccagc atttcatgtg cacaaatctc   13740
attagttgag atcaagactg gtttcaaatt gagatctgcg gtaatgggtg ataatcaatg   13800
catcacagtt ctttccgtat ttcctctaga gacagattcc aatgagcaag agcatagctc   13860
cgaggacaat gctgctcgcg tagcagccag tttagccaaa gtcacgagtg cctgtggcat   13920
cttcctaaaa ccagatgaga cttttgtgca ttcaggcttt atttatttcg gtaagaagca   13980
atatttaaat ggcgttcaat tgccacaatc actcaagact gctaccagga ttgctcccctt   14040 gtcagatgca atctttgatg accttcaggg aactctggct agtataggaa cggcatttga   14100
gagatctata tccgagacta gacatgtata cccttgccgg gtggttgccg cattccatac   14160
attcttctcc gttaggatcc tccaatacca ccaccttggt ttcaacaaag gaaccgatct   14220
aggtcaacta tcactaagca aaccgttgga tttcggaact atcactcttg ctttagcggt   14280 accctcaagtt ctaggaggtt tatcgttttt aaacccagag aaatgttttt atcgcaacct   14340
tggagacccc gtgacctccg gcctattcca acttaggact tacctgcaaa tgatcaacat   14400
ggacgactta tttctacctt taattgccaa gaaccccggg aactgtagtg caattgactt   14460
tgtactcaac ccaagcggat tgaatgtccc tgggtcacaa gacctaacat ctttttttacg   14520 tcagatagtg cgtagaacaa tcacattgag tgcaaaaaat aagctaataa acacattgtt   14580
tcactcctca gccgatttag aagatgagat ggtatgtaaa tggctacttt cttcaacacc   14640
tgtaatgagt cggtttgctg ctgatatatt ctctcgtact ccgagtggga agcgcttgca   14700
gatcctaggt tatttagaag ggactagaac cttgctagcc tccaaagtca tcaataacaa   14760
tgcagagact cctatttttag ataggttgag gaaaatcaca ctgcagagat ggagtttgtg   14820
gtttagctac ctagaccact gtgatcaggt tctagcagat gctttaataa aagtttcttg   14880
tacagttgat ttggcgcaaa ttttacgtga atatacctgg gcacacatac tagagggaag   14940
acagctcatt ggtgcaacac ttccttgcat gttagaacaa tttaatgtgt tttggctcaa   15000
atcgtacgaa caatgcccta atgtgcaaaa atctagaaat ccaaaaggag agccatttgt   15060
gtcaattgca attaagaaac aagttgtgag tgcatggccg aatcagtcac ggttaaattg   15120
gaccattggg gacggtgtac cttacatcgg gtctcgaaca gaggacaaga ttgggcagcc   15180
agcaatcaag cctaagtgtc cctctgctgc cttacgtgaa gcaatagagt tgacatctag   15240
actaacatgg gttacccaag gtggtgccaa tagtgatttg ctagttaaac cttttgtaga   15300
ggcacgagta aacctgagtg tgcaggagat ccttcaaatg acgccttctc attattcagg   15360
gaacatcgta catcggtata atgaccaata cagccctcat tctttcatgg caaatagaat   15420
gagtaattcc gcgacgagat tggtggtgtc gacaaatact ctcgggagt tctcaggtgg   15480
```

```
ggggcaatca gcaagggaca gcaatatcat ctttcaaaat gtaatcaatt tttcggttgc   15540
cctatttgat ttacgatttc ggaacaccga aacatcctcc attcagcata atcgtgccca   15600
tctccatctt tcacagtgtt gcacacggga agtcccagct caatacctaa cctacacgtc   15660
tacgctttcc ttggatctca caaggtaccg agagaatgag ttaatttatg ataacaatcc   15720
gttaaaaggt ggacttaatt gcaacctatc ctttgataat ccacttttca agggccaaag   15780
gctcaatatc atagaggagg atttgattag atttcctcat ctatctgggt gggaacttgc   15840
gaaaaccatc attcagtcca ttatctcaga cagcaataac tcatccacag accccattag   15900
cagtggagaa acacgatcat tcacaactca ctttctcaca tatcctaagg ttgggctcct   15960
ctatagtttc ggcgccatcg tgagttatta cttagggaat accattatta ggaccaaaaa   16020
gctagacctc agtcatttta tgtattactt aacaactcaa atccataatt tgccacatcg   16080
ctcgttgagg atacttaagc ccacctttaa acatgttagt gtgatatcaa gactaatgag   16140
tattgatcct cattttcaa tctacatcgg gggtacggca ggtgatcgag ggctttcgga    16200
tgctaccaga ctattccttc gagtggccat ttcttccttc cttcaattta tcaaaaaatg   16260
gatcgtggaa tacaagacag ctattcctct gtgggttata tacccttttgg agggacaaaa   16320 tccagatcca attaatagct ttctacatct gattatagcc ttactgcaaa atgaatcccc   16380
tcaaaacaac atccaattcc aagaagacag aaataatcaa cagttgtccg ataatctagt   16440
ttacatgtgc aagagcactg ccagtaattt cttccatgca tcacttgcct attggaggag   16500
ccggcacaaa ggacggccca aaaatcgatc gaccgaagaa cagacagtta aacccatacc   16560
atatgataat tttcattctg ttaaatgtgc ctcaaaccca ccaagcatcc ccaaatctaa   16620
gtcaggaact caaggttcaa gcgcattttt tgagaaactt gaatatgata agaaagaga    16680 attgccaaca gcttccacac cagccgaaca atccaagacc tatatcaagg ccctatccag   16740
ccgaatttat catggtaaaa caccatccaa tgccgcaaaa gatgattcaa caacctccaa   16800
gggctgcgat tccaaagaag aaaatgccgt tcaagcttca caccgaattg tcctaccatt   16860
ttttacattg tcacagaacg actacagaac tccctcagct aaaaagtcag agtatataac   16920
tgaaatcacc aaactaattc gacaattaaa ggcaattcca gataccactg tatactgtcg   16980
ctttacaggg gttgtatctt caatgcatta taagcttgat gaggttctct gggaattcga   17040
tagtttcaaa actgctgtga ctctagctga aggagaaggg tcaggtgcct tattactact   17100
acaaaaatat aaggtcagaa caatctttt taacactta gctacagagc atagcatcga    17160
ggcagaaata gtttctggga caaccacacc tcgaatgctc cttcctgtaa tggccaaact   17220
tcatgatgat caaataaatg taatattaaa caattctgct agccaggtta ctgatatcac   17280
taaccctgca tggttcactg accagaaatc tagaatcccc acacaagttg agattatgac   17340
tatggatgct gaaacgacag aaaatattaa tcggtcaaaa ttatatgagg ctattcagca   17400
attaattgtt tcacacattg atacaagggg gctaaagatt gttattataa aggttttttt   17460
aagtgatatt gaaggtctcc tgtggcttaa tgaccatctt gcccctttat tcggatccgg   17520
ctatttaatt aaacctatta cttcgagtcc aaagtcaagc gaatggtact tatgtctttc   17580
aaatttcctt tcagcctctc gacgacggcc tcatcagggt catgctacct gtatgcaagt   17640
catccaaaca gcgctacgac tccaagttca aaggagttca tactggctta gccatttagt   17700
gcaatatgct gatattaatt tgcacttgag ttatgttaat ttgggtttcc cttcattgga   17760
aaaggttctt taccatcgat ataacctagt tgattcacgg aagggtccac tggtctcgat   17820
```

```
cctttaccat ttaacacact tgcaagcaga gattagagaa ttagtgtgtg actataatca   17880
gcaacgacaa agtcgaaccc aaacatacca cttcatcaaa acgacaaagg gccggattac   17940
aaaattagtc aatgactacc ttaaatttta tctcgtagtg caagcactga agcataattg   18000
tctttggcag gaagaactca gaacacttcc tgacttaatc aatgtttgca atcgatttta   18060
ccatataagg gactgctcat gtgaagatcg attttaatt caaactcttt acttaacccg    18120
tatgcaagac tcagaagcaa aattaatgga gagattaacc gggtttctag gattgtatcc   18180
taatggtatt aacgcttaag atccccttag aggcatcgca atatgactcc aaacattaaa   18240
tgatattgct gtcaatacat ctacctgacc gagagcaagg tttattataa aaacctata    18300 cacatgactg caatgcgtaa tttataccga aacacagtga gggctgcaca tgcaggttcc   18360
tgttgagctt taaaagatca tgcaatataa aatgatattt gtatactaat catgttagta   18420
ctaactaaca gtactcactg catatactct atcaattaag aaaaattact gtggtttatg   18480
catttaaatg acatcacaga tggatataat atagttaatt cttacctaaa tgttgagtta   18540
tagtaatttg aagttataat tatgattagt gcttatacta taaataatag ctataccaag   18600
tatacacaag aagttatgat tttgtattca aattatattc acaggaactt gtgattaata   18660
ataaaagtct cagttgttgg ttgttgagtt gtaaaactcc cgttaaaaat ttattttcca   18720
cttataacta ataataatca tagatcagta tgagttgagg ctattcaaac cttagaaaaa   18780
ttgtgcgatg ttttttacca tgtcaatctt gatttcaatg atattggagg gcttgtcgat   18840
aaattcagta attaacatta agtcagtgtg gaacctcatt ggatatttga tcgtacacaa   18900 aatatctttta caaaattgtt ttctcttttt tgtgtgtcca                         18940
```

<210> SEQ ID NO 6
<211> LENGTH: 18891
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

```
cggacacaca aaagaaaaa aggttttta agatttttg tgtgcgagta actatgagga       60
agattaacag ttttcctcag tttaaggtat acactgaaat tgagattgag attctcctct   120
ttgctattct gtaactttcc ctggttgtga caattgaatc agttttatct attaccaatt   180
accatcaaca tggtatgtct agtgatcttg ggactcttct tcatctggtt tttcctagag   240
ctctgaatct attttgtgag aagttcatcc aaacgaccca gtgtctgaaa atacaagagg   300 ttccccttttc cgtcaagttt aaggggttgt tttgattgtg tgtagatttt ataatcctag   360
agtgccaagg agttgcgtgt catcattaat tgggaagatc aaggaaacaa tttgttccaa   420
taatatcgta catcttgact aagtcgaaca aggggaagtc gatatggatc gtgggaccag   480
aagaatctgg gtgtcgcaaa atcaaggtga tactgattta gattatcata aaattttgac   540
agctggcctt actgttcaac agggaattgt caggcagaaa ataatttctg tatatcttgt   600
tgataacttg gaggctatgt gtcaattggt aatacaagcc tttgaggccg gaattgattt   660
ccaagaaaat gccgacagct tccttctgat gctttgccta catcatgctt accaaggtga   720
ctataaattg ttcttggaga gcaatgctgt acagtatttg gaaggtcatg gattcaaatt   780
tgagctccgg aagaaggacg gtgtcaatcg gctcgaggaa ttgcttcctg ctgcaacgag   840
tggaaaaaac atcaggcgta cgttggccgc actgcctgaa gaggagacta cagaagcaaa   900
```

```
tgcagggcaa tttctctcat ttgcgagttt gtttcttccc aaactggttg tgggagagaa    960
ggcttgcttg gaaaaagtcc agcgacaaat tcaggttcat gcagaacagg gtttaattca   1020
atatcccact gcatggcaat cagttggaca catgatggta atcttcagat tgatgaggac   1080
taatttcttg attaaatatt tactgatcca ccagggtatg catatggtag ctggccacga   1140
tgccaatgat gctgtcattg ctaattcagt tgctcaggct cgcttttcag gactcctaat   1200
tgtcaaaacc gttcttgatc atattctgca gaaaaccgac caaggagtaa gacttcaccc   1260
tttggcccga acagccaaag tgcgtaatga ggttaatgca tttaaggccg ccctaagctc   1320
acttgctaag catggggaat atgccccttt tgctcgcctt ctcaatctct cgggagttaa   1380
caacctagaa catggtctct acccacagtt atcagcaatt gctcttggag ttgccacagc   1440
acatggtagc acccttgcag gagttaatgt tggtgagcag tatcagcagc ttagagaggc   1500
tgccactgaa gctgagaagc aactccaaca atatgctgag tccagagaac tcgacagcct   1560
aggcctagac gatcaggaaa gaagaatact aatgaacttc catcagaaga aaaatgaaat   1620
tagtttccag cagaccaatg caatggtaac ccttaggaaa gagcgactgg ccaaattaac   1680
agaagctata acgctggcct caagacctaa cctcgggtct agacaagacg acgacaatga   1740
aataccgttc cctgggccta taagcaacaa cccagaccaa gatcatctgg aggatgatcc   1800
tagagactcc agagacacta tcattcctaa tagtgcaatt gaccccgagg atggtgattt   1860
tgaaaattac aatggctatc atgatgatga agttgggacg gcaggtgact tggtcttgtt   1920
cgatcttgac gatcatgagg atgacaataa agcttttgag ctacaggaca gctcaccaca   1980
atcccaaagg gaaatagaga gagaaagatt aattcatcca cccccaggca acaacaagga   2040
cgacaatcgg gcctcagaca acaatcaaca atcagcagat tctgaggaac aagaaggtca   2100
atacaacagg caccgaggcc cagaacgtac gaccgccaat cgaagactct caccagtgca   2160
cgaagaggac acccctatag atcaaggcga tgatgatccc tcaagcccac ctccgctgga   2220
atctgatgat gacgatgcat caagtagcca acaagatccc gattatacag ctgttgcccc   2280
tcctgctcct gtataccgca gtgcagaagc ccacgagcct ccccacaaat cctcgaacga   2340
gccagctgaa acatcacaat gaatgaagaa ccctgatatc ggtcaatcaa agtctatgca   2400
aaaattagaa gagacatatc accatctgct gagaactcaa ggtccatttg aagctatcaa   2460
ttattatcac atgatgaagg atgagccggt aatatttagc actgatgatg ggaaggaata   2520
cacctacccg gattcacttg aggaagccta tcctccatgg ctcaccgaga agaacgact   2580
ggacaatgaa aatcgataca tttacataaa taatcaacag ttcttctggc ctgtcatgag   2640
tcccagagac aaatttcttg caatcttgca gcaccatcag taaccacagc acaaagcgcg   2700
gtccacttcg taaagctaaa tacacttaaa gcttgaccga ttcatctaca aaaactaatc   2760
cattataact tattagtgct acttttctat aagtgattct caatctaagg ccattaagag   2820
tttaagcaat atacatatac acttacaccg gtctatccaa gatgtggctc aatgttctta   2880
atttgaacat agtcataagg ggataaataa tactttatat ttctgattgt ggattgaccc   2940
attctgctta aaatgcttcg cccattaaaa atgtgatcta atagatagcc ctgactagac   3000
caattaagaa aaacatttga tgaagattaa aaccttcatc gccagtaaat gattatattg   3060
tctgtaggca ggtgtttact ccaccttaaa gtcggaaata tcctacctta ggaccattgt   3120
taagaggtgc ataggcatta ccatccttga gaacatgtat aataataaat tgaagatatg   3180
ttcaggccca gaaacaactg gatggatttc tgagcaacta atgacaggta agattccagt   3240
aactgatata ttcattgata ttgataacaa gccagatcaa atggaagtcc ggctcaaacc   3300
```

```
atcatcaagg agctcaacca gaacttgtac aagtagcagt cagacggagg tcaactatgt    3360
acctctcctt aaaaaggttg aggatacatt aactatgcta gtgagtgcaa ccagtcgtca    3420
gaatgctgca atcgaggccc ttgaaaaccg cctcagcaca cttgagagta gcttaaagcc    3480
aatccaagac atgggtaaag tgatttcatc attgaatcgc agttgtgccg aaatggtggc    3540
aaaatatgat cttctagtta tgacaactgg acgggctact tcaaccgcag ctgcagtaga    3600
tgcgtactgg aaagagcaca aacagccacc accagggcca gcgttgtatg aagagaatgc    3660
gcttaaagga aaaatcgatg atccaaacag ctatgtacca gatgctgtgc aggaggctta    3720
caagaacctt gacagtacat cgaccctgac cgaggaaaat tttgggaaac cttatatatc    3780
tgctaaagat ctgaaggaga tcatgtatga tcatctacct ggttttggga ctgcctttca    3840
ccaacttgtt caagtgattt gtaaaatagg aaaggataac aacctcttgg acacaatcca    3900
tgctgagttc caggcaagtc tagcagatgg tgactctccc caatgtgcac tcatacagat    3960
aaccaaaaga gtcccaatct ttcaggatgt gccgcccccg acaatccaca ttagatcccg    4020
tggtgatatc ccacgagcat gccaaaagag tctccgacca gcaccaccat cacccaaaat    4080
tgatcgtggt tgggtttgtt tgtttaagat gcaagatggt aaaacgcttg acttaagat    4140
ctaaggatca agatttattt aacaaggcaa gccacaacct tagatagaac ctcagccaga    4200
ctattgaact attgacgctg ttgatgataa tatataatta atggtcatat ttgaatatga    4260
caacatcttg cttcttgttt tgccttgtat ctctttgagt tggaagatca ttccaaactt    4320
acaaacatgc acaagatgtt atggtttagc aaagaattga taggagtact ggtatataat    4380
gtaaatataa caagtgatga agattaagaa aaaccagtcg gtattttcca gacttggcat    4440
ttcttatctt catcttctaa agtgagatat tttatcatca aaaaatgaga cgcggagtgt    4500
taccaacggc tcctccagca tataatgata ttgcatactc tatgagcata ctcccaaccc    4560
gaccaagtgt catagtcaat gagaccaaat cagatgtact ggcagtgcca ggagcagatg    4620
ttccatcaaa ctccatgaga ccagtggctg atgataacat tgatcactca agccatactc    4680
caagcggagt agcttctgcc tttatattgg aagctaaagt gaatgtaatt tcgggaacaa    4740
aagtcctgat gaagcaaata cctatttggc ttccactggg tgtagctgat cagaagatat    4800
acagctttga ttcaacaaca gccgcaatta tgttggcttc ctacacagtg acacacttcg    4860
ggaagatatc taacccgctg gtacgtgtca acaggctagg cccaggaata cccgatcatc    4920
cgctacgact cctaaggttg ggcaatcagg cattccttca agagtttgtt cttccaccag    4980
tccagcttcc ccagtatttc acatttgatc taacagctct aaagctcatc actcaaccat    5040
tgccagctgc aacctggaca gacgaaactc cagcaggagc agtcaatgct cttcgtcctg    5100
ggctctcact ccatcccaag cttcgtccaa ttcttctacc ggggaagata ggaaagaaag    5160
gtcatgcttc agacttaaca tcacctgaca aaattcaaac aatcatgaat gcaataccgg    5220
acctcaaaat tgtcccgatt gatccaatca agaacatagt tggaattgag gttccagaat    5280
tactagttca aaggctgacc ggcaaaaaac cacaacccaa aaatggccaa ccaattattc    5340
cagttcttct tccgaaatat gttggacttg atcctatatc gccaggggac ttaactatgg    5400
ttatcaccca ggattgtgat tcatgccact ctccagccag ccatccgtat cacatggaca    5460
agcaggatag ttaccaataa tttaaattcc attcgagcta ttattctgct agtaattccg    5520
acgggatcaa tagactaaaa atctgattgt atagaattat aaaagaatca agcagaggca    5580
acagactcac agcttacgcc tagatgacta atattaagga gtttttaat ctaatttcc      5640
```

```
agtcttaagt aataatcatt tcttttgtaa ttaattatgc atttgttaac ttatcggtgc   5700
gagatttcct tgagaacccg gcggggcttc tactatctgt agtaaccaga agagaagttc   5760
aacccagtca aaactaaacc aagcaatatt ctgaatgctc tatagtctat tctaatcaga   5820
ggtataacaa tggctaagat ttcaatgact cgttaacaat cgctagtaat tttaatctcc   5880
agattaagaa aaagatatac gatgaagatt aaggcgacaa cgagtcgaaa cttcatctct   5940
tttaaagatc taacattatc tgttccaaag tcatacaagg acacattcaa atcagggatt   6000
gtaagctgct atttcttacc tccccaaatc acctatacaa catgggtca ggatatcaac    6060 ttctccaatt gcctcgggaa cgttttcgta aaacttcgtt cttagtatgg gtaatcatcc   6120
tcttccagcg agcaatctcc atgccgcttg gtatagtgac aaatagcact ctcaaagcaa   6180
cagaaattga tcaattggtt tgtcgggaca actgtcatc aaccagtcag ctcaagtctg    6240
tggggctgaa tctggaagga aatggaattg caaccgatgt cccatcagca acaaaacgct   6300
ggggattccg ttcaggtgtg cctcccaagg tggtcagcta tgaagccgga gaatgggcag   6360
aaaattgcta caatctggag atcaaaaagt cagacggaag tgagtgcctc cctctccctc   6420
ccgacggtgt acggggattc cctagatgtc gctatgtcca caaagttcaa ggaacaggtc   6480
cttgtcccgg tgacttagct ttccataaaa atggggcttt tttcttgtat gatagattgg   6540
cctcaactgt catctaccgt gggacaactt ttgctgaagg tgtcatagct tttttaattc   6600
tgtcagagcc caagaagcat ttttggaagg ctacaccagc tcatgaaccg gtgaacacaa   6660
cagatgattc cacaagctac tacatgaccc tgacactcag ctacgagatg tcaaattttg   6720
gaggcgagga agtaacacc cttttttaagg tagacaacca cacatatgtg caactagatc    6780
gtccacacac tccgcagttc cttgttcagc tcaatgaaac acttcgaaga aataatcgcc   6840
ttagcaacag tacaggaga ttgacttgga cattggatcc caaaattgaa ccagatgttg     6900
gtgagtgggc cttctgggaa actaaaaaa cttttcccaa caacttcatg gagaaaactt     6960
gcatttccaa attctatcaa cccacaccaa caactcctca gatcagagcc cggcgggaac   7020
tgtccaagga aaaattagct accacccacc caccaacaac tccgagctgg ttccaacgga   7080
ttcccctcca gtggtttcag tgctcactgc aggacggaca gaggaaatgt cgacccaagg   7140
tctaactaac ggagagacaa tcacaggttt caccgcgaac ccaatgacaa ccaccattgc   7200
cccaagtcca accatgacaa gcgaggttga taacaatgta ccaagtgaac aaccgaacaa   7260
cacagcatcc attgaagact cccccccatc ggcaagcaac gagacaattg accactccga   7320
aatgaattcg atccaaggct cgaacaactc cgcccagagc ccacagacca aggccacgcc   7380
agcgcccaca gcatccccga tgaccctgga cccgcaagag acggccaaca gcagcaaacc   7440
aggaaccagc ccaggaagcg cagccgaacc aagtcagccc ggactcacta taaatacaat   7500
aagtaaggta gctgattcac tgagtccac caggaaacaa aagcgatcgg ttcgacaaaa     7560
caccgctaat aaatgtaacc cagatcttca ctattggaca gctgttgatg aggggcagc    7620 agtaggattg gcatggattc catattttgg acctgcagca gaaggcatct acattgaggg   7680
tgtaatgcat aatcagaatg ggcttatttg cgggctacgt cagctagcca atgaaactac   7740
ccaggctctt caattattc tgcgggccac aacagaactg aggacttact cacttcttaa    7800
cagaaaagct attgattttc ttcttcaacg atggggaggt acctgtcgaa tcctaggacc   7860
atcttgttgc attgagccac atgattggac aaaaaatatt actgatgaaa ttaaccaaat   7920
taaacatgac tttattgaca atcccctacc agaccacgga gatgatctta atctatggac   7980
aggttggaga caatggatcc cggctggaat tgggattatt ggagttataa ttgctataat   8040
```

```
agccctactt tgtatatgta agattttgtg ttgatttatt ctgagatctg agagaaaaaa    8100
atctcagggt tactctaagg agaaatatta tttttaaaat ttacttaaat gctgaccact    8160
tatcttaaat gagcaattaa taatatgttt ttctgcttct ttgcttgatt tacaatatga    8220
tatttctctt aataatgatt aatatattaa gaaaaactta tgacgaagat taaaggggag    8280
gatcgttaac gggaaaatct cccatctcgt tcgtcgaagc cacgttggtg gtgcttgcag    8340
ctgagaacaa ctccagagat tgtaggtaga aaggaccagc atttataggt aggggtcaga    8400
aagcaacaat agccataaaa ggagagcctg acattgctat ttaatatcct agaacctgat    8460
ttctaggttc tagttgtaca atccggatga tggagcattc aagagaacgg ggtagatcta    8520
gcaacatgcg acataatagc cgggaaccat acgaaaatcc atcaaggtct cgctcattat    8580
ctcgggaccc taatcaggtt gatcgtaggc agcctcgaag tgcatcccaa attcgtgttc    8640
cgaatctgtt ccatcggaaa aagactgatg cactcatagt tcctccggct cccaaagata    8700
tatgcccaac actcaaaaaa ggattcctct gcgatagtaa attttgcaaa aaagatcacc    8760
aattggatag cttaaatgat catgaattac tactgctaat tgcaagaaga acatgtggaa    8820
ttatcgagag caattcgcag attacatccc caaaagatat gcggttagcg aatccaacag    8880
ctgaagactt ctcacaaggt aatagtccta aattaacact tgcagtcctt cttcaaattg    8940
ctgaacattg gcaaccaga gacctaaggc aaattgagga ctctaaactt agagctcttt    9000
taaccctttg tgccgtatta acaaggaaat tttctaaatc ccaactgggt cttctatgtg    9060
agacccacct acggcatgag ggcctcggac aggaccaagc tgattctgta ttagaggtct    9120
accaaagact ccacagtgat aaaggaggga attttgaggc tgccctgtgg caacaatggg    9180
accgacagtc gttaataatg ttcatctctg cttttctcaa cattgctctc cagacacctt    9240
gtgaaagttc tagtgtcgta gtctcaggtc ttgccacatt gtacccagca caagacaatt    9300
ctacaccatc cgaggcaact aatgatacca cctggtcaag tacagttgaa tagaaaacca    9360
ctggagctat ttttccacga ttgctctcag tcaataaatt aatatagata taatacgact    9420
tcggtgtgca attgtcaagg gttccatttg gtaataatga ttcttaaaac aatctactat    9480
cgtaattatc gatggatcta ccctatttga cggtacatga cttgaatgta ataaggtaag    9540
ttggtatctg aggtattttg tctagagtat actcaaaatc gtatgtctag caaattatca    9600
atagcaaagt taaattctcc taacctcata ttttgatcaa gtaatcatga ttttatggta    9660
attctttgca gattatcggt ttaatcttta ttaagaaaaa atcatgattg tagacaattt    9720
actggtagtc cctgggtatc caagtttatg aacagagcta gagagaattt gctacttccg    9780
aggtataact ttattatttg ctacttcgaa tgcctaaaac cagtaatgca ggatgaagat    9840
taattgcgga ggaatcagga attcaacttt agttccttaa ggcctcgtct gaatcttcat    9900
cagttagtaa gttcttttat agaagtcatt agcttctaag gtgattatat tttagtatta    9960
aattttgtta attgcttgct ataaagttga agtgtcaat gcttaaatga acatttcttt    10020
gaagctgaca tacgaataca tcatatcata tgaaaacatc gcaattagag cgtccttgaa    10080
gtctggcatt gacagtcacc aggctgttct cagtagtctg tccttggaag ctcttgggga    10140
gacaagaaga ggtcccagag agtcccaaca ggttggcata aggtcattaa caccagcata    10200
gtcagctcga tcaagactgt aagcgagtcg attgcaacta aaaagattat ttcttgttgt    10260
ttaaacaaat tccttttgtg tgagacaccc tcaaggcaca agatggctaa agccacaggc    10320
cgatacaatc tcgtgccccc aaagaaagat atggaaaagg gagtgatttt tagtgatctt    10380
```

```
tgtaatttct tgattactca aaccctgcaa ggttggaagg tttattgggc aggaattgag   10440
tttgatgtaa gtcaaaaagg catggctctt ctgacaagac tcaaaacaaa tgactttgct   10500
cctgcctggg cgatgacaag aaatctcttc ccacatctgt tccaaaaccc aaattcggtt   10560
attcaatctc ccatctgggc tttgagggta attttggcag ccggattgca ggatcagttg   10620
ttagaccatt cattggttga gccattgaca ggggctctcg gtctaatttc tgattggctc   10680
ctaactacaa cgtcaacaca tttcaatctt cgtactagaa gcgtaaagga ccagcttagt   10740
tttcgtatgt tatctttgat caggtcaaac atcttgcagt tcatcaacaa gcttgacgcc   10800
ctgcatgttg tcaattacaa tggtttactc agtagtattg agatcgggac ttctacacac   10860
acaatcatta taactcgtac aaatatgggt tttctcgtgg aagttcagga gcctgacaaa   10920
tcagctatga attctaagcg cccaggacca gtcaagttct cattacttca tgagtctgcc   10980
ttcaaacctt tcactcgtgt tccacaatct gggatgcaat cattaataat ggagttcaac   11040
agtttgttgg caatttaaca aggtgatctt aaaataagta catgaatgag aattagttgt   11100
gggtcttacc tagcattgtt gagttagcta tctaatctat tttcactaat tgcattgagc   11160
actgctagta ggtttgcacc acgttaaaga ttcagagtgt atgaattgtg cagatttaaa   11220
cttgggtttt gccttatgct tcataggtgg tcttttttaaa atggagatta tcagcatttc   11280
ttcaatggga ggagttagca atcagaaatt ggagataaat ggacatcggg atagaacaat   11340
gcctaactat tgggcggctt tcattttttaa atgtgtatat aaccaatctt ttcctatctt   11400
tgcttatatt ggtgtaactt tactttaata acatgtcaat gctatactgt taagagaagg   11460
tctgaggaag attaagaaaa aggtctcgtg ttcacttggt tgccgtcaag tatcctgtgg   11520 ttttttttcta cctaacttcc tcatgccata tggctaccca gcatacccag tacccggatg   11580
cacgtttatc ttcacctata gtcctggatc aatgtgattt ggtaactcga gcatgtgggt   11640
tatattcatc ttattctcta aatcctcagc taaggcaatg taaattacca aaacatatat   11700
atcgacttaa gttcgacaca atagtatcca aattcctaag tgatacacct gtagcaacac   11760
tgccgataga ctatttagta ccaattctcc tgcgttccct aacggggcac ggtgataggc   11820 cgttgaccccc gacttgtaat caattccttg atggaattat taattacact cttcatgatg   11880
cagcctttct tgattactat ctcaaggcaa caggtgcaca ggaccatttg acaaacatta   11940
caactagaga gaagcttaaa aacgaaattc taaacaatga ttatgtccat caattgttct   12000
tctggcatga cctgtctatt ttggctcgac gtgggcgtct gaatcgcggg aacaaccgtt   12060
caacctggtt tgttcatgat gaattcattg atattttagg atatggcgat tatattttt   12120 ggaaaatacc tttatcatta ttaccagtta ctatagacgg ggtcccacac gcggcaactg   12180
actggtatca accgactctt tttaaagaat ccatcctagg gcacagccaa atcctatctg   12240
tgtcgacagc tgaaatacta attatgtgta aagatattat cacctgtagg tttaatacat   12300
cactgattgc atccattgca aaattagagg atgtagatgt gtctgattat cctgacccga   12360
gtgatattct taagatatac aatgctggag actatgtaat atctattctt ggctcagaag   12420
gttataagat aataaagtac cttgaaccac tttgtttggc caaaatccaa ctttgctcta   12480
aattcacaga aagaaaaggt cgtttcctca cacagatgca tttatcagta ataaatgatc   12540
ttcgggagtt gatttctaac cgcaggttaa aggactatca gcaagagaag attagggatt   12600
ttcacaaaat attattacaa ttgcaattat ctcctcaaca gttttgtgaa ttattctctg   12660
ttcaaaaaca ttgggggcat ccaatttttac atagtgagaa agctatacaa aaagtaaaac   12720
ggcatgcaac catccttaag gctctcagac ctaatgtcat ttttgagaca tattgtgtat   12780
```

```
tcaagtacaa tattgccaag cactatttcg acagccaagg aacttggtac agtgtaatct    12840
cagacaggaa tttaactcca ggactcaact ccttcataaa acgtaatcac tttccttcac    12900
tacccatgat taaggatctt ctatgggaat tctatcatct taatcaccct ccgttattct    12960
ctacaaaggt gattagtgac ttaagtattt tcatcaagga tagggccaca gctgttgaac    13020
agacatgttg ggatgcagtc tttgaaccca atgtgctagg ttacaatcct ccaaacaaat    13080
tctccactaa aagggtgccg gaacaatttc tagaacagga ggattttca atcgaaagtg    13140 tcctgaatta tgcacaggaa ttacattatt tattaccaca gaataggaat ttttccttt    13200 ctcttaaaga aaaagaatta aatattggac gaacatttgg taagctacca tatctcacac    13260
ggaatgtcca aactttatgt gaggctctgt tagcagatgg actggctaag gccttcccca    13320
gtaacatgat ggtagtaact gaacgtgaac aaaaagagag ccttcttcat caggcatcat    13380
ggcaccacac cagtgatgat tttggagaga atgctaccgt tcgagggagt agttttgtaa    13440
ctgatttaga gaagtacaat cttgcatttc gctatgagtt cactgcacca tttattgagt    13500
actgcaacca ttgctatggt gtgcgtaatg tctttaattg gatgcattat ttaatcccgc    13560
agtgttacat gcatgtaagt gattattata atccgcctca caatgttaat cttagcaatc    13620
gagaatatcc tcctgaaggc ccgagttcgt accgagggca cttaggaggc atagagggat    13680
tacaacaaaa actgtggacg agtatatcct gtgcacaaat ctccttagtg gaaattaaaa    13740
ctggttttaa gttacgatca gcggtcatgg gagacaatca gtgtataacc gtattgtctg    13800 ttttccact tgaaacagac cctgaagagc aggagcaaag cgccgaagac aatgctgcaa    13860
gagtagcagc aagtcttgca aaagtaacca gtgcatgtgg gatctttctt aaaccagaag    13920
agacattcgt acactcaggt ttcatttatt tcggaaaaaa acaatatctc aatggtgtac    13980
aattaccgca atcactcaaa acagcagcaa gaatggcgcc actctctgat gctatattcg    14040
atgatctaca aggaacactt gccagtattg gaactgcctt cgaacgtgct atatcggaaa    14100
cgcgacatat cctcccatgt cgtattgtag cagctttcca tacgtatttc gccgttcgga    14160
ttttacaata tcaccatctt ggatttaata aaggcatcga tttagggcag ttgtcactta    14220
gtaaaccatt agactatggg actattactc taacattggc ggttccacaa gtccttgggg    14280
gattgtcttt tctaaatcca gaaaagtgtt tttatcgaaa cttcggagat cctgtgactt    14340
ctggactttt ccagctacgg gtgtacctag aaatggttaa catgaaagac ctatttatc    14400 cattaatatc gaaaaatcca ggaaattgta gtgccattga ttttgtctta aatccatccg    14460
gattaaatgt tccaggatca caagacttga catccttttt gcgacagatc gttaggcgta    14520
gtattacact aactgcaaga aataagttaa ttaacactct cttccatgcc tctgctgatt    14580
tggaagatga gatggtttgt aaatggctcc tttcatcaaa ccctgtcatg agtcgctttg    14640
cagcggatat ttttccagg acacctagtg gtaaacgtct ccaaatatta ggttatcttg    14700
aagggaccag gactctattg gcctccaaaa tcataaacaa caacagtgag acacctgtac    14760
ttgataagct gaggaagatc accctacaaa gatggaatct gtggttcagt tatttggacc    14820
attgtgacca attactagca gatgctctac agaaaattag ttgcacagtg gatttggccc    14880
agattttgcg tgagtataca tggtcacaca tcttagaggg tagaccattg atcggagcga    14940
cattaccatg tatggtggag caattcaaag ttaagtggct aagacaatat gaaccttgtc    15000
cagaatgcct caacaaaaaa ggctcaaatg cttatgtctc agttgcagtc aaagatcaag    15060
tggtcagtgc ttggcctaat acttctcgaa taagttggac aataggagt ggtgtcccct    15120
```

```
atatagggtc aagaaccgag gataaaatcg gacagcctgc aatcaagccg cgatgccctt    15180
catctgccct caaggaggct atagaattag catcaaggct cacttgggtt acacaaggaa    15240
gttctaatag tgaacaatta atccggcctt tcttagaagc gagagtcaac cttagtgtca    15300
gtgaagtcct gcaaatgaca ccatcacatt attcaggaaa tattgtccat cgatataacg    15360
accaatatag cccgcactca tttatggcga atcgcatgag caatactgcg acccgtctca    15420
tagtgtcaac taatacactt ggagaatttt caggtggagg gcaggccgcc agggatagca    15480
atataatttt ccagaatgtt ataaatttag cagttgccct ttatgatatt agattccgga    15540
atacgaacac ctctgatata aggcataata gggctcatct tcacctgaca gagtgctgta    15600
ctaaagaggt cccggcccag tatttgacat atacaagtgc actcaatctg gatttaagcc    15660
gttatcgtga taatgaacta atatatgact caaatccact gaggggagga ttgaactgca    15720
atttaacaat ggatagtcct ttagtgaagg gtcctaggct taacatgatt gaagatgatc    15780
ttctccgctt tccacacctt tctggatggg agttagcgaa aacggtggta caatccatca    15840
tctcagacaa tagcaactca tcaacagatc caatcagtag cggagaaaca cgctctttca    15900
caactcattt tctcacttac cctcagattg gccttcttta cagtttcggg gcagtattat    15960
gcttttatct aggcaatact atcctatgga ctaaaaaact tgattatgaa cagtttctat    16020
attatttgca taaccagctg cacaacttac ctcatcgagc actccgtgtt tttaaaccaa    16080
catttaagca tgccagtgtg atgtcccgat taatggaaat tgattccaac ttctcaattt    16140
atattggcgg gacatctgga gatcgagggc tgtctgatgc tgctcgactg tttcttcgga    16200
cagcaatcgc gagttttta caatttctta aaagctggat catcgatcgc caaaagacaa    16260
ttcctttatg gatagtatat ccgcttgaag gtcaacagcc ggaatccatc aatgaatttc    16320
tacataaaat ttttggtctg ctcaaacaag gccccaaaaa tattccaaag gaggtcagca    16380
ttcaaaatga tggacatttg gatttggcag aaaataatta tgtttacaat agtaagagca    16440
ctgctagtaa tttcttccat gcatccttag cttactggag aagtaggaaa tctcggaaaa    16500
ctcaagacca taatgatttc tcaagagggg atggaacact tacagaaccc gtgtgtaagt    16560
tctcaagcaa tcatcagtca gatgaaaagt actacaatgt gacatgtgga aagtcaccga    16620
agccgcaaga acgcaaagac ttctcgcaat acagactcag caataacggg caaacaatga    16680
gtaatcatcg taagaaaggg aagttccaca agtggaatcc ctgcaaagtg ttaatggaga    16740
gtcaaagggg aactgttcta aaagagggtg actactttca aaacaatact ccaccaacag    16800
atgatgtatc aagtcctcac cgactcattc taccatttt taaattggga atcacaaacc    16860
atgcacatga tcaagatgcc caagaattga taaatcaaaa tattaaacag tacctacatc    16920
agctaaggtc tatgttggac accactatat attgtagatt cacagggatt gtctcatcca    16980
tgcattacaa attggacgaa gttcttctag aatacaatgg tttcgattca gctatcacat    17040
tagctgaagg tgaggggtca ggggctctat tactttttgca gaaatatagt acaaggttat    17100
tatttttgaa cacattggca acagaacaca gtatagagtc agaagttgta tcaggttttt    17160
ctactccgag aatgttgtta ccaataatgc aaaaggttca tgaaggacaa gtcactgtta    17220
tcttaaataa ttcagcaagt cagataactg acataactag ctcaatgtgg ttaagtaatc    17280
aaaaatataa tctaccttgt caagttgaaa tcattacgat ggatgctgaa acaacagaga    17340
acttaaacag gtcccaactc taccgagcag tatataactt aatacttgat cacattgatc    17400
cgcagtatct caaggtggtg gtactcaaag tatttctgag tgatatagaa ggaatattat    17460
ggattaatga ttacttggct ccattattcg gggctggtta cttgattaaa ccgattacat    17520
```

-continued

```
caagtgcccg gtcaagtgaa tggtacctttt gcttatcaaa tttgatatct actaacagga    17580
gatcggccca tcagactcac aaggcatgtc ttggtgttat cagagatgct ttgcaagcac    17640
aagtccagcg aggcgtgtac tggttgagtc acatcgcaca gtatgctaca aagaatctcc    17700
attgtgaata catatgcctt ggtttcccac ctctagaaaa ggtcctatat cacaggtata    17760
atctagttga tactggactc ggtccattgt cgtcagttat tagacattta actaacctcc    17820
aggcagagat acgagactta gtattagatt ataccctgat gagagagagt cgcactcaaa    17880
cgtaccattt tattaagact gcaaaaggca gaatcacaaa gttagtcaat gactttctga    17940
agttttcttt aattgtccag gcactcaaaa ataattcttc ttggtatact gagcttaaaa    18000
aattacctga ggtgattaat gtgtgtaatc gattttatca tactcacagt tgcgaatgtc    18060
aggaaaaatt ctttgtccag acgctttatt tacaacgcct acgcgatgca gaaatcaagc    18120
taattgaacg ccttaccggg ttaatgcgat tttatccaga aggttaata tattccaatc    18180 acacataggt actaaatcat catagtatga ggaataaaat aatgataatt cctgacgaca    18240
gttttagttc cgattctaag tatatcggaa gagagtatgc caatcttaat tattaaaggt    18300
aacaagctat tagttattac ttattgataa gaataaactt tatcatagcg taacacatca    18360
taactttata gcgattttgc atttctaatc ctagtattta ttagaatgta ctatcagaga    18420
aatgacccca gttcctatct ttaaataatg attgtgtgta ttaaattatt agtttattag    18480
gtttatgagt tggttacaca gtgagtatta gtaattgagg attatgtaga taggtaatct    18540
aacactgaat cacccatctg atgtcaccat atccaaatat tgtgctagtc gcatttaaac    18600
atgctatctt cagttaagta acatagactg aaaatgctaa gaagagattg gagtaaaagt    18660
ataaaataaa tttaattaaa cttcaaagtg attaaatgat aatgatcttg ggaactcgat    18720
atgacctcaa gtcaaaaata atgtcaatat aattgtttag taatatgagt tataatgtga    18780
attttgataa ctaactagct ttagtagtta agatcaaatg caaacattct aagaatgtta    18840
agcgcacaca aaaacattat aaaaaaccaa ttttttcctt tttgtgtgtc c              18891
```

<210> SEQ ID NO 7
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: a, c, t, g, unknown or other

<400> SEQUENCE: 7 tctctccna                                                                  9

HUMAN ADENOVIRUS SEROTYPE 5 VECTORS CONTAINING E1 AND E2B DELETIONS ENCODING THE EBOLA VIRUS GLYCOPROTEIN

CROSS REFERENCE

This application is a U.S. National Phase Application under 35 U.S.C. § 371 of International Application No. PCT/US2016/012482, filed Jan. 7, 2016, which claims priority to U.S. Provisional Application No. 62/101,968, filed Jan. 9, 2015, which are incorporated herein by reference in their entirety.

SEQUENCE LISTING

The instant application contains a Sequence Listing which has been submitted electronically in ASCII format and is hereby incorporated by reference in its entirety. Said ASCII copy, created on Jan. 25, 2016, is named 39891-715601_SL.txt and is 166,679 bytes in size.

BACKGROUND OF THE INVENTION

Ebola viruses, members of the family Filoviridae, are associated with outbreaks of highly lethal hemorrhagic fever in humans and nonhuman primates. The Bundibugyo ebolavirus, Zaire ebolavirus, and Sudan ebolavirus have all been associated with large outbreaks in Africa. The severity of the current Ebola outbreak in West Africa as highlighted the medical need for long-lasting and compressive Ebola vaccine that covers many strains for at-risk populations that do not have routine access to medical care. While some recombinant adenovirus-based vaccines have conferred good protection against multiple strains of Ebola after a single immunization, their efficacy if often impaired in human by pre-existing immunity to the adenovirus as discussed above.

Of particular interest are Ad5-based immunotherapeutics that have been repeatedly used in humans to induce robust T cell-mediated immune (CMI) responses, all while maintaining an extensive safety profile. In addition, Ad5 vectors can be reliably manufactured in large quantities and are stable for storage and delivery for outpatient administration. Nonetheless, a major obstacle to the use of first generation (E1-deleted) Ad5-based vectors is the high frequency of pre-existing anti-adenovirus type 5 neutralizing antibodies. These antibodies can be present in a potential vaccine receiver due to either prior wild type adenovirus infection and/or induction of adenovirus neutralizing antibodies by repeated injections with Ad5-based vaccines, resulting in inadequate immune stimulation against the target EA.

A major problem with adenovirus vectors has been their inability to sustain long-term transgene expression due largely to the host immune response that eliminates the adenovirus vector and virally transduced cells in immune-competent subjects. Thus, the Use of first generation adenovirus vector vaccines is severely limited by preexisting or induced immunity of vaccines to adenovirus (Ad) (Yang, et al. J Virol 77/799-803 (2003); Casimiro, et al. J Virol 77/6305-6313 (2003)). One group reported that a preponderance of humans have antibody against adenovirus type 5 (Ad5), the most widely used serotype for gene transfer vectors, and that two-thirds of humans studied have lymphoproliferative responses against Ad (Chirmule, et al. Gene Ther 6/1574-1583 (1999)). In another study, an adenovirus vector vaccine carrying an HIV-1 envelope gene was incapable of reimmunizing a primed immune response using non-adjuvanted DNA (Barouch, et al. J. Virol 77/8729-8735 (2003)). Another group reported that non-human primates having pre-existing immunity against Ad5 due to a single immunization with Ad5 were unable to generate transgene-specific antibodies to HIV proteins, as well as altering the overall T-cell responses (McCoy, et al. J. Virol 81/6594-6604 (2007)).

There are numerous mechanisms by which preexisting immunity interferes with adenovirus vector vaccines but one major concern is the presence of neutralizing antibody followed by cell mediated immune elimination of Ad infected antigen harboring cells. Both of these responses can be directed to several Ad proteins. One approach is to increase the vector vaccine dose. Although there is evidence that increasing vaccine doses can increase induction of desired cell mediated immune (CMI) responses in Ad-immune animals (Barouch, et al. J. Virol 77/8729-8735 (2003)), it often results in unacceptable adverse effects in animals and humans. When using first generation Ad5 vector vaccines, one option can be to use the approach of a heterologous prime-boost regimen, using naked (non-vectored) DNA as the priming vaccination, followed by an Ad5 vector immunization. This protocol may result in a subsequent immune response against Ad5 such that one cannot administer a further re-immunization (boost) with the same (or a different) adenovirus vector vaccine that utilizes the same viral backbone. Therefore, with the current First Generation of Ad5 vectors, using this approach can also abrogate any further use of Ad5 vector immunization in the Ad5 immunized vaccinee.

First generation (E1-deleted) adenovirus vector vaccines express Ad late genes, albeit at a decreased level and over a longer time period than wild-type Ad virus (Nevins, et al. Cell 26/213-220 (1981); Gaynor, et al. Cell 33/683-693 (1983); Yang, et al. J Virol 70/7209-7212 (1996)). When using First Generation adenovirus vectors for immunization, vaccine antigens are presented to the immune system simultaneously with highly immunogenic Ad capsid proteins. The major problem with these adenovirus vectors is that the immune responses generated are less likely to be directed to the desired vaccine epitopes (McMichael, et al. Nat Rev Immunol 2/283-291 (2002)) and more likely to be directed to the adenovirus-derived antigens, i.e., antigenic competition. There is controversy about the mechanism by which First Generation adenovirus vectors are potent immunogens. It has been hypothesized that the composition of the Ad capsid or a toxic effect of viral genes creates generalized inflammation resulting in a nonspecific immune stimulatory effect. The E1 proteins of Ad act to inhibit inflammation following infection (Schaack, et al. PNAS 101/3124-3129 (2004)). Removal of the gene segments for these proteins, which is the case for First Generation adenovirus vectors, results in increased levels of inflammation (Schaack, et al. PNAS 101/3124-3129 (2004); Schaack, et al. Viral Immunol 18/79-88 (2005)).

Thus, it is apparent that there remains a need for a more effective Ebola vaccine vector candidate. Ad vaccine vectors that allow for long-term immune response, multiple vaccinations and vaccinations in individuals with preexisting immunity to Ad. The present invention provides this and other advantages.

SUMMARY OF THE INVENTION

The present invention relates to methods and adenovirus vectors for generating immune responses against target antigens, in particular, those related to Ebola cells. As such, the present invention further provides nucleic acid sequences that encode one or more target antigens of interest, or fragments or variants thereof. As such, the present invention provides polynucleotides that encode target antigens from any source as described further herein, vectors comprising such polynucleotides and host cells transformed or transfected with such expression vectors.

Attempts to overcome anti-Ad immunity have included use of alternative Ad serotypes and/or alternations in the Ad5 viral capsid protein each with limited success and the potential for significantly altering biodistribution of the resultant vaccines. Therefore, a completely novel approach was attempted by further reducing the expression of viral proteins from the E1 deleted Ad5 vectors, proteins known to be targets of pre-existing Ad immunity. Specifically, a novel recombinant Ad5 platform has been described with deletions in the early 1 (E1) gene region and additional deletions in the early 2b (E2b) gene region (Ad5 [E1-, E2b-]). Deletion of the E2b region (that encodes DNA polymerase and the pre-terminal protein) results in decreased viral DNA replication and late phase viral protein expression. This vector platform has been previously reported to successfully induce CMI responses in animal models of cancer and infectious disease and more importantly, this recombinant Ad5 gene delivery platform overcomes the barrier of Ad5 immunity and can be used in the setting of pre-existing and/or vector-induced Ad immunity thus enabling multiple homologous administrations of the vaccine.

The present disclosure provides compositions, methods and kits for generating an immune response against one or multiple Ebola antigens in an individual A composition comprising a replication defective adenovirus vector comprising a nucleic acid sequence encoding an Ebola virus antigen, wherein the Ebola virus antigen encoding sequence has 70%-100% sequence identity to a sequence selected from the group consisting of SEQ ID NO:1, SEQ ID NO:2, SEQ ID NO:4, SEQ ID NO:5, SEQ ID NO:6, and combinations thereof.

In one aspect, a composition is provided comprising a recombinant nucleic acid vector, wherein the recombinant nucleic acid vector comprises a replication defective adenovirus vector; and wherein upon administration to a human, the composition is capable of inducing an immune response directed towards cells expressing an Ebola virus antigen antigen in said human, wherein the immune response comprises cell mediated immunity.

In some embodiments, the replication defective adenovirus vector comprises a replication defective adenovirus 5 vector. In some embodiments, the replication defective adenovirus vector comprises a deletion in an E2b gene region. In some embodiments, the Ebola virus antigen comprises a modification of 25 or less amino acids.

In one aspect, a composition is provided comprising a recombinant replication defective adenovirus 5 vector having a deletion in an E2b gene region comprising a sequence encoding an Ebola virus antigen, wherein the Ebola virus antigen comprises a modification of 25 or less amino acids. In some embodiments, the Ebola virus antigen comprises a modification 20, 15, 10, 5, or less amino acids. In some embodiments, the Ebola virus antigen comprises a modification in 2, 3, or 4 amino acids. In some embodiments, the Ebola virus antigen comprises a modification in 1 amino acid. In some embodiments, the replication defective adenovirus vector comprises a deletion in an E1 gene region. In some embodiments, the replication defective adenovirus vector comprises a deletion in an E3 gene region. In some embodiments, the replication defective adenovirus vector comprises a deletion in an E4 gene region. In some embodiments, the Ebola virus is selected from the group consisting of EBOV, SUDV, TAFV, BDBV, RESTV, and any combination thereof. In some embodiments, the Ebola virus antigen comprises a sequence with at least 80% sequence identity to a sequence selected from the group consisting of SEQ ID NO:1, SEQ ID NO:2, SEQ ID NO:4, SEQ ID NO:5, SEQ ID NO:6, and combinations thereof. In some embodiments, the Ebola virus antigen is encoded by a sequence with at least 90% sequence identity to a sequence selected from the group consisting of SEQ ID NO:1, SEQ ID NO:2, SEQ ID NO:4, SEQ ID NO:5, SEQ ID NO:6, and combinations thereof. In some embodiments, the Ebola virus antigen is encoded by a sequence with at least 95% sequence identity to a sequence selected from the group consisting of SEQ ID NO:1, SEQ ID NO:2, SEQ ID NO:4, SEQ ID NO:5, SEQ ID NO:6, and combinations thereof. In some embodiments, the Ebola virus antigen is encoded by a sequence with at least 97% sequence identity to a sequence selected from the group consisting of SEQ ID NO:1, SEQ ID NO:2, SEQ ID NO:4, SEQ ID NO:5, SEQ ID NO:6, and combinations thereof. In some embodiments, the Ebola virus antigen is encoded by a sequence with at least 99% sequence identity to a sequence selected from the group consisting of SEQ ID NO:1, SEQ ID NO:2, SEQ ID NO:4, SEQ ID NO:5, SEQ ID NO:6, and combinations thereof. In some embodiments, the Ebola virus antigen is encoded by a sequence with 100% sequence identity to a sequence selected from the group consisting of SEQ ID NO:1, SEQ ID NO:2, SEQ ID NO:4, SEQ ID NO:5, SEQ ID NO:6, and combinations thereof. In some embodiments, the recombinant nucleic acid vector is capable of effecting overexpression of the Ebola virus antigen in transfected cells. In some embodiments, the recombinant nucleic acid vector is capable of inducing a specific immune response against cells expressing the Ebola virus antigen in a human that is at least 2, 3, 4, 5, 6, 7, 8, 9, 10, 15, 20, or 25 fold over basal. In some embodiments, the human has an inverse Ad5 neutralizing antibody titer of greater than 50, 75, 100, 125, 150, 175, or 200. In some embodiments, the human has an inverse Ad5 neutralizing antibody titer of greater than 250, 500, 750, 1000, 1500, 2000, 2500, 3000, 3500, 4000, 4500, or 4767. In some embodiments, the immune response is measured as an Ebola virus antigen specific antibody response. In some embodiments, the immune response is measured as a neutralizing Ebola virus antigen specific antibody response. In some embodiments, the immune response is measured as Ebola virus antigen specific cell-mediated immunity (CMI). In some embodiments, the immune response is measured as Ebola virus antigen antigen specific IFN-γ secretion. In some embodiments, the immune response is measured as Ebola virus antigen antigen specific IL-2 secretion. In some embodiments, the immune response against the Ebola virus antigen is measured by an ELISspot assay. In some embodiments, the Ebola virus antigen specific CMI is greater than 25, 50, 75, 100, 150, 200, 250, or 300 IFN-γ spot forming cells (SFC) per $10^6$ peripheral blood mononuclear cells (PBMC). In some embodiments, the immune response is measured by T cell lysis of CAP-1 pulsed antigen-presenting cells, allogeneic Ebola virus antigen expressing cells from an Ebola-infected cell line or from an autologous Ebola-infected cell. In some embodiments, the composition further comprises an immunogenic component. In some embodiments, the immunogenic component comprises a cytokine selected from the group consisting of IFN-γ, TNFα IL-2, IL-8, IL-12, IL-18, IL-7, IL-3, IL-4, IL-5, IL-6, IL-9, IL-10, and IL-13. In some embodiments, the immunogenic component is selected from the group consisting of IL-7, a nucleic acid encoding IL-7, a protein with substantial identity to IL-7, and a nucleic acid encoding a protein with substantial identity to IL-7.

In one aspect, a vial is provided comprising a composition consisting of a therapeutic solution of a volume in the range of 0.8-1.2 mL, the therapeutic solution comprising 2.5-7.5× $10^{11}$ virus particles; wherein the virus particles comprise a replication defective adenovirus comprising a nucleic acid sequence encoding an Ebola virus antigen.

In some embodiments, the recombinant nucleic acid vector is capable of effecting overexpression of the Ebola virus antigen in transfected cells. In some embodiments, the in transfected cells are E.C7 cells. In some embodiments, the replication defective adenovirus vector comprises a replication defective adenovirus 5 vector. In some embodiments, the replication defective adenovirus comprises a nucleic acid sequence encoding a protein that is capable of inducing a specific immune response against Ebola virus antigen expressing cells in a human. In some embodiments, the immune response is measured as an Ebola virus antigen specific antibody response. In some embodiments, the immune response is measured as a neutralizing Ebola virus antigen specific antibody response. In some embodiments, the immune response is measured as Ebola virus antigen specific cell-mediated immunity (CMI). In some embodiments, the immune response is measured as Ebola virus antigen specific IFN-γ secretion. In some embodiments, the immune response is measured as Ebola virus antigen specific IL-2 secretion. In some embodiments, the immune response against the Ebola virus antigen is measured by an ELISspot assay In some embodiments, the Ebola virus antigen specific CMI is greater than 25, 50, 75, 100, 150, 200, 250, or 300 IFN-γ spot forming cells (SFC) per $10^6$ peripheral blood mononuclear cells (PBMC). In some embodiments, the immune response is measured by T cell lysis of CAP-1 pulsed antigen-presenting cells, allogeneic Ebola virus antigen expressing cells from an Ebola-infected cell line, or from an autologous Ebola-infected cell. In some embodiments, the therapeutic solution comprises at least $1.0×10^{11}$, $1.5×10^{11}$, $2.0×10^{11}$, $2.5×10^{11}$, $3.0×10^{11}$, $3.5×10^{11}$, $4.0×10^{11}$, $4.5×10^{11}$, $4.8×10^{11}$, $4.9×10^{11}$, $4.95×10^{11}$, or $4.99×10^{11}$ virus particles comprising the recombinant nucleic acid vector. In some embodiments, the therapeutic solution comprises at most $7.0×10^{11}$, $6.5×10^{11}$, $6.0×10^{11}$, $5.5×10^{11}$, $5.2×10^{11}$, $5.1×10^{11}$, $5.05×10^{11}$, or $5.01×10^{11}$, virus particles comprising the recombinant nucleic acid vector. In some embodiments, the therapeutic solution comprises $1.0-7.0×10^{11}$ virus particles comprising the recombinant nucleic acid vector. In some embodiments, the therapeutic solution comprises $4.5-5.5×10^{11}$ virus particles comprising the recombinant nucleic acid vector. In some embodiments, the therapeutic solution comprises $4.8-5.2×10^{11}$ virus particles comprising the recombinant nucleic acid vector. In some embodiments, the therapeutic solution comprises $4.9-5.1×10^{11}$ virus particles comprising the recombinant nucleic acid vector. In some embodiments, the therapeutic solution comprises $4.95-5.05×10^{11}$ virus particles comprising the recombinant nucleic acid vector. In some embodiments, the therapeutic solution comprises $4.99-5.01×10^{11}$ virus particles comprising the recombinant nucleic acid vector. In some embodiments, the vial further comprises an immunogenic component. In some embodiments, the immunogenic component comprises a cytokine selected from the group of IFN-γ, TNFα IL-2, IL-8, IL-12, IL-18, IL-7, IL-3, IL-4, IL-5, IL-6, IL-9, IL-10, and IL-13. In some embodiments, the immunogenic component is selected from the group consisting of IL-7, a nucleic acid encoding IL-7, a protein with substantial identity to IL-7, and a nucleic acid encoding a protein with substantial identity to IL-7.

In one aspect, a method of generating an immune response against an Ebola virus antigen in a human is provided, the method comprising administering to the human a composition described herein.

In one aspect, a method of generating an immune response against an Ebola virus antigen in a human is provided, the method comprising administering to the human the composition a vial described herein.

In some embodiments, the administering step is repeated at least once. In some embodiments, the administering step is repeated after about 3 weeks following a previous administering step. In some embodiments, the administering step is repeated after about 3 months following a previous administering step. In some embodiments, the administering step is repeated twice.

In one aspect, method of generating an immune response against an Ebola virus antigen in a human is provided comprising: a first phase of treatment comprising administering to the human a first composition comprising a first replication defective adenovirus vector encoding an Ebola virus antigen that induces an immune response against cells expressing the Ebola virus antigen antigen in the human; and a subsequent second phase of treatment comprising administering to the human a second composition comprising a second replication defective adenovirus vector encoding an Ebola virus antigen that induces an immune response against cells expressing the Ebola virus antigen in the human.

In one aspect, method of treatment is provided comprising: selecting a first phase of treatment and a second phase of treatment; during the first phase, administering to a human, a total of n times, a first composition comprising a first replication defective adenovirus vector encoding an Ebola virus antigen induces an immune response against cells expressing the Ebola virus antigen antigen in the human; and during the second phase of treatment, administering the human, a total of m times, a second composition comprising a second replication defective adenovirus vector encoding an Ebola virus antigen that induces an immune response against cells expressing the Ebola virus antigen in the human.

In some embodiments, n is greater than 1. In some embodiments, n is 3. In some embodiments, m is greater than 1. In some embodiments, m is 3. In some embodiments, the first phase is at least 2, 3, 4, 5, 6, 7, or 8 weeks. In some embodiments, the second phase is at least 2, 3, 4, 5, 6, 7, or 8 months. In some embodiments, the second phase starts 3-16 weeks after first phase ends. In some embodiments, in the first phase two administrations of the replication defective adenovirus are at least 18 days apart. In some embodiments, in the first phase two administrations of the replication defective adenovirus are about 21 days apart. In some embodiments, in the first phase two administrations of the replication defective adenovirus are at most 24 days apart. In some embodiments, in the second phase two administrations of the replication defective adenovirus are at least 10 weeks apart. In some embodiments, in the second phase two administrations of the replication defective adenovirus are about 13 weeks apart. In some embodiments, in the second phase two administrations of the replication defective adenovirus are at most 16 weeks apart.

In one aspect, method of treatment is provided comprising: selecting a first phase and a second phase of treatment; during the first phase, administering to a human a total of 3 times, in about 3 week intervals, a first composition comprising a first replication defective adenovirus vector encoding an Ebola virus antigen that induces an immune response against cells expressing the Ebola virus antigen in the human; and during the second phase, administering to said human a total of 3 times, in about 3 month intervals, a second composition comprising a second replication defective adenovirus vector encoding an an Ebola virus antigen that induces an immune response against cells expressing an Ebola virus antigen in the human; wherein the second phase starts about 3 months after the end of the first phase.

In some embodiments, the Ebola virus antigen encoded by the first replication defective adenovirus vector is the same as the Ebola virus antigen encoded by the second replication defective adenovirus vector. In some embodiments, the Ebola virus antigen encoded by the first replication defective adenovirus vector is different from the Ebola virus antigen encoded by the second replication defective adenovirus vector. In some embodiments, the first replication defective adenovirus vector and the second replication defective adenovirus vector are the same. In some embodiments, the first replication defective adenovirus vector comprises a replication defective adenovirus 5 vector. In some embodiments, the second replication defective adenovirus vector comprises a replication defective adenovirus 5 vector. In some embodiments, the first replication defective adenovirus vector comprises a sequence with 60%-100% sequence identity to a sequence selected from the group consisting of SEQ ID NO:1, SEQ ID NO:2, SEQ ID NO:4, SEQ ID NO:5, SEQ ID NO:6, and any combination thereof In some embodiments, the second replication defective adenovirus vector comprises a sequence with 60%-100% sequence identity to a sequence selected from the group consisting of SEQ ID NO:1, SEQ ID NO:2, SEQ ID NO:4, SEQ ID NO:5, SEQ ID NO:6, and any combination thereof. In some embodiments, the Ebola virus antigen encoded by the first or the second replication defective adenovirus vector comprises a modification of 25 amino acids or less. In some embodiments, the Ebola virus antigen encoded by the first or the second replication defective adenovirus vector comprises a modification of 20, 15, 10, or 5 amino acids or less. In some embodiments, the Ebola virus antigen encoded by the first or the second replication defective adenovirus vector comprises a modification of 1 amino acid. In some embodiments, the first replication defective adenovirus vector comprises a deletion in an E2b gene region. In some embodiments, the first replication defective adenovirus vector further comprises a deletion in an E1 gene region. In some embodiments, the first replication defective adenovirus vector further comprises a deletion in an E3 gene region. In some embodiments, the first replication defective adenovirus vector further comprises a deletion in an E4 gene region. In some embodiments, the second replication defective adenovirus vector comprises a deletion in an E2b gene region. In some embodiments, the second replication defective adenovirus vector further comprises a deletion in an E1 gene region. In some embodiments, the second replication defective adenovirus vector further comprises a deletion in an E3 gene region. In some embodiments, the second replication defective adenovirus vector further comprises a deletion in an E4 gene region. In some embodiments, the first composition, the second composition, or both, comprises at least $1.0 \times 10^{11}$, $1.5 \times 10^{11}$, $2.0 \times 10^{11}$, $2.5 \times 10^{11}$, $3.0 \times 10^{11}$, $3.5 \times 10^{11}$, $4.0 \times 10^{11}$, $4.5 \times 10^{11}$, $4.8 \times 10^{11}$, $4.9 \times 10^{11}$, $4.95 \times 10^{11}$, or $4.99 \times 10^{11}$ virus particles comprising the recombinant nucleic acid vector. In some embodiments, the first composition, the second composition, or both, comprises at most $7.0 \times 10^{11}$, $6.5 \times 10^{11}$, $6.0 \times 10^{11}$, $5.5 \times 10^{11}$, $5.2 \times 10^{11}$, $5.1 \times 10^{11}$, $5.05 \times 10^{11}$, or $5.01 \times 10^{11}$ virus particles. In some embodiments, the first composition, the second composition, or both, comprises $1.0$-$7.0 \times 10^{11}$ virus particles. In some embodiments, the first composition, the second composition, or both, comprises $4.5$-$5.5 \times 10^{11}$ virus particles. In some embodiments, the first composition, the second composition, or both, comprises $4.8$-$5.2 \times 10^{11}$ virus particles. In some embodiments, the first composition, the second composition, or both, comprises $4.9$-$5.1 \times 10^{11}$ virus particles. In some embodiments, the first composition, the second composition, or both, comprises $4.95$-$5.05 \times 10^{11}$ virus particles. In some embodiments, the first composition, the second composition, or both, comprises $4.99$-$5.01 \times 10^{11}$ virus particles. In some embodiments, the immune response to the Ebola virus antigen is increased by at least 2, 3, 4, 5, 6, 7, 8, 9, 10, 15, 20, or 25 fold. In some embodiments, the immune response is measured as an Ebola virus antigen specific antibody response. In some embodiments, the immune response is measured as a neutralizing Ebola virus antigen specific antibody response. In some embodiments, the immune response is measured as Ebola virus antigen specific cell-mediated immunity (CMI). In some embodiments, the immune response is measured as Ebola virus antigen specific IFN-γ secretion. In some embodiments, the immune response is measured as Ebola virus antigen specific IL-2 secretion. In some embodiments, the immune response against the Ebola virus antigen is measured by ELISspot assay. In some embodiments, the Ebola virus antigen specific CMI is greater than 25, 50, 75, 100, 150, 200, 250, or 300 IFN-γ spot forming cells (SFC) per $10^6$ peripheral blood mononuclear cells (PBMC). In some embodiments, the immune response is measured by T cell lysis of CAP-1 pulsed antigen-presenting cells, allogeneic Ebola virus antigen expressing cells from an Ebola-infected cell line or from an autologous Ebola-infected cell. In some embodiments, a first or a second replication defective adenovirus infects dendritic cells in the human, and wherein the infected dendritic cells present the Ebola virus antigen, thereby inducing the immune response. In some embodiments, the administering steps comprise subcutaneous administration. In some embodiments, the human carries an inverse Ad5 neutralizing antibody titer that is of greater than 50, 75, 100, 125, 150, 160, 175, 200, 225, 250, 275, or 300 prior to the administering step. In some embodiments, the human has an inverse Ad5 neutralizing antibody titer of greater than 250, 500, 750, 1000, 1500, 2000, 2500, 3000, 3500, 4000, 4500, or 4767. In some embodiments, the human is not concurrently being treated by any one of steroids, corticosteroids, immunosuppressive agents, and immunotherapy. In some embodiments, the human has not been treated by any one of steroids, corticosteroids, immunosuppressive agents, and immunotherapy prior to the administering step. In some embodiments, the human does not have an autoimmune disease. In some embodiments, the human does not have inflammatory bowel disease, systemic lupus erythematosus, ankylosing spondylitis, scleroderma, multiple sclerosis, viral hepatitis, or HIV. In some embodiments, the human has autoimmune related thyroid disease or vitiligo. In some embodiments, the human has cells expressing the Ebola virus antigen. In some embodiments, the human does not have cells expressing the Ebola virus antigen. In some embodiments, the human has at least one, two, or three symptoms of an Ebola virus infection. In some embodiments, the human has received a therapy prior to the administering. In some embodiments, prior to the first phase, the human has received at least one medication selected from the group consisting of: rehydration with oral or intravenous fluids, blood products, immune therapies, drug or therapies for specific symptoms such as fever, fatigue, muscle pain, headache and sore throat, vomiting, diarrhoea, rash, impaired kidney and liver function, and internal and external bleeding. In some embodiments, the human concurrently receives chemotherapy or radiation therapy treatment. In some embodiments, the human concurrently receives a therapy comprising the administration of at least one medication of the group consisting of fluoropyrimidine, irinotecan, oxaliplatin, bevacizumab, Capecitabine, Mitomycin, Regorafenib, cetuxinab, panitumumab, and acetinophen. In some embodiments, the human comprises cells overexpressing the Ebola virus antigen. In some embodiments, the cells overexpressing the Ebola virus antigen overexpress the Ebola virus antigen by at least 2, 3, 4, 5, 10, 15, or 20 times over a baseline expression of an Ebola virus antigen in a non-infected cell In some embodiments, the cells overexpressing the Ebola virus antigen comprise Ebola-infected cells. In some embodiments, the cells overexpressing the Ebola virus antigen comprise immune cells. In some embodiments, the cells overexpressing the Ebola virus antigen comprise blood cells. In some embodiments, the cells overexpressing the Ebola virus antigen comprise epithelium cells. In some embodiments, the Ebola virus antigen is an antigen from EBOV, SUDV, TAFV, BDBV, RESTV, or any combination thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 8 exemplifies four Ad5 [E1-, E2b-]-EA based vaccines that have been generated.

DETAILED DESCRIPTION OF THE INVENTION

Figure 1:
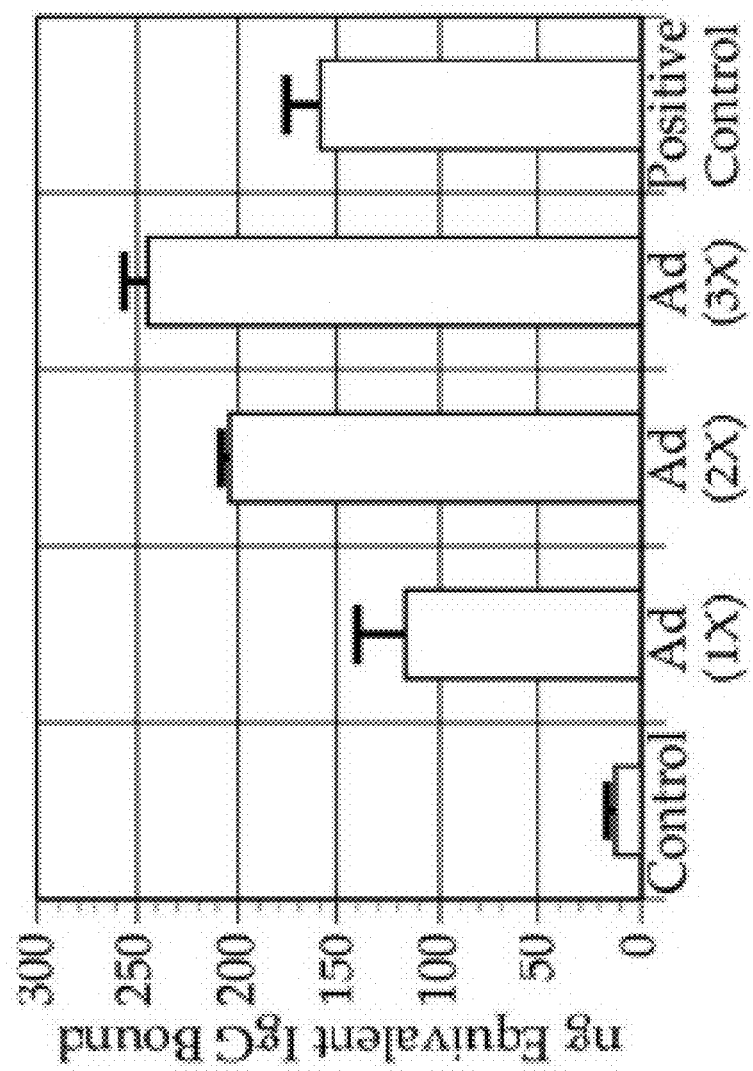
FIG. 1 exemplifies a bar graph showing antibody levels from mice immunized with Ad5-null (empty vector). Mice were immunized three times with Ad5-null viral particles (VPs) at 14 day intervals. Anti-Ad antibody (neutralizing antibody) levels increased after each immunization.

The following passages describe different aspects of the invention in greater detail. Each aspect of the invention may be combined with any other aspect or aspects of the invention unless clearly indicated to the contrary. In particular, any feature indicated as being preferred or advantageous may be combined with any other feature of features indicated as being preferred or advantageous. As used herein, unless otherwise indicated, the article "a" means one or more unless explicitly otherwise provided for. As used herein, unless otherwise indicated, terms such as "contain," "containing," "include," "including," and the like mean "comprising." As used herein, unless otherwise indicated, the term "or" can be conjunctive or disjunctive. As used herein, unless otherwise indicated, any embodiment can be combined with any other embodiment.

It has been discovered that Ad5 [E1-, E2b-] vectors are not only are safer than, but appear to be superior to Ad5 [E1-] vectors in regard to induction of antigen specific immune responses, making them much better suitable as a platform to deliver Ebola vaccines that can result in a clinical response. In other cases, immune induction may take months. Ad5 [E1-, E2b-] vectors not only are safer than, but appear to be superior to Ad5 [E1-] vectors in regard to induction of antigen specific immune responses, making them much better suitable as a platform to deliver Ebola vaccines that can result in a clinical response.

Various embodiments of the invention, by taking advantage of the new Ad5 [E1-, E2b-] vector system in delivering a long sought-after need for a develop a therapeutic vaccine against Ebola, overcome barriers found with other Ad5 systems and permit the immunization of people who have previously been exposed to Ad5. In other embodiments of the invention, by taking advantage of the new Ad5 [E1-, E2b-] vector system in delivering a long sought-after need for a develop a therapeutic vaccine against Ebola, overcome barriers found with other Ad5 systems and permit the immunization of people who have previously been exposed to Ad5. In other embodiments of the invention, by taking advantage of the new Ad5 [E1-, E2b-] vector system in delivering a long sought-after need for a develop a therapeutic vaccine against Ebola, overcome barriers found with other Ad5 systems and permit the immunization of people who have previously been exposed to Ad5.

An "adenovirus" (Ad) refers to non-enveloped DNA viruses from the family Adenoviridae. These viruses can be found in, but are not limited to, human, avian, bovine, porcine and canine species. The present invention contemplates the use of any Ad from any of the four genera of the family Adenoviridae (e.g., Aviadenovirus, Mastadenovirus, Atadenovirus and Siadenovirus) as the basis of an E2b deleted virus vector, or vector containing other deletions as described herein. In addition, several serotypes are found in each species. Ad also pertains to genetic derivatives of any of these viral serotypes, including but not limited to, genetic mutations, deletions or transpositions.

A "helper adenovirus" or "helper virus" refers to an Ad that can supply viral functions that a particular host cell cannot (the host may provide Ad gene products such as E1 proteins). This virus is used to supply, in trans, functions (e.g., proteins) that are lacking in a second virus, or helper dependent virus (e.g., a gutted or gutless virus, or a virus deleted for a particular region such as E2b or other region as described herein); the first replication-incompetent virus is said to "help" the second, helper dependent virus thereby permitting the production of the second viral genome in a cell.

An "adenovirus 5 null (Ad5-null)" refers to a non-replicating Ad that does not contain any heterologous nucleic acid sequences for expression.

A "first generation adenovirus" refers to an Ad that has the early region 1 (E1) deleted. In additional cases, the early region 3 (E3) may also be deleted.

"Gutted" or "gutless" refers to an Ad vector that has been deleted of all viral coding regions.

"Transfection" refers to the introduction of foreign nucleic acid into eukaryotic cells. Exemplary means of transfection include calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

"Stable transfection" or "stably transfected" refers to the introduction and integration of foreign nucleic acid, DNA or RNA, into the genome of the transfected cell. The term "stable transfectant" refers to a cell which has stably integrated foreign DNA into the genomic DNA.

A "reporter gene" indicates a nucleotide sequence that encodes a reporter molecule (e.g., an enzyme). A "reporter molecule" is detectable in any of a variety of detection systems, including, but not limited to, enzyme-based detection assays (e.g., ELISA, histochemical assays), fluorescent, radioactive, and luminescent systems. The E. coli β-galactosidase gene, green fluorescent protein (GFP), the human placental alkaline phosphatase gene, the chloramphenicol acetyltransferase (CAT) gene; and other reporter genes may be employed.

A "heterologous sequence" refers to a nucleotide sequence that is ligated to, or is manipulated to become ligated to, a nucleic acid sequence to which it is not ligated in nature, or to which it is ligated at a different location in nature. Heterologous nucleic acid may include a naturally occurring nucleotide sequence or some modification relative to the naturally occurring sequence.

A "transgene" refers to any gene coding region, either natural or heterologous nucleic acid sequences or fused homologous or heterologous nucleic acid sequences, introduced into cells or a genome of subject. Transgenes may be carried on any viral vector used to introduce transgenes to the cells of the subject.

A "second generation adenovirus" refers to an Ad that has all or parts of the E1, E2, E3, and, in certain embodiments, E4 DNA gene sequences deleted (removed) from the virus.

A "subject" refers to any animal, including, but not limited to, humans, non-human primates (e.g., rhesus or other types of macaques), mice, pigs, horses, donkeys, cows, sheep, rats and fowls.

An "immunogenic fragment" refers to a fragment of a polypeptide that is specifically recognized (i.e., specifically bound) by a B-cell and/or T-cell surface antigen receptor resulting in a generation of an immune response specifically against a fragment.

A "target antigen" or "target protein" refers to a molecule, such as a protein, against which an immune response is to be directed.

"E2b deleted" refers to a DNA sequence mutated in such a way so as to prevent expression and/or function of at least one E2b gene product. Thus, in certain embodiments, "E2b deleted" is used in relation to a specific DNA sequence that is deleted (removed) from an Ad genome. E2b deleted or "containing a deletion within an E2b region" refers to a deletion of at least one base pair within an E2b region of an Ad genome. Thus, in certain embodiments, more than one base pair is deleted and in further embodiments, at least 20, 30, 40, 50, 60, 70, 80, 90, 100, 110, 120, 130, 140, or 150 base pairs are deleted. In another embodiment, a deletion is of more than 150, 160, 170, 180, 190, 200, 250, or 300 base pairs within an E2b region of an Ad genome. An E2b deletion may be a deletion that prevents expression and/or function of at least one E2b gene product and therefore, encompasses deletions within exons of encoding portions of E2b-specific proteins as well as deletions within promoter and leader sequences. In certain embodiments, an E2b deletion is a deletion that prevents expression and/or function of one or both a DNA polymerase and a preterminal protein of an E2b region. In a further embodiment, "E2b deleted" refers to one or more point mutations in a DNA sequence of this region of an Ad genome such that one or more encoded proteins is non-functional. Such mutations include residues that are replaced with a different residue leading to a change in an amino acid sequence that result in a nonfunctional protein.

"E1-deleted" refers to a DNA sequence that is mutated in such a way so as to prevent expression and/or function of at least one E1 gene product. Thus, in certain embodiments, "E1 deleted" is used in relation to a specific DNA sequence that is deleted (removed) from the Ad genome. E1 deleted or "containing a deletion within the E1 region" refers to a deletion of at least one base pair within the E1 region of the Ad genome. Thus, in certain embodiments, more than one base pair is deleted and in further embodiments, at least 20, 30, 40, 50, 60, 70, 80, 90, 100, 110, 120, 130, 140, or 150 base pairs are deleted. In another embodiment, the deletion is of more than 150, 160, 170, 180, 190, 200, 250, or 300 base pairs within the E1 region of the Ad genome. An E1 deletion may be a deletion that prevents expression and/or function of at least one E1 gene product and therefore, encompasses deletions within exons of encoding portions of E1-specific proteins as well as deletions within promoter and leader sequences. In certain embodiments, an E1 deletion is a deletion that prevents expression and/or function of one or both of a trans-acting transcriptional regulatory factor of the E1 region. In a further embodiment, "E1 deleted" refers to one or more point mutations in the DNA sequence of this region of an Ad genome such that one or more encoded proteins is non-functional. Such mutations include residues that are replaced with a different residue leading to a change in the amino acid sequence that result in a nonfunctional protein.

"Generating an immune response" or "inducing an immune response" refers to a statistically significant change, e.g., increase or decrease, in the number of one or more immune cells (T-cells, B-cells, antigen-presenting cells, dendritic cells, neutrophils, and the like) or in the activity of one or more of these immune cells (CTL activity, HTL activity, cytokine secretion, change in profile of cytokine secretion, etc.).

The terms "nucleic acid" and "polynucleotide" are used essentially interchangeably herein. Polynucleotides of the invention may be single-stranded (coding or antisense) or double-stranded, and may be DNA (e.g., genomic, cDNA, or synthetic) or RNA molecules. RNA molecules may include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials. An isolated polynucleotide, as used herein, means that a polynucleotide is substantially away from other coding sequences. For example, an isolated DNA molecule as used herein does not contain large portions of unrelated coding DNA, such as large chromosomal fragments or other functional genes or polypeptide coding regions. This refers to the DNA molecule as originally isolated, and does not exclude genes or coding regions later added to the segment recombinantly in the laboratory.

As will be understood by those skilled in the art, the polynucleotides of this invention can include genomic sequences, extra-genomic and plasmid-encoded sequences and smaller engineered gene segments that express, or may be adapted to express target antigens as described herein, fragments of antigens, peptides and the like. Such segments may be naturally isolated, or modified synthetically by the hand of man.

When comparing polynucleotide sequences, two sequences are "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned. Optimal alignment of sequences for comparison may be conducted using the Megalign program in the Lasergene suite of bioinformatics software (DNASTAR, Inc., Madison, Wis.), using default parameters. This program embodies several alignment schemes.

Alternatively, optimal alignment of sequences for comparison may be conducted by the local identity algorithm of Smith and Waterman, Add. APL. Math 2:482 (1981), by the identity alignment algorithm of Needleman and Wunsch, J. Mol. Biol. 48:443 (1970), by the search for similarity methods of Pearson and Lipman, Proc. Natl. Acad. Sci. USA 85: 2444 (1988), by computerized implementations of these algorithms (GAP, BESTFIT, BLAST, FASTA, and TFASTA), or by inspection.

One example of algorithms that are suitable for determining percent sequence identity and sequence similarity are the BLAST and BLAST 2.0 algorithms. BLAST and BLAST 2.0 can be used, for example with the parameters described herein, to determine percent sequence identity for the polynucleotides of the invention. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program uses as defaults a word length (W) of 11, and expectation (E) of 10, and the BLOSUM62 scoring matrix alignments, (B) of 50, expectation (E) of 10, M=5, N=−4 and a comparison of both strands.

The "percentage of sequence identity" can be determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence and multiplying the results by 100 to yield the percentage of sequence identity.

It will be appreciated by those of ordinary skill in the art that, as a result of the degeneracy of the genetic code, there are many nucleotide sequences that encode a particular antigen of interest, or fragment thereof, as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

As would be understood by the skilled artisan upon reading the present disclosure, other regions of the Ad genome can be deleted. Thus to be "deleted" in a particular region of the Ad genome, as used herein, refers to a specific DNA sequence that is mutated in such a way so as to prevent expression and/or function of at least one gene product encoded by that region. In certain embodiments, to be "deleted" in a particular region refers to a specific DNA sequence that is deleted (removed) from the Ad genome in such a way so as to prevent the expression and/or the function encoded by that region (e.g., E2b functions of DNA polymerase or preterminal protein function). "Deleted" or "containing a deletion" within a particular region refers to a deletion of at least one base pair within that region of the Ad genome. Thus, in certain embodiments, more than one base pair is deleted and in further embodiments, at least 20, 30, 40, 50, 60, 70, 80, 90, 100, 110, 120, 130, 140, or 150 base pairs are deleted from a particular region. In another embodiment, the deletion is more than 150, 160, 170, 180, 190, 200, 250, or 300 base pairs within a particular region of the Ad genome. These deletions are such that expression and/or function of the gene product encoded by the region is prevented. Thus deletions encompass deletions within exons encoding portions of proteins as well as deletions within promoter and leader sequences. In a further embodiment, "deleted" in a particular region of the Ad genome refers to one or more point mutations in the DNA sequence of this region of an Ad genome such that one or more encoded proteins is non-functional. Such mutations include residues that are replaced with a different residue leading to a change in the amino acid sequence that result in a nonfunctional protein. Deletions or mutations in the Ad genome can be within one or more of E1a, E1b, E2a, E2b, E3, E4, L1, L2, L3, L4, L5, TP, POL, IV, and VA regions. The deleted adenovirus vectors of the present invention can be generated using recombinant techniques.

As would be recognized by the skilled artisan, the adenovirus vectors for use in the present invention can be successfully grown to high titers using an appropriate packaging cell line that constitutively expresses E2b gene products and products of any of the necessary genes that may have been deleted. In certain embodiments, HEK-293-derived cells that not only constitutively express the E1 and DNA polymerase proteins, but also the Ad-preterminal protein, can be used. In one embodiment, E.C7 cells are used to successfully grow high titer stocks of the adenovirus vectors.

In order to delete critical genes from self-propagating adenovirus vectors, the proteins encoded by the targeted genes can first be coexpressed in HEK-293 cells, or similar, along with the E1 proteins. For example, only those proteins which are non-toxic when coexpressed constitutively (or toxic proteins inducibly-expressed) can be selectively utilized. Coexpression in HEK-293 cells of the E1 and E4 genes is possible. The E1 and protein IX genes, a virion structural protein, can be coexpressed. Further coexpression of the E1, E4, and protein IX genes is also possible. The E1 and 100 k genes can be successfully expressed in transcomplementing cell lines, as can E1 and protease genes.

Cell lines coexpressing E1 and E2b gene products for use in growing high titers of E2b deleted Ad particles are described. The E2b region encodes viral replication proteins, which are essential for Ad genome replication. Useful cell lines constitutively express the approximately 140 kDa Ad-DNA polymerase and/or the approximately 90 kDa preterminal protein. In particular, cell lines that have high-level, constitutive coexpression of the E1, DNA polymerase, and preterminal proteins, without toxicity (e.g., E.C7), are desirable for use in propagating Ad for use in multiple vaccinations. These cell lines permit the propagation of adenovirus vectors deleted for the E1, DNA polymerase, and preterminal proteins.

Further information on viral delivery systems can be found in Fisher-Hoch et al., Proc. Natl. Acad. Sci. USA 86:317-321, 1989; Flexner et al., Ann. N.Y. Acad. Sci. 569:86-103, 1989; Flexner et al., Vaccine 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, Biotechniques 6:616-627, 1988; Rosenfeld et al., Science 252:431-434, 1991; Kolls et al., Proc. Natl. Acad. Sci. USA 91:215-219, 1994; Kass-Eisler et al., Proc. Natl. Acad. Sci. USA 90:11498-11502, 1993; Guzman et al., Circulation 88:2838-2848, 1993; and Guzman et al., Cir. Res. 73:1202-1207, 1993.

Heterologous Nucleic Acid

The adenovirus vectors of the present invention typically comprise modified or heterologous nucleic acid sequences that encode one or more target antigens of interest, or variants, fragments or fusions thereof, against which it is desired to generate an immune response. In some embodiments, the adenovirus vectors of the present invention comprise modified or heterologous nucleic acid sequences that encode one or more proteins, variants thereof, fusions thereof, or fragments thereof, that can modulate the immune response. In a further embodiment of the invention, the adenovirus vector of the present invention encodes one or more antibodies against specific antigens, such as anthrax protective antigen, permitting passive immunotherapy. In certain embodiments, the adenovirus vectors of the present invention comprise modified or heterologous nucleic acid sequences encoding one or more proteins having therapeutic effect (e.g., anti-viral, anti-bacterial, anti-parasitic, or anti-Ebola function). Thus the present invention provides the Second Generation E2b deleted adenovirus vectors that comprise a heterologous nucleic acid sequence. In some embodiments, the heterologous modified or nucleic acid sequence is an EBOV, SUDV, TAFV, BDBV, or RESTV antigen, a variant thereof, a fragment thereof, or a combination thereof. In some embodiments, the heterologous modified or nucleic acid sequence is a combination or fusion of an EBOV, SUDV, TAFV, BDBV, or RESTV antigen, a variant thereof, a fragment thereof, or a combination thereof. In some embodiments, the heterologous modified or nucleic acid sequence is a combination or fusion of an EBOV, SUDV, TAFV, BDBV, or RESTV antigen, a variant thereof, a fragment thereof, or a combination thereof.

In particular, the present invention provides an improved adenovirus (Ad)-based vaccine such that multiple vaccinations against one or more antigenic target entity can be achieved. In some embodiments, the improved adenovirus (Ad)-based vaccine comprises a replication defective adenovirus carrying a target antigen, a fragment, a variant or a variant fragment thereof, such as Ad5 [E1-, E2b-]-SEQ. ID. NO.:1, Ad5 [E1-, E2b-]-SEQ. ID. NO.:2, Ad5 [E1-, E2b-]-SEQ. ID. NO.:4, Ad5 [E1-, E2b-]-SEQ. ID. NO.:5, Ad5 [E1-, E2b-]-SEQ. ID. NO.:6. In some embodiments, the improved adenovirus (Ad)-based vaccine comprises a replication defective adenovirus carrying a target antigen, a fragment, a variant or a variant fragment thereof, such as Ad5 [E1-, E2b-]-GP, Ad5 [E1-, E2b-]-NP, Ad5 [E1-, E2b-]-VP40, Ad5 [E1-, E2b-]-VP35, Ad5 [E1-, E2b-]-VP30, and Ad5 [E1-, E2b-]-VP24. Variants and/or fragments of target antigens, for example EBOV, SUDV, TAFV, BDBV, or RESTV antigens, such as GP, NP, VP40, VP35, VP30, or VP24, can be selected based on a variety of factors, including immunogenic potential. Accordingly, a mutant of an EBOV, SUDV, TAFV, BDBV, or RESTV antigen, such as a mutant of a GP, NP, VP40, VP35, VP30, or VP24 antigen is utilized in various embodiments of the invention for its increased capability to raise an immune response relative to the wild type form. Importantly, vaccination can be performed in the presence of preexisting immunity to the Ad and/or administered to subjects previously immunized multiple times with the adenovirus vector of the present invention or other adenovirus vectors. The adenovirus vectors of the invention can be administered to subjects multiple times to induce an immune response against an antigen of interest, for example an EBOV, SUDV, TAFV, BDBV, or RESTV antigen, such as GP, NP, VP40, VP35, VP30, or VP24, including but not limited to, the production of antibodies and cell-mediated immune responses against one or more target antigens of EBOV, SUDV, TAFV, BDBV, or RESTV, such as GP, NP, VP40, VP35, VP30, or VP24 and/or one or more Ebola virus strains, as described herein and publically available on GenBank.

The immunogenic polypeptide may be RNA sequence from Ebola Zaire (GenBank: KJ660347.2) or a fragment thereof. In some embodiments, the replication defective adenovirus vector comprises a sequence encoding a nucleotide or polypeptide with at least 70%, 75%, 80%, 85%, 90%, 95%, 98%, 99%, 99.5%, or 99.9% identity to the immunogenic polypeptide.

In some embodiments, the sequence encoding the immunogenic polypeptide comprises the sequence of SEQ. ID. NO.:1. In some embodiments, the sequence encoding the immunogenic nucleotide or polypeptide comprises a sequence with at least 70%, 75%, 80%, 85%, 90%, 95%, 98%, 99%, 99.5%, or 99.9% identity to SEQ. ID. NO.:1 or a sequence generated from SEQ. ID. NO.:1 by alternative codon replacements optimized for the human genome. In some embodiments, the immunogenic polypeptide encoded by the adenovirus vectors described herein comprising up to 1, 2, 3, 4, 5, 6, 7, 8, 9, 10, 11, 12, 13, 14, 15, 16, 17, 18, 19, 20, 25, 30, 35, 40, or more point mutations, such as single amino acid substitutions or deletions, as compared to a wild-type GenBank sequence (Zaire KJ660347).

In some embodiments, the sequence encoding the immunogenic polypeptide comprises the sequence of SEQ. ID. NO.:2. In some embodiments, the sequence encoding the immunogenic nucleotide or polypeptide comprises a sequence with at least 70%, 75%, 80%, 85%, 90%, 95%, 98%, 99%, 99.5%, or 99.9% identity to SEQ. ID. NO.:2 or a sequence generated from SEQ. ID. NO.:2 by alternative codon replacements optimized for the human genome. In some embodiments, the immunogenic polypeptide encoded by the adenovirus vectors described herein comprising up to 1, 2, 3, 4, 5, 6, 7, 8, 9, 10, 11, 12, 13, 14, 15, 16, 17, 18, 19, 20, 25, 30, 35, 40, or more point mutations, such as single amino acid substitutions or deletions, as compared to a wild-type GenBank sequence (Sudan KC545392.1).

In some embodiments, the sequence encoding the immunogenic polypeptide comprises the sequence of SEQ. ID. NO.:4. In some embodiments, the sequence encoding the immunogenic nucleotide or polypeptide comprises a sequence with at least 70%, 75%, 80%, 85%, 90%, 95%, 98%, 99%, 99.5%, or 99.9% identity to SEQ. ID. NO.:4 or a sequence generated from SEQ. ID. NO.:4 by alternative codon replacements optimized for the human genome. In some embodiments, the immunogenic polypeptide encoded by the adenovirus vectors described herein comprising up to 1, 2, 3, 4, 5, 6, 7, 8, 9, 10, 11, 12, 13, 14, 15, 16, 17, 18, 19, 20, 25, 30, 35, 40, or more point mutations, such as single amino acid substitutions or deletions, as compared to a wild-type NCBI sequence (Tai Forest NC_014372.1).

In some embodiments, the sequence encoding the immunogenic polypeptide comprises the sequence of SEQ. ID. NO.:5. In some embodiments, the sequence encoding the immunogenic nucleotide or polypeptide comprises a sequence with at least 70%, 75%, 80%, 85%, 90%, 95%, 98%, 99%, 99.5%, or 99.9% identity to SEQ. ID. NO.:5 or a sequence generated from SEQ. ID. NO.:5 by alternative codon replacements optimized for the human genome. In some embodiments, the immunogenic polypeptide encoded by the adenovirus vectors described herein comprising up to 1, 2, 3, 4, 5, 6, 7, 8, 9, 10, 11, 12, 13, 14, 15, 16, 17, 18, 19, 20, 25, 30, 35, 40, or more point mutations, such as single amino acid substitutions or deletions, as compared to a wild-type NCBI sequence Bundibugyo ebolavirus (NC_014373.1).

In some embodiments, the sequence encoding the immunogenic polypeptide comprises the sequence of SEQ. ID. NO.:6. In some embodiments, the sequence encoding the immunogenic nucleotide or polypeptide comprises a sequence with at least 70%, 75%, 80%, 85%, 90%, 95%, 98%, 99%, 99.5%, 99.9% identity to SEQ. ID. NO.:6 or a sequence generated from SEQ. ID. NO.:6 by alternative codon replacements optimized for the human genome. In some embodiments, the immunogenic polypeptide encoded by the adenovirus vectors described herein comprising up to 1, 2, 3, 4, 5, 6, 7, 8, 9, 10, 11, 12, 13, 14, 15, 16, 17, 18, 19, 20, 25, 30, 35, 40, or more point mutations, such as single amino acid substitutions or deletions, as compared to a wild-type Reston ebolavirus (GenBank: JX477166.1).

In various embodiments, the adenovirus-derived vectors described herein have a deletion in the E2b region, and optionally, in the E1 region, the deletion conferring a variety of advantages to the use of the vectors in immunotherapy as described herein.

Certain regions within the adenovirus genome serve essential functions and may need to be substantially conserved when constructing the replication defective adenovirus vectors of the invention. (See, Lauer et al., J. Gen. Virology, 85, 2615-2625 (2004)); Leza et al., J. Virology, pp. 3003-3013 (1988); and Miralles et al., JBC. Vol. 264, No. 18, pp. 10763-10772 (1983).

First generation, E1-deleted Adenovirus subtype 5 (Ad5)-based vectors, although promising platforms for use as vaccines, are impeded in activity by naturally occurring or induced Ad-specific neutralizing antibodies. Ad5-based vectors with deletions of the E1 and the E2b regions (Ad5 [E1-, E2b-]), the latter encoding the DNA polymerase and the pre-terminal protein, by virtue of diminished late phase viral protein expression, provide an opportunity to avoid immunological clearance and induce more potent immune responses against the encoded antigen transgene in Ad-immune hosts.

Multiple homologous immunizations with Ad5 [E1-, E2b-]-EA, encoding an Ebola antigen may be used according to the present invention to induce EA-specific cell-mediated immune (CMI) responses with anti-Ebola activity in mice despite the presence of pre-existing or induced Ad5-neutralizing antibody. Cohorts of patients with Ebola can be immunized with escalating doses of Ad5 [E1-, E2b-]-EA. EA-specific CMI responses may be observed despite the presence of pre-existing Ad5 immunity in many or a majority of patients. Importantly, minimal toxicity, and overall patient survival may be similar regardless of pre-existing Ad5 neutralizing antibody titers. In Ebola infected subjects, the novel Ad5 [E1-, E2b-] gene delivery platform can be used to generate significant CMI responses to Ebola antigens in the setting of both naturally acquired and immunization-induced Ad5 specific immunity. An Ebola antigen specific CMI can be, for example, greater than 10, 20, 30, 40, 50, 100, 200, 300, 400, 500, 600, 700, 800, 900, 1000, 5000, 10000, or more IFN-γ spot forming cells (SFC) per $10^6$ peripheral blood mononuclear cells (PBMC). Thus, the methods and compositions of the invention relate to a recombinant nucleic acid vector, wherein the recombinant nucleic acid vector comprises a replication defective adenovirus vector, and wherein upon administration to a human, the composition is capable of inducing an immune response directed towards cells expressing an Ebola antigen in said human. The immune response may be induced even in the presence of preexisting immunity against Ad5. In some embodiments, the immune response is raised in a human subject with a preexisting inverse Ad5 neutralizing antibody titer of greater than 50, 100, 150, 200, 300, 400, 500, 600, 700, 800, 900, 1000, 1500, 2000, 2500, 3000, 3500, 4000, 4500, 5000, 6000, 7000, 8000, 9000, 1000, 12000, 15000 or higher. The immune response may comprise a cell-mediated immunity and/or a humoral immunity as described herein. The immune response may be measured by one or more of intracellular cytokine staining (ICS), ELISpot, proliferation assays, cytotoxic T cell assays including chromium release or equivalent assays, and gene expression analysis using any number of polymerase chain reaction (PCR) or RT-PCR based assays, as described herein and to the extent they are available to a person skilled in the art, as well as any other suitable assays known in the art for measuring immune response.

While Ebola immunotherapy achieved by delivering Ebola-associated antigens (EA) provides some survival benefits, limitations to these strategies exist and more immunologically potent vaccines are needed. To address the low immunogenicity a variety of advanced, multi-component vaccination strategies including co-administration of adjuvants and immune stimulating cytokines are provided. The invention relates to recombinant viral vectors that inherently provide innate pro-inflammatory signals, while simultaneously engineered to express the antigen of interest. Of particular interest is adenovirus serotype-5 (Ad5)-based immunotherapeutics that have been repeatedly used in humans to induce robust T cell-mediated immune (CMI) responses, all while maintaining an extensive safety profile. In addition, Ad5 vectors can be reliably manufactured in large quantities and are stable for storage and delivery for outpatient administration. Nonetheless, a major obstacle to the use of first generation (E1-deleted) Ad5-based vectors is the high frequency of pre-existing anti-adenovirus type 5 neutralizing antibodies. These antibodies can be present in a potential vaccinee due to either prior wild type adenovirus infection and/or induction of adenovirus neutralizing antibodies by repeated injections with Ad5-based vaccines, each resulting in inadequate immune stimulation against the target EA.

Provided herein is an Ad5 [E1-, E2b-] platform containing a gene insert for a EBOV, SUDV, TAFV, BDBV, or RESTV antigen with a modification that enhances T cell responses and is used in various embodiments of the invention for therapies raising an immune response against at least one EBOV, SUDV, TAFV, BDBV, or RESTV antigen. Multiple immunizations with this Ad5 platform can be used to induce EBOV, SUDV, TAFV, BDBV, or RESTV antigen specific CMI responses with anti-Ebola activity despite the presence of existing Ad5 immunity in mice. In some embodiments the Ad5 [E1-, E2B-] comprises SEQ. ID. NO.:1, SEQ. ID. NO.:2, SEQ. ID. NO.:4, SEQ. ID. NO.:5, SEQ. ID. NO.:6, or a combination thereof. In some embodiments the Ad5 [E1-, E2B-] comprises an EBOV, SUDV, TAFV, BDBV, or RESTV antigen encoding sequence from GenBank. In some embodiments the Ad5 [E1-, E2B-] comprises a sub-species of EBOV, SUDV, TAFV, BDBV, or RESTV antigen encoding sequence from a human isolate from GenBank or NCBI. It is contemplated, that a phase I/II clinical trial of EBOV, SUDV, TAFV, BDBV, or RESTV immunotherapies, as provided herein, would demonstrate safety and immunogenicity in humans CMI can be induced without a substantial effect on clinical outcome relative to the existence of pre-existing Ad5-immunity.

EBOV as Target for Immune Response

Ebola virus (EBOV) is a member of the family Filoviridae. Its genome comprises a single-stranded, RNA molecule of approximately 19-kb in size. Ebola virions are filamentous particles that may appear in the shape of a shepherd's crook, of a "U" or of a "6," and they may be coiled, toroid or branched. In general, Ebola virions are 80 nanometers (nm) in width and may be as long as 14,000 nm. EBOV can be subdivided into at least five distinct species with different levels of pathogenicities. The genomes of the five different Ebolaviruses (BDBV, EBOV, RESTV, SUDV and TAFV) differ in sequence and the number and location of gene overlaps.

Ebola viruses display filamentous particles that give the virus its characteristic name, are enveloped, non-segmented, have negative stranded RNA and varying morphology. The Ebola virus genome contains seven genes, the nucleoprotein (NP), virion protein (VP) 35, VP40, glycoprotein (GP), VP30, VP24, and an RNA-dependent RNA polymerase (L). Except for GP, all genes are monocistronic and encode one structural protein. The inner ribonucleoprotein complex of the virus contains the RNA genome that is encapsulated by the NP, which associates with VP35, VP30, and RNA-dependent RNA polymerase to the functional transcriptase-replicase complex. Proteins of the ribonucleoprotein complex have additional functions such as VP35 that is an interferon antagonist. VP40 is a matrix protein and mediates virus particle formation. VP24 is another structural protein associated with the membrane and interferes with interferon signaling. The GP is the only transmembrane surface protein and forms trimeric spikes consisting of GP-1 and GP-2 that are two disulphide linked furin-cleavage fragment. An important feature of the Ebola virus as compared to other Mononegavirales is the production of soluble GP (from the GP gene) secreted out of infected cells.

In some aspects, the disclosure provides for a recombinant vector as provided herein comprising at least one target virus antigen from the BDBV. In some aspects, the disclosure provides for a recombinant vector as provided herein comprising at least one target virus antigen from EBOV. In some aspects, the disclosure provides for a recombinant vector as provided herein comprising at least one target virus antigen from RESTV. In another aspect the disclosure provides for a recombinant vector as provided herein comprising at least one target virus antigen from SUDV. In another aspect the disclosure provides for a recombinant vector as provided herein comprising at least one target virus antigen from TAFV. In another aspect the disclosure provides for a recombinant vector as provided herein comprising the target virus antigens from Ebola viruses described in GenBank and NCBI.

In another aspect the disclosure provides for a recombinant vector as provided herein comprising the target virus antigens from a combination of Ebola strains, for example BDBV, EBOV, RESTV, SUDV and TAFV, and others as described in GenBank and NCBI.

Figure 3:
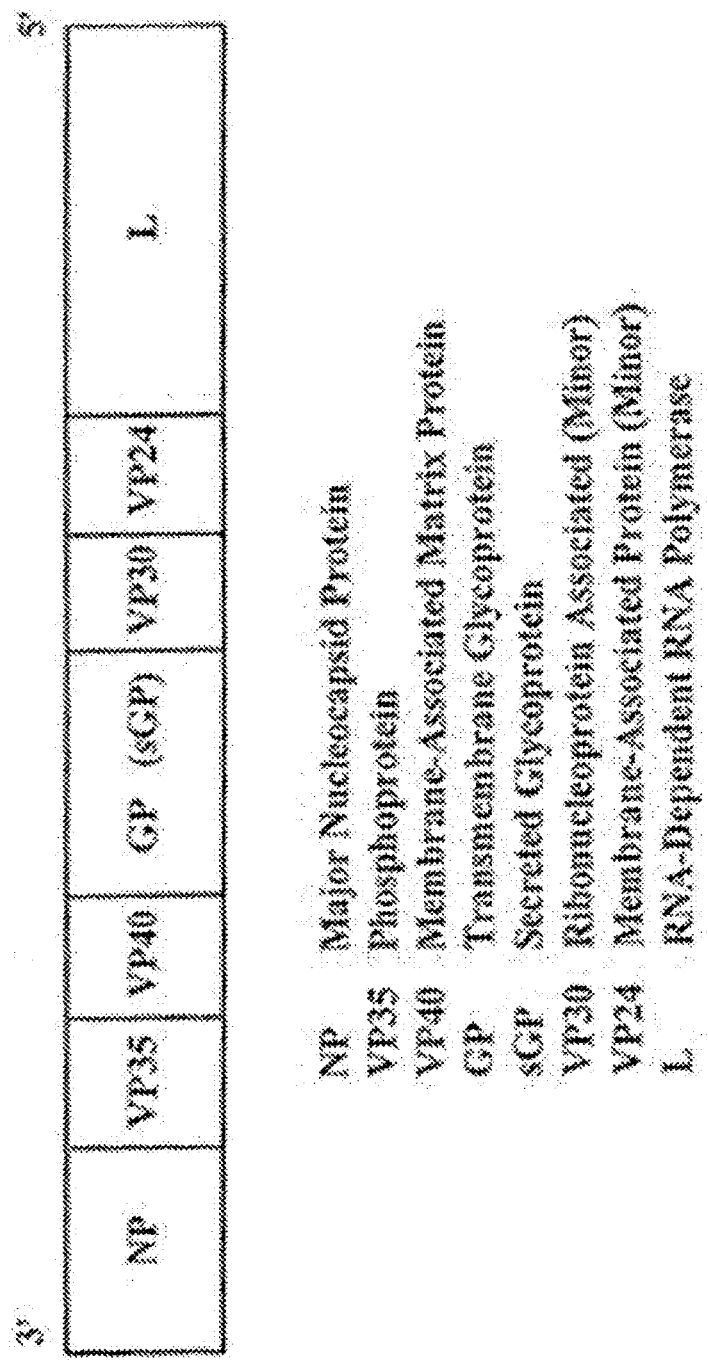
FIG. 3 exemplifies one structure of an Ebola virus genome.
Figure 4:
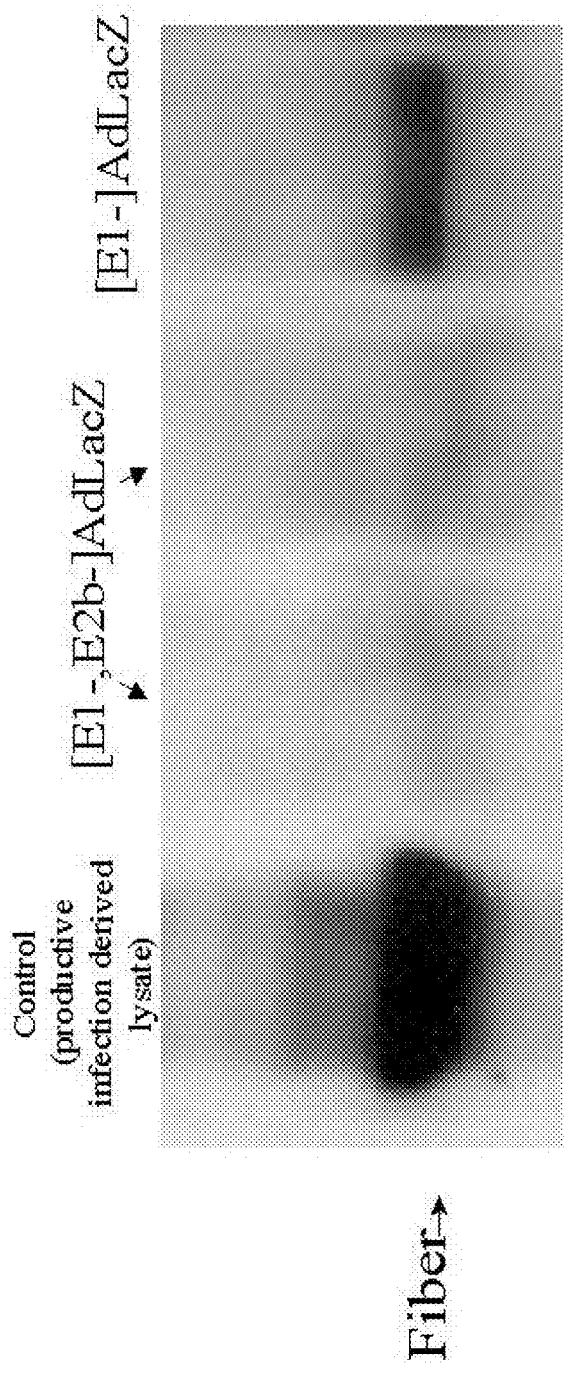
FIG. 4 exemplifies lack of late gene expression by Ad5 [E1-, E2b-] vectors in Hela cells. Hela cells were infected with Ad5 [E1-]-LacZ, or with an Ad5 [E1-, E2b-]-LacZ vector. Protein lysates were harvested and the 66 kD fiber protein was detected by Western blotting. As a positive control, a portion of a protein lysate from the productive infection of an Ad virus grown in a complementing cell line is included.
Figure 5:
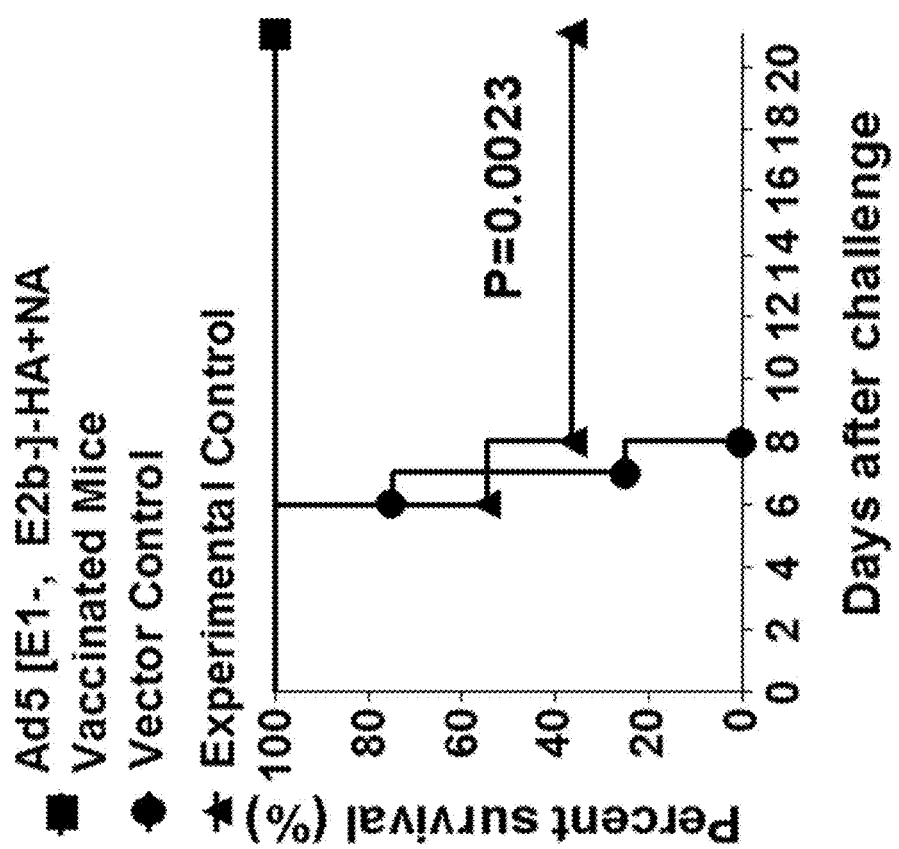
FIG. 5 exemplifies survival in vaccinated mice and control mice injected with saline or Ad5-null.
Figure 6:
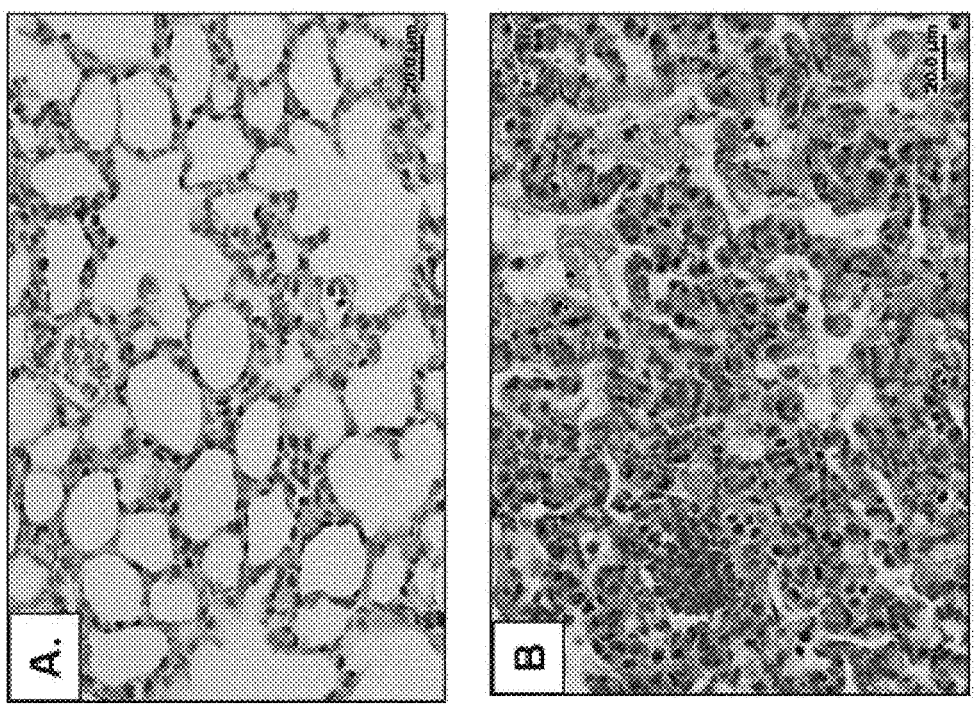
FIG. 6 exemplifies vaccinated mice (top) or control mice (below). Note the extensive inflammation in control mice, but not in vaccinated mice after challenge.
Figure 7:
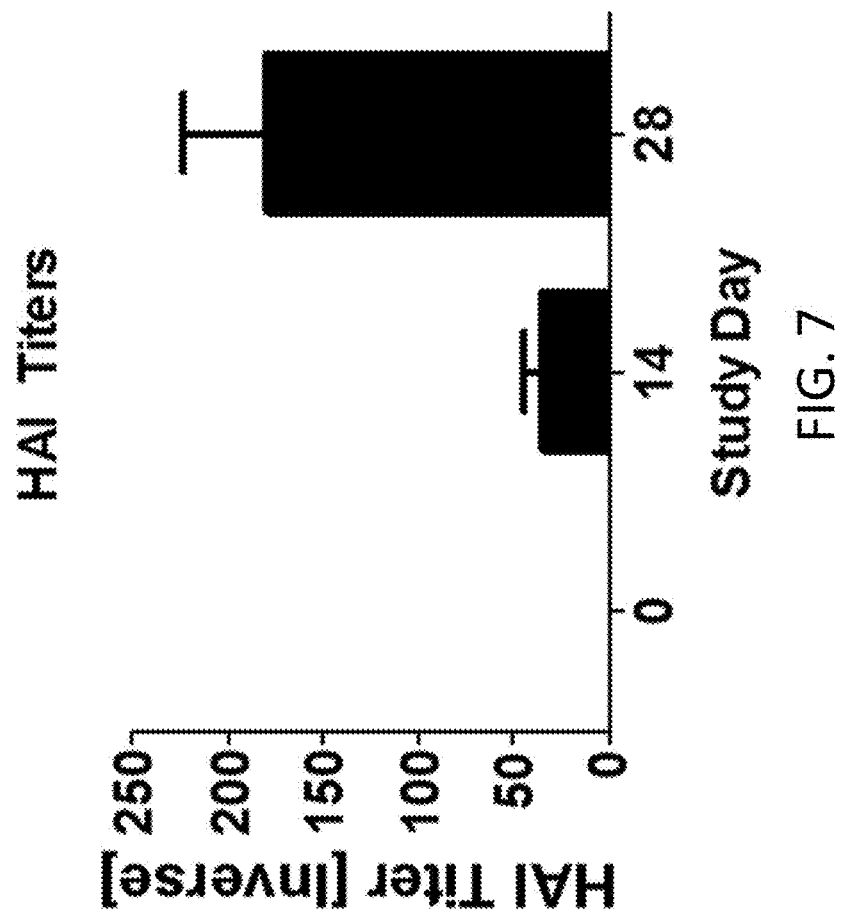
FIG. 7 exemplifies hemagglutination inhibition (HAI) titers were induced in Ad5-immune monkeys after 1 vaccination with Ad5 [E1-, E2b-]-HA. Note that HAI activity was detected 14 days after immunization and significantly increased above day 14 levels by day 28 (P<0.01). Mean±SEM.

Ebola virions, like virions of other filoviruses, can contain seven proteins (see FIG. 3): a surface glycoprotein (GP), a nucleoprotein (NP), four virion structural proteins (VP40, VP35, VP30, and VP24), and an RNA-dependent RNA polymerase (L).

The glycoprotein of Ebola virus is unusual in that it is encoded in two open reading frames. Transcriptional editing is needed to express the transmembrane form that is incorporated into the virion. The unedited form produces a nonstructural secreted glycoprotein (sGP) that is synthesized in large amounts early during the course of infection. In some cases, the encoded protein is cut after translation, generating a mature secreted form that sits on the surfaces of viral particles, as well as a sugar-coated smaller part.

In some aspects, the disclosure provides for a recombinant vector as provided herein comprising a target virus antigen from the glycoprotein (GP) of at least one Ebola virion. In some aspects the disclosure provides for a recombinant vector as provided herein comprising a target virus antigen from a nucleoprotein (NP) of at least one Ebola virion. In some aspects, the disclosure provides for a recombinant vector as provided herein comprising the target virus antigens from at least one of the four virion structural proteins (VP40, VP35, VP30, and VP24), from at least one Ebola virion. For example, a recombinant vector can comprise a target virus antigen from VP40 of at least one Ebola virion. For example, a recombinant vector can comprise a target virus antigen from VP35 of at least one Ebola virion. For example, a recombinant vector can comprise a target virus antigen from VP30 of at least one Ebola virion. For example, a recombinant vector can comprise a target virus antigen from VP24 of at least one Ebola virion. In some aspects, the disclosure provides for a recombinant vector as provided herein comprising a target virus antigen from the L protein of at least one Ebola virion.

The Ebola life cycle is thought to begin with a virion contacting a host cell. The structural glycoprotein (known as GP1,2) is responsible for the virus' ability to bind to and infect targeted cells. The virion is thought to attach to specific cell-surface receptors on the host cell such as, for example, C-type lectins, DC-SIGN, or integrins, which is followed by fusion of the viral envelope with host cell's cellular membranes. After the virions taken up by the host cell they then travel to acidic endosomes and lysosomes where the viral envelope glycoprotein GP is cleaved.

The viral RNA polymerase, encoded by the L gene, partially uncoats the nucleocapsid and transcribes the genes into positive-strand mRNAs, which are then translated into structural and nonstructural proteins that comprise the virion. The most abundant protein produced is the nucleoprotein, whose concentration in the host cell determines when L switches from gene transcription to genome replication. Replication of the viral genome results in full-length, positive-strand antigenomes that are, in turn, transcribed into genome copies of negative-strand virus progeny. Newly synthesized structural proteins and genomes self-assemble and accumulate near the inside of the cell membrane. Virions bud off from the host cell, gaining their envelopes from the cellular membrane from which they bud from. The mature viral progeny particles then infect other cells to repeat the cycle.

In some aspects, the disclosure provides for a recombinant vector as provided herein comprising the target virus antigens from the L gene of at least one Ebola virion. In one aspect the disclosure provides for a recombinant vector as provided herein comprising the target virus that inhibits the production of the nucleoprotein of at least one Ebola virion. In one aspect the disclosure provides for a recombinant vector as provided herein comprising the target virus antigens that inhibit the genome replication of at least one Ebola virion. In one aspect the disclosure provides for a recombinant vector as provided herein comprising the target virus antigens that inhibit the budding process of at least one Ebola virion. In one aspect, the disclosure provides for a recombinant vector as provided herein comprising the target virus antigens that inhibit the infection process of at least one Ebola virion.

In various embodiments, Ad5 [E1-, E2B-]-SEQ. ID. NO.: 1, Ad5 [E1-, E2B-]-SEQ. ID. NO.:2, Ad5 [E1-, E2B-]-SEQ. ID. NO.:4, Ad5 [E1-, E2B-]-SEQ. ID. NO.:5, and/or Ad5 [E1-, E2B-]-SEQ. ID. NO.:6 increase the capability to transduce dendritic cells, improving antigen specific immune responses in the vaccine by taking advantage of the reduced inflammatory response against Ad5 [E1-, E2b-] vector viral proteins and the resulting evasion of pre-existing Ad immunity.

For example, Ad5 [E1-, E2B-]-GP, Ad5 [E1-, E2B-]-NP, Ad5 [E1-, E2B-]-VP40, Ad5 [E1-, E2B-]-VP35, Ad5 [E1-, E2b-]-VP30, [E1-, E2b-]-VP24, and/or [E1-, E2b-]-L can increase the capability to transduce dendritic cells, improving antigen specific immune responses in the vaccine by taking advantage of the reduced inflammatory response against Ad5 [E1-, E2b-] vector viral proteins and the resulting evasion of pre-existing Ad immunity.

In various embodiments Ad5 [E1-, E2B-]-SEQ. ID. NO.: 1, Ad5 [E1-, E2B-]-SEQ. ID. NO.:2, Ad5 [E1-, E2B-]-SEQ. ID. NO.:4, Ad5 [E1-, E2B-]-SEQ. ID. NO.:5, Ad5 [E1-, E2B-]-SEQ. ID. NO.:6 therapeutic and preventative vaccines can be used to increase overall survival (OS) of a human and have a toxicity profile bounds of technical safety. For example, Ad5 [E1-, E2B-]-GP, Ad5 [E1-, E2B-]-NP, Ad5 [E1-, E2B-]-VP40, Ad5 [E1-, E2B-]-VP35, Ad5 [E1-, E2b-]-VP30, [E1-, E2b-]-VP24, and/or [E1-, E2b-]-L therapeutic and preventative vaccines can be used to increase overall survival (OS) of a human and have a toxicity profile bounds of technical safety.

Further, in various embodiments, the composition and methods of the invention lead to clinical responses, such as altered disease progression or life expectancy of human infected with Ebola. Further, in various embodiments, the composition and methods of the invention lead to clinical responses, such as altered disease progression or life expectancy of human at low, medium and high risk for infection with Ebola.

In some aspects, the disclosure provides compositions and methods using adenovirus based vectors expressing at least one antigen selected from the group consisting of: an EBOV, SUDV, TAFV, BDBV, and RESTV antigen. For example, the disclosure provides compositions and methods using adenovirus based vectors expressing at least one antigen selected from the group consisting of GP, NP, VP40, VP35, VP30, VP24, and L antigens.

Further, in various embodiments, the composition and methods of the invention lead to clinical responses, such as altered disease progression or life expectancy of human infected with Ebola. Further, in various embodiments, the composition and methods of the invention lead to clinical responses, such as altered disease progression or life expectancy of human at low, medium and high risk for infection with Ebola.

Ad5-Based Ebola Vaccines

Adenoviruses are a family of DNA viruses characterized by an icosahedral, non-enveloped capsid containing a linear double-stranded genome. Of the human Ads, none are associated with any neoplastic disease, and only cause relatively mild, self-limiting illness in immunocompetent individuals. The first genes expressed by the virus are the E1 genes, which act to initiate high-level gene expression from the other Ad5 gene promoters present in the wild type genome. Viral DNA replication and assembly of progeny virions occur within the nucleus of infected cells, and the entire life cycle takes about 36 hr with an output of approximately $10^4$ virions per cell. The wild type Ad5 genome is approximately 36 kb, and encodes genes that are divided into early and late viral functions, depending on whether they are expressed before or after DNA replication. The early/late delineation is nearly absolute, since it has been demonstrated that super-infection of cells previously infected with an Ad5 results in lack of late gene expression from the super-infecting virus until after it has replicated its own genome. Without bound by theory, this is likely due to a replication dependent cis-activation of the Ad5 major late promoter (MLP), preventing late gene expression (primarily the Ad5 capsid proteins) until replicated genomes are present to be encapsulated. The composition and methods of the invention take advantage of feature in the development of advanced generation Ad vectors/vaccines.

Ad5 Vectors

First generation, or E1-deleted adenovirus vectors Ad5 [E1-] are constructed such that a transgene replaces only the E1 region of genes. Typically, about 90% of the wild-type Ad5 genome is retained in the vector. Ad5 [E1-] vectors have a decreased ability to replicate and cannot produce infectious virus after infection of cells not expressing the Ad5 E1 genes. The recombinant Ad5 [E1-] vectors are propagated in human cells (typically 293 cells) allowing for Ad5 [E1-] vector replication and packaging. Ad5 [E1-] vectors have a number of positive attributes; one of the most important is their relative ease for scale up and cGMP production. Currently, well over 220 human clinical trials utilize Ad5 [E1-] vectors, with more than two thousand subjects given the virus sc, im, or iv. Additionally, Ad5 vectors do not integrate; their genomes remain episomal. Generally, for vectors that do not integrate into the host genome, the risk for insertional mutagenesis and/or germline transmission is extremely low if at all. Conventional Ad5 [E1-] vectors have a carrying capacity that approaches 7 kb.

Ad5 [E1-] Vectors Used as a Vaccine

Ad5 [E1-] vectors encoding a variety of antigens can efficiently transduce 95% of ex vivo exposed DCs to high titers of the vector. Importantly, increasing levels of foreign gene expression were noted in the DCs with increasing multiplicities of infection (MOI) with the vector. DCs infected with Ad5 [E1-] vectors encoding a variety of antigens (including the tumor antigens MART-1, MAGE-A4, DF3/MUC1, p53, hugp100 melanoma antigen, polyoma virus middle-T antigen) have the propensity to induce antigen specific CTL responses, have an enhanced antigen presentation capacity, and have an improved ability to initiate T-cell proliferation in mixed lymphocyte reactions. Immunization of animals with DCs transduced by Ad5 vectors encoding tumor specific antigens have been demonstrated to result in significant levels of protection for the animals when challenged with tumor cells expressing the respective antigen. Interestingly, intra-tumoral injection of Ads encoding IL-7 was less effective than injection of DCs transduced with IL-7 encoding Ad5 vectors at inducing antitumor immunity, further heightening the interest in ex vivo transduction of DCs by Ad5 vectors. Ex vivo DC transduction strategies have also been used to attempt to induce tolerance in recipient hosts, for example, by Ad5 mediated delivery of the CTLA4Ig into DCs, blocking interactions of the DCs CD80 with the CD28 molecule present on T-cells.

Ad5 vector capsid interactions with DCs in and of themselves may trigger several beneficial responses, which may be enhancing the propensity of DCs to present antigens encoded by Ad5 vectors. For example, immature DCs, though specialized in antigen uptake, are relatively inefficient effectors of T-cell activation. DC maturation coincides with the enhanced ability of DCs to drive T-cell immunity. In some instances, the compositions and methods of the invention take advantage of an Ad5 infection resulting in direct induction of DC maturation. Studies of immature bone marrow derived DCs from mice suggest that Ad vector infection of immature bone marrow derived DCs from mice resulted may upregulate cell surface markers normally associated with DC maturation (MHC I and II, CD40, CD80, CD86, and ICAM-1) as well as down-regulation of CD11c, an integrin known to be down regulated upon myeloid DC maturation. In some instances, Ad vector infection triggers IL-12 production by DCs, a marker of DC maturation. Without being bound by theory, these events may possibly be due to Ad5 triggered activation of NF-κB pathways. Mature DCs can be efficiently transduced by Ad vectors, and did not lose their functional potential to stimulate the proliferation of naive T-cells at lower MOI, as demonstrated by mature CD83+ human DC (derived from peripheral blood monocytes. However, mature DCs may also be less infectable than immature ones. Modification of capsid proteins can be used as a strategy to optimize infection of DC by Ad vectors, as well as enhancing functional maturation, for example using the CD40L receptor as a viral vector receptor, rather than using the normal CAR receptor infection mechanisms.

Most dramatically, when the potential of non-viral vectors to induce anti-HIV immune responses was directly compared to Ad5 based vectoring systems, the Ad5 based systems were found to be far superior. For example, in Ad5 naïve primate models, vaccination with a Ad5 [E1-] expressing the HIV gag was superior in protecting the animals from SHIV infections as compared to similar efforts utilizing naked DNA vaccines expressing HIV-gag. Thus, viral vectors can be superior to naked DNA approaches. Combined strategies (building upon their clinical experiences with naked DNA-gag vectors alone) using naked DNA-gag vaccines as a priming vaccination, followed by boosting with the Ad5 [E1-]-gag vaccine further improved T cell responses in human trials than those previously noted with the DNA-HIV-gag encoding vector alone.

In a recent phase 1 clinical trial evaluating safety and immunogenicity, 20 healthy adults were vaccinated once intramuscularly with a recombinant chimpanzee Ad-based (cAd) vaccine containing the GP component of the Zaire and Sudan strains of Ebola virus (cAd-EBO). GP-specific antibodies were induced in all 20 subjects. The antibody titers were highest in the group (n=10) that received $2 \times 10^{11}$ virus particles (VP) as compared to the group (n=10) that received $2 \times 10^{10}$ VP. The antibody responses attained were observed to be in the range reported to be associated with vaccine-induced protective immunity in challenge studies involving nonhuman primates (NHP). GP-specific T-cell responses were also more frequent among those who received the $2 \times 10^{11}$ VP dose as compared to those that received the $2 \times 10^{10}$ VP dose. The vaccine was safely tolerated and no serious adverse effects were observed. Importantly, it was demonstrated that anti-chimpanzee Ad antibodies were also induced in the subjects and these antibodies will prevent further vaccination (boost) that may be required to maintain protective immune responses. In order to circumvent the boosting challenge, these investigators propose to perform an additional clinical trial evaluating the safety and immunogenicity of the cAd-EBO vaccine combined with a booster vaccine composed of a recombinant modified vaccinia virus Ankara (MVA) containing GP of the Ebola virus (MVA-EBO). Even if this approach is successful, the development of neutralizing antibodies to both cAd and MVA must be considered, as that could mitigate further immunizations using these two recombinant vaccines.

Ad5 vectors offer a unique opportunity to allow for high level and efficient transduction of EAs such as EBOV, SUDV, TAFV, BDBV, and RESTV antigens, such as GP, NP, VP40, VP35, VP30, VP24, and L. One of the major problems facing Ad5 based vectors is the high propensity of pre-existing immunity to Ads in the human population, and how this may preclude the use of conventional, Ad5 [E1-] deleted (first generation Ads) in most human populations, for any additional vaccine application.

Ad5 [E1-, E2B-]-Ebola Vaccine: The Use of Ad5 [E1-, E2b-] Vaccines to Overcome the Challenge of Pre-Existing Anti-Ad5 Immunity Studies in humans and animals have demonstrated that pre-existing immunity against Ad5 can be an inhibitory factor to commercial use of Ad-based vaccines. The preponderance of humans have antibody against Ad5, the most widely used subtype for human vaccines, with two-thirds of humans studied having lympho-proliferative responses against Ad5. This pre-existing immunity can inhibit immunization or re-immunization using typical Ad5 vaccines and may preclude the immunization of a vaccinee against a second antigen, using an Ad5 vector, at a later time. Overcoming the problem of pre-existing anti-vector immunity has been a subject of intense investigation. Investigations using alternative human (non-Ad5 based) Ad5 subtypes or even non-human forms of Ad5 have been examined. Even if these approaches succeed in an initial immunization, subsequent vaccinations may be problematic due to immune responses to the novel Ad5 subtype. To avoid the Ad5 immunization barrier, and improve upon the limited efficacy of first generation Ad5 [E1-] vectors to induce optimal immune responses, various embodiments of the invention relate to a next generation Ad5 vector based vaccine platform. The new Ad5 platform has additional deletions in the E2b region, removing the DNA polymerase and the preterminal protein genes. The Ad5 [E1-, E2b-] platform has an expanded cloning capacity that is sufficient to allow inclusion of many possible genes. Ad5 [E1-, E2b-] vectors have up to about 12 kb gene-carrying capacity as compared to the 7 kb capacity of Ad5 [E1-] vectors, providing space for multiple genes if needed. In some embodiments, an insert of more than 1, 2, 3, 4, 5, 6, 7, 8, 9, 10, or 11 kb is introduced into an Ad5 vector, such as the Ad5 [E1-, E2b-] vector. Deletion of the E2b region confers advantageous immune properties on the Ad5 vectors of the invention, often eliciting potent immune responses to target transgene antigens while minimizing the immune responses to Ad viral proteins.

In various embodiments, Ad5 [E1-, E2b-] vectors of the invention induce a potent CMI, as well as antibodies against the vector expressed vaccine antigens even in the presence of Ad immunity. Ad5 [E1-, E2b-] vectors also have reduced adverse reactions as compared to Ad5 [E1-] vectors, in particular the appearance of hepatotoxicity and tissue damage. A key aspect of these Ad5 vectors is that expression of Ad late genes is greatly reduced. For example, production of the capsid fiber proteins could be detected in vivo for Ad5 [E1-] vectors, while fiber expression was ablated from Ad5 [E1-, E2b-] vector vaccines. The innate immune response to wild type Ad is complex. Proteins deleted from the Ad5 [E1-, E2b-] vectors generally play an important role. Specifically, Ad5 [E1-, E2b-] vectors with deletions of preterminal protein or DNA polymerase display reduced inflammation during the first 24 to 72 hours following injection compared to Ad5 [E1-] vectors. In various embodiments, the lack of Ad5 gene expression renders infected cells invisible to anti-Ad activity and permits infected cells to express the transgene for extended periods of time, which develops immunity to the target.

Various embodiments of the invention contemplate increasing the capability for the Ad5 [E1-, E2b-] vectors to transduce dendritic cells, improving antigen specific immune responses in the vaccine by taking advantage of the reduced inflammatory response against Ad5 [E1-, E2b-] vector viral proteins and the resulting evasion of pre-existing Ad immunity.

In some cases, this immune induction may take months. Ad5 [E1-, E2b-] vectors not only are safer than, but appear to be superior to Ad5 [E1-] vectors in regard to induction of antigen specific immune responses, making them much better suitable as a platform to deliver Ebola vaccines that can result in a clinical response.

Various embodiments of the invention, by taking advantage of the new Ad5 [E1-, E2b-] vector system in delivering a long sought-after need for a develop a therapeutic vaccine against Ebola, overcome barriers found with other Ad5 systems and permit the immunization of people who have previously been exposed to Ad5.

In various embodiments the compositions and methods of the invention comprising an Ad5 [E1-, E2b-] vector Ebola vaccine effect of increased overall survival (OS) within the bounds of technical safety.

Adenovirus Vectors

Compared to first generation adenovirus vectors, certain embodiments of the Second Generation E2b deleted adenovirus vectors of the present invention contain additional deletions in the DNA polymerase gene (pol) and deletions of the pre-terminal protein (pTP). E2b deleted vectors have up to a 13 kb gene-carrying capacity as compared to the 5 to 6 kb capacity of First Generation adenovirus vectors, easily providing space for nucleic acid sequences encoding any of a variety of target antigens. The E2b deleted adenovirus vectors also have reduced adverse reactions as compared to First Generation adenovirus vectors. E2b deleted vectors have reduced expression of viral genes, and this characteristic leads to extended transgene expression in vivo.

The innate immune response to wild type Ad can be complex, and it appears that Ad proteins expressed from adenovirus vectors play an important role. Specifically, the deletions of pre-terminal protein and DNA polymerase in the E2b deleted vectors appear to reduce inflammation during the first 24 to 72 hours following injection, whereas First Generation adenovirus vectors stimulate inflammation during this period. In addition, it has been reported that the additional replication block created by E2b deletion also leads to a 10,000 fold reduction in expression of Ad late genes, well beyond that afforded by E1, E3 deletions alone. The decreased levels of Ad proteins produced by E2b deleted adenovirus vectors effectively reduce the potential for competitive, undesired, immune responses to Ad antigens, responses that prevent repeated use of the platform in Ad immunized or exposed individuals. The reduced induction of inflammatory response by second generation E2b deleted vectors results in increased potential for the vectors to express desired vaccine antigens during the infection of antigen presenting cells (i.e. dendritic cells), decreasing the potential for antigenic competition, resulting in greater immunization of the vaccine to the desired antigen relative to identical attempts with First Generation adenovirus vectors. E2b deleted adenovirus vectors provide an improved Ad-based vaccine candidate that is safer, more effective, and more versatile than previously described vaccine candidates using First Generation adenovirus vectors.

Thus, first generation, E1-deleted Adenovirus subtype 5 (Ad5)-based vectors, although promising platforms for use as vaccines, are impeded in activity by naturally occurring or induced Ad-specific neutralizing antibodies. Without being bound by theory, Ad5-based vectors with deletions of the E1 and the E2b regions (Ad5 [E1-, E2b-]), the latter encoding the DNA polymerase and the pre-terminal protein, for example by virtue of diminished late phase viral protein expression, may avoid immunological clearance and induce more potent immune responses against the encoded antigen transgene in Ad-immune hosts.

The present invention contemplates the use of E2b deleted adenovirus vectors, such as those described in U.S. Pat. Nos. 6,063,622; 6,451,596; 6,057,158; 6,083,750; and 8,298,549. The vectors with deletions in the E2b regions in many cases cripple viral protein expression and/or decrease the frequency of generating replication competent Ad (RCA). Propagation of these E2b deleted adenovirus vectors can be done utilizing cell lines that express the deleted E2b gene products. The present invention also provides such packaging cell lines; for example E.C7 (formally called C-7), derived from the HEK-293 cell line.

Further, the E2b gene products, DNA polymerase and preterminal protein, can be constitutively expressed in E.C7, or similar cells along with the E1 gene products. Transfer of gene segments from the Ad genome to the production cell line has immediate benefits: (1) increased carrying capacity; and, (2) a decreased potential of RCA generation, typically requiring two or more independent recombination events to generate RCA. The E1, Ad DNA polymerase and/or preterminal protein expressing cell lines used in the present invention can enable the propagation of adenovirus vectors with a carrying capacity approaching 13 kb, without the need for a contaminating helper virus. In addition, when genes critical to the viral life cycle are deleted (e.g., the E2b genes), a further crippling of Ad to replicate or express other viral gene proteins occurs. This can decrease immune recognition of virally infected cells, and allow for extended durations of foreign transgene expression.

E1, DNA polymerase, and preterminal protein deleted vectors are typically unable to express the respective proteins from the E1 and E2b regions. Further, they may show a lack of expression of most of the viral structural proteins. For example, the major late promoter (MLP) of Ad is responsible for transcription of the late structural proteins L1 through L5. Though the MLP is minimally active prior to Ad genome replication, the highly toxic Ad late genes are primarily transcribed and translated from the MLP only after viral genome replication has occurred. This cis-dependent activation of late gene transcription is a feature of DNA viruses in general, such as in the growth of polyoma and SV-40. The DNA polymerase and preterminal proteins are important for Ad replication (unlike the E4 or protein IX proteins). Their deletion can be extremely detrimental to adenovirus vector late gene expression, and the toxic effects of that expression in cells such as APCs.

In certain embodiments, the adenovirus vectors contemplated for use in the present invention include E2b deleted adenovirus vectors that have a deletion in the E2b region of the Ad genome and, optionally, the E1 region. In some cases, such vectors do not have any other regions of the Ad genome deleted. In another embodiment, the adenovirus vectors contemplated for use in the present invention include E2b deleted adenovirus vectors that have a deletion in the E2b region of the Ad genome and, optionally, deletions in the E1 and E3 regions. In some cases, such vectors have no other regions deleted. In a further embodiment, the adenovirus vectors contemplated for use in the present invention include adenovirus vectors that have a deletion in the E2b region of the Ad genome and, optionally, deletions in the E1, E3 and, also optionally, partial or complete removal of the E4 regions. In some cases, such vectors have no other deletions. In another embodiment, the adenovirus vectors contemplated for use in the present invention include adenovirus vectors that have a deletion in the E2b region of the Ad genome and, optionally deletions in the E1 and/or E4 regions. In some cases, such vectors contain no other deletions. In an additional embodiment, the adenovirus vectors contemplated for use in the present invention include adenovirus vectors that have a deletion in the E2a, E2b and/or E4 regions of the Ad genome. In some cases, such vectors have no other deletions. In one embodiment, the adenovirus vectors for use herein comprise vectors having the E1 and/or DNA polymerase functions of the E2b region deleted. In some cases, such vectors have no other deletions. In a further embodiment, the adenovirus vectors for use herein have the E1 and/or the preterminal protein functions of the E2b region deleted. In some cases, such vectors have no other deletions. In another embodiment, the adenovirus vectors for use herein have the E1, DNA polymerase and/or the preterminal protein functions deleted. In some cases, such vectors have no other deletions. In one particular embodiment, the adenovirus vectors contemplated for use herein are deleted for at least a portion of the E2b region and/or the E1 region. In some cases, such vectors are not "gutted" adenovirus vectors. In this regard, the vectors may be deleted for both the DNA polymerase and the preterminal protein functions of the E2b region. In an additional embodiment, the adenovirus vectors for use in the present invention include adenovirus vectors that have a deletion in the E1, E2b and/or 100 K regions of the adenovirus genome. In one embodiment, the adenovirus vectors for use herein comprise vectors having the E1, E2b and/or protease functions deleted. In some cases, such vectors have no other deletions. In a further embodiment, the adenovirus vectors for use herein have the E1 and/or the E2b regions deleted, while the fiber genes have been modified by mutation or other alterations (e.g., to alter Ad tropism). Removal of genes from the E3 or E4 regions may be added to any of the mentioned adenovirus vectors. In certain embodiments, the adenovirus vector may be a "gutted" adenovirus vector.

The present invention also provides compositions and methods for immunotherapy against Ebola using a viral gene delivery platform to immunize against Ebola genes combined with an immune pathway checkpoint modulator. For example, compositions and methods for immunotherapy against Ebola using a viral gene delivery platform can be used immunize against Ebola genes combined with an immune pathway checkpoint modulator, such as an inhibitor of PD1. These compositions and methods can utilize an Ad5 [E1-, E2b-]-Ebola vaccine combined with an immune pathway checkpoint modulator, such as an inhibitor of a checkpoint inhibitor.

The compositions and methods can be used to generate an immune response against a target antigen expressed and/or presented by a cell. For example, the compositions and methods can be used to generate immune responses against an Ebola antigen, such as an Ebola antigen expressed or presented by a cell. For example, the compositions and methods can be used to generate an immune response against an EBOV, SUDV, TAFV, BDBV, or RESTV antigen, such as GP, NP, VP40, VP35, VP30, VP24, L, or any combination thereof, expressed or presented by a cell. For example, the compositions and methods can be used to generate an immune response against an EBOV antigen expressed and/or presented by a cell. For example, the compositions and methods can be used to generate an immune response against a SUDV antigen expressed and/or presented by a cell. For example, the compositions and methods can be used to generate an immune response against a TAFV antigen expressed and/or presented by a cell. For example, the compositions and methods can be used to generate an immune response against a BDBV antigen expressed and/or presented by a cell. For example, the compositions and methods can be used to generate an immune response against a RESTV antigen expressed and/or presented by a cell. For example, the compositions and methods can be used to generate an immune response against GP expressed and/or presented by a cell. For example, the compositions and methods can be used to generate an immune response against NP expressed and/or presented by a cell. For example, the compositions and methods can be used to generate an immune response against VP40 expressed and/or presented by a cell. For example, the compositions and methods can be used to generate an immune response against VP35 expressed and/or presented by a cell. For example, the compositions and methods can be used to generate an immune response against VP30 expressed and/or presented by a cell. For example, the compositions and methods can be used to generate an immune response against VP24 expressed and/or presented by a cell. For example, the compositions and methods can be used to generate an immune response against L expressed and/or presented by a cell.

The compositions and methods can be used to generate an immune response against multiple target antigens expressed and/or presented by a cell. For example, the compositions and methods can be used to generate an immune response against two or more EBOV, SUDV, TAFV, BDBV, or RESTV antigens, such as two or more of GP, NP, VP40, VP35, VP30, VP24, and L antigens. For example, the compositions and methods can be used to generate an immune response against an EBOV antigen and a SUDV antigen. For example, the compositions and methods can be used to generate an immune response against a TAFV antigen and a BDBV antigen. For example, the compositions and methods can be used to generate an immune response against a RESTV antigen and an EBOV antigen. For example, the compositions and methods can be used to generate an immune response against GP and NP. For example, the compositions and methods can be used to generate an immune response against GP and VP40. For example, the compositions and methods can be used to generate an immune response against GP and VP35. For example, the compositions and methods can be used to generate an immune response against GP and VP30. For example, the compositions and methods can be used to generate an immune response against GP and VP24. For example, the compositions and methods can be used to generate an immune response against GP and L. For example, the compositions and methods can be used to generate an immune response against NP and VP40. For example, the compositions and methods can be used to generate an immune response against NP and VP35. For example, the compositions and methods can be used to generate an immune response against NP and VP30. For example, the compositions and methods can be used to generate an immune response against NP and VP24. For example, the compositions and methods can be used to generate an immune response against NP and L. For example, the compositions and methods can be used to generate an immune response against VP40 and VP35. For example, the compositions and methods can be used to generate an immune response against VP40 and VP30. For example, the compositions and methods can be used to generate an immune response against VP40 and VP24. For example, the compositions and methods can be used to generate an immune response against VP40 and L. For example, the compositions and methods can be used to generate an immune response against VP35 and VP30. For example, the compositions and methods can be used to generate an immune response against VP35 and VP24. For example, the compositions and methods can be used to generate an immune response against VP35 and L. For example, the compositions and methods can be used to generate an immune response against VP30 and VP24. For example, the compositions and methods can be used to generate an immune response against VP30 and L. For example, the compositions and methods can be used to generate an immune response against VP24 and L.

A modified form of an EBOV, SUDV, TAFV, BDBV, or RESTV antigen, such as GP, NP, VP40, VP35, VP30, VP24, or L can be used in a vaccine directed to raising an immune response against an EBOV, SUDV, TAFV, BDBV, or RESTV antigen, such as GP, NP, VP40, VP35, VP30, VP24, or L; or cells expressing and/or presenting an EBOV, SUDV, TAFV, BDBV, or RESTV antigen, such as GP, NP, VP40, VP35, VP30, VP24, or L. Typically, polynucleotide variants will contain one or more substitutions, additions, deletions and/or insertions, preferably such that the immunogenicity of the epitope of the polypeptide encoded by the variant polynucleotide or such that the immunogenicity of the heterologous target protein is not substantially diminished relative to a polypeptide encoded by the native polynucleotide sequence. In some cases, said one or more substitutions, additions, deletions and/or insertions may result in an increased immunogenicity of the epitope of the polypeptide encoded by the variant polynucleotide. As described elsewhere herein, the polynucleotide variants can encode a variant of the target antigen, or a fragment (e.g., an epitope) thereof wherein the propensity of the variant polypeptide or fragment (e.g., epitope) thereof to react with antigen-specific antisera and/or T-cell lines or clones is not substantially diminished relative to the native polypeptide. The polynucleotide variants can encode a variant of the target antigen, or a fragment thereof wherein the propensity of the variant polypeptide or fragment thereof to react with antigen-specific antisera and/or T-cell lines or clones is substantially increased relative to the native polypeptide.

In particular, the present invention provides an improved Ad-based vaccine such that multiple vaccinations against one or more antigenic target entity can be achieved. In some embodiments, the improved Ad-based vaccine comprises a replication defective adenovirus carrying a target antigen, a fragment, a variant or a variant fragment thereof, such as Ad5 [E1-, E2b-]-EBOV. Variants or fragments of target antigens, such as GP, NP, VP40, VP35, VP30, VP24, or L, can be selected based on a variety of factors, including immunogenic potential. A mutant GP, NP, VP40, VP35, VP30, VP24, or L can utilized for its increased capability to raise an immune response relative to the wild-type GP, NP, VP40, VP35, VP30, VP24, or L, respectively. Importantly, vaccination can be performed in the presence of preexisting immunity to the Ad or administered to subjects previously immunized multiple times with the Ad vector of the present invention or other Ad vectors. The Ad vectors can be administered to subjects multiple times to induce an immune response against an antigen of interest, such as GP, NP, VP40, VP35, VP30, VP24, or L, including but not limited to, the production of antibodies and CMI responses against one or more target antigens. In particular embodiments, variants or fragments of target antigens are modified such that they have one or more reduced biological activities. For example, an Ebola protein target antigen may be modified to reduce or eliminate the viral activity of the protein, or a viral protein may be modified to reduce or eliminate one or more activities or the viral protein. An example of a modified Ebola protein is a GP, NP, VP40, VP35, VP30, VP24, or L, having a point mutation that results in a variant protein, such as a variant protein with increased immunogenicity.

In order to express a desired target antigen polypeptide or fragment or variant thereof, or fusion protein comprising any of the above, as described herein, the nucleotide sequences encoding the polypeptide, or functional equivalents, are inserted into an appropriate Ad as described elsewhere herein using recombinant techniques known in the art.

Compositions

Viral Vectors for Ebola Immunotherapies and Vaccines

Recombinant viral vectors can be used to express protein coding genes or antigens (e.g., EAs). The advantages of recombinant viral vector based vaccines and immunotherapy include high efficiency gene transduction, highly specific delivery of genes to target cells, induction of robust immune responses, and increased cellular immunity. The present disclosure provides for recombinant adenovirus vectors comprising deletions or insertions of crucial regions of the viral genome. The viral vectors of provided by the present disclosure can comprise heterologous nucleic acid sequences that encode one or more target antigens of interest, or variants, fragments or fusions thereof, against which it is desired to generate an immune response.

Suitable viral vectors that can be used with the methods and compositions of the present disclosure include but are not limited to retroviruses, lentiviruses, provirus, Vaccinia virus, adenoviruses, adeno-associated viruses, self-complementary adeno-associated virus, Cytomegalovirus, or Sendai virus. In some embodiments, the viral vector can be replication-competent. In some embodiments, the viral vector can be replication-defective. For replication-defective viral vectors, the viruses' genome can have the coding regions necessary for additional rounds of replication and packaging replaced with other genes, or deleted. These viruses are capable of infecting their target cells and delivering their viral payload, but then fail to continue the typical lytic pathway that leads to cell lysis and death. Depending on the viral vector, the typical maximum length of an allowable DNA or cDNA insert in a replication-defective viral vector is can be about 8-10 kilobases (kb).

Retroviruses have been used to express antigens, such as an enveloped, single-stranded RNA virus that contains reverse transcriptase. Retrovirus vectors can be replication-defective. Retrovirus vectors can be of murine or avian origin. Retrovirus vectors can be from Moloney murine leukemia virus (MoMLV). Retrovirus vectors can be used that require genome integration for gene expression. Retrovirus vectors can be used to provide long-term gene expression. For example, retrovirus vectors can have a genome size of approximately 7-11 kb and the vector can harbor 7-8 kb long foreign DNA inserts. Retrovirus vectors can be used to display low immunogenicity and most patients do not show pre-existing immunity to retroviral vectors. Retrovirus vectors can be used to infect dividing cells. Retrovirus vectors can be used to not infect non-dividing cells.

Lentivirus vectors have been used to express antigens. Lentiviruses constitute a subclass of retroviruses. Lentivirus vectors can be used to infect non-dividing cells. Lentivirus vectors can be used to infect dividing cells. Lentivirus vectors can be used to infect both non-dividing and dividing cells. Lentiviruses generally exhibit broader tropism than retroviruses. Several proteins such as tat and rev regulate the replication of lentiviruses. These regulatory proteins are typically absent in retroviruses. HIV is an exemplary lentivirus that can be engineered into a transgene delivery vector. The advantages of lentivirus vectors are similar to those of retroviral vectors. Although lentiviruses can potentially trigger tumorigenesis, the risk is lower than that of retroviral vectors, as the integration sites of lentiviruses are away from the sites harboring cellular promoters. HIV-based vectors can be generated, for example, by deleting the HIV viral envelope and some of the regulatory genes not required during vector production. Instead of parental envelope, several chimeric or modified envelope vectors are generated because it determines the cell and tissue specificity.

Cytomegalovirus (CMV) vectors have been used to express antigens. CMV is a member of the herpesviruses. Species-specific CMVs can be used (e.g., human CMV (HCMV), e.g., human herpesvirus type 5. HCMV contains a 235 kb double-stranded linear DNA genome surrounded by a capsid. The envelope contains glycoproteins gB and gH, which bind to cellular receptors.

Sendai virus (SeV) vectors have been used to express antigens. SeV is an enveloped, single-stranded RNA virus of the family Paramyxovirus. The SeV genome encodes six protein and two envelope glycoproteins, HN and F proteins, that mediate cell entry and determine its tropism. SeV vectors that lack F protein can be used as a replication-defective virus to improve the safety of the vector. SeV vector produced in a packaging cell can be used to expresses the F protein. An F gene-deleted and transgene-inserted genome can be transfected into a packaging cell. SeV contains RNA dependent RNA polymerase and viral genome localizes to the cytoplasm. This ensures that fast gene expression occurs soon after infection and the genotoxic advantage of SeV. SeV vectors can be used to exhibit highly efficient gene transfer. SeV vectors can be used to transduce both dividing and non-dividing cells. SeV vectors can be used to transduce non-dividing cells. SeV vectors can be used to transduce dividing cells. SeV vectors can be used, for example, to efficiently transduce human airway epithelial cells. SeV vectors can be, for example, administered by a mucosal (e.g., oral and nasal) route. Intranasal administration can be used to potentially reduce the influence of a pre-existing immunity to SeV, as compared to intramuscular administration. Compared to other viral vectors, its transgene capacity (3.4 kb) is low. SeV is highly homologous to the human parainfluenza type 1 (hPIV-1) virus; thus, a pre-existing immunity against hPIV-1 can work against the use of SeV.

Adenovirus Vectors

In general, adenoviruses are attractive for clinical because they can have a broad tropism, they can infect a variety of dividing and non-dividing cell types and hey can be used systemically as well as through more selective mucosal surfaces in a mammalian body. In addition, their relative thermostability further facilitates their clinical use. Adenoviruses are a family of DNA viruses characterized by an icosahedral, non-enveloped capsid containing a linear double-stranded genome. Generally, adenoviruses are found as non-enveloped viruses comprising double-stranded DNA genome approximated ~30-35 kilobases in size. Of the human Ads, none are associated with any neoplastic disease, and only cause relatively mild, self-limiting illness in immunocompetent individuals. The first genes expressed by the virus are the E1 genes, which act to initiate high-level gene expression from the other Ad5 gene promoters present in the wild type genome. Viral DNA replication and assembly of progeny virions occur within the nucleus of infected cells, and the entire life cycle takes about 36 hr with an output of approximately $10^4$ virions per cell. The wild type Ad5 genome is approximately 36 kb, and encodes genes that are divided into early and late viral functions, depending on whether they are expressed before or after DNA replication. The early/late delineation is nearly absolute, since it has been demonstrated that super-infection of cells previously infected with an Ad5 results in lack of late gene expression from the super-infecting virus until after it has replicated its own genome. Without bound by theory, this is likely due to a replication dependent cis-activation of the Ad5 major late promoter (MLP), preventing late gene expression (primarily the Ad5 capsid proteins) until replicated genomes are present to be encapsulated. The composition and methods of the invention take advantage of feature in the development of advanced generation Ad vectors/vaccines. The linear genome of the adenovirus is generally flanked by two origins for DNA replication (ITRs) and has eight units for RNA polymerase II-mediated transcription. The genome carries five early units E1A, E1B, E2, E3, E4, and E5, two units that are expressed with a delay after initiation of viral replication (IX and IVa2), and one late unit (L) that is subdivided into L1-L5. Some adenoviruses can further encode one or two species of RNA called virus-associated (VA) RNA.

Adenoviruses that induce innate and adaptive immune responses in human patient are provided. By deletion or insertion of crucial regions of the viral genome, recombinant vectors are provided that have been engineered to increase their predictability and reduce unwanted side effects. In some aspects, the invention provides for an adenovirus vector comprising the genome deletion or insertion selected from the group consisting of: E1A, E1B, E2, E3, E4, E5, IX, IVa2, L1, L2, L3, L4, and L5, and any combination thereof.

The present disclosure provides for recombinant adenovirus vectors comprising an altered capsid. Generally, the capsid of an adenovirus is primarily comprises 20 triangular facets of an icosahedron each icosahedron contains 12 copies of hexon trimers. In addition there are also other several additional minor capsid proteins, IIIa, VI, VIII, and IX.

The present disclosure provides for recombinant adenovirus vectors comprising one or more altered fiber proteins. In general the fiber proteins, which also form trimers, are inserted at the 12 vertices into the pentameric penton bases. The fiber can comprise of a thin N-terminal tail, a shaft, and a knob domain. The shaft can comprise a variable numbers of β-strand repeats. The knob can comprise one or more loops A, B, C, D, E, F, G, H, I, J. The fiber knob loops can bind to cellular receptors. The present disclosure provides for adenovirus vectors to be used in vaccine systems for the treatment of Ebola Suitable adenoviruses that can be used with the present methods and compositions of the disclosure include but are not limited to species-specific adenovirus including human subgroups A, B1, B2, C, D, E and F or their crucial genomic regions as provided herein, which subgroups can further classified into immunologically distinct serotypes. Further, suitable adenoviruses that can be used with the present methods and compositions of the disclosure include, but are not limited to, species-specific adenovirus or their crucial genomic regions identified from primates, bovines, fowls, reptiles, or frogs.

Some adenoviruses serotypes preferentially target distinct organs. Serotypes such as AdHu1, AdHu2, and AdHu5 (subgenus C), generally effect the infect upper respiratory, while subgenera A and F effect gastrointestinal organs. The present disclosure provides for recombinant adenovirus vectors to be used in preferentially target distinct organs for the treatment of Ebola. In some applications the recombinant adenovirus vector is altered to reduce tropism to a specific organ in a mammal. In some applications the recombinant adenovirus vector is altered to increase tropism to a specific organ in a mammal.

The tropism of an adenovirus can be determined by their ability to attach to host cell receptors. In some instances the process of host cell attachment can involve the initial binding of the distal knob domain of the fiber to a host cell surface molecule followed by binding of the RGD motif within the penton base with αV integrins. The present disclosure provides for recombinant adenovirus vectors with altered tropism such that they can be genetic engineered to infect specific cell types of a host. The present disclosure provides for recombinant adenovirus vectors with altered tropism for the treatment of cell-specific Ebola infections. The present disclosure provides for recombinant adenovirus vectors with altered fiber knob from one or more adenoviruses of subgroups A, B, C, D, or F, or a combination thereof or the insertion of RGD sequences. In some applications the recombinant adenovirus vectors comprising an altered fiber knob results in a vector with reduced tropism for one or more particular cell types. In some applications the recombinant adenovirus vectors comprising an altered fiber knob results in a vector with enhanced tropism for one or more particular cell types. In some applications the recombinant adenovirus vectors comprising an altered fiber knob results in a vector with reduced product-specific B or T-cell responses. In some applications the recombinant adenovirus vectors comprising an altered fiber knob results in a vector with enhanced product-specific B or T-cell responses.

The present disclosure provides for recombinant adenovirus vectors that are coated with other molecules to circumvent the effects of virus-neutralizing antibodies or improve transduction in to a host cell. The present disclosure provides for recombinant adenovirus vectors that are coated with an adaptor molecule that aids in the attachment of the vector to a host cell receptor. By way of example an adenovirus vector can be coated with adaptor molecule that connects coxsackie Ad receptor (CAR) with CD40L resulting in increased transduction of dendritic cells, thereby enhancing immune responses in a subject. Other adenovirus vectors similarly engineered for enhancing the attachment to other target cell types are also included by the present disclosure.

Ad5 Vectors

Studies in humans and animals have demonstrated that pre-existing immunity against Ad5 can be an inhibitory factor to commercial use of Ad-based vaccines. The preponderance of humans have antibody against Ad5, the most widely used subtype for human vaccines, with two-thirds of humans studied having lympho-proliferative responses against Ad5. This pre-existing immunity can inhibit immunization or re-immunization using typical Ad5 vaccines and may preclude the immunization of a vaccine against a second antigen, using an Ad5 vector, at a later time. Overcoming the problem of pre-existing anti-vector immunity has been a subject of intense investigation. Investigations using alternative human (non-Ad5 based) Ad5 subtypes or even non-human forms of Ad5 have been examined. Even if these approaches succeed in an initial immunization, subsequent vaccinations may be problematic due to immune responses to the novel Ad5 subtype. To avoid the Ad5 immunization barrier, and improve upon the limited efficacy of first generation Ad5 [E1-] vectors to induce optimal immune responses, various embodiments of the invention relate to a next generation Ad5 vector based vaccine platform.

First generation, or E1-deleted adenovirus vectors Ad5 [E1-] are constructed such that a transgene replaces only the E1 region of genes. Typically, about 90% of the wild-type Ad5 genome is retained in the vector. Ad5 [E1-] vectors have a decreased ability to replicate and cannot produce infectious virus after infection of cells that do not express the Ad5 E1 genes. The recombinant Ad5 [E1-] vectors are propagated in human cells (e.g., 293 cells) allowing for Ad5 [E1-] vector replication and packaging. Ad5 [E1-] vectors have a number of positive attributes; one of the most important is their relative ease for scale up and cGMP production. Currently, well over 220 human clinical trials utilize Ad5 [E1-] vectors, with more than two thousand subjects given the virus sc, im, or iv. Additionally, Ad5 vectors do not integrate; their genomes remain episomal. Generally, for vectors that do not integrate into the host genome, the risk for insertional mutagenesis and/or germline transmission is extremely low if at all. Conventional Ad5 [E1-] vectors have a carrying capacity that approaches 7 kb.

Ad5-based vectors with deletions of the E1 and the E2b regions (Ad5 [E1-, E2b-]), the latter encoding the DNA polymerase and the pre-terminal protein, by virtue of diminished late phase viral protein expression, provide an opportunity to avoid immunological clearance and induce more potent immune responses against the encoded Ebola antigen transgene in Ad-immune hosts. The new Ad5 platform has additional deletions in the E2b region, removing the DNA polymerase and the preterminal protein genes. The Ad5 [E1-, E2b-] platform has an expanded cloning capacity that is sufficient to allow inclusion of many possible genes. Ad5 [E1-, E2b-] vectors have up to about 12 kb gene-carrying capacity as compared to the 7 kb capacity of Ad5 [E1-] vectors, providing space for multiple genes if needed. In some embodiments, an insert of more than 1, 2, 3, 4, 5, 6, 7, 8, 9, 10, or 11 kb is introduced into an Ad5 vector, such as the Ad5 [E1-, E2b-] vector. Deletion of the E2b region confers advantageous immune properties on the Ad5 vectors of the invention, often eliciting potent immune responses to target transgene antigens while minimizing the immune responses to Ad viral proteins.

In various embodiments, Ad5 [E1-, E2b-] vectors of the invention induce a potent CMI, as well as antibodies against the vector expressed vaccine antigens even in the presence of Ad immunity. Ad5 [E1-, E2b-] vectors also have reduced adverse reactions as compared to Ad5 [E1-] vectors, in particular the appearance of hepatotoxicity and tissue damage. A key aspect of these Ad5 vectors is that expression of Ad late genes is greatly reduced. For example, production of the capsid fiber proteins could be detected in vivo for Ad5 [E1-] vectors, while fiber expression was ablated from Ad5 [E1-, E2b-] vector vaccines. The innate immune response to wild type Ad is complex. Proteins deleted from the Ad5 [E1-, E2b-] vectors generally play an important role. Specifically, Ad5 [E1-, E2b-] vectors with deletions of preterminal protein or DNA polymerase display reduced inflammation during the first 24 to 72 h following injection compared to Ad5 [E1-] vectors. In various embodiments, the lack of Ad5 gene expression renders infected cells invisible to anti-Ad activity and permits infected cells to express the transgene for extended periods of time, which develops immunity to the target.

Various embodiments of the invention contemplate increasing the capability for the Ad5 [E1-, E2b-] vectors to transduce dendritic cells, improving antigen specific immune responses in the vaccine by taking advantage of the reduced inflammatory response against Ad5 [E1-, E2b-] vector viral proteins and the resulting evasion of pre-existing Ad immunity.

Replication Defective Ad5 Vector

Attempts to overcome anti-Ad immunity have included use of alternative Ad serotypes and/or alternations in the Ad5 viral capsid protein each with limited success and the potential for significantly altering biodistribution of the resultant vaccines. Therefore, a completely novel approach was attempted by further reducing the expression of viral proteins from the E1 deleted Ad5 vectors, proteins known to be targets of pre-existing Ad immunity. Specifically, a novel recombinant Ad5 platform has been described with deletions in the early 1 (E1) gene region and additional deletions in the early 2b (E2b) gene region (Ad5 [E1-, E2b-]). Deletion of the E2b region (that encodes DNA polymerase and the pre-terminal protein) results in decreased viral DNA replication and late phase viral protein expression. This vector platform can be used to induce CMI responses in animal models of Ebola infection and more importantly, this recombinant Ad5 gene delivery platform overcomes the barrier of Ad5 immunity and can be used in the setting of pre-existing and/or vector-induced Ad immunity thus enabling multiple homologous administrations of the vaccine. In particular embodiments, the present invention relates to a replication defective adenovirus vector of serotype 5 comprising a sequence encoding an immunogenic polypeptide. The immunogenic polypeptide may be a mutant, natural variant, or a fragment thereof.

In some embodiments, the replication defective adenovirus vector comprises a modified sequence encoding a polypeptide with at least 70%, 75%, 80%, 85%, 90%, 95%, 98%, 99%, 99.5%, 99.9% identity to a wild-type immunogenic polypeptide or a fragment thereof. In some embodiments, the replication defective adenovirus vector comprises a modified sequence encoding a subunit of a wild-type polypeptide. The compositions and methods of the invention, in some embodiments, relate to an adenovirus-derived vector comprising at least 60% sequence identity to SEQ. ID. NO.: 1, 2, 4, 5, or 6.

In some embodiments, an adenovirus-derived vector, optionally relating to a replication defective adenovirus, comprises a sequence with at least 75%, 80%, 85%, 90%, 95%, 98%, 99%, 99.5%, 99.8%, 99.9% identity to SEQ. ID. NO.: 1, 2, 4, 5, or 6 or a sequence generated from SEQ. ID. NO.:3 by alternative codon replacements. In various embodiments, the adenovirus-derived vectors described herein have a deletion in the E2b region, and optionally, in the E1 region, the deletion conferring a variety of advantages to the use of the vectors in immunotherapy as described herein.

Certain regions within the adenovirus genome serve essential functions and may need to be substantially conserved when constructing the replication defective adenovirus vectors of the invention. These regions are further described in Lauer et al., J. Gen. Virol., 85, 2615-25 (2004), Leza et al., J. Virol., p. 3003-13 (1988), and Miralles et al., J. Bio Chem., Vol. 264, No. 18, p. 10763-72 (1983), which are incorporated by reference in their entirety. Recombinant nucleic acid vectors comprising a sequence with identity values of at least 75%, 80%, 85%, 90%, 95%, 98%, 99%, 99.5%, 99.8%, 99.9% to a portion of SEQ. ID. NO.: 1, 2, 4, 5, or 6, such as a portion comprising at least about 100, 250, 500, 1000 or more bases of SEQ. ID. NO.: 1, 2, 4, 5, or 6 are within the bounds of the invention.

The present invention contemplates the use of E2b deleted adenovirus vectors, such as those described in U.S. Pat. Nos. 6,063,622; 6,451,596; 6,057,158; 6,083,750; and 8,298,549. The vectors with deletions in the E2b regions in many cases cripple viral protein expression and/or decrease the frequency of generating replication competent Ad (RCA). Propagation of these E2b deleted adenovirus vectors can be done utilizing cell lines that express the deleted E2b gene products. Such packaging cell lines are provided herein; e.g., E.C7 (formally called C-7), derived from the HEK-293 cell line.

Further, the E2b gene products, DNA polymerase and preterminal protein, can be constitutively expressed in E.C7, or similar cells along with the E1 gene products. Transfer of gene segments from the Ad genome to the production cell line has immediate benefits: (1) increased carrying capacity; and, (2) a decreased potential of RCA generation, typically requiring two or more independent recombination events to generate RCA. The E1, Ad DNA polymerase and/or preterminal protein expressing cell lines used in the present invention can enable the propagation of adenovirus vectors with a carrying capacity approaching 13 kb, without the need for a contaminating helper virus. In addition, when genes critical to the viral life cycle are deleted (e.g., the E2b genes), a further crippling of Ad to replicate or express other viral gene proteins occurs. This can decrease immune recognition of infected cells, and extend durations of foreign transgene expression.

E1, DNA polymerase, and preterminal protein deleted vectors are typically unable to express the respective proteins from the E1 and E2b regions. Further, they may show a lack of expression of most of the viral structural proteins. For example, the major late promoter (MLP) of Ad is responsible for transcription of the late structural proteins L1 through L5. Though the MLP is minimally active prior to Ad genome replication, the highly toxic Ad late genes are primarily transcribed and translated from the mLP only after viral genome replication has occurred. This cis-dependent activation of late gene transcription is a feature of DNA viruses in general, such as in the growth of polyoma and SV-40. The DNA polymerase and preterminal proteins are important for Ad replication (unlike the E4 or protein IX proteins). Their deletion can be extremely detrimental to adenovirus vector late gene expression, and the toxic effects of that expression in cells such as APCs.

The adenovirus vectors can include a deletion in the E2b region of the Ad genome and, optionally, the E1 region. In some cases, such vectors do not have any other regions of the Ad genome deleted. The adenovirus vectors can include a deletion in the E2b region of the Ad genome and deletions in the E1 and E3 regions. In some cases, such vectors have no other regions deleted. The adenovirus vectors can include a deletion in the E2b region of the Ad genome and deletions in the E1, E3 and partial or complete removal of the E4 regions. In some cases, such vectors have no other deletions. The adenovirus vectors can include a deletion in the E2b region of the Ad genome and deletions in the E1 and/or E4 regions. In some cases, such vectors contain no other deletions. The adenovirus vectors can include a deletion in the E2a, E2b and/or E4 regions of the Ad genome. In some cases, such vectors have no other deletions. The adenovirus vectors can have the E1 and/or DNA polymerase functions of the E2b region deleted. In some cases, such vectors have no other deletions. The adenovirus vectors can have the E1 and/or the preterminal protein functions of the E2b region deleted. In some cases, such vectors have no other deletions. The adenovirus vectors can have the E1, DNA polymerase and/or the preterminal protein functions deleted. In some cases, such vectors have no other deletions. The adenovirus vectors can have at least a portion of the E2b region and/or the E1 region. In some cases, such vectors are not gutted adenovirus vectors. In this regard, the vectors may be deleted for both the DNA polymerase and the preterminal protein functions of the E2b region. The adenovirus vectors can have a deletion in the E1, E2b and/or 100 K regions of the adenovirus genome. The adenovirus vectors can comprise vectors having the E1, E2b and/or protease functions deleted. In some cases, such vectors have no other deletions. The adenovirus vectors can have the E1 and/or the E2b regions deleted, while the fiber genes have been modified by mutation or other alterations (for example to alter Ad tropism). Removal of genes from the E3 or E4 regions may be added to any of the adenovirus vectors mentioned. In certain embodiments, the adenovirus vector may be a gutted adenovirus vector.

Other regions of the Ad genome can be deleted. A "deletion" in a particular region of the Ad genome refers to a specific DNA sequence that is mutated or removed in such a way so as to prevent expression and/or function of at least one gene product encoded by that region (e.g., E2b functions of DNA polymerase or preterminal protein function). Deletions encompass deletions within exons encoding portions of proteins as well as deletions within promoter and leader sequences. A deletion within a particular region refers to a deletion of at least one base pair within that region of the Ad genome. More than one base pair can be deleted. For example, at least 20, 30, 40, 50, 60, 70, 80, 90, 100, 110, 120, 130, 140, or 150 base pairs can be deleted from a particular region. The deletion can be more than 150, 160, 170, 180, 190, 200, 250, or 300 base pairs within a particular region of the Ad genome. These deletions can prevent expression and/or function of the gene product encoded by the region. For example, a particular region of the Ad genome can include one or more point mutations such that one or more encoded proteins is non-functional. Such mutations include residues that are replaced with a different residue leading to a change in the amino acid sequence that result in a nonfunctional protein. Exemplary deletions or mutations in the Ad genome include one or more of E1a, E1b, E2a, E2b, E3, E4, L1, L2, L3, L4, L5, TP, POL, IV, and VA regions. Deleted adenovirus vectors can be made, for example, using recombinant techniques.

Ad vectors for use in the present invention can be successfully grown to high titers using an appropriate packaging cell line that constitutively expresses E2b gene products and products of any of the necessary genes that may have been deleted. HEK-293-derived cells that not only constitutively express the E1 and DNA polymerase proteins, but also the Ad-preterminal protein, can be used. E.C7 cells can be used, for example, to grow high titer stocks of the adenovirus vectors.

To delete critical genes from self-propagating adenovirus vectors, proteins encoded by the targeted genes can first be coexpressed in HEK-293 cells, or similar, along with E1 proteins. For example, those proteins which are non-toxic when coexpressed constitutively (or toxic proteins inducibly-expressed) can be selectively utilized. Coexpression in HEK-293 cells of the E1 and E4 genes is possible (for example utilizing inducible, not constitutive, promoters). The E1 and protein IX genes, a virion structural protein, can be coexpressed. Further coexpression of the E1, E4, and protein IX genes is also possible. E1 and 100 K genes can be expressed in trans-complementing cell lines, as can E1 and protease genes.

Cell lines coexpressing E1 and E2b gene products for use in growing high titers of E2b deleted Ad particles can be used. Useful cell lines constitutively express the approximately 140 kDa Ad-DNA polymerase and/or the approximately 90 kDa preterminal protein. Cell lines that have high-level, constitutive coexpression of the E1, DNA polymerase, and preterminal proteins, without toxicity (e.g., E.C7), are desirable for use in propagating Ad for use in multiple vaccinations. These cell lines permit the propagation of adenovirus vectors deleted for the E1, DNA polymerase, and preterminal proteins.

The recombinant Ad of the present invention can be propagated using, for example, tissue culture plates containing E.C7 cells infected with Ad vector virus stocks at an appropriate MOI (e.g., 5) and incubated at 37° C. for 40-96 h. The infected cells can be harvested, resuspended in 10 mM Tris-Cl (pH 8.0), and sonicated, and the virus can be purified by two rounds of cesium chloride density centrifugation. The virus containing band can be desalted over a column, sucrose or glycerol can be added, and aliquots can be stored at −80° C. Virus can be placed in a solution designed to enhance its stability, such as A195. The titer of the stock can be measured (e.g., by measurement of the optical density at 260 nm of an aliquot of the virus after lysis). Plasmid DNA, either linear or circular, encompassing the entire recombinant E2b deleted adenovirus vector can be transfected into E.C7, or similar cells, and incubated at 37° C. until evidence of viral production is present (e.g., cytopathic effect). Conditioned media from cells can be used to infect more cells to expand the amount of virus produced before purification. Purification can be accomplished, for example, by two rounds of cesium chloride density centrifugation or selective filtration. Virus may be purified by chromatography using commercially available products or custom chromatographic columns.

The compositions of the present invention can comprise enough virus to ensure that cells to be infected are confronted with a certain number of viruses. Thus, in various embodiments, the present invention provides a stock of recombinant Ad, such as an RCA-free stock of recombinant Ad. Viral stocks can vary considerably in titer, depending largely on viral genotype and the protocol and cell lines used to prepare them. Viral stocks can have a titer of at least about $10^6$, $10^7$, or $10^8$ pfu/ml, or higher, such as at least about $10^9$, $10^{10}$, $10^{11}$, or $10^{12}$ pfu/ml. Depending on the nature of the recombinant virus and the packaging cell line, a viral stock of the present invention can have a titer of even about $10^{13}$ particles/ml or higher.

Polynucleotides and Variants Encoding Antigen Targets

The present disclosure further provides nucleic acid sequences, also referred to herein as polynucleotides that encode one or more target antigens of interest, or fragments or variants thereof. As such, the present invention provides polynucleotides that encode target antigens from any source as described further herein, vectors comprising such polynucleotides and host cells transformed or transfected with such expression vectors. In order to express a desired target antigen polypeptide, nucleotide sequences encoding the polypeptide, or functional equivalents, can be inserted into an appropriate Ad vector (e.g., using recombinant techniques). The appropriate adenovirus vector may contain the necessary elements for the transcription and translation of the inserted coding sequence and any desired linkers. Methods which are well known to those skilled in the art may be used to construct these adenovirus vectors containing sequences encoding a polypeptide of interest and appropriate transcriptional and translational control elements. These methods include in vitro recombinant DNA techniques, synthetic techniques, and in vivo genetic recombination.

Polynucleotides may comprise a native sequence (i.e., an endogenous sequence that encodes a target antigen polypeptide/protein/epitope of the invention or a portion thereof) or may comprise a sequence that encodes a variant, fragment, or derivative of such a sequence. Polynucleotide sequences can encode target antigen proteins. In some embodiments, polynucleotides represent a novel gene sequence optimized for expression in specific cell types that may substantially vary from the native nucleotide sequence or variant but encode a similar protein antigen.

In other related embodiments, polynucleotide variants have substantial identity to native sequences encoding proteins (e.g., target antigens of interest), for example those comprising at least 70% sequence identity, preferably at least 75%, 80%, 85%, 90%, 95%, 96%, 97%, 98%, or 99% or higher, sequence identity compared to a native polynucleotide sequence encoding the polypeptides (e.g., BLAST analysis using standard parameters). These values can be appropriately adjusted to determine corresponding identity of proteins encoded by two nucleotide sequences by taking into account codon degeneracy, amino acid similarity, reading frame positioning and the like. Polynucleotides can encode a protein comprising for example at least 70% sequence identity, preferably at least 75%, 80%, 85%, 90%, 95%, 96%, 97%, 98%, or 99% or higher, sequence identity compared to a protein sequence encoded by a native polynucleotide sequence.

Polynucleotides can comprise at least about 5, 10, 15, 20, 25, 30, 35, 40, 45, 50, 55, 60, 65, 70, 75, 80, 85, 90, 95, 100, 11, 120, 130, 140, 150, 160, 170, 180, 190, 200, 210, 220, 230, 240, 250, 260, 270, 280, 290, 300, 350, 400, 450, 500, 550, 600, 650, 700, 750, 800, 850, 900, 950, or 1000 or more contiguous nucleotides encoding a polypeptide (e.g., target protein antigens), and all intermediate lengths there between. "Intermediate lengths", in this context, refers to any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like. A polynucleotide sequence may be extended at one or both ends by additional nucleotides not found in the native sequence encoding a polypeptide, such as an epitope or heterologous target protein. This additional sequence may consist of 1, 2, 3, 4, 5, 6, 7, 8, 9, 10, 11, 12, 13, 14, 15, 16, 17, 18, 19, or 20 nucleotides or more, at either end of the disclosed sequence or at both ends of the disclosed sequence.

The polynucleotides, regardless of the length of the coding sequence itself, may be combined with other DNA sequences, such as promoters, expression control sequences, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. Illustrative polynucleotide segments with total lengths of about 1000, 2000, 3000, 4000, 5000, 6000, 7000, 8000, 9000, 10,000, about 500, about 200, about 100, about 50 base pairs in length, and the like, (including all intermediate lengths) are contemplated to be useful in many implementations of this invention.

A mutagenesis approach, such as site-specific mutagenesis, can be employed to prepare target antigen sequences. Specific modifications in a polypeptide sequence can be made through mutagenesis of the underlying polynucleotides that encode them. Site-specific mutagenesis can be used to make mutants through the use of oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. For example, a primer comprising about 14 to about 25 nucleotides or so in length can be employed, with about 5 to about 10 residues on both sides of the junction of the sequence being altered. Mutations may be made in a selected polynucleotide sequence to improve, alter, decrease, modify, or otherwise change the properties of the polynucleotide, and/or alter the properties, activity, composition, stability, or primary sequence of the encoded polypeptide.

Mutagenesis of polynucleotide sequences can be used to alter one or more properties of the encoded polypeptide, such as the immunogenicity of an epitope comprised in a polypeptide or the immunogenicity of a target antigen. Assays to test the immunogenicity of a polypeptide include, but are not limited to, T-cell cytotoxicity assays (CTL/chromium release assays), T-cell proliferation assays, intracellular cytokine staining, ELISA, ELISpot, etc. Other ways to obtain sequence variants of peptides and the DNA sequences encoding them can be employed. For example, recombinant vectors encoding the desired peptide sequence may be treated with mutagenic agents, such as hydroxylamine, to obtain sequence variants.

Polynucleotide segments or fragments encoding the polypeptides of the present invention may be readily prepared by, for example, directly synthesizing the fragment by chemical means. Fragments may be obtained by application of nucleic acid reproduction technology, such as PCR, by introducing selected sequences into recombinant vectors for recombinant production, and by other recombinant DNA techniques generally known to those of skill in the art of molecular biology.

A variety of vector/host systems may be utilized to contain and produce polynucleotide sequences. Exemplary systems include microorganisms such as bacteria transformed with recombinant bacteriophage, plasmid, or cosmid DNA vectors; yeast transformed with yeast vectors; insect cell systems infected with virus vectors (e.g., baculovirus); plant cell systems transformed with virus vectors (e.g., cauliflower mosaic virus, CaMV; tobacco mosaic virus, TMV) or with bacterial vectors (e.g., Ti or pBR322 plasmids); or animal cell systems.

Control elements or regulatory sequences present in an Ad vector may include those non-translated regions of the vector-enhancers, promoters, and 5' and 3' untranslated regions. Such elements may vary in their strength and specificity. Depending on the vector system and host utilized, any number of suitable transcription and translation elements, including constitutive and inducible promoters, may be used. For example, sequences encoding a polypeptide of interest may be ligated into an Ad transcription/translation complex consisting of the late promoter and tripartite leader sequence. Insertion in a non-essential E1 or E3 region of the viral genome may be used to obtain a viable virus which is capable of expressing the polypeptide in infected host cells. In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest (e.g., ATG initiation codon and adjacent sequences). Exogenous translational elements and initiation codons may be of various origins, both natural and synthetic. The efficiency of expression may be enhanced by the inclusion of enhancers which are appropriate for the particular cell system which is used. Specific termination sequences, either for transcription or translation, may also be incorporated in order to achieve efficient translation of the sequence encoding the polypeptide of choice.

A variety of protocols for detecting and measuring the expression of polynucleotide-encoded products (e.g., target antigens), can be used (e.g., using polyclonal or monoclonal antibodies specific for the product). Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed.

The Ad vectors can comprise a product that can be detected or selected for, such as a reporter gene whose product can be detected, such as by fluorescence, enzyme activity on a chromogenic or fluorescent substrate, and the like, or selected for by growth conditions. Exemplary reporter genes include green fluorescent protein (GFP), β-galactosidase, chloramphenicol acetyltransferase (CAT), luciferase, neomycin phosphotransferase, secreted alkaline phosphatase (SEAP), and human growth hormone (HGH). Exemplary selectable markers include drug resistances, such as neomycin (G418), hygromycin, and the like.

The Ad vectors can also comprise a promoter or expression control sequence. The choice of the promoter will depend in part upon the targeted cell type and the degree or type of control desired. Promoters that are suitable within the context of the present invention include, without limitation, constitutive, inducible, tissue specific, cell type specific, temporal specific, or event-specific. Examples of constitutive or nonspecific promoters include the SV40 early promoter, the SV40 late promoter, CMV early gene promoter, bovine papilloma virus promoter, and adenovirus promoter. In addition to viral promoters, cellular promoters are also amenable within the context of this invention. In particular, cellular promoters for the so-called housekeeping genes are useful (e.g., β-actin). Viral promoters are generally stronger promoters than cellular promoters. Inducible promoters may also be used. These promoters include MMTV LTR, inducible by dexamethasone, metallothionein, inducible by heavy metals, and promoters with cAMP response elements, inducible by cAMP, heat shock promoter. By using an inducible promoter, the nucleic acid may be delivered to a cell and will remain quiescent until the addition of the inducer. This allows further control on the timing of production of the protein of interest. Event-type specific promoters (e.g., HIV LTR) can be used, which are active or upregulated only upon the occurrence of an event, such as Ebola infection, for example. The HIV LTR promoter is inactive unless the tat gene product is present, which occurs upon viral infection. Some event-type promoters are also tissue-specific. Preferred event-type specific promoters include promoters activated upon viral infection.

Examples of promoters include promoters for α-fetoprotein, α-actin, myo D, carcinoembryonic antigen, VEGF-receptor; FGF receptor; TEK or tie 2; tie; urokinase receptor; E- and P-selectins; VCAM-1; endoglin; endosialin; αV-β3 integrin; endothelin-1; ICAM-3; E9 antigen; von Willebrand factor; CD44; CD40; vascular-endothelial cadherin; notch 4, high molecular weight melanoma-associated antigen; prostate specific antigen-1, probasin, FGF receptor, VEGF receptor, erb B2; erb B3; erb B4; MUC-1; HSP-27; int-1; int-2, CEA, HBEGF receptor; EGF receptor; tyrosinase, MAGE, IL-2 receptor; prostatic acid phosphatase, probasin, prostate specific membrane antigen, α-crystallin, PDGF receptor, integrin receptor, α-actin, SM1 and SM2 myosin heavy chains, calponin-hl, SM22 α-angiotensin receptor, IL-1, IL-2, IL-3, IL-4, IL-5, IL-6, IL-7, IL-8, IL-9, IL-10, IL-11, IL-12, IL-13, IL-14, immunoglobulin heavy chain, immunoglobulin light chain, and CD4.

Repressor sequences, negative regulators, or tissue-specific silencers may be inserted to reduce non-specific expression of the polynucleotide. Multiple repressor elements may be inserted in the promoter region. Repression of transcription is independent of the orientation of repressor elements or distance from the promoter. One type of repressor sequence is an insulator sequence. Such sequences inhibit transcription and can silence background transcription. Negative regulatory elements can be located in the promoter regions of a number of different genes. The repressor element can function as a repressor of transcription in the absence of factors, such as steroids, as does the NSE in the promoter region of the ovalbumin gene. These negative regulatory elements can bind specific protein complexes from oviduct, none of which are sensitive to steroids. Three different elements are located in the promoter of the ovalbumin gene. Oligonucleotides corresponding to portions of these elements can repress viral transcription of the TK reporter. One of the silencer elements shares sequence identity with silencers in other genes (TCTCTCCNA (SEQ. ID. NO.:7)).

Further, repressor elements can be located in the promoter region of a variety of genes, including the collagen II gene, for example. Nuclear factors from HeLa cells can bind specifically to DNA fragments containing the silencer region. Repressor elements may play a role regulating transcription in the carbamyl phosphate synthetase gene. This gene is expressed in only two different cell types, hepatocytes and epithelial cells of the intestinal mucosa. Negative regulatory regions are also found in the promoter region of the choline acetyltransferase gene, the albumin promoter, phosphoglycerate kinase (PGK-2) gene promoter, and in the 6-phosphofructo-2-kinase/fructose-2, 6-bisphosphatase gene, in which the negative regulatory element inhibits transcription in non-hepatic cell lines. Furthermore, the negative regulatory element Tse-1 is located in a number of liver specific genes, including tyrosine aminotransferase (TAT). TAT gene expression is liver specific and inducible by both glucocorticoids and the cAMP signaling pathway. The cAMP response element (CRE) can ask as the target for repression by Tse-1 and hepatocyte-specific elements. Accordingly, it is clear that varieties of such elements are known or are readily identified.

In certain embodiments, Elements that increase the expression of the desired target antigen can be incorporated into the nucleic acid sequence of the Ad vectors described herein. Exemplary elements include internal ribosome binding sites (IRESs). IRESs can increase translation efficiency. As well, other sequences may enhance expression. For some genes, sequences especially at the 5' end may inhibit transcription and/or translation. These sequences are usually palindromes that can form hairpin structures. In some cases, such sequences in the nucleic acid to be delivered are deleted. Expression levels of the transcript or translated product can be assayed to confirm or ascertain which sequences affect expression. Transcript levels may be assayed by any known method, including Northern blot hybridization, RNase probe protection and the like. Protein levels may be assayed by any known method, including ELISA.

Ebola Antigen-Specific Immunotherapies and Vaccines

The present disclosure provides for single antigen or combination antigen immunization against Ebola antigens, such as GP, NP, VP40, VP35, VP30, VP24, and/or L, utilizing such vectors and other vectors as provided herein. The present disclosure provides for therapeutic vaccines against Ebola antigens. The present disclosure provides for prophylactic vaccines against Ebola antigens. Further, in various embodiments, the composition and methods provide herein can lead to clinical responses, such as altered disease progression or life expectancy.

Ad5 [E1-] vectors encoding a variety of antigens can be used to efficiently transduce 95% of ex vivo exposed DC's to high titers of the vector. Importantly, the inventors have discovered increasing levels of foreign gene expression in the DC with increasing multiplicities of infection (MOI) with the vector. DCs infected with Ad5 [E1-] vectors can encode a variety of Ebola antigens that have the propensity to induce antigen specific CTL responses, have an enhanced antigen presentation capacity, and/or have an improved ability to initiate T-cell proliferation in mixed lymphocyte reactions. Immunization of animals with dendritic cells (DCs) previously transduced by Ad5 vectors encoding tumor specific antigens can be used to induce significant levels of protection for the animals when challenged with tumor cells expressing the respective antigen. Interestingly, intra-tumoral injection of Ads encoding IL-7 is less effective than injection of DCs transduced with IL-7 encoding Ad5 vectors at inducing anti-tumor immunity. Ex vivo transduction of DCs by Ad5 vectors is contemplated by the present disclosure. Ex vivo DC transduction strategies can been used to induce recipient host tolerance. For example, Ad5 mediated delivery of the CTLA4Ig into DCs can block interactions of the DCs CD80 with CD28 molecules present on T-cells.

Ad5 vector capsid interactions with DCs may trigger several beneficial responses, which may be enhancing the propensity of DCs to present antigens encoded by Ad5 vectors. For example, immature DCs, though specialized in antigen uptake, are relatively inefficient effectors of T-cell activation. DC maturation coincides with the enhanced ability of DCs to drive T-cell immunity. In some instances, the compositions and methods of the invention take advantage of an Ad5 infection resulting in direct induction of DC maturation Ad vector infection of immature bone marrow derived DCs from mice may upregulate cell surface markers normally associated with DC maturation (MHC I and II, CD40, CD80, CD86, and ICAM-1) as well as down-regulation of CD11c, an integrin down regulated upon myeloid DC maturation. In some instances, Ad vector infection triggers IL-12 production by DCs, a marker of DC maturation. Without being bound by theory, these events may possibly be due to Ad5 triggered activation of NF-κB pathways. Mature DCs can be efficiently transduced by Ad vectors, and do not lose their functional potential to stimulate the proliferation of naive T-cells at lower MOI, as demonstrated by mature CD83+ human DC (derived from peripheral blood monocytes). However, mature DCs may also be less infectable than immature ones.

Modification of capsid proteins can be used as a strategy to optimize infection of DC by Ad vectors, as well as enhancing functional maturation, for example using the CD40L receptor as a viral vector receptor, rather than using the normal CAR receptor infection mechanisms.

In various embodiments the compositions and methods of the invention comprising an Ad5 [E1-, E2b-]-GP, NP, VP40, VP35, VP30, VP24, L, or any combination thereof, vaccine effect of increased overall survival (OS) within the bounds of technical safety. For example, the compositions and methods of the invention can comprise an Ad5 [E1-, E2b-] vector(s) GP vaccine effect of increased overall survival (OS) within the bounds of technical safety. For example, the compositions and methods of the invention can comprise an Ad5 [E1-, E2b-] vector(s) NP vaccine effect of increased overall survival (OS) within the bounds of technical safety. For example, the compositions and methods of the invention can comprise an Ad5 [E1-, E2b-] vector(s) VP40 vaccine effect of increased overall survival (OS) within the bounds of technical safety. For example, the compositions and methods of the invention can comprise an Ad5 [E1-, E2b-] vector(s) VP35 vaccine effect of increased overall survival (OS) within the bounds of technical safety. For example, the compositions and methods of the invention can comprise an Ad5 [E1-, E2b-] vector(s) VP30 vaccine effect of increased overall survival (OS) within the bounds of technical safety. For example, the compositions and methods of the invention can comprise an Ad5 [E1-, E2b-] vector(s) VP24 vaccine effect of increased overall survival (OS) within the bounds of technical safety. For example, the compositions and methods of the invention can comprise an Ad5 [E1-, E2b-] vector(s) L vaccine effect of increased overall survival (OS) within the bounds of technical safety.

As noted above, the adenovirus vectors of the present invention comprise nucleic acid sequences that encode one or more target proteins or antigens of interest. In this regard, the vectors may contain nucleic acid encoding 1, 2, 3, 4, 5, 6, 7, 8, 9, 10, 11, 12, 13, 14, 15, 16, 17, 18, 19, 20 or more different target antigens of interest. The target antigens may be a full length protein or may be a fragment (e.g., an epitope) thereof. The adenovirus vectors may contain nucleic acid sequences encoding multiple fragments or epitopes from one target protein of interest or may contain one or more fragments or epitopes from numerous different target proteins of interest.

A target antigen may comprise any substance against which it is desirable to generate an immune response but generally, the target antigen is a protein. A target antigen may comprise a full length protein, a subunit of a protein, an isoform of a protein, or a fragment thereof that induces an immune response (i.e., an immunogenic fragment). A target antigen or fragment thereof may be modified, e.g., to reduce one or more biological activities of the target antigen or to enhance its immunogenicity.

In certain embodiments, immunogenic fragments bind to an MHC class I or class II molecule. An immunogenic fragment may "bind to" an MHC class I or class II molecule if such binding is detectable using any assay known in the art. For example, the ability of a polypeptide to bind to MHC class I may be evaluated indirectly by monitoring the ability to promote incorporation of $^{125}$I labeled β-2-microglobulin (β-2m) into MHC class I/β2m/peptide heterotrimeric complexes (see Parker et al., J. Immunol. 152:163, 1994). Alternatively, functional peptide competition assays that are known in the art may be employed. Immunogenic fragments of polypeptides may generally be identified. Representative techniques for identifying immunogenic fragments include screening polypeptides for the ability to react with antigen-specific antisera and/or T-cell lines or clones. An immunogenic fragment of a particular target polypeptide is a fragment that reacts with such antisera and/or T-cells at a level that is not substantially less than the reactivity of the full length target polypeptide (e.g., in an ELISA and/or T-cell reactivity assay). In other words, an immunogenic fragment may react within such assays at a level that is similar to or greater than the reactivity of the full length polypeptide. Such screens may be performed using methods known in the art.

In some embodiments, the viral vectors of the present invention comprise heterologous nucleic acid sequences that encode one or more proteins, variants thereof, fusions thereof, or fragments thereof, that can modulate the immune response. In some embodiments, the viral vector of the present invention encodes one or more antibodies against specific antigens, such as anthrax protective antigen, permitting passive immunotherapy. In some embodiments, the viral vectors of the present invention comprise heterologous nucleic acid sequences encoding one or more proteins having therapeutic effect (e.g., anti-viral, anti-bacterial, anti-parasitic, or anti-Ebola function). In some embodiments the Second Generation E2b deleted adenovirus vectors comprise a heterologous nucleic acid sequence. In some embodiments, the heterologous nucleic acid sequence is GP, NP, VP40, VP35, VP30, VP24, L, a variant, a portion, or any combination thereof.

Target antigens include, but are not limited to, antigens derived from a variety of Ebola viruses. In some embodiments, parts or variants of Ebola proteins are employed as target antigens. In some embodiments, parts or variants of Ebola proteins being employed as target antigens have a modified, for example, increased ability to effect and immune response against the Ebola protein or cells containing the same. A vaccine of the present invention can vaccinate against an antigen. A vaccine can also target an epitope. An antigen can be an Ebola virus antigen. An epitope can be an Ebola virus epitope. Such a Ebola virus epitope may be derived from a wide variety of Ebola viruses, such as antigens from Ebola viruses resulting from mutations and shared Ebola species specific antigens. Ebola antigens (EAs) may be antigens not normally expressed by the host. Ebola-associated antigens may be, for example, proteins or protein fragments, complex carbohydrates, gangliosides, haptens, nucleic acids, other biological molecules or any combinations thereof.

Illustrative Ebola proteins useful in the present invention include, but are not limited to any one or more of GP, NP, VP40, VP35, VP30, VP24, and L. In some embodiments, the viral vector comprises a target antigen sequence encoding a modified polypeptide selected from GP, NP, VP40, VP35, VP30, VP24, and L wherein the polypeptide or a fragment thereof has at least 60%, 65%, 70%, 75%, 80%, 85%, 90%, 95%, 98%, 99%, 99.5%, 99.9% identity to the described sequence.

The inventors have discovered that multiple homologous immunizations with Ad5 [E1-, E2b-]-GP, NP, VP40, VP35, VP30, VP24, and/or L, induced GP, NP, VP40, VP35, VP30, VP24, and/or L-specific cell-mediated immune (CMI) responses with anti-Ebola activity in animals despite the presence of pre-existing or induced Ad5-neutralizing antibody. Cohorts of patients with Ebola can be immunized with escalating doses of Ad5 [E1-, E2b-]-GP, NP, VP40, VP35, VP30, VP24, and/or L. In subjects with Ebola infections, the novel Ad5 [E1-, E2b-] gene delivery platform generates significant CMI responses to the EAs GP, NP, VP40, VP35, VP30, VP24, and/or L in the setting of both naturally acquired and immunization-induced Ad5 specific immunity.

GP, NP, VP40, VP35, VP30, VP24, and/or L antigen specific CMI can be, for example, greater than 10, 20, 30, 40, 50, 100, 200, 300, 400, 500, 600, 700, 800, 900, 1000, 5000, 10000, or more IFN-γ spot forming cells (SFC) per $10^6$ peripheral blood mononuclear cells (PBMC). In some embodiments, the immune response is raised in a human subject with a preexisting inverse Ad5 neutralizing antibody titer of greater than 50, 100, 150, 200, 300, 400, 500, 600, 700, 800, 900, 1000, 1500, 2000, 2500, 3000, 3500, 4000, 4500, 5000, 6000, 7000, 8000, 9000, 1000, 12000, 15000 or higher. The immune response may comprise a cell-mediated immunity and/or a humoral immunity as described herein. The immune response may be measured by one or more of intracellular cytokine staining (ICS), ELISpot, proliferation assays, cytotoxic T-cell assays including chromium release or equivalent assays, and gene expression analysis using any number of polymerase chain reaction (PCR) or RT-PCR based assays, as described herein and to the extent they are available to a person skilled in the art, as well as any other suitable assays known in the art for measuring immune response.

In some embodiments, the replication defective adenovirus vector comprises a modified sequence encoding a subunit with at least 75%, 80%, 85%, 90%, 95%, 98%, 99%, 99.5%, 99.9% identity to a wild-type subunit of the polypeptide. The immunogenic polypeptide may be a mutant GP, NP, VP40, VP35, VP30, VP24, or L, or a fragment thereof. In some embodiments, the replication defective adenovirus vector comprises a sequence encoding a polypeptide with at least 75%, 80%, 85%, 90%, 95%, 98%, 99%, 99.5%, 99.9% identity to the immunogenic polypeptide. In some embodiments, the sequence encoding the immunogenic polypeptide comprises the sequence of SEQ. ID. NO.:1.

In some embodiments, the sequence encoding the immunogenic polypeptide comprises a sequence with at least 70% 75%, 80%, 85%, 90%, 95%, 98%, 99%, 99.5%, 99.9% identity to SEQ. ID. NO.:1, 2, 4, 5, or 6, or a sequence generated from SEQ. ID. NO.: 1, 2, 4, 5, or 6 by alternative codon replacements. In some embodiments, the immunogenic polypeptide encoded by the adenovirus vectors comprise up to 1, 2, 3, 4, 5, 6, 7, 8, 9, 10, 11, 12, 13, 14, 15, 16, 17, 18, 19, 20, 25, 30, 35, 40, or more point mutations, such as single amino acid substitutions or deletions, as compared to a wild-type human GP, NP, VP40, VP35, VP30, VP24, or L sequence.

In certain embodiments Ebola antigens may be identified directly from an individual infected with an Ebola virus. In this regard, screens can be carried out using a variety of known technologies. For example, in one embodiment, a cell or tissue biopsy is taken from a patient, RNA is isolated from the sample cells and screened using a gene chip (for example, from Affymetrix, Santa Clara, Calif.) and a Ebola virus antigen is identified. Once the Ebola virus target antigen is identified, it may then be cloned, expressed and purified using techniques known in the art.

This target antigen can then linked to one or more epitopes or incorporated or linked to cassettes or viral vectors described herein and administered to the patient in order to alter the immune response to the target molecule isolated from a sample from he Ebola infected patient. In this manner, "personalized" immunotherapy and vaccines are contemplated within the context of the invention. In some embodiments, a personalized Ebola antigen related to SEQ. ID. NO.:1, SEQ. ID. NO.:2, SEQ. ID. NO.:4, SEQ. ID. NO.:5, SEQ. ID. NO.:6 or a combination thereof is characterized from a patient and further utilized as the target antigen as a whole, in part or as a variant.

Combination Immunotherapies and Vaccines

The present disclosure provides for a combination immunotherapy and vaccine compositions for the treatment of Ebola infections. In some aspects, combination immunotherapies and vaccines provided herein can comprise a multi-targeted immunotherapeutic approach against antigens associated with Ebola infections. In some aspects, combination immunotherapies and vaccines provided herein can comprise a multi-targeted antigen signature immunotherapeutic approach against antigens associated with Ebola infections. The compositions and methods of the invention, in various embodiments, provide viral based vectors expressing a wild-type or variant of GP, NP, VP40, VP35, VP30, VP24, and/or L for immunization of Ebola, as provided herein. These vectors can raise an immune response against GP, NP, VP40, VP35, VP30, VP24, and/or L.

In some aspects, the vector comprises at least one antigen. In some aspects, the vector comprises at least two antigens. In some aspects, the vector comprises at least three antigens. In some aspects, the vector comprises more than three antigens. In some aspects, the vaccine formulation comprises 1:1 ratio of vector to antigen. In some aspects, the vaccine comprises 1:2 ratio of vector to antigen. In some aspects, the vaccine comprises 1:3 ratio of vector to antigen. In some aspects, the vaccine comprises 1:4 ratio of vector to antigen. In some aspects, the vaccine comprises 1:5 ratio of vector to antigen. In some aspects, the vaccine comprises 1:6 ratio of vector to antigen. In some aspects, the vaccine comprises 1:7 ratio of vector to antigen. In some aspects, the vaccine comprises 1:8 ratio of vector to antigen. In some aspects, the vaccine comprises 1:9 ratio of vector to antigen. In some aspects, the vaccine comprises 1:10 ratio of vector to antigen.

In some aspects, the vaccine is a combination vaccine, wherein the vaccine comprises at least two vectors each containing at least a single antigen. In some aspects the vaccine is a combination vaccine, wherein the vaccine comprises at least three vectors each containing at least a single antigen target. In some aspects the vaccine is a combination vaccine, wherein the vaccine comprises more than three vectors each containing at least a single antigen.

In some aspects, the vaccine is a combination vaccine, wherein the vaccine comprises at least two vectors, wherein a first vector of the at least two vectors comprises at least a single antigen and wherein a second vector of the at least two vectors comprises at least two antigens. In some aspects, the vaccine is a combination vaccine, wherein the vaccine comprises at least three vectors, wherein a first vector of the at least three vectors comprises at least a single antigen and wherein a second vector of the at least three vectors comprises at least two antigens. In some aspects, the vaccine is a combination vaccine, wherein the vaccine comprises three or more vectors, wherein a first vector of the three or more vectors comprises at least a single antigen and wherein a second vector of the three or more vectors comprises at least two antigens. In some aspects the vaccine is a combination vaccine, wherein the vaccine comprises more than three vectors each containing at least two antigens.

When a mixture of different antigens are simultaneously administered or expressed from a same or different vector in an individual, they may compete with one another. As a result the formulations comprising different concentration and ratios of expressed antigens in a combination immunotherapy or vaccine must be evaluated and tailored to the individual or group of individuals to ensure that effective and sustained immune responses occur after administration.

Composition that comprises multiple antigens can be present at various ratios. For example, formulations with more than vector can have various ratios. For example, immunotherapies or vaccines can have two different vectors in a stoichiometry of 1:1, 1:2, 1:3, 1:4, 1:5, 1:6, 1:7, 1:8, 1:9, 1:10, 1:15, 1:20, 1:30, 2:1, 2:3, 2:4, 2:5, 2:6, 2:7, 2:8, 3:1, 3:3, 3:4, 3:5, 3:6, 3:7, 3:8, 3: 1, 3:3, 3:4, 3:5, 3:6, 3:7, 3:8, 4: 1, 4:3, 4:5, 4:6, 4:7, 4:8, 5: 1, 5:3, 5:4, 5:6, 5:7, 5:8, 6:1, 6:3, 6:4, 6:5, 6:7, 6:8, 7: 1, 7:3, 7:4, 7:5, 7:6, 7:8, 8: 1, 8:3, 8:4, 8:5, 8:6, or 8:7. For example, immunotherapies or vaccines can have three different vectors in a stoichiometry of: 1:1:1, 1:2:1, 1:3:1, 1:4:1, 1:5:1, 1:6:1, 1:7:1, 1:8:1, 2:1:1, 2:3:1, 2:4:1, 2:5:1, 2:6:1, 2:7:1, 2:8:1, 3:1, 3:3:1, 3:4:1, 3:5:1, 3:6:1, 3:7:1, 3:8:1, 3:1:1, 3:3:1, 3:4:1, 3:5:1, 3:6:1, 3:7:1, 3:8:1, 4:1:1, 4:3:1, 4:4:1, 4:5:1, 4:6:1, 4:7:1, 4:8:1, 5:1:1, 5:3:1, 5:4:1, 5:5:1, 5:6:1, 5:7:1, 5:8:1, 6:1:1, 6:3:1, 6:4:1, 6:5:1, 6:6:1, 6:7:1, 6:8:1, 7:1:1, 7:3:1, 7:4:1, 7:5:1, 7:6:1, 7:7:1, 7:8:1, 8:1:1, 8:3:1, 8:4:1, 8:5:1, 8:6:1, 8:7:1, 8:8:1, 1:1:2, 1:2:2, 1:3:2, 1:4:2, 1:5:2, 1:6:2, 1:7:2, 1:8:2, 2:1:2, 2:3:2, 2:4:2, 2:5:2, 2:6:2, 2:7:2, 2:8:2, 3:1:2, 3:3:2, 3:4:2, 3:5:2, 3:6:2, 3:7:2, 3:8:2, 3:1:2, 3:3:2, 3:4:2, 3:5:2, 3:6:2, 3:7:2, 3:8:2, 4:1:2, 4:3:2, 4:4:2, 4:5:2, 4:6:2, 4:7:2, 4:8:2, 5:1:2, 5:3:2, 5:4:2, 5:5:2, 5:6:2, 5:7:2, 5:8:2, 6:1:2, 6:3:2, 6:4:2, 6:5:2, 6:6:2, 6:7:2, 6:8:2, 7:1:2, 7:3:2, 7:4:2, 7:5:2, 7:6:2, 7:7:2, 7:8:2, 8:1:2, 8:3:2, 8:4:2, 8:5:2, 8:6:2, 8:7:2, 8:8:2, 1:1:3, 1:2:3, 1:3:3, 1:4:3, 1:5:3, 1:6:3, 1:7:3, 1:8:3, 2:1:3, 2:3:3, 2:4:3, 2:5:3, 2:6:3, 2:7:3, 2:8:3, 3:1:3, 3:3:3, 3:4:3, 3:5:3, 3:6:3, 3:7:3, 3:8:3, 3:1:3, 3:3:3, 3:4:3, 3:5:3, 3:6:3, 3:7:3, 3:8:3, 4:1:3, 4:3:3, 4:4:3, 4:5:3, 4:6:3, 4:7:3, 4:8:3, 5:1:3, 5:3:3, 5:4:3, 5:5:3, 5:6:3, 5:7:3, 5:8:3, 6:1:3, 6:3:3, 6:4:3, 6:5:3, 6:6:3, 6:7:3, 6:8:3, 7:1:3, 7:3:3, 7:4:3, 7:5:3, 7:6:3, 7:7:3, 7:8:3, 8:1:3, 8:3:3, 8:4:3, 8:5:3, 8:6:3, 8:7:3, 8:8:3, 1:1:4, 1:2:4, 1:3:4, 1:4:4, 1:5:4, 1:6:4, 1:7:4, 1:8:4, 2:1:4, 2:3:4, 2:4:4, 2:5:4, 2:6:4, 2:7:4, 2:8:4, 3:1:4, 3:3:4, 3:4:4, 3:5:4, 3:6:4, 3:7:4, 3:8:4, 3:1:4, 3:3:4, 3:4:4, 3:5:4, 3:6:4, 3:7:4, 3:8:4, 4:1:4, 4:3:4, 4:4:4, 4:5:4, 4:6:4, 4:7:4, 4:8:4, 5:1:4, 5:3:4, 5:4:4, 5:5:4, 5:6:4, 5:7:4, 5:8:4, 6:1:4, 6:3:4, 6:4:4, 6:5:4, 6:6:4, 6:7:4, 6:8:4, 7:1:4, 7:3:4, 7:4:4, 7:5:4, 7:6:4, 7:7:4, 7:8:4, 8:1:4, 8:3:4, 8:4:3, 8:5:4, 8:6:4, 8:7:4, 8:8:4, 1:1:5, 1:2:5, 1:3:5, 1:4:5, 1:5:5, 1:6:5, 1:7:5, 1:8:5, 2:1:5, 2:3:5, 2:4:5, 2:5:5, 2:6:5, 2:7:5, 2:8:5, 3:1:5, 3:3:5, 3:4:5, 3:5:5, 3:6:5, 3:7:5, 3:8:5, 3:1:5, 3:3:5, 3:4:5, 3:5:5, 3:6:5, 3:7:5, 3:8:5, 4:1:5, 4:3:5, 4:4:5, 4:5:5, 4:6:5, 4:7:5, 4:8:5, 5:1:5, 5:3:5, 5:4:5, 5:5:5, 5:6:5, 5:7:5, 5:8:5, 6:1:5, 6:3:5, 6:4:5, 6:5:5, 6:6:5, 6:7:5, 6:8:5, 7:1:5, 7:3:5, 7:4:5, 7:5:5, 7:6:5, 7:7:5, 7:8:5, 8:1:5, 8:3:5, 8:4:5, 8:5:5, 8:6:5, 8:7:5, 8:8:5, 1:1:6, 1:2:6, 1:3:6, 1:4:6, 1:5:6, 1:6:6, 1:7:6, 1:8:6, 2:1:6, 2:3:6, 2:4:6, 2:5:6, 2:6:6, 2:7:6, 2:8:6, 3:1:6, 3:3:6, 3:4:6, 3:5:6, 3:6:6, 3:7:6, 3:8:6, 3:1:6, 3:3:6, 3:4:6, 3:5:6, 3:6:6, 3:7:6, 3:8:6, 4:1:6, 4:3:6, 4:4:6, 4:5:6, 4:6:6, 4:7:6, 4:8:6, 5:1:6, 5:3:6, 5:4:6, 5:5:6, 5:6:6, 5:7:6, 5:8:6, 6:1:6, 6:3:6, 6:4:6, 6:5:6, 6:6:6, 6:7:6, 6:8:6, 7:1:6, 7:3:6, 7:4:6, 7:5:6, 7:6:6, 7:7:6, 7:8:6, 8:1:6, 8:3:6, 8:4:6, 8:5:6, 8:6:6, 8:7:6, 8:8:6, 1:1:7, 1:2:7, 1:3:7, 1:4:7, 1:5:7, 1:6:7, 1:7:7, 1:8:7, 2:1:7, 2:3:7, 2:4:7, 2:5:7, 2:6:7, 2:7:7, 2:8:7, 3:1:7, 3:3:7, 3:4:7, 3:5:7, 3:6:7, 3:7:7, 3:8:7, 3:1:7, 3:3:7, 3:4:7, 3:5:7, 3:6:7, 3:7:7, 3:8:7, 4:1:7, 4:3:7, 4:4:7, 4:5:7, 4:6:7, 4:7:7, 4:8:7, 5:1:7, 5:3:7, 5:4:7, 5:5:7, 5:6:7, 5:7:7, 5:8:7, 6:1:7, 6:3:7, 6:4:7, 6:5:7, 6:6:7, 6:7:7, 6:8:7, 7:1:7, 7:3:7, 7:4:7, 7:5:7, 7:6:7, 7:7:7, 7:8:7, 8:1:7, 8:3:7, 8:4:7, 8:5:7, 8:6:5, 8:7:7, or 8:8:7.

The present disclosure provides for a combination immunotherapies or vaccines comprising: at least two, at least three, or more than three different target antigens comprising a sequence encoding a GP, NP, VP40, VP35, VP30, VP24, and/or L. For example, a combination immunotherapy or vaccine can comprise at least two, at least three, or more than three different target antigens comprising a sequence encoding a wild-type or modified GP, NP, VP40, VP35, VP30, VP24, and/or L, wherein a wild-type or modified target antigen comprises a sequence with at least 70%, 75%, 80%, 85%, 90%, 95%, 98%, 99%, 99.5%, or 99.9% sequence identity to SEQ. ID. NO.:1. For example, a combination immunotherapy or vaccine can comprise at least two, at least three, or more than three different target antigens comprising a sequence encoding a wild-type or modified GP, NP, VP40, VP35, VP30, VP24, and/or L, wherein a wild-type or modified target antigen comprises a sequence with at least 70%, 75%, 80%, 85%, 90%, 95%, 98%, 99%, 99.5%, or 99.9% sequence identity to SEQ. ID. NO.:2. For example, a combination immunotherapy or vaccine can comprise at least two, at least three, or more than three different target antigens comprising a sequence encoding a wild-type or modified GP, NP, VP40, VP35, VP30, VP24, and/or L, wherein a wild-type or modified target antigen comprises a sequence with at least 70%, 75%, 80%, 85%, 90%, 95%, 98%, 99%, 99.5%, or 99.9% sequence identity to SEQ. ID. NO.:4. For example, a combination immunotherapy or vaccine can comprise at least two, at least three, or more than three different target antigens comprising a sequence encoding a wild-type or modified GP, NP, VP40, VP35, VP30, VP24, and/or L, wherein a wild-type or modified target antigen comprises a sequence with at least 70%, 75%, 80%, 85%, 90%, 95%, 98%, 99%, 99.5%, or 99.9% sequence identity to SEQ. ID. NO.:5. For example, a combination immunotherapy or vaccine can comprise at least two, at least three, or more than three different target antigens comprising a sequence encoding a wild-type or modified GP, NP, VP40, VP35, VP30, VP24, and/or L, wherein a wild-type or modified target antigen comprises a sequence with at least 70%, 75%, 80%, 85%, 90%, 95%, 98%, 99%, 99.5%, or 99.9% sequence identity to SEQ. ID. NO.:6.

In some aspects the present disclosure provides combination immunotherapies comprising multi-targeted immunotherapeutic directed to EAs and molecular compositions comprising an immune pathway checkpoint modulator that targets at least one immune-checkpoint protein of the immune inhibitory pathway. The present disclosure provides for a combination immunotherapies or vaccines comprising: at least two, at least three, or more than three different target antigens comprising a sequence encoding a wild-type or modified GP, NP, VP40, VP35, VP30, VP24, and/or L, and at least one molecular composition comprising an immune pathway checkpoint modulator. For example, a combination immunotherapy or vaccine can comprise at least two, at least three, or more than three different target antigens comprising a sequence encoding a modified wild-type or modified GP, NP, VP40, VP35, VP30, VP24, and/or L, wherein the modified target antigen comprises a sequence with an at least 70%, 75%, 80%, 85%, 90%, 95%, 98%, 99%, 99.5%, or 99.9% sequence identity to SEQ. ID. NO.:1, 2, 4, 5, and/or 6, and at least one molecular composition of the immune-checkpoint inhibitory pathway.

In some embodiments, the least one molecular composition comprises an immune pathway checkpoint modulator that targets CTLA4. In some embodiments, the least one molecular comprises an immune pathway checkpoint modulator that targets PD1. In some embodiments, the least one molecular composition comprises an immune pathway checkpoint modulator that targets PDL1. In some embodiments, the least one molecular composition comprises an immune pathway checkpoint modulator that targets LAG3. In some embodiments, the least one molecular composition comprises an immune pathway checkpoint modulator that targets B7-H3. In some embodiments, the least one molecular composition comprises an immune pathway checkpoint modulator that targets B7-H4. In some embodiments, the least one molecular composition comprises an immune pathway checkpoint modulator that targets TIM3. In some embodiment the molecular composition comprises an immune pathway checkpoint modulator that is a monoclonal or polyclonal antibody directed to PD1, PDL1, PDL2, CD28, CD80, CD86, CTLA4, B7RP1, ICOS, B7RPI, B7-H3, B7-H4, BTLA, HVEM, KIR, TCR, LAG3, CD137, CD137L, OX40, OX40L, CD27, CD70, CD40, CD40L, TIM3 (i.e., HAVcr2), GALS, and A2aR.

Immunological Fusion Partner Antigen Targets

The viral vectors of the present invention may also include nucleic acid sequences that encode proteins that increase the immunogenicity of the target antigen. In this regard, the protein produced following immunization with the adenovirus vector containing such a protein may be a fusion protein comprising the target antigen of interest fused to a protein that increases the immunogenicity of the target antigen of interest.

In one embodiment, such an immunological fusion partner is derived from a *Mycobacterium* sp., such as a *Mycobacterium tuberculosis*-derived Ra12 fragment. Ra12 compositions and methods for their use in enhancing the expression and/or immunogenicity of heterologous polynucleotide/polypeptide sequences are described in U.S. Patent Application 60/158,585 and U.S. Pat. No. 7,009,042. Briefly, Ra12 refers to a polynucleotide region that is a subsequence of a *Mycobacterium tuberculosis* MTB32A nucleic acid. MTB32A is a serine protease of 32 kDa encoded by a gene in virulent and avirulent strains of *M. tuberculosis*. The nucleotide sequence and amino acid sequence of MTB32A have been described (see, e.g., U.S. Patent Application 60/158,585; Skeiky et al., Infection and Immun. 67:3998-4007 (1999)). C-terminal fragments of the MTB32A coding sequence express at high levels and remain as soluble polypeptides throughout the purification process. Moreover, Ra12 may enhance the immunogenicity of heterologous immunogenic polypeptides with which it is fused. One Ra12 fusion polypeptide comprises a 14 kDa C-terminal fragment corresponding to amino acid residues 192 to 323 of MTB32A. Other Ra12 polynucleotides generally comprise at least about 15, 30, 60, 100, 200, 300, or more nucleotides that encode a portion of a Ra12 polypeptide. Ra12 polynucleotides may comprise a native sequence (i.e., an endogenous sequence that encodes a Ra12 polypeptide or a portion thereof) or may comprise a variant of such a sequence. Ra12 polynucleotide variants may contain one or more substitutions, additions, deletions and/or insertions such that the biological activity of the encoded fusion polypeptide is not substantially diminished, relative to a fusion polypeptide comprising a native Ra12 polypeptide. Variants can have at least about 70%, 80%, or 90% identity, or more, to a polynucleotide sequence that encodes a native Ra12 polypeptide or a portion thereof.

An immunological fusion partner can be derived from protein D, a surface protein of the gram-negative bacterium *Haemophilus* influenza B. In some cases, a protein D derivative comprises approximately the first third of the protein (e.g., the first N-terminal 100-110 amino acids). A protein D derivative may be lipidated. Within certain embodiments, the first 109 residues of a Lipoprotein D fusion partner is included on the N-terminus to provide the polypeptide with additional exogenous T-cell epitopes, which may increase the expression level in *E. coli* and may function as an expression enhancer. The lipid tail may ensure optimal presentation of the antigen to antigen presenting cells. Other fusion partners include the non-structural protein from influenza virus, NS1 (hemagglutinin). Typically, the N-terminal 81 amino acids are used, although different fragments that include T-helper epitopes may be used.

The immunological fusion partner can be the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus can be employed. Within another embodiment, a repeat portion of LYTA may be incorporated into a fusion polypeptide. A repeat portion can, for example, be found in the C-terminal region starting at residue 178. One particular repeat portion incorporates residues 188-305.

In some embodiments, the antigen target comprises an immunogenic component comprising a cytokine selected from the group of IFN-γ, TNFα IL-2, IL-8, IL-12, IL-18, IL-7, IL-3, IL-4, IL-5, IL-6, IL-9, IL-10, and IL-13. In some embodiments, the antigen target further comprises one or more immunogenic component comprises a cytokine selected from the group of IFN-γ, TNFα IL-2, IL-8, IL-12, IL-18, IL-7, IL-3, IL-4, IL-5, IL-6, IL-9, IL-10, and IL-13. In some embodiments, the antigen target comprises an immunogenic component comprising a nucleic acid encoding of IFN-γ, TNFα IL-2, IL-8, IL-12, IL-18, IL-7, IL-3, IL-4, IL-5, IL-6, IL-9, IL-10, and IL-13, a protein with substantial identity to of IFN-γ, TNFα IL-2, IL-8, IL-12, IL-18, IL-7, IL-3, IL-4, IL-5, IL-6, IL-9, IL-10, and IL-13, and a nucleic acid encoding a protein with substantial identity to of IFN-γ, TNFα IL-2, IL-8, IL-12, IL-18, IL-7, IL-3, IL-4, IL-5, IL-6, IL-9, IL-10, and IL-13.

In some embodiments, the antigen target is fused or linked to an immunogenic component comprising a cytokine selected from the group of IFN-γ, TNFα IL-2, IL-8, IL-12, IL-18, IL-7, IL-3, IL-4, IL-5, IL-6, IL-9, IL-10, and IL-13. In some embodiments, the antigen target is co-expressed in a cell with an immunogenic component comprising a cytokine selected from the group of IFN-γ, TNFα IL-2, IL-8, IL-12, IL-18, IL-7, IL-3, IL-4, IL-5, IL-6, IL-9, IL-10, and IL-13.

Immune Pathway Checkpoint Modulators

In some embodiments, compositions of the present invention are administered with one or more immune pathway checkpoint modulators. A balance between activation and inhibitory signals regulates the interaction between T lymphocytes and disease cells, wherein T-cell responses are initiated through antigen recognition by the T-cell receptor (TCR). The inhibitory pathways and signals are referred to as immune checkpoints. In normal circumstances, immune checkpoints play a critical role in control and prevention of autoimmunity and also protect from tissue damage in response to pathogenic infection.

The present disclosure provides combination immunotherapies comprising viral vector based vaccines and compositions for modulating immune checkpoint inhibitory pathways for the treatment of Ebola infections. In some embodiments, modulating is increasing expression or activity of a gene or protein. In some embodiments, modulating is decreasing expression or activity of a gene or protein. In some embodiments, modulating affects a family of genes or proteins.

In general, the immune inhibitory pathways are initiated by ligand-receptor interactions. It is now clear that in diseases, the disease can co-opt immune-checkpoint pathways as mechanism for inducing immune resistance in a subject.

The induction of immune resistance or immune inhibitory pathways in a subject by a given disease can be blocked by molecular compositions such as siRNAs, antisense, small molecules, mimic, a recombinant form of ligand, receptor or protein, or antibodies (which can be an Ig fusion protein) that are known to modulate one or more of the Immune Inhibitory Pathways. For example, preliminary clinical findings with blockers of immune-checkpoint proteins, such as Cytotoxic T-lymphocyte-associated antigen 4 (CTLA4) and programmed cell death protein 1 (PD1) have shown promise for enhancing anti-tumor immunity.

Because diseased cells can express multiple inhibitory ligands, and disease-infiltrating lymphocytes express multiple inhibitory receptors, dual or triple blockade of immune checkpoints proteins may enhance anti-disease immunity. Combination immunotherapies as provide herein can comprise one or more molecular compositions comprising an immune pathway checkpoint modulator that targets one or more of the following immune-checkpoint proteins: PD1, PDL1, PDL2, CD28, CD80, CD86, CTLA4, B7RP1, ICOS, B7RPI, B7-H3 (also known as CD276), B7-H4 (also known as B7-S1, B7x and VCTN1), BTLA (also known as CD272), HVEM, KIR, TCR, LAG3 (also known as CD223), CD137, CD137L, OX40, OX40L, CD27, CD70, CD40, CD40L, TIM3 (also known as HAVcr2), GALS, A2aR and Adenosine. In some embodiments, the molecular composition comprises a siRNAs. In some embodiments, the molecular composition comprises a small molecule. In some embodiments, the molecular composition comprises a recombinant form of a ligand. In some embodiments, the molecular composition comprises a recombinant form of a receptor. In some embodiments, the molecular composition comprises an antibody. In some embodiments, the combination therapy comprises more than one molecular composition and/or more than one type of molecular composition. As it will be appreciated by those in the art, future discovered proteins of the immune checkpoint inhibitory pathways are also envisioned to be encompassed by the present disclosure.

In some embodiments, combination immunotherapies comprise molecular compositions for the modulation of CTLA4. In some embodiments, combination immunotherapies comprise molecular compositions for the modulation of PD1. In some embodiments, combination immunotherapies comprise molecular compositions for the modulation of PDL1. In some embodiments, combination immunotherapies comprise molecular compositions for the modulation of LAG3. In some embodiments, combination immunotherapies comprise molecular compositions for the modulation of B7-H3. In some embodiments, combination immunotherapies comprise molecular compositions for the modulation of B7-H4. In some embodiments, combination immunotherapies comprise molecular compositions for the modulation of TIM3. In some embodiments, modulation is an increase or enhancement of expression. In other embodiments, modulation is the decrease of absence of expression.

Two exemplary immune checkpoint inhibitors include the cytotoxic T lymphocyte associated antigen-4 (CTLA-4) and the programmed cell death protein-1 (PD1). CTLA-4 can be expressed exclusively on T-cells where it regulates early stages of T-cell activation. CTLA-4 interacts with the co-stimulatory T-cell receptor CD28 which can result in signaling that inhibits T-cell activity. Once TCR antigen recognition occurs, CD28 signaling may enhances TCR signaling, in some cases leading to activated T-cells and CTLA-4 inhibits the signaling activity of CD28. The present disclosure provides immunotherapies as provided herein in combination with anti-CTLA-4 monoclonal antibody for the treatment of Ebola. The present disclosure provides immunotherapies as provided herein in combination with CTLA-4 molecular compositions for the treatment of Ebola.

Programmed death cell protein ligand-1 (PDL1) is a member of the B7 family and is distributed in various tissues and cell types. PDL1 can interact with PD1 inhibiting T-cell activation and CTL mediated lysis. Significant expression of PDL1 has been demonstrated on various human tumors and PDL1 expression is one of the key mechanisms in which tumors evade host anti-tumor immune responses. Programmed death-ligand 1 (PDL1) and programmed cell death protein-1 (PD1) interact as immune checkpoints. This interaction can be a major tolerance mechanism which results in the blunting of anti-tumor immune responses and subsequent tumor progression. PD1 is present on activated T cells and PDL1, the primary ligand of PD1, is often expressed on tumor cells and antigen-presenting cells (APC) as well as other cells, including B cells. Significant expression of PDL1 has been demonstrated on various human tumors including HPV-associated head and neck cancers. PDL1 interacts with PD1 on T cells inhibiting T cell activation and cytotoxic T lymphocyte (CTL) mediated lysis. The present disclosure provides immunotherapies as provided herein in combination with anti-PD1 or anti-PDL1 monoclonal antibody for the treatment of Ebola. The present disclosure provides immunotherapies as provided herein in combination with PD1 or anti-PDL1 molecular compositions for the treatment of Ebola. The present disclosure provides immunotherapies as provided herein in combination with anti-CTLA-4 and anti-PD1 monoclonal antibodies for the treatment of Ebola. The present disclosure provides immunotherapies as provided herein in combination with anti-CTLA-4 and PDL1 monoclonal antibodies for the treatment of Ebola. The present disclosure provides immunotherapies as provided herein in combination with anti-CTLA-4, anti-PD1, PDL1, monoclonal antibodies, or a combination thereof, for the treatment of Ebola.

Immune checkpoint molecules can be expressed by T cells. Immune checkpoint molecules can effectively serve as "brakes" to down-modulate or inhibit an immune response. Immune checkpoint molecules include, but are not limited to Programmed Death 1 (PD1, also known as PDCD1 or CD279, accession number: NM_005018), Cytotoxic T-Lymphocyte Antigen 4 (CTLA-4, also known as CD152, GenBank accession number AF414120.1), LAG3 (also known as CD223, accession number: NM_002286.5), Tim3 (also known as HAVCR2, GenBank accession number: JX049979.1), BTLA (also known as CD272, accession number: NM_181780.3), BY55 (also known as CD160, GenBank accession number: CR541888.1), TIGIT (also known as IVSTM3, accession number: NM_173799), LAIR1 (also known as CD305, GenBank accession number: CR542051.1), SIGLECIO (GenBank accession number: AY358337.1), 2B4 (also known as CD244, accession number: NM_001166664.1), PPP2CA, PPP2CB, PTPN6, PTPN22, CD96, CRTAM, SIGLEC7, SIGLEC9, TNFRSF10B, TNFRSF10A, CASP8, CASP10, CASP3, CASP6, CASP7, FADD, FAS, TGFBRII, TGFRBRI, SMAD2, SMAD3, SMAD4, SMAD10, SKI, SKIL, TGIF1, ILIORA, IL10RB, HMOX2, IL6R, IL6ST, EIF2AK4, CSK, PAG1, SIT1, FOXP3, PRDM1, BATF, GUCY1A2, GUCY1A3, GUCY1B2, GUCY1B3 which directly inhibit immune cells. For example, PD1 can be combined with an adenoviral vaccine of the present invention to treat a patient in need thereof.

Table 1, without being exhaustive, shows exemplary immune checkpoint genes that can be inactivated to improve the efficiency of the adenoviral vaccine of the present invention. Immune checkpoints gene can be selected from such genes listed in Table 1 and others involved in co-inhibitory receptor function, cell death, cytokine signaling, arginine tryptophan starvation, TCR signaling, Induced T-reg repression, transcription factors controlling exhaustion or anergy, and hypoxia mediated tolerance.

TABLE 1

| # | Gene Symbol | NCBI # (GRCh38.p2) | Start | Stop | Genome location |
|---|---|---|---|---|---|
| 1 | ADORA2A | 135 | 24423597 | 24442360 | 22q11.23 |
| 2 | CD276 | 80381 | 73684281 | 73714518 | 15q23-q24 |
| 3 | VTCN1 | 79679 | 117143587 | 117270368 | 1p13.1 |
| 4 | BTLA | 151888 | 112463966 | 112499702 | 3q13.2 |
| 5 | CTLA4 | 1493 | 203867788 | 203873960 | 2q33 |
| 6 | IDO1 | 3620 | 39913809 | 39928790 | 8p12-p11 |
| 7 | KIR3DL1 | 3811 | 54816438 | 54830778 | 19q13.4 |
| 8 | LAG3 | 3902 | 6772483 | 6778455 | 12p13.32 |
| 9 | PDCD1 | 5133 | 241849881 | 241858908 | 2q37.3 |
| 10 | HAVCR2 | 84868 | 157085832 | 157109237 | 5q33.3 |
| 11 | VISTA | 64115 | 71747556 | 71773580 | 10q22.1 |
| 12 | CD244 | 51744 | 160830158 | 160862902 | 1q23.3 |
| 13 | CISH | 1154 | 50606454 | 50611831 | 3p21.3 |

The combination of an adenoviral-based vaccine and an immune pathway checkpoint modulator may result in reduction in Ebola infection, progression, or symptoms in treated patients, as compared to either agent alone. In another embodiment of this invention the combination of an adenoviral-based vaccine and an immune pathway checkpoint modulator may result improved overall survival of treated patients, as compared to either agent alone. In some cases, the combination of an adenoviral vaccine and an immune pathway checkpoint modulator may increase the frequency or intensity of Ebola-specific T cell responses in treated patients as compared to either agent alone.

The present invention also discloses the use of immune checkpoint inhibition to improve performance of an adenoviral vector-based vaccine. Said immune checkpoint inhibition may be administered at the time of the vaccine. Said immune checkpoint inhibition may also be administered after a vaccine. Immune checkpoint inhibition may occur simultaneously to an adenoviral vaccine administration. Immune checkpoint inhibition may occur 1, 2, 3, 4, 5, 6, 7, 8, 9, 10, 15, 20, 30, 40, 50, or 60 minutes after vaccination. Immune checkpoint inhibition may also occur 1, 2, 3, 4, 5, 6, 7, 8, 9, 10, 11, 12, 13, 14, 15, 16, 17, 18, 19, 20, 21, 22, 23, or 24 hours post vaccination. In some cases, immune inhibition may occur 1, 2, 3, 4, 5, 6, or 7 days after vaccination. Immune checkpoint inhibition may occur at any time before or after vaccination.

In another aspect, the invention pertains to a vaccine comprising an antigen and an immune pathway checkpoint modulator. The invention can pertain to a method for treating a subject having a condition that would benefit from downregulation of an immune checkpoint protein, PD1 for example, and its natural binding partner(s) on cells of the subject.

An immune pathway checkpoint modulator may be combined with an adenoviral vaccine comprising any antigen. For example, an antigen can be GP, NP, VP40, VP35, VP30, VP24, and/or L. An immune pathway checkpoint modulator may produce a synergistic effect when combined with a vaccine. An immune pathway checkpoint modulator may also produce an additive effect when combined with a vaccine.

Formulations

The present invention provides pharmaceutical compositions comprising a vaccination regime that can be administered either alone or together with a pharmaceutically acceptable carrier or excipient, by any routes, and such administration can be carried out in both single and multiple dosages. More particularly, the pharmaceutical composition can be combined with various pharmaceutically acceptable inert carriers in the form of tablets, capsules, lozenges, troches, hand candies, powders, sprays, aqueous suspensions, injectable solutions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes. The compositions described throughout can be formulated into a pharmaceutical medicament and be used to treat a human or mammal, in need thereof, diagnosed with a disease, e.g., Ebola.

For administration, the adenovirus vector stock can be combined with an appropriate buffer, physiologically acceptable carrier, excipient or the like. In certain embodiments, an appropriate number of virus vector particles (VP) are administered in an appropriate buffer, such as, sterile PBS or saline. In certain embodiment's viral vector compositions disclosed herein are provided in specific formulations for administration subcutaneously, parenterally, intravenously, intramuscularly, or even intraperitoneally. In certain embodiments, formulations in a solution of the active compounds as free base or pharmacologically acceptable salts may be prepared in water suitably mixed with a surfactant, such as hydroxypropylcellulose. Dispersions may also be prepared in glycerol, liquid polyethylene glycols, squalene-based emulsion, Squalene-based oil-in-water emulsions, water-in-oil emulsions, oil-in-water emulsions, nonaqueous emulsions, water-in-paraffin oil emulsion, and mixtures thereof and in oils. In other embodiments, viral vectors may are provided in specific formulations for pill form administration by swallowing or by suppository.

Illustrative pharmaceutical forms suitable for injectable use include sterile aqueous solutions or dispersions and sterile powders for the extemporaneous preparation of sterile injectable solutions or dispersions (see, e.g., U.S. Pat. No.

5,466,468). Fluid forms to the extent that easy syringability exists may be preferred. Forms that are stable under the conditions of manufacture and storage are within the bounds of this invention. In various embodiments, forms are preserved against the contaminating action of microorganisms, such as bacteria, molds and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, and thimerosal. It may be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution can be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 mL of isotonic NaCl solution and either added to 1000 mL of hypodermoclysis fluid or injected at the proposed site of infusion. Some variation in dosage may occur depending on the condition of the subject being treated.

Carriers of formulation can comprise any and all solvents, dispersion media, vehicles, coatings, diluents, antibacterial and antifungal agents, isotonic and absorption delaying agents, buffers, carrier solutions, suspensions, colloids, and the like. Except insofar as any conventional media or agent is incompatible with the active ingredient, its use in the therapeutic compositions is contemplated. Supplementary active ingredients can also be incorporated into the compositions. GP, NP, VP40, VP35, VP30, VP24, and L.

In certain embodiments, the viral vectors of the invention may be administered in conjunction with one or more immunostimulants, such as an adjuvant. An immunostimulant refers to essentially any substance that enhances or potentiates an immune response (antibody and/or cell-mediated) to an antigen. One type of immunostimulant comprises an adjuvant. Many adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Certain adjuvants are commercially available as, for example, Freund's Incomplete Adjuvant and Complete Adjuvant (Difco Laboratories); Merck Adjuvant 65 (Merck and Company, Inc.) AS-2 (SmithKline Beecham); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF, IFN-γ, TNFα, IL-2, IL-8, IL-12, IL-18, IL-7, IL-3, IL-4, IL-5, IL-6, IL-9, IL-10, and/or IL-13, and others, like growth factors, may also be used as adjuvants.

Within certain embodiments of the invention, the adjuvant composition can be one that induces an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient may support an immune response that includes Th1- and/or Th2-type responses. Within certain embodiments, in which a response is predominantly Th1-type, the level of Th1-type cytokines will increase to a greater extent than the level of Th2-type cytokines. The levels of these cytokines may be readily assessed using standard assays. Thus, various embodiments of the invention relate to therapies raising an immune response against a target antigen, for example SEQ. ID. NO.:1, SEQ. ID. NO.:2, SEQ. ID. NO.:4, SEQ. ID. NO.:5, or SEQ. ID. NO.:6 using cytokines, e.g., IFN-γ, TNFα, IL-2, IL-8, IL-12, IL-18, IL-7, IL-3, IL-4, IL-5, IL-6, IL-9, IL-10, and/or IL-13 supplied concurrently with a replication defective viral vector treatment. In some embodiments, a cytokine or a nucleic acid encoding a cytokine, is administered together with a replication defective viral described herein. In some embodiments, cytokine administration is performed prior or subsequent to viral vector administration. In some embodiments, a replication defective viral vector capable of raising an immune response against a target antigen, for example, SEQ. ID. NO.:1, SEQ. ID. NO.:2, SEQ. ID. NO.:4, SEQ. ID. NO.:5, or SEQ. ID. NO.:6 further comprises a sequence encoding a cytokine.

Certain illustrative adjuvants for eliciting a predominantly Th1-type response include, for example, a combination of monophosphoryl lipid A, such as 3-de-O-acylated monophosphoryl lipid A, together with an aluminum salt. MPL® adjuvants are commercially available. CpG-containing oligonucleotides (in which the CpG dinucleotide is unmethylated) also induce a predominantly Th1 response. Such oligonucleotides are well known and are described. Immunostimulatory DNA sequences are also described. Another adjuvant for use in the present invention comprises a saponin, such as Quil A, or derivatives thereof, including QS21 and QS7; escin; digitonin; or gypsophila or chenopodium quinoa saponins. Other formulations may include more than one saponin in the adjuvant combinations of the present invention, for example combinations of at least two of the following group comprising QS21, QS7, Quil A, β-escin, or digitonin.

In certain embodiments, the compositions may be delivered by intranasal sprays, inhalation, and/or other aerosol delivery vehicles. The delivery of drugs using intranasal microparticle resins and lysophosphatidyl-glycerol compounds (U.S. Pat. No. 5,725,871) are well-known in the pharmaceutical arts. Likewise, illustrative transmucosal drug delivery in the form of a polytetrafluoroetheylene support matrix is described.

In certain embodiments, Liposomes, nanocapsules, microparticles, lipid particles, vesicles, and the like, are used for the introduction of the compositions of the present invention into suitable host cells/organisms. In particular, the Compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

The formation and use of liposome and liposome-like preparations as potential drug carriers is generally known to those of skill in the art (see, Lasic, Trends Biotechnol 1998 July; 16(7):307-21; Takakura, Nippon Rinsho 1998 March; 56(3):691-5; Chandran et al., Indian J Exp Biol. 1997 August; 35(8):801-9; Margalit, Crit. Rev Ther Drug Carrier Syst. 1995; 12(2-3):233-61; U.S. Pat. Nos. 5,567,434; 5,552,157; 5,565,213; 5,738,868 and 5,795,587).

Liposomes have been used successfully with a number of cell types that are normally difficult to transfect by other procedures, including T cell suspensions, primary hepatocyte cultures and PC 12 cells. Liposomes have been used effectively to introduce genes, various drugs, radiotherapeutic agents, enzymes, viruses, transcription factors, allosteric effectors and the like, into a variety of cultured cell lines and animals. Furthermore, the use of liposomes does not appear to be associated with autoimmune responses or unacceptable toxicity after systemic delivery.

In certain embodiments, liposomes are formed from phospholipids that are dispersed in an aqueous medium and spontaneously form multilamellar concentric bilayer vesicles (also termed multilamellar vesicles (MLVs).

Alternatively, in other embodiments, the invention provides for pharmaceutically-acceptable nanocapsule formulations of the compositions of the present invention. Nanocapsules can generally entrap compounds in a stable and reproducible way. To avoid side effects due to intracellular polymeric overloading, such ultrafine particles (sized around 0.1 μm) may be designed using polymers able to be degraded in vivo. Such particles can be made as described by Couvreur et al., Crit. Rev Ther Drug Carrier Syst. 1988; 5(1):1-20; zur Muhlen et al., Eur J Pharm Biopharm. 1998 March; 45(2):149-55; Zambaux et al. J Controlled Release. 1998 Jan. 2; 50(1-3):31-40; and U.S. Pat. No. 5,145,684.

Methods

Compositions and methods of the invention, in various embodiments, take advantage of human cytolytic T-cells (CTLs), such as those that recognize GP, NP, VP40, VP35, VP30, VP24, and/or L epitopes which bind to selected MHC molecules, e.g., HLA-A2, A3, and A24. Individuals expressing MHC molecules of certain serotypes, e.g., HLA-A2, A3, and A24 may be selected for therapy using the methods and compositions of the invention. For example, individuals expressing MHC molecules of certain serotypes, e.g., HLA-A2, A3, and A24, may be selected for a therapy including raising an immune response against GP, NP, VP40, VP35, VP30, VP24, and/or L, using the methods and compositions described herein.

In various embodiments, these T-cells can be generated by in vitro cultures using antigen-presenting cells pulsed with the epitope of interest to stimulate peripheral blood mononuclear cells. In addition, T-cell lines can also be generated after stimulation with GP, NP, VP40, VP35, VP30, VP24, and/or L latex beads, GP, NP, VP40, VP35, VP30, VP24, and/or L protein-pulsed plastic adherent peripheral blood mononuclear cells, or DCs sensitized with GP, NP, VP40, VP35, VP30, VP24, and/or L RNA. T-cells can also be generated from patients immunized with a vaccine vector encoding GP, NP, VP40, VP35, VP30, VP24, and/or L immunogen. HLA A2-presented peptides from GP, NP, VP40, VP35, VP30, VP24, and/or L can further be found in patients infected with Ebola. In various embodiments, the invention relates to an HLA A2 restricted epitope of GP, NP, VP40, VP35, VP30, VP24, and/or L, with ability to stimulate CTLs from patients immunized with vaccine-GP, NP, VP40, VP35, VP30, VP24, and/or L.

Methods of Treatment

The adenovirus vectors of the present invention can be used in a number of vaccine settings for generating an immune response against one or more target antigens as described herein. The present invention provides methods of generating an immune response against any target antigen, such as those described elsewhere herein. The adenovirus vectors are of particular importance because of the unexpected finding that they can be used to generate immune responses in subjects who have preexisting immunity to Ad and can be used in vaccination regimens that include multiple rounds of immunization using the adenovirus vectors, regimens not possible using previous generation adenovirus vectors.

Generally, generating an immune response comprises an induction of a humoral response and/or a cell-mediated response. It may desirable to increase an immune response against a target antigen of interest. Generating an immune response may involve a decrease in the activity and/or number of certain cells of the immune system or a decrease in the level and/or activity of certain cytokines or other effector molecules. A variety of methods for detecting alterations in an immune response (e.g., cell numbers, cytokine expression, cell activity) are known in the art and are useful in the context of the instant invention. Illustrative methods useful in this context include intracellular cytokine staining (ICS), ELISpot, proliferation assays, cytotoxic T-cell assays including chromium release or equivalent assays, and gene expression analysis using any number of polymerase chain reaction (PCR) or RT-PCR based assays.

Generating an immune response can comprise an increase in target antigen-specific CTL activity of between 1.5 and 5 fold in a subject administered the adenovirus vectors of the invention as compared to a control. In another embodiment, generating an immune response comprises an increase in target-specific CTL activity of about 2, 2.5, 3, 3.5, 4, 4.5, 5, 5.5, 6, 6.5, 7, 7.5, 8, 8.5, 9, 9.5, 10, 10.5, 11, 11.5, 12, 12.5, 15, 16, 17, 18, 19, 20, or more fold in a subject administered the adenovirus vectors as compared to a control.

Generating an immune response can comprise an increase in target antigen-specific HTL activity, such as proliferation of helper T-cells, of between 1.5 and 5 fold in a subject administered the adenovirus vectors of the invention that comprise nucleic acid encoding the target antigen as compared to an appropriate control. In another embodiment, generating an immune response comprises an increase in target-specific HTL activity of about 2, 2.5, 3, 3.5, 4, 4.5, 5, 5.5, 6, 6.5, 7, 7.5, 8, 8.5, 9, 9.5, 10, 10.5, 11, 11.5, 12, 12.5, 15, 16, 17, 18, 19, 20, or more fold as compared to a control. In this context, HTL activity may comprise an increase as described above, or decrease, in production of a particular cytokine, such as interferon-γ (IFN-γ), interleukin-1 (IL-1), IL-2, IL-3, IL-6, IL-7, IL-12, IL-15, tumor necrosis factor-α (TNF-α), granulocyte macrophage colony-stimulating factor (GM-CSF), granulocyte-colony stimulating factor (G-CSF), or other cytokine. In this regard, generating an immune response may comprise a shift from a Th2 type response to a Th1 type response or in certain embodiments a shift from a Th1 type response to a Th2 type response. In other embodiments, generating an immune response may comprise the stimulation of a predominantly Th1 or a Th2 type response.

Generating an immune response can comprise an increase in target-specific antibody production of between 1.5 and 5 fold in a subject administered the adenovirus vectors of the present invention as compared to an appropriate control. In another embodiment, generating an immune response comprises an increase in target-specific antibody production of about 2, 2.5, 3, 3.5, 4, 4.5, 5, 5.5, 6, 6.5, 7, 7.5, 8, 8.5, 9, 9.5, 10, 10.5, 11, 11.5, 12, 12.5, 15, 16, 17, 18, 19, 20, or more fold in a subject administered the adenovirus vector as compared to a control.

Thus the present invention provides methods for generating an immune response against a target antigen of interest comprising administering to the individual an adenovirus vector comprising: a) a replication defective adenovirus vector, wherein the adenovirus vector has a deletion in the E2b region, and b) a nucleic acid encoding the target antigen; and readministering the adenovirus vector at least once to the individual; thereby generating an immune response against the target antigen. In certain embodiments, the present invention provides methods wherein the vector administered is not a gutted vector. In particular embodiments, the target antigen may be a wild-type protein, a fragment, a variant, or a variant fragment thereof. In some embodiments, the target antigen comprises GP, NP, VP40, VP35, VP30, VP24, L, a fragment, a variant, or a variant fragment thereof.

In a further embodiment, the present invention provides methods for generating an immune response against a target antigen in an individual, wherein the individual has preexisting immunity to Ad, by administering to the individual an adenovirus vector comprising: a) a replication defective adenovirus vector, wherein the adenovirus vector has a deletion in the E2b region, and b) a nucleic acid encoding the target antigen; and readministering the adenovirus vector at least once to the individual; thereby generating an immune response against the target antigen. In particular embodiments, the target antigen may be a wild-type protein, a fragment, a variant, or a variant fragment thereof. In some embodiments, the target antigen comprises GP, NP, VP40, VP35, VP30, VP24, L, a fragment, a variant, or a variant fragment thereof.

With regard to preexisting immunity to Ad, this can be determined using methods known in the art, such as antibody-based assays to test for the presence of Ad antibodies. Further, in certain embodiments, the methods of the present invention include first determining that an individual has preexisting immunity to Ad then administering the E2b deleted adenovirus vectors of the invention as described herein.

One embodiment of the invention provides a method of generating an immune response against one or more target antigens in an individual comprising administering to the individual a first adenovirus vector comprising a replication defective adenovirus vector, wherein the adenovirus vector has a deletion in the E2b region, and a nucleic acid encoding at least one target antigen; administering to the individual a second adenovirus vector comprising a replication defective adenovirus vector, wherein the adenovirus vector has a deletion in the E2b region, and a nucleic acid encoding at least one target antigen, wherein the at least one target antigen of the second adenovirus vector is the same or different from the at least one target antigen of the first adenovirus vector. In particular embodiments, the target antigen may be a wild-type protein, a fragment, a variant, or a variant fragment thereof. In some embodiments, the target antigen comprises GP, NP, VP40, VP35, VP30, VP24, L, a fragment, a variant, or a variant fragment thereof.

Thus, the present invention contemplates multiple immunizations with the same E2b deleted adenovirus vector or multiple immunizations with different E2b deleted adenovirus vectors. In each case, the adenovirus vectors may comprise nucleic acid sequences that encode one or more target antigens as described elsewhere herein. In certain embodiments, the methods comprise multiple immunizations with an E2b deleted adenovirus encoding one target antigen, and re-administration of the same adenovirus vector multiple times, thereby inducing an immune response against the target antigen. In some embodiments, the target antigen comprises GP, NP, VP40, VP35, VP30, VP24, L, a fragment, a variant, or a variant fragment thereof.

In a further embodiment, the methods comprise immunization with a first adenovirus vector that encodes one or more target antigens, and then administration with a second adenovirus vector that encodes one or more target antigens that may be the same or different from those antigens encoded by the first adenovirus vector. In this regard, one of the encoded target antigens may be different or all of the encoded antigens may be different, or some may be the same and some may be different. Further, in certain embodiments, the methods include administering the first adenovirus vector multiple times and administering the second adenovirus multiple times. In this regard, the methods comprise administering the first adenovirus vector 1, 2, 3, 4, 5, 6, 7, 8, 9, 10, 11, 12, 13, 14, 15, or more times and administering the second adenovirus vector 1, 2, 3, 4, 5, 6, 7, 8, 9, 10, 11, 12, 13, 14, 15, or more times. The order of administration may comprise administering the first adenovirus one or multiple times in a row followed by administering the second adenovirus vector one or multiple times in a row. In certain embodiments, the methods include alternating administration of the first and the second adenovirus vectors as one administration each, two administrations each, three administrations each, and so on. In certain embodiments, the first and the second adenovirus vectors are administered simultaneously. In other embodiments, the first and the second adenovirus vectors are administered sequentially. In some embodiments, the target antigen comprises GP, NP, VP40, VP35, VP30, VP24, L, a fragment, a variant, or a variant fragment thereof.

As would be readily understood by the skilled artisan, more than two adenovirus vectors may be used in the methods of the present invention. Three, 4, 5, 6, 7, 8, 9, 10 or more different adenovirus vectors may be used in the methods of the invention. In certain embodiments, the methods comprise administering more than one E2b deleted adenovirus vector at a time. In this regard, immune responses against multiple target antigens of interest can be generated by administering multiple different adenovirus vectors simultaneously, each comprising nucleic acid sequences encoding one or more target antigens.

Methods are also provided for treating or ameliorating the symptoms of Ebola. The methods of treatment comprise administering the adenovirus vectors one or more times to individuals suffering from an Ebola infection or at risk from suffering from an Ebola infection as described herein. As such, the present invention provides methods for vaccinating against Ebola in individuals who are at risk of being infected with such a virus. Individuals at risk may be individuals who may be exposed to Ebola at some time or have been previously exposed but do not yet have symptoms of Ebola infection or being particularly susceptible to an Ebola infection. Individuals suffering from an Ebola infection may be determined to express and/or present a target antigen, which may be use to guide the therapies herein. For example, an example can be found to express and/or present a target antigen and an adenovirus vector encoding the target antigen, a variant, a fragment or a variant fragment thereof may be administered subsequently.

The present invention contemplates the use of adenovirus vectors for the in vivo delivery of nucleic acids encoding a target antigen, or a fragment, a variant, or a variant fragment thereof. Once injected into a subject, the nucleic acid sequence is expressed resulting in an immune response against the antigen encoded by the sequence. The adenovirus vector vaccine can be administered in an "effective amount", that is, an amount of adenovirus vector that is effective in a selected route or routes of administration to elicit an immune response as described elsewhere herein. An effective amount can induce an immune response effective to facilitate protection or treatment of the host against the target Ebola. The amount of vector in each vaccine dose is selected as an amount which induces an immune, immunoprotective or other immunotherapeutic response without significant adverse effects generally associated with typical vaccines. Once vaccinated, subjects may be monitored to determine the efficacy of the vaccine treatment. Monitoring the efficacy of vaccination may be performed by any method known to a person of ordinary skill in the art. In some embodiments, blood or fluid samples may be assayed to detect levels of antibodies. In other embodiments, ELISpot assays may be performed to detect a cell-mediated immune response from circulating blood cells or from lymphoid tissue cells.

Routes and frequency of administration of the therapeutic compositions described herein, as well as dosage, may vary from individual to individual, and from disease to disease, and may be readily established using standard techniques. In general, the pharmaceutical compositions and vaccines may be administered by injection (e.g., intracutaneous, intramuscular, intravenous or subcutaneous), intranasally (e.g., by aspiration), in pill form (e.g., swallowing, suppository for vaginal or rectal delivery). In certain embodiments, between 1 and 10 doses may be administered over a 52 week period. In certain embodiments, 6 doses are administered, at intervals of 1 month, and further booster vaccinations may be given periodically thereafter. Alternate protocols may be appropriate for individual patients. As such, 1, 2, 3, 4, 5, 6, 7, 8, 9, 10, 11, 12, 13, 14, 15, 16, 17, 18, 19, 20, or more doses may be administered over a 1 year period or over shorter or longer periods, such as over 35, 40, 45, 50, 55, 60, 65, 70, 75, 80, 85, 90, 95 or 100 week periods. Doses may be administered at 1, 2, 3, 4, 5, or 6 week intervals or longer intervals.

A vaccine can be infused over a period of less than about 4 hours, and more preferably, over a period of less than about 3 hours. For example, the first 25-50 mg could be infused within 30 minutes, preferably even 15 min, and the remainder infused over the next 2-3 hrs. More generally, the dosage of an administered vaccine construct may be administered as one dosage every 2 or 3 weeks, repeated for a total of at least 3 dosages. Or, the construct may be administered twice per week for 4-6 weeks. The dosing schedule can optionally be repeated at other intervals and dosage may be given through various parenteral routes, with appropriate adjustment of the dose and schedule. Compositions of the present invention can be administered to a patient in conjunction with (e.g., before, simultaneously, or following) any number of relevant treatment modalities.

A suitable dose is an amount of an adenovirus vector that, when administered as described above, is capable of promoting a target antigen immune response as described elsewhere herein. In certain embodiments, the immune response is at least 10-50% above the basal (i.e., untreated) level. In certain embodiments, the immune response is at least 2, 3, 4, 5, 6, 7, 8, 9, 10, 12, 15, 20, 25, 30, 35, 40, 45, 50, 55, 60, 65, 70, 75, 80, 85, 90, 100, 110, 125, 150, 200, 250, 300, 400, 500 or more over the basal level. Such response can be monitored by measuring the target antigen(s) antibodies in a patient or by vaccine-dependent generation of cytolytic effector cells capable of killing patient infected cells in vitro, or other methods known in the art for monitoring immune responses. Such vaccines should also be capable of causing an immune response that leads to an improved clinical outcome of the disease in question in vaccinated patients as compared to non-vaccinated patients. In some embodiments, the improved clinical outcome comprises treating disease, reducing the symptoms of a disease, changing the progression of a disease, or extending life.

In general, an appropriate dosage and treatment regimen provides the adenovirus vectors in an amount sufficient to provide therapeutic and/or prophylactic benefit. Such a response can be monitored by establishing an improved clinical outcome for the particular disease being treated in treated patients as compared to non-treated patients. The monitoring data can be evaluated over time. The progression of a disease over time can be altered. Such improvements in clinical outcome would be readily recognized by a treating physician. Increases in preexisting immune responses to a target protein can generally correlate with an improved clinical outcome. Such immune responses may generally be evaluated using standard proliferation, cytotoxicity or cytokine assays, which may be performed using samples obtained from a patient before and after treatment.

While one advantage of the present invention is the capability to administer multiple vaccinations with the same or different adenovirus vectors, particularly in individuals with preexisting immunity to Ad, the adenoviral vaccines of this invention may also be administered as part of a prime and boost regimen. A mixed modality priming and booster inoculation scheme may result in an enhanced immune response. Thus, one aspect of this invention is a method of priming a subject with a plasmid vaccine, such as a plasmid vector comprising a target antigen of interest, by administering the plasmid vaccine at least one time, allowing a predetermined length of time to pass, and then boosting by administering the adenovirus vector. Multiple primings, e.g., 1-4, may be employed, although more may be used. The length of time between priming and boost may typically vary from about four months to a year, but other time frames may be used. In certain embodiments, subjects may be primed 1, 2, 3, 4, 5, 6, 7, 8, 9, 10, or more times with plasmid vaccines, and then boosted 4 months later with the adenovirus vector.

Patient Selection

Various embodiments of the invention relate to compositions and methods for raising an immune response against one or more SEQ. ID. NO.:1, SEQ. ID. NO.:2, SEQ. ID. NO.:4, SEQ. ID. NO.:5, or SEQ. ID. NO.:6 antigens in selected patient populations. Any of the compositions provided herein may be administered to an individual. "Individual" may be used interchangeably with "subject" or "patient." An individual may be a mammal, for example a human or animal such as a non-human primate, a rodent, a rabbit, a rat, a mouse, a horse, a donkey, a goat, a cat, a dog, a cow, a pig, or a sheep. In embodiments, the individual is a human. In embodiments, the individual is a fetus, an embryo, or a child. In some cases, the compositions provided herein are administered to a cell ex vivo. In some cases, the compositions provided herein are administered to an individual as a method of treating an Ebola infection.

In some cases, a subject does not have an Ebola infection. In some cases, the treatment of the present invention is administered before an Ebola infection. A subject may have an undetected Ebola infection. A subject may have a low Ebola infection burden. A subject may also have a high Ebola infection burden.

In some embodiments, patients may be required to have received and, optionally, progressed through other therapies. In some cases, individual's refusal to accept such therapies may allow the patient to be included in a therapy eligible pool with methods and compositions of the invention. In some embodiments, individuals to receive therapy using the methods and compositions of the invention may be required to have an estimated life expectancy of at least, 1, 2, 3, 4, 5, 6, 7, 8, 9, 10, 11, 12, 14, 15, 18, 21, or 24 months. The patient pool to receive a therapy using the methods and compositions of the invention may be limited by age. For example, individuals who are older than 2, 3, 4, 5, 6, 7, 8, 9, 10, 11, 12, 13, 14, 15, 16, 17, 18, 19, 20, 21, 25, 30, 35, 40, 50, 60, or more years old can be eligible for therapy with methods and compositions of the invention. For another example, individuals who are younger than 75, 70, 65, 60, 55, 50, 40, 35, 30, 25, 20, or fewer years old can be eligible for therapy with methods and compositions of the invention.

In some embodiments, patients receiving therapy using the methods and compositions of the invention are limited to individuals with adequate hematologic function, for example with one or more of a WBC count of at least 1000, 1500, 2000, 2500, 3000, 3500, 4000, 4500, 5000 or more per microliter, a hemoglobin level of at least 5, 6, 7, 8, 9, 10, 11, 12, 13, 14 or higher g/dL, a platelet count of at least 50,000; 60,000; 70,000; 75,000; 90,000; 100,000; 110,000; 120,000; 130,000; 140,000; 150,000 or more per microliter; with a PT-INR value of less than or equal to 0.8, 1.0, 1.2, 1.3, 1.4, 1.5, 1.6, 1.8, 2.0, 2.5, 3.0, or higher, a PTT value of less than or equal to 1.2, 1.4, 1.5, 1.6, 1.8, 2.0×ULN or more. In various embodiments, hematologic function indicator limits are chosen differently for individuals in different gender and age groups, for example 0-5, 5-10, 10-15, 15-18, 18-21, 21-30, 30-40, 40-50, 50-60, 60-70, 70-80 or older than 80.

In various embodiments, samples, for example serum or urine samples, from the individuals or candidate individuals for a therapy using the methods and compositions of the invention may be collected. Samples may be collected before, during, and/or after the therapy for example, within 2, 4, 6, 8, 10 weeks prior to the start of the therapy, within 1 week, 10 day, 2 weeks, 3 weeks, 4 weeks, 6 weeks, 8 weeks, or 12 weeks from the start of the therapy, within 2, 4, 6, 8, 10 weeks prior to the start of the therapy, within 1 week, 10 day, 2 weeks, 3 weeks, 4 weeks, 6 weeks, 8 weeks, 9 weeks, or 12 weeks from the start of the therapy, in 1 week, 10 day, 2 weeks, 3 weeks, 4 weeks, 6 weeks, 8 weeks, 9 weeks, or 12 weeks intervals during the therapy, in 1 month, 3 month, 6 month, 1 year, 2 year intervals after the therapy, within 1 month, 3 months, 6 months, 1 year, 2 years, or longer after the therapy, for a duration of 6 months, 1, 2, 3, 4, 5, 6, 7, 8, 9, 10 years or longer. The samples may be tested for any of the hematologic, renal, or hepatic function indicators described herein as well as suitable others known in the art, for example a ß-HCG for women with childbearing potential. In that regard, hematologic and biochemical tests, including cell blood counts with differential, PT, INR and PTT, tests measuring Na, K, Cl, $CO_2$, BUN, creatinine, Ca, total protein, albumin, total bilirubin, alkaline phosphatase, AST, ALT and glucose are within the bounds of the invention. In some embodiments, the presence or the amount of HIV antibody, Hepatitis BsAg, or Hepatitis C antibody are determined in a sample from individuals or candidate individuals for a therapy using the methods and compositions of the invention. Biological markers, such as antibodies to SEQ. ID. NO.:1, SEQ. ID. NO.:2, SEQ. ID. NO.:4, SEQ. ID. NO.:5, SEQ. ID. NO.:6, or the neutralizing antibodies to Ad5 vector can be tested in a sample, such as serum, from individuals or candidate individuals for a therapy using the methods and compositions of the invention. In some cases, one or more samples, such as a blood sample can be collected and archived from an individuals or candidate individuals for a therapy using the methods and compositions of the invention. Collected samples can be assayed for immunologic evaluation. Individuals or candidate individuals for a therapy using the methods and compositions of the invention can be evaluated in imaging studies, for example using CT scans or MRI of the chest, abdomen, or pelvis. Imaging studies can be performed before, during, or after therapy using the methods and compositions of the invention, during, and/or after the therapy, for example, within 2, 4, 6, 8, 10 weeks prior to the start of the therapy, within 1 week, 10 day, 2 weeks, 3 weeks, 4 weeks, 6 weeks, 8 weeks, or 12 weeks from the start of the therapy, within 2, 4, 6, 8, 10 weeks prior to the start of the therapy, within 1 week, 10 day, 2 weeks, 3 weeks, 4 weeks, 6 weeks, 8 weeks, 9 weeks, or 12 weeks from the start of the therapy, in 1 week, 10 day, 2 week, 3 week, 4 week, 6 week, 8 week, 9 week, or 12 week intervals during the therapy, in 1 month, 3 month, 6 month, 1 year, 2 year intervals after the therapy, within 1 month, 3 months, 6 months, 1 year, 2 years, or longer after the therapy, for a duration of 6 months, 1, 2, 3, 4, 5, 6, 7, 8, 9, 10 years or longer.

Dosages and Administration

Compositions and methods of the invention contemplate various dosage and administration regimens during therapy. Patients may receive one or more replication defective adenovirus or adenovirus vector, for example Ad5 [E1-, E2B-]-SEQ. ID. NO.:1, Ad5 [E1-, E2b-]-SEQ. ID. NO.:2, Ad5 [E1-, E2b-]-SEQ. ID. NO.:4, Ad5 [E1-, E2b-]-SEQ. ID. NO.:5, Ad5 [E1-, E2b-]-SEQ. ID. NO.:6 that is capable of raising an immune response in an individual against a target antigen described herein, for example SEQ. ID. NO.:1, SEQ. ID. NO.:2, SEQ. ID. NO.:4, SEQ. ID. NO.:5, or SEQ ID. NO.6. In various embodiments, the replication defective adenovirus is administered at a dose that suitable for affecting such immune response. In some cases, the replication defective adenovirus is administered at a dose that is greater than or equal to $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $1.5\times10^{12}$, $2\times10^{12}$, $3\times10^{12}$, or more virus particles (VP) per immunization. In some cases, the replication defective adenovirus is administered at a dose that is less than or equal to $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $1.5\times10^{12}$, $2\times10^{12}$, $3\times10^{12}$, or more virus particles per immunization. In various embodiments, a desired dose described herein is administered in a suitable volume of formulation buffer, for example a volume of about 0.1-10 mL, 0.2-8 mL, 0.3-7 mL, 0.4-6 mL, 0.5-5 mL, 0.6-4 mL, 0.7-3 mL, 0.8-2 mL, 0.9-1.5 mL, 0.95-1.2 mL, or 1.0-1.1 mL. Those of skill in the art appreciate that the volume may fall within any range bounded by any of these values (e.g., about 0.5 mL to about 1.1 mL). Administration of virus particles can be through a variety of suitable paths for delivery, for example it can be by injection (e.g., intracutaneously, intramuscularly, intravenously or subcutaneously), intranasally (e.g., by aspiration), in pill form (e.g., swallowing, suppository for vaginal or rectal delivery. In some embodiments, a subcutaneous delivery may be preferred and can offer greater access to dendritic cells.

Administration of virus particles to an individual may be repeated. Repeated deliveries of virus particles may follow a schedule or alternatively, may be performed on an as needed basis. For example, the individual's immunity against a target antigen, for example SEQ. ID. NO.:1, SEQ. ID. NO.:2, SEQ. ID. NO.:4, SEQ. ID. NO.:5, or SEQ. ID. NO.:6 may be tested and replenished as necessary with additional deliveries. In some embodiments, schedules for delivery include administrations of virus particles at regular intervals. Joint delivery regimens may be designed comprising one or more of a period with a schedule and/or a period of need based administration assessed prior to administration. For example, a therapy regimen may include an administration, such as subcutaneous administration once every three weeks then another immunotherapy treatment every three months until removed from therapy for any reason including death. Another example regimen comprises three administrations every three weeks then another set of three immunotherapy treatments every three months. Another example regimen comprises a first period with a first number of administrations at a first frequency, a second period with a second number of administrations at a second frequency, a third period with a third number of administrations at a third frequency, etc., and optionally one or more periods with undetermined number of administrations on an as needed basis. The number of administrations in each period can be independently selected and can for example be 1, 2, 3, 4, 5, 6, 7, 8, 9, 10, 11, 12, 13, 14, 15, 16, 17, 18, 19, 20 or more. The frequency of the administration in each period can also be independently selected, can for example be about every day, every other day, every third day, twice a week, once a week, once every other week, every three weeks, every month, every six weeks, every other month, every third month, every fourth month, every fifth month, every sixth month, once a year etc. The therapy can take a total period of up to 1, 2, 3, 4, 5, 6, 7, 8, 9, 10, 11, 12, 13, 14, 15, 16, 17, 18, 19, 20, 21, 22, 23, 24, 30, 36 months or more. The scheduled interval between immunizations may be modified so that the interval between immunizations is revised by up to a fifth, a fourth, a third, or half of the interval. For example, for a 3-week interval schedule, an immunization may be repeated between 20 and 28 days (3 weeks −1 day to 3 weeks +7 days). For the first 3 immunizations, if the second and/or third immunization is delayed, the subsequent immunizations may be shifted allowing a minimum amount of buffer between immunizations. For example, for a three week interval schedule, if an immunization is delayed, the subsequent immunization may be scheduled to occur no earlier than 17, 18, 19, or 20 days after the previous immunization.

Compositions of the invention, such as Ad5 [E1-, E2B-]-SEQ. ID. NO.:1, Ad5 [E1-, E2B-]-SEQ. ID. NO.:2, Ad5 [E1-, E2B-]-SEQ. ID. NO.:4, Ad5 [E1-, E2B-]-SEQ. ID. NO.:5, and Ad5 [E1-, E2B-]-SEQ. ID. NO.:6 vectors and virus particles produced using these vectors, can be provided in various states, for example, at room temperature, on ice, or frozen. Compositions may be provided in a container of a suitable size, for example a vial of 2 mL vial. In one embodiment, 12 ml vial with 1.0 mL of extractable vaccine contains $5\times10^{11}$ total virus particles/mL. Storage conditions including temperature and humidity may vary. For example, compositions for use in therapy may be stored at room temperature, 4° C., −20° C., or lower.

In various embodiments, general evaluations are performed on the individuals receiving treatment according to the methods and compositions of the invention. One or more of any tests may be performed as needed or in a scheduled basis, such as on weeks 0, 3, 6 etc. A different set of tests may be performed concurrent with immunization vs. at time points without immunization.

General evaluations may include one or more of medical history, ECOG Performance Score, Karnofsky performance status, and complete physical examination with weight by the attending physician. Any other treatments, medications, biologics, or blood products that the patient is receiving or has received since the last visit may be recorded. Patients may be followed at the clinic for a suitable period, for example approximately 30 minutes, following receipt of vaccine to monitor for any adverse reactions. Local and systemic reactogenicity after each dose of vaccine will may be assessed daily for a selected time, for example for 3 days (on the day of immunization and 2 days thereafter). Diary cards may be used to report symptoms and a ruler may be used to measure local reactogenicity. Immunization injection sites may be assessed. CT scans or MRI of the chest, abdomen, and pelvis may be performed.

In various embodiments, hematological and biochemical evaluations are performed on the individuals receiving treatment according to the methods and compositions of the invention. One or more of any tests may be performed as needed or in a scheduled basis, such as on weeks 0, 3, 6 etc. A different set of tests may be performed concurrent with immunization vs. at time points without immunization. Hematological and biochemical evaluations may include one or more of blood test for chemistry and hematology, CBC with differential, Na, K, Cl, $CO_2$, BUN, creatinine, Ca, total protein, albumin, total bilirubin, alkaline phosphatase, AST, ALT, glucose, and ANA.

In various embodiments, biological markers are evaluated on individuals receiving treatment according to the methods and compositions of the invention. One or more of any tests may be performed as needed or in a scheduled basis, such as on weeks 0, 3, 6 etc. A different set of tests may be performed concurrent with immunization vs. at time points without immunization.

Biological marker evaluations may include one or more of measuring antibodies to SEQ. ID. NO.:1, SEQ. ID. NO.:2, SEQ. ID. NO.:4, SEQ. ID. NO.:5, SEQ. ID. NO.:6 or the Ad5 vector, from a serum sample of adequate volume, for example about 5 mL. Biomarkers may be reviewed if determined and available.

In various embodiments, an immunological assessment is performed on individuals receiving treatment according to the methods and compositions of the invention. One or more of any tests may be performed as needed or in a scheduled basis, such as on weeks 0, 3, 6 etc. A different set of tests may be performed concurrent with immunization vs. at time points without immunization.

Peripheral blood, for example about 90 mL may be drawn prior to each immunization and at a time after at least some of the immunizations, to determine whether there is an effect on the immune response at specific time points during the study and/or after a specific number of immunizations. Immunological assessment may include one or more of assaying peripheral blood mononuclear cells (PBMC) for T-cell responses to SEQ. ID. NO.:1, SEQ. ID. NO.:2, SEQ. ID. NO.:4, SEQ. ID. NO.:5, or SEQ. ID. NO.:6 using ELISpot, proliferation assays, multi-parameter flow cytometric analysis, and cytotoxicity assays. Serum from each blood draw may be archived and sent and determined.

In various embodiments, an Ebola infection assessment or Ebola replication assay is performed on individuals receiving treatment according to the methods and compositions of the invention. One or more of any tests may be performed as needed or in a scheduled basis, such as prior to treatment, on weeks 0, 3, 6 etc. A different set of tests may be performed concurrent with immunization vs. at time points without immunization. Ebola infection may include one or more Ebola immonospecific tests prior to treatment, at a time after at least some of the immunizations and at approximately every week to three months following the completion of a selected number, for example 2, 3, or 4, of first treatments and for example until removal from treatment.

Immune responses against a target antigen described herein, such as SEQ. ID. NO.:1, SEQ. ID. NO.:2, SEQ. ID. NO.:4, SEQ. ID. NO.:5, or SEQ ID. NO.6 may be evaluated from a sample, such as a peripheral blood sample of an individual using one or more suitable tests for immune response, such as ELISpot, cytokine flow cytometry, or antibody response. A positive immune response can be determined by measuring a T-cell response. A T-cell response can be considered positive if the mean number of spots adjusted for background in six wells with antigen exceeds the number of spots in six control wells by 10 and the difference between single values of the six wells containing antigen and the six control wells is statistically significant at a level of $p \leq 0.05$ using the Student's t-test. Immunogenicity assays may occur prior to each immunization and at scheduled time points during the period of the treatment. For example, a time point for an immunogenicity assay at around week 1, 2, 3, 4, 5, 6, 7, 8, 9, 10, 11, 12, 13, 14, 15, 18, 20, 24, 30, 36, or 48 of a treatment may be scheduled even without a scheduled immunization at this time. In some cases, an individual may be considered evaluable for immune response if they receive at least a minimum number of immunizations, for example 1, 2, 3, 4, 5, 6, 7, 8, 9, or more immunizations.

Determination of Clinical Response

In some embodiments, disease progression or clinical response determination is made according to the RECIST 1.1 criteria among patients with measurable/evaluable disease. In some embodiments, therapies using the methods and compositions of the invention affect a Complete Response (CR; disappearance of all antigens or symptoms target sites or disappearance of all non-target sites and normalization of antigens or symptoms level for non-target sites) in an individual receiving the therapy. In some embodiments, therapies using the methods and compositions of the invention affect a Partial Response (PR; at least a 30% decrease in the sum of the LD of target sites, taking as reference the baseline sum LD for target sites) in an individual receiving the therapy.

In some embodiments, therapies using the methods and compositions of the invention affect a Stable Disease (SD; neither sufficient reduction of antigens or symptoms to qualify for PR nor sufficient increase to qualify for PD, taking as reference the smallest sum LD since the treatment started for target sites) in an individual receiving the therapy. In some embodiments, therapies using the methods and compositions of the invention affect an Incomplete Response/Stable Disease (SD; persistence of one or more non-target sites) or/and maintenance of antigens or symptoms above the normal limits for non-target sites) in an individual receiving the therapy. In some embodiments, therapies using the methods and compositions of the invention affect a Progressive Disease (PD; at least a 20% increase in the sum of the LD of antigens or symptoms, taking as reference the smallest sum LD recorded since the treatment started or the appearance of one or more new antigens or symptoms or persistence of one or more non-target antigens or symptoms or/and maintenance of antigens level above the normal limits for in an individual receiving the therapy.

Kits

The compositions, immunotherapy or vaccines may be supplied in the form of a kit. The kits of the present disclosure may further comprise instructions regarding the dosage and or administration including treatment regimen information.

In some embodiments, kits comprise the compositions and methods for providing combination multi-targeted Ebola immunotherapy. In some embodiments, kits comprise the compositions and methods for the combination multi-targeted treatment of an Ebola infection. In some embodiment's kits may further comprise components useful in administering the kit components and instructions on how to prepare the components. In some embodiments, the kit can further comprise software for conducting monitoring patient before and after treatment with appropriate laboratory tests, or communicating results and patient data with medical staff. The components comprising the kit may be in dry or liquid form. If they are in dry form, the kit may include a solution to solubilize the dried material. The kit may also include transfer factor in liquid or dry form. If the transfer factor is in dry form, the kit will include a solution to solubilize the transfer factor. The kit may also include containers for mixing and preparing the components. The kit may also include instrument for assisting with the administration such for example needles, tubing, applicator, inhalant, syringe, pipette, forceps, measured spoon, eye dropper or any such medically approved delivery vehicle. The kits or drug delivery systems of the present invention also will typically include a means for containing compositions of the present disclosure in close confinement for commercial sale and distribution.

EXAMPLES

Example 1: Multiple Injections of Ad5Null Adenovirus Vector Produces Anti-Adenovirus Antibodies This example shows that multiple injections of Ad5-null results in the production of anti-adenovirus antibodies in the injected subjects.

It was demonstrated that the Ad5-null adenovirus vector that does not contain any heterologous nucleic acid sequences, generated a neutralizing immune response in mice. In one experiment, female Balb/c mice aged 5-7 weeks were immunized with Ad5-null viral particles at 14 day intervals. To determine the presence of anti-adenovirus antibodies, an enzyme linked immunosorbent assay (ELISA) was used. For this ELISA, $10^9$ viral particles were coated onto microtiter wells in 100 μL of 0.05M carbonate/bicarbonate buffer, pH 9.6, and incubated overnight at room temperature. For a standard immunoglobulin G (IgG) reference curve, 200 ng, 100 ng, 50 ng, 25 ng, and 0 ng of purified mouse IgG were coated onto microtiter wells as described above. After incubation, all wells were washed 3 times with 250 μL of 1% bovine serum albumin (BSA) in phosphate buffered saline (PBS), pH 7.4. After washing, 250 μL of BSA/PBS was added to all and incubated for 30 minutes at room temperature to block unbound sites. After incubation, all wells were washed 3 times with 250 μL of BSA/PBS. After washing, 200 μL of a 1/100 serum dilution in BSA/PBS was added to wells and incubated for 1 hour at room temperature. For a positive control, 200 µL of a 1/10000 dilution of anti-adenovirus antiserum in BSA/PBS was added to wells. Control wells contained BSA/PBS only. After incubation, all wells were washed 3 times with 250 µL of BSA/PBS. After washing, 200 µL of a 1/10000 dilution of peroxidase conjugated γ-chain specific goat anti-mouse IgG (Sigma Chemicals) in BSA/PBS were added to each well and incubated for 1 hour at room temperature. After incubation, all wells were washed 3 times with 250 µL of BSA/PBS. After washing, 200 µL of developing reagent (0.5 mg/mL 1,2-phenylene-diamine in 0.2M potassium phosphate buffer, pH 5.0, containing 0.06% hydrogen peroxide) was added to each well and incubated for 30-40 minutes at room temperature. After incubation, the color reaction was stopped by addition of 50 µL 5N HCl to each well. All wells were then read in a microwell plate reader at 492 nm. After readings were obtained, the optical density readings of unknown samples were correlated with the standard IgG curve to obtain the ngs of IgG bound per well. This was performed using the INSTAT statistical package.

ELISA to Detect Antibodies Against EAs

ELISA plates will be coated with 100 ng of GP, NP, VP40, VP35, VP30, VP24, or L in 0.05 M carbonate-bicarbonate buffer pH 9.6 and incubated overnight at room temperature. Plates were washed three times with phosphate buffered saline containing 1% Tween-20 (PBS-T) and then blocked with PBS containing 1% BSA for 60 min at room temperature. After an additional three washes, serum diluted 1/50 in PBS-T will be added to the wells and the plates will be incubated for 1 hour at room temperature. Peroxidase labeled goat anti-mouse immunoglobulin (Ig) G (γ-chain specific) (Sigma-Aldrich) antibody at a 1:5000 dilution will be added to the wells after washings and plates were incubated for 1 hour. Plates will be washed three times and 1,2-phenylene-diamine substrate solution will be added to each well. The reaction will be stopped by adding 10% phosphoric acid. Absorbance will be measured at 492 nm on a SpectraMax 190 ELISA reader. The nanogram equivalents of IgG bound to GP, NP, VP40, VP35, VP30, VP24, or L, per well will be obtained by reference to a standard curve generated using purified mouse IgG and developed at the same time as the GP, NP, VP40, VP35, VP30, VP24, or L ELISA. The results were analyzed and quantitated using SoftMax Pro 6.3 software.

Significant levels ($P<0.001$) of anti-adenovirus IgG antibody were detected in mice 2 weeks after a first injection with $10^{10}$ Ad-5-null (FIG. 1). A significantly higher level ($P<0.001$) was observed 2 weeks after a second injection with $10^{10}$ adenovirus. Significantly higher ($P<0.001$) levels of antibody were continued to be observed 2 weeks after a third injection with $10^{10}$ Ad5-null. Each value represents the average of triplicate determinations from pooled sera of 5 mice in each group. Multiple injections of Ad5-null resulted in production of anti-adenovirus antibodies in the subjects.

To determine the presence of neutralizing antibody to Ad, the following assay was utilized. A HEK-293T-cell line was cultured in 200 µL of culture medium consisting of DMEM containing 10% fetal calf serum (DMEM/FCS) in microwell tissue culture plates at a cell concentration of $2\times10^3$ cells per well for 24 hours at 37° C. in 5% $CO_2$. After incubation, 100 µL of culture medium was removed from triplicate wells and mixed with 20 µL of DMEM/FCS containing viral particles (VP). After mixing, the 120 µL mixture was added back to the respective microwells. In another set of triplicate wells, 100 µL of culture medium was removed and mixed with 20 µL of heat inactivated (56° C. for 1 h) Ad immune mouse serum previously incubated with VP for one hour at room temperature. After mixing, the 120 µL mixture was added back to the respective wells. In triplicate cell control wells, 20 µL of DMEM/FCS was added to control for total culture medium volume. Triplicate medium-only control wells contained 220 µL of DMEM/FCS. The tissue culture plate was incubated for an additional 3 days at 37° C. in 5% $CO_2$. After incubation, 40 µL of PROMEGA cell viability reagent (Owen's reagent) was added to all wells and incubated for 75 minutes at 37° C. in 5% $CO_2$. In this assay, the Owen's reagent (MTS tetrazolium compound) is bioreduced by viable cells into a colored formazan product that is soluble in tissue culture medium. The quantity of formazan product as measured by absorbance at 490 nm is directly proportional to the number of living cells in culture. After incubation, 150 µL was removed from each well and transferred to another microwell plate for optical density readings. Optical density readings at 492 nm were subsequently obtained using a microwell plate reader.

Figure 2:
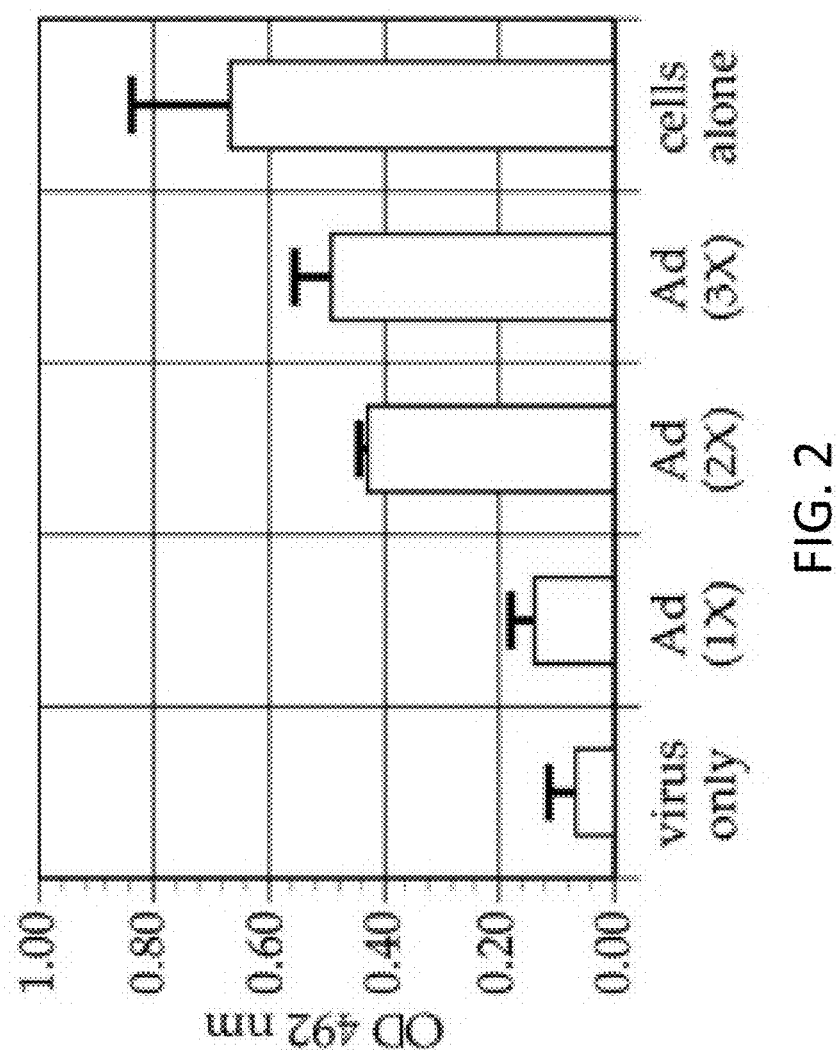
FIG. 2 exemplifies a bar graph showing neutralizing antibody (NAb) levels from mice immunized with Ad5-null. Mice were immunized three times with Ad5-null VPs at 14 day intervals. Neutralizing antibody levels increased after each immunization. Optical density readings indicate the presence of viable target cells.

To detect the presence of neutralizing antibodies to Ad, groups of 5 mice each were injected once, twice, or three times with $10^{10}$ Ad5-null at two week intervals. Two weeks after the final injection of virus, mice were bled, pooled, and assessed for neutralizing antibody as described above using $4\times10^7$ VP incubated with or without heat inactivated sera. Cells cultured alone served as a control group. Normal mice and mice injected one time with Ad5null did not exhibit significant levels of neutralizing antibody (FIG. 2). Mice injected two times with Ad exhibited significant ($P<0.05$) levels of neutralizing antibody as compared with cells incubated with virus only. Mice injected three times with Ad5-null also exhibited significant ($P<0.01$) levels of neutralizing antibody as compared with cells incubated with virus only.

Example 2: The Ad5 [E1-]-EA Vector Vaccine Induces EA Specific Immune Response Upon Re-Immunization in Ad5 Immune Mice This example shows that the Ad5 [E1-, E2b-] vector platform induces CMI responses against the Ebola associated antigens GP, NP, VP40, VP35, VP30, VP24, and/or L in the presence of pre-existing Ad5 immunity in mice.

Ad5 [E1-, E2B-]-GP, Ad5 [E1-, E2B-]-NP, Ad5 [E1-, E2B-]-VP40, Ad5 [E1-, E2B-]-VP35, Ad5 [E1-, E2b-]-VP30, [E1-, E2b-]-VP24, and/or [E1-, E2b-]-L will constructed and produced. Briefly, the transgenes will be subcloned into the E1 region of the Ad5 [E1-, E2b-] vector using a homologous recombination-based approach. The replication deficient virus will be propagated in the E.C7 packaging cell line, $CsCl_2$ purified, and titered. Viral infectious titer will be determined as plaque-forming units (PFUs) on an E.C7 cell monolayer. The VP concentration will be determined by sodium dodecyl sulfate (SDS) disruption and spectrophotometry at 260 nm and 280 nm.

Characterization of Ad5 CEA Vectors

Initial studies were performed to confirm GP, NP, VP40, VP35, VP30, VP24, and/or L gene expression of two Ad5-GP, NP, VP40, VP35, VP30, VP24, and/or L vector platforms. It was first determined that the antigens could be expressed on cells transfected with the vaccine vector platforms. A549 cells were obtained from ATCC and transfected with Ad5 [E1-]-GP, Ad5 [E1-]-NP, Ad5 [E1-]-VP40, Ad5 [E1-]-VP35, Ad5 [E1-]-VP30, [E1-]-VP24, and/or [E1-]-L; or Ad5 [E1-, E2B-]-GP, Ad5 [E1-, E2B-]-NP, Ad5 [E1-, E2B-]-VP40, Ad5 [E1-, E2B-]-VP35, Ad5 [E1-, E2b-]-VP30, [E1-, E2b-]-VP24, and/or [E1-, E2b-]-L. Western blot analysis revealed that cells transfected with the vector platforms expressed the indicated antigens.

Methods

A549 cells were inoculated at a MOI of 555 VPs/cell with Ad5 [E1-, E2B-]-GP, Ad5 [E1-, E2B-]-NP, Ad5 [E1-, E2B-]-VP40, Ad5 [E1-, E2B-]-VP35, Ad5 [E1-, E2b-]-VP30, [E1-, E2b-]-VP24, and/or [E1-, E2b-]-L. Cells were incubated for 48 hours at 37° C. in 5% $CO_2$ After 48 hours cells were harvested and washed with PBS and freeze/thawed three times. The whole cell lysate was heated for 70° C. for 10 min prior to loading on the gel. Recombinant GP, NP, VP40, VP35, VP30, VP24, and/or L control was loaded at 30 ng/lane and the prepared lysate at 20 µL/lane. Sample loading buffer was included as an additional negative control and the positive controls were Magic Mark CP Western markers and the recombinant GP, NP, VP40, VP35, VP30, VP24, and/or L. The gel was transferred to a nitrocellulose membrane and blocked with SuperBlock Blocking solution for 60 min. The membrane was probed with mouse monoclonal anti-GP, NP, VP40, VP35, VP30, VP24, or L primary antibody (1:1000) and a secondary anti-mouse HRP (1:2500) conjugated antibody. The membrane was washed three times then incubated with SuperSignal chemiluminescent reagent and banding was visualized by exposing X-ray film to the membrane followed by development.

Induction of Ad5 Immunity in Mice

To assess the levels of Ad5 immunity that could be induced, groups of Ad5 naive C57Bl/6 mice will be injected subcutaneously with the Ad5 vector platform (VP). Twenty eight to forty two days later, serum samples will be collected and assessed for endpoint Ad5 NAb titers. Undetectable Ad5 NAb titers (endpoint Ad5 NAb titer <1/25) may be observed in normal control mice. Ad5 NAb (endpoint titers of 1/25 to 1/50) may be detectable after one injection but may dramatically increase after three injections of $10^{10}$ Ad5. Therefore, in additional Ad5 immune studies, mice will be injected twice with $10^{10}$ Ad5 VP to render the animals Ad5 immune.

Immunization of Ad5 Immune Mice with Ad5 [E1-]-EAs or Ad5 [E1-, E2b-]-EAs.

These experiments will be designed to determine and compare the immunization induction potential of Ad5 [E1-]-EA and Ad5 [E1-, E2b-]-EA vaccines in Ad5 immune mice. Groups of female C57Bl/6 mice, 4 to 8 weeks old, will be immunized 2 times at 2 week intervals with $10^{10}$ Ad5-null VP. Two weeks following the last Ad5-null immunization, the mice will be immunized 3 times at weekly intervals with $10^{10}$ VP of Ad5 [E1-]-EA or Ad5 [E1-, E2b-]-EA. Two weeks following the last immunization, mice will be euthanized and their spleens and sera harvested for analyses.

CMI responses will be assessed by ELISpot assays performed on splenocytes exposed to intact EA antigen. Splenocytes from Ad5 immune C57Bl/6 mice that were immunized subcutaneously with Ad5 E1-]-EA or Ad5 [E1-, E2b-]-EA will be harvested and assessed for the number of IFN-γ and IL-2 secreting cells. Significantly elevated numbers of both IFN-γ and IL-2 secreting cells may be observed in spleens assayed from mice immunized with Ad5 [E1-, E2b-]-EA as compared to immunized Ad5 [E1-]-EA mice. Immunization of Ad5 immune mice with Ad5 [E1-, E2b-]-CEA may be shown to induce significantly higher CMI responses.

Lack of Adverse Liver Effects in Immunized Mice

Toxicity studies will be performed on serum from Ad5 immune female C57Bl/6 mice immunized with Ad5 [E1-]-EAs, Ad5 [E1-, E2b-]-EAs as described above. Ad5 naive or Ad5 immune mice injected with buffer alone will serve as controls. Three days after the third immunization, aspartate aminotransferase (AST) levels will be assessed on the blood samples to determine liver toxicity due to the treatment. AST levels may not be elevated over controls following immunization with either vector. Alanine aminotransferase (ALT) levels will also be assessed and similar results may be observed.

Ad5 [E1-, E2b-]-CEA Immunotherapy in Ad5 Immune Ebola Infected Mice

Based upon the successful immunological results observed above, studies in which Ebola infections were established in mice and then treated were performed as described below. After Ebola infection, the mice will be treated with the novel Ad5 [E1-, E2b-]-EA vector platform. To determine if Ad5 immune Ebola infected mice could be treated with the Ad5 [E1-, E2b-]-EA vector, C57Bl/6 mice will be injected two times subcutaneously with $10^{10}$ Ad5 [E1-]-null VP at 14 day intervals to render the mice Ad5 immune. Two weeks after the last injection, two groups of 7 C57Bl/6 mice will be injected subcutaneously with $10^6$ EA expressing cells. Seven days later, when Ebola infection may be palpable, one group of mice will be treated by distal subcutaneous injection with $10^{10}$ VP of Ad5 [E1-, E2b-]-EA on days 7, 13 and 19. A group of injection buffer only treated C57Bl/6 mice will serve as untreated controls. All mice will be monitored for Ebola infection regression over a 21 day period and Ebola virus infection titer will be determined. At the termination of the study, spleens will be collected from mice and the CEA specific CMI response will be determined by ELISpot assay.

Analysis of CMI Responses by ELISpot Assay.

An ELISpot assay for IFN-γ secreting lymphocytes will be performed. Briefly, isolated PBMCs ($2\times10^5$ cells/well) from individual patient samples will be incubated 36-40 h with a EA peptide pool to stimulate IFN-γ producing T-cells. CMI responses to Ad5 will be determined after exposure of patient PBMC to Ad5-null (empty vector). Cells will be stimulated with concanavalin A (Con A) at a concentration of 0.25 μg/well served as positive controls. Colored spot-forming cells (SFC) will be counted using an Immunospot ELISpot plate reader and responses will be considered to be positive if 50 SFC were detected/$10^6$ cells after subtraction of the negative control and SFC were ≥2-fold higher than those in the negative control wells.

Determination of Ad5 Neutralizing Antibody (NAb) Titers.

Endpoint Ad5 NAb titers will be determined. Briefly, dilutions of heat inactivated test sera in 100 μL of DMEM containing 10% fetal calf serum will be mixed with $4\times10^7$ VP of Ad5 [E1-]-null and incubated for 60 minutes at room temperature. The samples will be added to microwells containing HEK293 cells cultured in DMEM containing 10% heat inactivated calf serum at $2\times10^3$ cells/well for 24 hours at 37° C. in 5% $CO_2$. The mixture will be incubated for an additional 72 hours at 37° C. in 5% $CO_2$. An MTS tetrazolium bioreduction assay will be used to measure cell killing and endpoint Ad5 NAb titers. Endpoint titers with a value less than 1:25 will be assigned a value of 0.

Statistics.

Statistical analyses comparing immune responses will be performed employing the Mann-Whitney test (PRISM, Graph Pad). Survival comparisons will be performed employing Kaplan-Meier plots (PRISM, Graph Pad). Ad5 NAb titer and EA-specific CMI will be analyzed as continuous variables. The association of Ad5 NAb titer with change in EA-specific CMI will be tested with the Spearman correlation coefficient. The association of Ad5 NAb titer with survival will be tested with the Wald test of the proportional hazards model.

A secondary objective will be to evaluate EA specific immune responses following immunization treatments with the product.

Dendritic cells will be generated from the peripheral blood mononuclear cells (PBMCs) of a Ebola infected subject; using PBMCs from this patient post-vaccination, individual T-cell lines specific for EAs, will be attempted to be established. Briefly, PBMCs will be isolated using lymphocyte separation medium gradient, resuspended in AIM-V medium ($2\times10^7$ cells) and allowed to adhere in a 6-well plate for 2 hours. Adherent cells will be cultured for 5 days in AIM-V medium containing 100 ng/mL of recombinant human (rh) GM-CSF and 20 ng/ml of rhIL-4 The culture medium will be replenished every 3 days.

Example 3: GLP Production of Clinical Grade Multi-Targeted Vaccine

This example shows the production of clinical-grade multi-target vaccine using good laboratory practice (GLP) standards. Previously, the Ad5 [E1-, E2b-]-CEA(6D) product was produced using a 5 L Cell Bioreactor under GLP conditions in accordance with good manufacturing practice standards. This example may show that the Ad5 [E1-, E2b-]-EA products GP, NP, VP40, VP35, VP30, VP24, and L can be produced in a 5 L Cell Bioreactor using a similar approaches.

Briefly, vials of the E.C7 manufacturing cell line will be thawed, transferred into a T225 flasks, and initially cultured at 37° C. in 5% $CO_2$ in DMEM containing 10% FBS/4 mM L-glutamine. After expansion, the E.C7 cells will be expanded using 10-layered CellSTACKS (CS-10) and transitioned to FreeStyle serum-free medium (SFM). The E.C7 cells will be cultured in SFM for 24 hours at 37° C. in 5% $CO_2$ to a target density of $5\times10^5$ cells/mL in the Cell Bioreactor. The E.C7 cells will then be infected with Ad5 [E1-, E2B-]-GP, Ad5 [E1-, E2B-]-NP, Ad5 [E1-, E2B-]-VP40, Ad5 [E1-, E2B-]-VP35, Ad5 [E1-, E2b-]-VP30, [E1-, E2b-]-VP24, and/or [E1-, E2b-]-L, respectively, and cultured for 48 hours.

Mid-stream processing will be performed in an identical manner as that used to prepare clinical grade Ad5 [E1-, E2B-]-GP, Ad5 [E1-, E2B-]-NP, Ad5 [E1-, E2B-]-VP40, Ad5 [E1-, E2B-]-VP35, Ad5 [E1-, E2b-]-VP30, [E1-, E2b-]-VP24, and/or [E1-, E2b-]-L product. 30 minutes before harvest, Benzonase nuclease will be added to the culture to promote better cell pelleting for concentration. After pelleting by centrifugation, the supernatant will be discarded and the pellets re-suspended in Lysis Buffer containing 1% Polysorbate-20 for 90 min at room temperature. The lysate will then be treated with Benzonase and the reaction quenched by addition of 5 M NaCl. The slurry will be centrifuged and the pellet discarded. The lysate will be clarified by filtration and subjected to a two-column ion exchange procedure.

To purify the vaccine products, a two-column anion exchange procedure will be performed. A first column will be packed with Q Sepharose XL resin, sanitized, and equilibrated with loading buffer. The clarified lysate will be loaded onto the column and washed with loading buffer. The vaccine product will be eluted and the main elution peak (eluate) containing Ad5 [E1-, E2B-]-GP, Ad5 [E1-, E2B-]-NP, Ad5 [E1-, E2B-]-VP40, Ad5 [E1-, E2B-]-VP35, Ad5 [E1-, E2b-]-VP30, [E1-, E2b-]-VP24, and/or [E1-, E2b-]-L carried forward to the next step. A second column will be packed with Source 15Q resin, sanitized, and equilibrated with loading buffer. The eluate from the first anion exchange column will be loaded onto the second column and the vaccine product eluted with a gradient starting at 100% Buffer A (20 mM Tris, 1 mM $MgCl_2$, pH 8.0) running to 50% Buffer B (20 mM Tris, 1 mM $MgCl_2$, 2 M NaCl, pH 8.0). The elution peak containing Ad5 [E1-, E2B-]-GP, Ad5 [E1-, E2B-]-NP, Ad5 [E1-, E2B-]-VP40, Ad5 [E1-, E2B-]-VP35, Ad5 [E1-, E2b-]-VP30, [E1-, E2b-]-VP24, and/or [E1-, E2b-]-L will be collected and stored overnight at 2-8° C. The peak elution fraction will be processed through a tangential flow filtration (TFF) system for concentration and diafiltration against formulation buffer (20 mM Tris, 25 mM NaCl, 2.5% (v/v) glycerol, pH 8.0). After processing, the final vaccine product will be sterile filtered, dispensed into aliquots, and stored at ≤−60° C. A highly purified product approaching 100% purity is typically produced and similar results for these products are predicted.

The concentration and total number of VP product produced will be determined spectrophotometrically. Product purity will be assessed by HPLC. Infectious activity will be determined by performing an Ad5 hexon-staining assay for infectious particles using kits.

Western blots will be performed using lysates from vector transfected cells to verify EA expression. Quality control tests will be performed to determine that the final vaccine products are mycoplasma-free, have no microbial bioburden, and exhibit endotoxin levels less than 2.5 endotoxin units (EU) per mL. To confirm immunogenicity, the individual vectors will be tested in mice.

Example 7: Immunogenicity of Single and Multi-Targeted GP, NP, VP40, VP35, VP30, VP24, L Viral Vectors Female C57BL/6 mice will be injected s.c. with $10^{10}$ VP of Ad5 [E1-, E2B-]-GP, Ad5 [E1-, E2B-]-NP, Ad5 [E1-, E2B-]-VP40, Ad5 [E1-, E2B-]-VP35, Ad5 [E1-, E2b-]-VP30, [E1-, E2b-]-VP24, or [E1-, E2b-]-L, or a combination of $10^{10}$ VP of two or more viruses at a ratio of 1:1:1. Control mice will be injected with $3\times10^{10}$ VP of Ad-null (no transgene insert). Doses will be administered in 25 μl of injection buffer (20 mM HEPES with 3% sucrose) and mice will be vaccinated three times at 14-day intervals. Fourteen days after the final injection spleens and sera will be collected. Sera will be frozen at −20° C. Splenocyte suspensions will be generated by gently crushing the spleens through a 70 μM nylon cell strainer (BD Falcon, San Jose, Calif.). Red cells will be removed by the addition of red cell lysis buffer (Sigma-Aldrich, St. Louis, Mo.) and the splenocytes will be washed twice and resuspended in R10 (RPMI 1640 supplemented with L-glutamine (2 mM), HEPES (20 mM), penicillin 100 U/mL and streptomycin 100 μg/ml, and 10% fetal bovine serum. Splenocytes will be assayed for cytokine production by ELISPOT and flow cytometry.

Immunogenicity Studies:

Two weeks after the last immunization, CMI activity will be determined employing ELISpot assays for IFN-γ secreting cells (SFC) after exposure of splenocytes to EA peptide pools.

Briefly, CMI responses against EAs as assessed by ELISpot assays for IFN-γ secreting splenocytes (SFC) will be detected in multi-targeted immunized mice but not control mice (injected with Ad5-Null empty vector). Specificity of the ELISpot assay responses will be confirmed by lack of reactivity to irrelevant SIV-nef or SIV-vif peptide antigens. A positive control will include cells exposed to concanavalin A (Con A).

ELISPOT Assay

GP, NP, VP40, VP35, VP30, VP24, or L-specific IFN-γ- or IL-2-secreting T cells will be determined by ELISPOT assay from freshly isolated mouse splenocytes. Briefly, $2 \times 10^5$ splenocytes will be stimulated with 0.2 µg/well of overlapping 15-mer peptides in a single pool derived from GP, NP, VP40, VP35, VP30, VP24, or L. Cells will be stimulated with Con A at a concentration of 0.0625 µg/per well as a positive control and overlapping 15-mer complete peptides pools derived from SIV-Nef and SIV-Vif will be used as irrelevant peptide controls. The numbers of SFCs will be determined using an Immunospot ELISpot plate reader and results will be reported as the number of SFCs per $10^6$ splenocytes.

To determine the level of complement dependent cellular cytotoxicity (CDCC), a CDCC test will be performed using EA target cells.

Intracellular Cytokine Stimulation

Splenocytes will be prepared. Stimulation assays will be performed using $1 \times 10^6$ live splenocytes per well in 96-well U-bottom plates. Pools of overlapping peptides spanning the entire coding sequences of GP, NP, VP40, VP35, VP30, VP24, and L will be synthesized as 15-mers with 11-amino acid overlaps and lyophilized peptide pools will be dissolved in DMSO. Similarly constructed peptide pools corresponding to SIV-Vif and SIV-Nef will serve as off-target controls. Splenocytes in R10 media (RPMI 1640, 10% fetal bovine serum, and antibiotics) will be stimulated by the addition of peptide pools at 2 µg/mL/peptide for 6 h at 37° C. and 5% $CO_2$, with protein transport inhibitor (GolgiStop) added 2 h into the incubation. Stimulated splenocytes will then be stained for lymphocyte surface markers CD8α and CD4, fixed, permeabilized, and then stained for the intracellular accumulation of IFN-γ and TNFα. Antibodies against mouse CD8α, CD4, IFN-γ, and TNFα will be used and staining was performed in the presence of anti-CD16/CD32. Flow cytometry will be performed and analyzed in BD Accuri C6 Software.

Complement-Dependent Cytotoxicity Assay (CDC)

EA cells will be cultured overnight at a density of $2 \times 10^4$ cells per well in 96-well tissue culture microplates. Pooled heat inactivated mouse sera will be added at a 1:50 dilution and incubated at 37° C. for 1 hour. Rabbit serum will then be added at a 1:50 dilution as a source of complement and cells will be incubated an additional 2.5 hours at 37° C. Cell culture supernatants will be assayed using Promega Cytotox 96 non-radioactive cytotoxicity assay, according to the manufacturer's instructions. Percent lysis of EA cells will be calculated by the formula % lysis=(experimental−target spontaneous)/(target maximum−target spontaneous)×100%.

Anti-Ebola Immunotherapy Studies:

Studies will be conducted to test the anti-Ebola capability of Ad5 [E1-, E2b-]-based multi-vaccines in immunotherapy studies in mice with established Ebola infections. In this study the anti-Ebola activity of the individual components of the Ad5 [E1-, E2b-]-based multi-vaccine will be assessed.

Groups of C57Bl/6 mice will be injected subcutaneously in the right flank with $5 \times 10^5$ EA expressing cells. Mice will be treated by 3 subcutaneous injections with $1 \times 10^{10}$ VP each of Ad5 [E1-, E2b-]-null (no transgene, e.g., empty vector), Ad5 [E1-, E2B-]-GP, Ad5 [E1-, E2B-]-NP, Ad5 [E1-, E2B-]-VP40, Ad5 [E1-, E2B-]-VP35, Ad5 [E1-, E2b-]-VP30, [E1-, E2b-]-VP24, and [E1-, E2b-]-L, respectively.

Example 8: Use of Ebola Virus GP and NP as Vaccine Targets

Earlier generation recombinant Ad5 based vector (Ad5 [E1-]) vaccines containing Ebola virus gene components, including GP and/or NP have been constructed, produced, and tested in a laboratory setting. Promising pre-clinical protective effects have been obtained in mice and non-human primates (NHP) using these vaccines but the effectiveness was negated when animals exhibited pre-existing or Ad5 vector induced immunity to adenovirus.

In this example, GP and NP components of the Ebola virus will be used in a vaccine. Since the Zaire and Sudan strains are responsible for the most species-specific case fatalities, virus components from these two strains will be initially used. GP will be employed because it is a surface glycoprotein that can be targeted. GP genes from both isolate strains of Ebola will be used in order to induce broadly reactive immune responses against Ebola. Since NP associates with VP35, VP30, and RNA-dependent RNA polymerase to the functional transcriptase-replicase complex, it will be used in the vaccine to induce immune responses that interfere and/or prevent virus replication. In this manner, a broadly reactive vaccine based upon an Ad5 [E1-, E2b-] platform that will induce humoral and cell-mediated immune (CMI) responses against Ebola will be developed. Use of Recombinant Ad5 [E1-, E2b-]-Based Vectors as Vaccines.

The vaccine will be delivered directly by subcutaneous injection for exposure of defined Ebola antigens to antigen-presenting cells (APC) that induce potent immune responses. Amplification of Ad5 [E1-, E2b-]-based vector Ebola vaccines.

Figure 8:
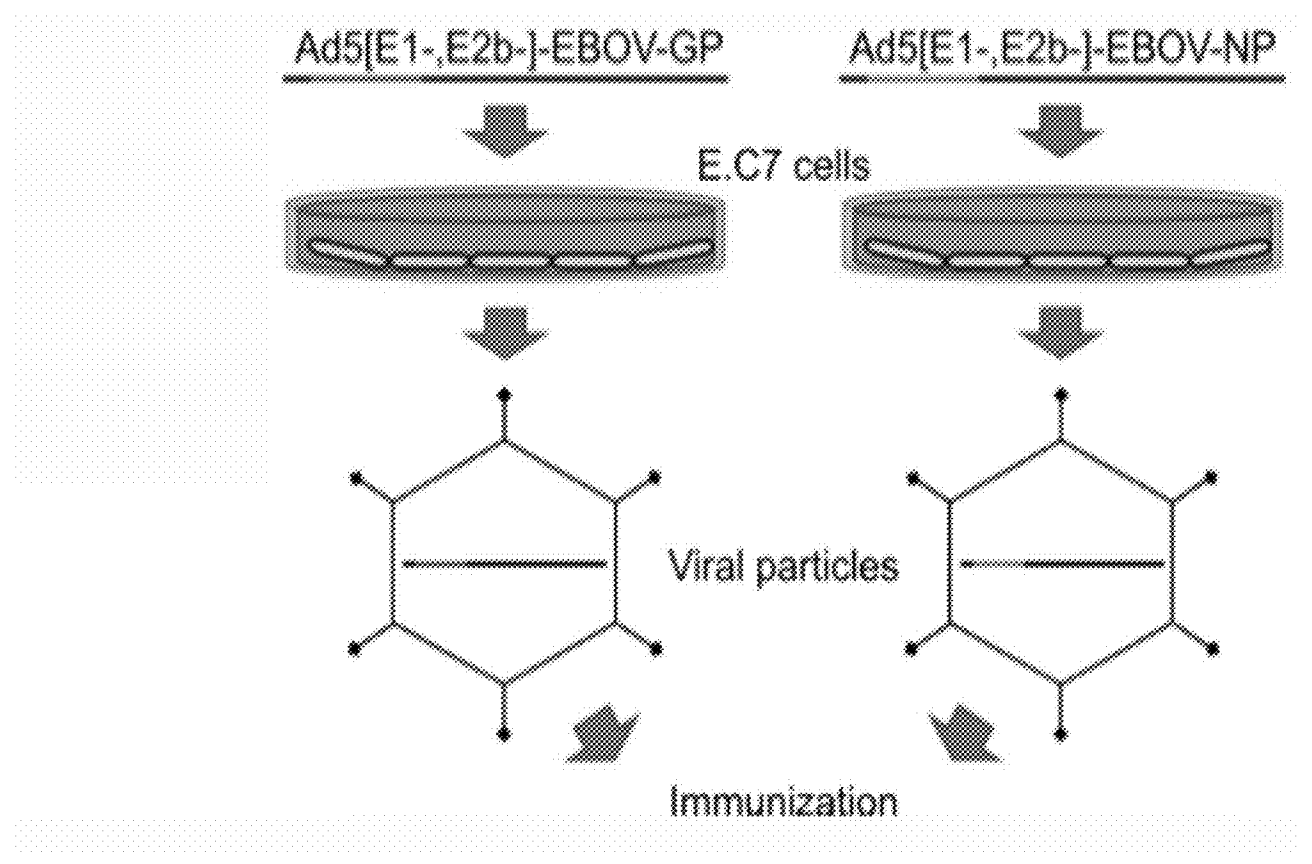

Four Ad5 [E1-, E2b-]-based vaccines were constructed (FIG. 8). For the Zaire strain vaccine, the nucleotide sequences of GP and NP from the current outbreak (Zaire Ebola virus isolate H. sapiens-wt/GIN/2014/Gueckedou-C07, GeneBank accession # KJ660347) were optimized to human codon usage and cloned into the Ad5 [E1-, E2b-] vector under the regulation of CMV promoter. Viral particles were rescued by transfecting E.C7 cells that stably express adenoviral E1 and E2b genes with linearized Ad5 [E1-, E2b-] plasmid constructs, producing an Ad5 [E1-, E2b-]-$GP_{EZ}$ product and an Ad5 [E1-, E2b-]-$NP_{EZ}$ product.

For the Sudan strain vaccine, the nucleotide sequences of GP and NP of a Sudan strain of Ebola virus (Sudan Ebola virus isolate EboSud-682 2012, complete genome GenBank: KC545392.1) were optimized to human codon usage and cloned into the Ad5 [E1-, E2b-] vector under the regulation of CMV promoter. Viral particles were rescued by transfecting E.C7 cells that stably express adenoviral E1 and E2b genes with linearized Ad5 [E1-, E2b-] plasmid constructs, producing an Ad5 [E1-, E2b-]-$GP_{ES}$ product and an Ad5 [E1-, E2b-]-$NP_{ES}$ product.

Production, Purification, and Testing of Recombinant Ad5 [E1-, E2b-]-Based Vaccines.

Figure 9:
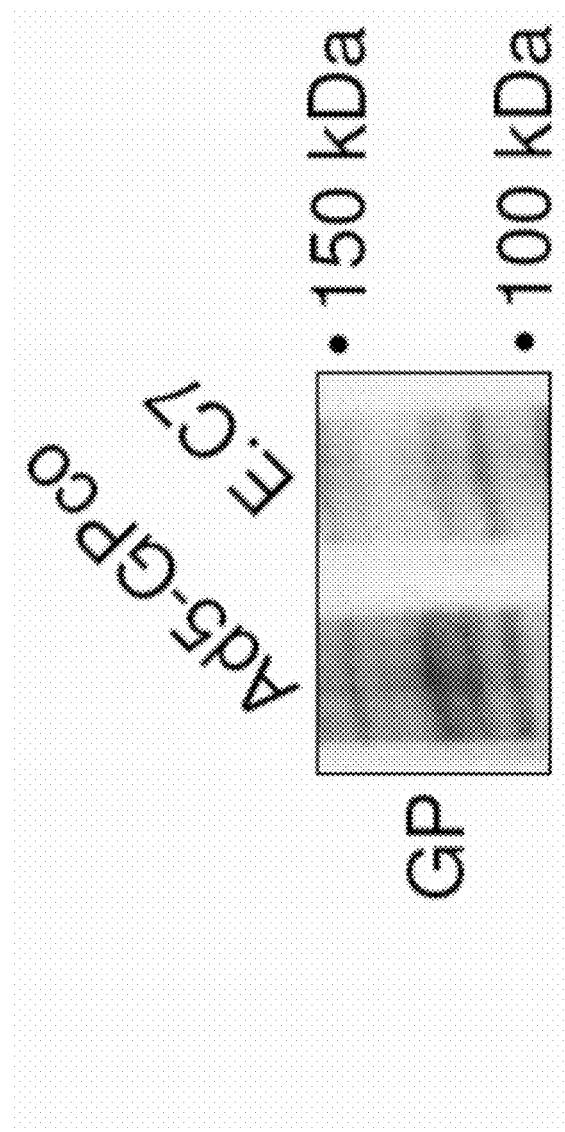
FIG. 9 exemplifies expression of Ebola GP from E.C7 cells infected for 24 hours with Ad5 [E1, Eb2-]-$GP_{EZ}$ (left lane). Note the presence of the GP protein band in the left lane migrating at approximately 125 kDA but not in the right lane (a lysate from non-infected cells).

Additional vaccines will be prepared for later studies with NHP. The E.C7 cell line allows Ad5 [E1-, E2b-] vectors to grow with high and reproducible yields. The Ad5 [E1-, E2b-] vectors will be manufactured and produced by release from E.C7 human cells using Triton X-100, purification on CsCl gradients or ion exchange chromatography, and dialysis against 20 mM HEPES (pH 7.4) containing 5% sucrose. The purified recombinant Ad5 [E1-, E2b-]-based virus vaccines will be aliquoted and frozen in a dry ice-ethanol bath. The infectivity of the virus particles is measured using a plaque assay. Virus particle (VP) concentrations will be calculated from the absorbance at 260 nm and used to determine the amounts of virus for in vivo immunizations. Western blots from transfected A549 cell lysates will verify antigen transgene expression. An example of Ebola GP (Zaire strain) expression in a cell lysate of E.C7 cells after 24 hours transfection with Ad5 [E1-, E2b-]-$GP_{EZ}$ is shown in FIG. 9.

Dose Escalation Immunogenicity Study.

These studies will be performed using a clinically relevant Ad5 immune mouse model. BALB/c mice will be made Ad5-immune by two subcutaneous injections with $10^{10}$ VPs of Ad5-null at two-week intervals. Two weeks after the second injection, sera will be tested for Ad5 neutralizing Ab (NAb) to verify that the mice are Ad5-immune. Mice and monkeys treated in this manner achieve Ad5 NAb titers of 1/100 to 1/200 and in a clinical trial the mean pre existing Ad5 NAb titer among all patients was 1:189±1:71 (mean±SEM). Immune responses that are induced after immunization with increasing doses of Ad5 [E1-, E2b-]-$GP_{EZ}/NP_{EZ}$ and Ad5 [E1-, E2b-]-$GP_{ES}/NP_{ES}$ (an equally combined mixture) will be assessed. Groups of Ad5 immune mice (n=5/group) will be immunized twice by subcutaneous route every two weeks using escalating doses of $4\times10^8$, $4\times10^9$, or $4\times10^{10}$ VPs (a vaccine mixture containing equal amounts of Ad5 [E1-, E2b-]-$GP_{EZ}/NP_{EZ}$ and Ad5 [E1-, E2b-]-$GP_{ES}/NP_{ES}$). Control mice (n=5) will be injected with $4\times10^{10}$ VPs of Ad5 [E1-, E2b-]-null on the same schedule. Fourteen days after the final immunization, antibody (Ab) and cell-mediated immune (CMI) responses will be assessed. For CMI evaluation, splenocytes from individual mice will be assessed using previously described ELISpot assays to measure the number of interferon-$\gamma$ (IFN-$\gamma$) and IL-2-secreting lymphoid cells after exposure to GP or NP peptide pools. Serum samples will be assessed for Ab activity using purified commercially available.

Using the highest immunogenic dose, a study employing one or two subcutaneous immunizations will be performed to determine if one or two doses are required for effective vaccination. Groups of mice (n=5/group) will be immunized one time or twice every two weeks using the most effective dose of vaccine. Control mice (n=5) will be injected with Ad5 [E1-, E2b-]-null (VP quantity same as vaccine) on the same schedule. Fourteen days after the final immunization, Ab and CMI responses will be assessed as described above. These studies will allow determination of whether or not one or two immunizations are required to induce significant immune responses.

Immunogenicity Studies in Ad5 Immune Mice by ELISA, ELISpot, and Flow Cytometry.

For these studies, the most effective dose and frequency of vaccination determined above will be used. In a proof-of-concept study in monkeys with influenza vaccine, it was observed that Ab responses, as assessed by hemagglutination inhibition (HAI) assays, might require up to 30 days to develop maximum levels (FIG. 9). Therefore, Ab activity and CMI responses in Ad5-immune BALB/c mice (n=5/group) at two weeks, 30 days, and 60 days after subcutaneous vaccination will be assessed with the most effective dose and frequency of vaccination (vaccine mixture containing equal amounts of Ad5 [E1-, E2b-]-$GP_{EZ}/NP_{EZ}$ and Ad5 [E1-, E2b-]-$GP_{ES}/NP_{ES}$). Control mice will be injected with Ad5 [E1-, E2b-]-null (VP quantity same as vaccine) on the same schedule. Two weeks, 30 days, or 60 days after vaccination, serum and spleen cells will be collected from individual mice. Splenocytes from individual mice will be assessed for CMI responses using ELISpot assays to measure the number of IFN-$\gamma$ and IL-2 secreting lymphoid cells after exposure to GP or NP peptide pools. Since cytotoxic T lymphocyte (CTL) responses will also be of importance in the evaluation of vaccines, granzyme B secretion will be analyzed by ELISpot assays on splenocytes after exposure to GP or NP peptide pools for CTL activity since this is a good assay to measure CD8 functional CTL activity. Serum samples will be assessed for Ab activity against purified commercially available Ebola virus proteins employing an ELISA technique. For virus neutralizing activity, plaque reduction neutralization assays will also be performed on sera from individual mice.

Based upon the above studies in which the highest CMI responses are observed, flow cytometry studies will also be performed to characterize T-cell immune responses induced by immunization with the vaccines. Ad5-immune BALB/c mice (n=5) will be immunized with the vaccine using the most effective dose and frequency of vaccination. Control mice (n=5) will be injected with Ad5 [E1-, E2b-]-null (VP quantity same as vaccine) on the same schedule. Based upon the optimal time after vaccination, spleens will be harvested and $CD4^+$ and $CD8^+$ T cells will be determined by flow cytometry for IFN-$\gamma$ and/or TNF-$\alpha$ expressing cells after exposure to GP or NP peptide pools. Briefly, splenocytes from immunized and control mice will be harvested and incubated for 5 hrs with 0.5 μg/ml of GP or NP peptide pools, in the presence of GolgiStop, a protein transport inhibitor. The $CD4^+$ or $CD8^+$ T cells will then be fixed, permeabilized, stained for IFN-$\gamma$ or TNF-$\alpha$, and analyzed by flow cytometry.

Protection of Vaccinated Ad5 Immune Mice Against Virus Challenge.

In a proof-of-principle test, a challenge study will be performed in mice. Two groups of BALB/c mice (n=15/group) will be made Ad5-immune as described above. Using the most effective dose and frequency for vaccination, one group will be immunized with the vaccine (vaccine mixture containing equal amounts of Ad5 [E1-, E2b-]-$GP_{EZ}/NP_{EZ}$ and Ad5 [E1-, E2b-]-$GP_{ES}/NP_{ES}$). A control group will be injected with Ad5 [E1-, E2b-]-null (VP quantity same as vaccine) on the same schedule. When induced virus neutralizing titers are achieved, the mice will be challenged by inoculations with a lethal mouse adapted strain of Ebola. Weight loss and time to death for the endpoints will be monitored. Mice will be observed daily for clinical signs of morbidity for over 21 days after challenge.

Phase 2 Studies

In phase 2 studies, the immunogenicity of the Ebola vaccines in NHP will be evaluated. The appropriate immunizing dose, boosting schedule, and live Ebola challenge potential will be determined. In addition, the Ad5 [E1-, E2b-]-based platform containing fused GP and NP genes from the Zaire and Sudan strains of Ebola virus will be evaluated. In this manner two recombinant vectors will be produced, an Ad5 [E1-, E2b-]-$GP_{EZ}/NP_{EZ}$ product and an Ad5 [E1-, E2b-]-$GP_{ES}/NP_{ES}$ product. By introducing multiple genes into one recombinant Ad5 [E1-, E2b-]-based vector, the number of viral particles that would be required will be significantly cut down compared to producing and combining each of 4 individual recombinant vectors.

The various embodiments described above can be combined to provide further embodiments. All of the U.S. patents, U.S. patent application publications, U.S. patent application, foreign patents, foreign patent application and non-patent publications referred to in this specification and/ or listed in the Application Data Sheet are incorporated herein by reference, in their entirety to the same extent as if each individual publication, patent, or patent application was specifically and individually indicated to be incorporated by reference.

Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A composition comprising an adenovirus 5 vector comprising a nucleotide sequence encoding a first antigen, wherein the first antigen is a glycoprotein (GP), wherein the adenovirus 5 vector comprises a deletion in an E1 gene region and a deletion in an E2b gene region, and wherein the GP is from an Ebola selected from the group consisting of Zaire ebolavirus (EBOV), Sudan virus (SUDV), Tai Forest ebolavirus (TAFV), Bundibugyo ebolavirus (BDBV), Reston virus (RESTV), and any combination thereof.

2. The composition of claim 1, wherein the adenovirus 5 vector further comprises a deletion in an E3 gene region, an E4 gene region, or any combination thereof.

3. The composition of claim 1, wherein the adenovirus 5 vector is a replication defective adenovirus 5 vector.

4. The composition of claim 1, further comprising an immunogenic component, wherein the immunogenic component comprises a cytokine selected from the group consisting of IFN-γ, TNFα IL-2, IL-8, IL-12, IL-18, IL-7, IL-3, IL-4, IL-5, IL-6, IL-9, IL-10, and IL-13.

5. The composition of claim 4, wherein the immunogenic component is IL-7.

6. The composition of claim 3, wherein the replication defective adenovirus vector is capable of generating an immune response to the GP following one round, two rounds, or multiple rounds of immunization with the same type of replication defective adenovirus vector.

7. The composition of claim 1, wherein the adenovirus 5 vector is capable of inducing an immune response against cells expressing the Ebola virus antigen in a human that is at least 2 fold over basal, as measured as an Ebola virus antigen specific antibody response, as a neutralizing Ebola virus antigen specific antibody response, as Ebola virus antigen specific cell-mediated immunity (CMI), as Ebola virus antigen specific IFN-γ secretion, as Ebola virus antigen specific IL-2 secretion, by ELISpot assay, or by any combination thereof.

8. The composition of claim 7, wherein the immune response is measured as an Ebola virus antigen specific antibody response.

9. The composition of claim 1, further comprising a nucleotide encoding an immunological fusion partner.

10. The composition of claim 8, wherein the immunological fusion partner comprises a *Mycobacterium tuberculosis*-derived Ra12 fragment, protein D fragment, NS1, or LYTA.

11. The composition of claim 1, wherein the adenovirus 5 vector comprises a nucleotide encoding a second antigen.

12. The composition of claim 11, wherein the adenovirus 5 vector comprises a nucleotide encoding a third antigen.

13. The composition of claim 11, wherein the second antigen is selected from NP, VP40, VP35, VP30, VP24, and L.

14. The composition of claim 12, wherein the third antigen is selected from NP, VP40, VP35, VP30, VP24, and L.

15. The composition of claim 1 in a single dose form comprising $5.0 \times 10^{11}$ virus particles (VPs).

16. A method of generating an immune response against an Ebola virus antigen in a human comprising:
(a) a first phase of treatment comprising administering to the human a first composition comprising the composition of claim 1; and
(b) a subsequent second phase of treatment comprising administering to the human a second composition comprising a second replication defective adenovirus vector encoding an Ebola virus antigen that induces an immune response against cells expressing the Ebola virus antigen in the human.

17. The method of claim 16, wherein the first phase is at least 2 weeks.

18. The method of claim 16, wherein the second phase is at least 2 months.

19. The method of claim 16, wherein the second phase starts 3-16 weeks after first phase ends.

20. The method of claim 16, wherein in the first phase two administrations of the composition are at least 18 days apart.

21. The method of claim 20, wherein in the first phase two administrations of the composition are about 21 days apart.

22. The method of claim 20, wherein in the first phase two administrations of the composition are at most 24 days apart.

23. The method of claim 16, wherein in the second phase two administrations of the replication defective adenovirus are at least 10 weeks apart.

24. The method of claim 23, wherein in the second phase two administrations of the replication defective adenovirus are about 13 weeks apart.

25. The method of claim 23, wherein in the second phase two administrations of the replication defective adenovirus are at most 16 weeks apart.

\* \* \* \* \*